(12) United States Patent
Vojan et al.

(10) Patent No.: US 11,638,840 B2
(45) Date of Patent: May 2, 2023

(54) RADIOTHERAPY METHODS, SYSTEMS, AND WORKFLOW-ORIENTED GRAPHICAL USER INTERFACES

(71) Applicant: VARIAN MEDICAL SYSTEMS, INC., Palo Alto, CA (US)

(72) Inventors: Filip Vojan, Palo Alto, CA (US); Brian Spatola, Palo Alto, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 163 days.

(21) Appl. No.: 17/138,155

(22) Filed: Dec. 30, 2020

(65) Prior Publication Data

US 2022/0203137 A1   Jun. 30, 2022

(51) Int. Cl.
*A61N 5/10* (2006.01)

(52) U.S. Cl.
CPC ............ *A61N 5/1081* (2013.01); *A61N 5/103* (2013.01); *A61N 2005/1074* (2013.01)

(58) Field of Classification Search
CPC .................. A61N 5/1081; A61N 5/103; A61N 2005/1074; A61N 5/1049
See application file for complete search history.

(56) References Cited

U.S. PATENT DOCUMENTS

| | | | |
|---|---|---|---|
| 3,783,251 A * | 1/1974 | Pavkovich | A61B 6/4441 378/68 |
| 5,446,548 A | 8/1995 | Gerig et al. | |
| 6,222,544 B1 * | 4/2001 | Tarr | A61N 5/103 128/845 |
| 6,614,036 B1 * | 9/2003 | Reinstein | A61N 5/1049 250/492.3 |
| 6,650,930 B2 | 11/2003 | Ding | |
| 6,810,108 B2 | 10/2004 | Clark et al. | |
| 6,937,696 B1 | 8/2005 | Mostafavi | |
| 7,154,991 B2 | 12/2006 | Earnst et al. | |
| 7,166,852 B2 | 1/2007 | Saracen et al. | |
| 7,372,053 B2 * | 5/2008 | Yamashita | F16D 55/40 250/398 |
| 7,397,054 B2 * | 7/2008 | Natori | A61N 5/1079 315/504 |

(Continued)

FOREIGN PATENT DOCUMENTS

| | | |
|---|---|---|
| EP | 3 436 912 | 2/2019 |
| KR | 101580935 | 12/2015 |

OTHER PUBLICATIONS

International Search Report and Written Opinion on PCT Appl. Ser. PCT/US2021/064511 dated May 31, 2022 (32 pages).

*Primary Examiner* — David P Porta
*Assistant Examiner* — Djura Malevic
(74) *Attorney, Agent, or Firm* — Foley & Lardner LLP

(57) ABSTRACT

Disclosed herein are radiotherapy methods and systems that can display a workflow-oriented graphical user interface(s). In an embodiment, a method comprises presenting, by a server, a graphical user interface for display on a screen positioned on a gantry of a radiotherapy machine, wherein the graphical user interface comprises a page corresponding to a radiotherapy treatment of a patient, wherein the page comprises a first graphical element indicating at least one attribute of alignment data corresponding to the radiotherapy treatment of the patient.

20 Claims, 65 Drawing Sheets

(56) References Cited

U.S. PATENT DOCUMENTS

| | | | |
|---|---|---|---|
| 7,492,858 B2* | 2/2009 | Partain | A61B 6/4441 5/601 |
| 7,511,286 B2 | 3/2009 | Manthey | |
| 7,586,112 B2* | 9/2009 | Chiba | A61N 5/1079 250/493.1 |
| 7,613,501 B2 | 11/2009 | Scherch | |
| 7,835,494 B2 | 11/2010 | Nord et al. | |
| 7,839,975 B2* | 11/2010 | Nakamura | A61B 6/032 378/65 |
| 7,860,550 B2* | 12/2010 | Saracen | A61B 6/548 5/601 |
| 7,869,859 B2* | 1/2011 | Shinno | A61B 6/465 378/98 |
| 8,095,203 B2 | 1/2012 | Wright et al. | |
| 8,130,904 B2 | 3/2012 | Bowers et al. | |
| 8,189,738 B2* | 5/2012 | Dussault | A61N 5/103 378/65 |
| 8,239,005 B2* | 8/2012 | Wright | A61N 5/1049 600/427 |
| 8,278,633 B2 | 10/2012 | Nord et al. | |
| 8,587,519 B2 | 11/2013 | Shaw et al. | |
| 8,655,429 B2* | 2/2014 | Kuduvalli | B25J 9/1682 600/407 |
| 8,693,633 B2 | 4/2014 | Hyde et al. | |
| 8,788,020 B2 | 7/2014 | Mostafavi et al. | |
| 8,836,697 B2 | 9/2014 | Nord et al. | |
| 8,849,633 B2 | 9/2014 | Core et al. | |
| 8,907,893 B2* | 12/2014 | Shaw | H04N 21/42222 345/158 |
| 9,020,235 B2 | 4/2015 | Krishnan et al. | |
| 9,421,397 B2 | 8/2016 | Purdie et al. | |
| 9,492,685 B2 | 11/2016 | Jeong | |
| 9,511,243 B2 | 12/2016 | Yan et al. | |
| 9,555,266 B2* | 1/2017 | Hishikawa | A61N 5/1045 |
| 9,586,059 B2 | 3/2017 | Herron et al. | |
| 9,764,162 B1 | 9/2017 | Willcut et al. | |
| 9,764,163 B2* | 9/2017 | Benner | A61N 5/1049 |
| 9,788,810 B2 | 10/2017 | Ancar | |
| 9,955,241 B2* | 4/2018 | Smith | G06F 21/44 |
| 9,990,711 B2 | 6/2018 | Lugosi et al. | |
| 10,029,122 B2* | 7/2018 | Michaud | A61N 5/1049 |
| 10,035,026 B2 | 7/2018 | Tijs et al. | |
| 10,065,049 B2 | 9/2018 | Lugosi et al. | |
| 10,183,177 B2 | 1/2019 | Meir et al. | |
| 10,258,811 B2 | 4/2019 | Kumar et al. | |
| 10,293,179 B2 | 5/2019 | Carpenter et al. | |
| 10,296,563 B2 | 5/2019 | Shaath | |
| 10,307,614 B2 | 6/2019 | Schnarr | |
| 10,307,617 B2* | 6/2019 | Michaud | A61N 5/107 |
| 10,315,049 B2 | 6/2019 | Gauthier et al. | |
| 10,342,997 B2 | 7/2019 | Spatola et al. | |
| 10,376,714 B2 | 8/2019 | Bharat et al. | |
| 10,383,585 B2 | 8/2019 | Konno | |
| 10,449,394 B2* | 10/2019 | Benner | A61N 5/1081 |
| 10,456,600 B2 | 10/2019 | Owens et al. | |
| 10,493,298 B2 | 12/2019 | Hampton et al. | |
| 10,493,300 B2 | 12/2019 | Kane et al. | |
| 10,561,861 B2 | 2/2020 | Dempsey | |
| 10,583,310 B1 | 3/2020 | Fram et al. | |
| 10,583,312 B2* | 3/2020 | Ono | A61N 5/1081 |
| 10,600,514 B2 | 3/2020 | Haas et al. | |
| 10,622,114 B2 | 4/2020 | Purwar et al. | |
| 10,643,371 B2 | 5/2020 | Bharadwaj et al. | |
| 10,653,893 B2 | 5/2020 | Kuusela et al. | |
| 10,668,302 B2* | 6/2020 | Knox | A61N 5/1065 |
| 10,737,117 B2 | 8/2020 | Mori et al. | |
| 10,765,889 B2 | 9/2020 | Koehl et al. | |
| 10,765,891 B2 | 9/2020 | Isola et al. | |
| 10,799,716 B2 | 10/2020 | Morgas et al. | |
| 10,799,718 B2 | 10/2020 | Smith | |
| 10,814,143 B2 | 10/2020 | Hardemark | |
| 10,835,761 B2 | 11/2020 | Bã© riault | |
| 10,835,762 B2 | 11/2020 | Mori et al. | |
| 10,850,119 B2 | 12/2020 | Meltsner et al. | |
| 10,888,714 B2 | 1/2021 | Dempsey et al. | |
| 10,940,331 B2 | 3/2021 | Mori et al. | |
| 10,940,334 B2 | 3/2021 | Fishman et al. | |
| 10,952,695 B2 | 3/2021 | Mori et al. | |
| 10,959,783 B2 | 3/2021 | Gregerson et al. | |
| 10,960,232 B2* | 3/2021 | Gaderlund | A61N 5/1067 |
| 10,966,680 B2 | 4/2021 | Kagermeier et al. | |
| 10,974,070 B2 | 4/2021 | Vahala et al. | |
| 10,993,680 B2* | 5/2021 | Ruebel | G21K 1/08 |
| 11,000,703 B2 | 5/2021 | Krishnaswamy et al. | |
| 11,024,084 B2 | 6/2021 | Friman et al. | |
| 11,077,320 B1 | 8/2021 | Hibbard | |
| 11,083,911 B2 | 8/2021 | Anto et al. | |
| 11,110,298 B2 | 9/2021 | Anto et al. | |
| 11,141,126 B2 | 10/2021 | Mori et al. | |
| 11,184,967 B2* | 11/2021 | Coleman | G01S 7/497 |
| 11,229,409 B2* | 1/2022 | Deutschmann | A61B 6/462 |
| 11,273,326 B2 | 3/2022 | Ohishi | |
| 11,273,328 B2 | 3/2022 | Schell et al. | |
| 11,278,737 B2 | 3/2022 | Peltola et al. | |
| 11,278,739 B2* | 3/2022 | Hannibal | H01H 13/023 |
| 11,285,338 B2 | 3/2022 | Schadewaldt et al. | |
| 11,311,264 B2 | 4/2022 | Szczykutowicz et al. | |
| 11,358,008 B2 | 6/2022 | Voronenko et al. | |
| 11,369,806 B2* | 6/2022 | Laurence, Jr. | A61N 5/1049 |
| 11,369,807 B2* | 6/2022 | Jacques | A61N 5/1081 |
| 11,452,491 B2 | 9/2022 | Toepfer | |
| 2004/0122308 A1 | 6/2004 | Ding | |
| 2004/0181142 A1* | 9/2004 | Shinno | A61B 6/548 600/407 |
| 2004/0183033 A1* | 9/2004 | Moriyama | A61N 5/1079 250/398 |
| 2005/0085710 A1* | 4/2005 | Earnst | A61B 6/0487 378/65 |
| 2005/0218341 A1 | 10/2005 | Saracen et al. | |
| 2006/0063999 A1 | 3/2006 | Herron et al. | |
| 2006/0072849 A1* | 4/2006 | Marc | A61N 5/1042 382/128 |
| 2006/0163495 A1* | 7/2006 | Hiramoto | A61N 5/1049 250/492.3 |
| 2008/0089463 A1* | 4/2008 | Nakamura | G01R 33/283 378/4 |
| 2009/0003975 A1* | 1/2009 | Kuduvalli | B25J 9/0084 901/19 |
| 2010/0008467 A1* | 1/2010 | Dussault | A61N 5/103 378/65 |
| 2010/0317968 A1* | 12/2010 | Wright | A61B 90/36 250/492.3 |
| 2011/0071380 A1* | 3/2011 | Goldenberg | A61N 5/1007 600/411 |
| 2013/0024213 A1 | 1/2013 | Poon | |
| 2013/0296687 A1 | 11/2013 | Dempsey | |
| 2014/0055351 A1* | 2/2014 | Shaw | G06F 3/0346 345/156 |
| 2015/0095045 A1* | 4/2015 | Kashyap | G16H 20/40 705/2 |
| 2015/0119625 A1* | 4/2015 | Knox | A61N 5/1047 600/1 |
| 2015/0328482 A1* | 11/2015 | Hishikawa | A61N 5/1049 250/208.1 |
| 2016/0243927 A1* | 8/2016 | Biderman | G07C 5/008 |
| 2016/0287907 A1* | 10/2016 | Michaud | A61N 5/107 |
| 2016/0302871 A1 | 10/2016 | Gregerson et al. | |
| 2017/0087389 A1* | 3/2017 | Benner | A61N 5/1082 |
| 2017/0238991 A1* | 8/2017 | Worrell | H05K 3/0011 |
| 2017/0245027 A1* | 8/2017 | Smith | G06F 21/44 |
| 2017/0259084 A1* | 9/2017 | Bennett | A61N 5/1049 |
| 2017/0259085 A1* | 9/2017 | Bennett | A61B 6/032 |
| 2018/0064959 A1* | 3/2018 | Benner | A61N 5/1049 |
| 2018/0078784 A1 | 3/2018 | Schnarr | |
| 2018/0125610 A1 | 5/2018 | Carrier et al. | |
| 2018/0264287 A1* | 9/2018 | Ono | A61N 5/1069 |
| 2018/0294052 A1 | 10/2018 | Fishman | |
| 2019/0021684 A1* | 1/2019 | Ruebel | A61N 5/1082 |
| 2019/0054320 A1 | 2/2019 | Owens et al. | |
| 2019/0103869 A1* | 4/2019 | Hannibal | H01H 13/023 |
| 2019/0143145 A1* | 5/2019 | Laurence, Jr. | A61B 34/10 600/1 |

(56) References Cited

U.S. PATENT DOCUMENTS

| | | |
|---|---|---|
| 2019/0240508 A1 | 8/2019 | Friman et al. |
| 2019/0243138 A1 | 8/2019 | Peltola et al. |
| 2019/0246873 A1 | 8/2019 | Lu et al. |
| 2019/0255362 A1 | 8/2019 | Voronenko et al. |
| 2020/0030636 A1* | 1/2020 | Gaderlund ............. A61B 6/541 |
| 2020/0121267 A1* | 4/2020 | Deutschmann ...... A61B 6/4452 |
| 2020/0121954 A1 | 4/2020 | Bodduluri et al. |
| 2020/0316408 A1* | 10/2020 | Jacques ................ A61N 5/1037 |
| 2021/0031057 A1 | 2/2021 | Nakagawa |
| 2021/0090716 A1* | 3/2021 | Deasy .................... A61B 5/055 |
| 2021/0112647 A1* | 4/2021 | Coleman ................ H05B 47/11 |
| 2022/0203126 A1* | 6/2022 | Vojan .................... A61N 5/1049 |
| 2022/0203137 A1* | 6/2022 | Vojan ..................... A61N 5/103 |
| 2022/0208366 A1* | 6/2022 | Vojan ..................... G16H 40/20 |

* cited by examiner

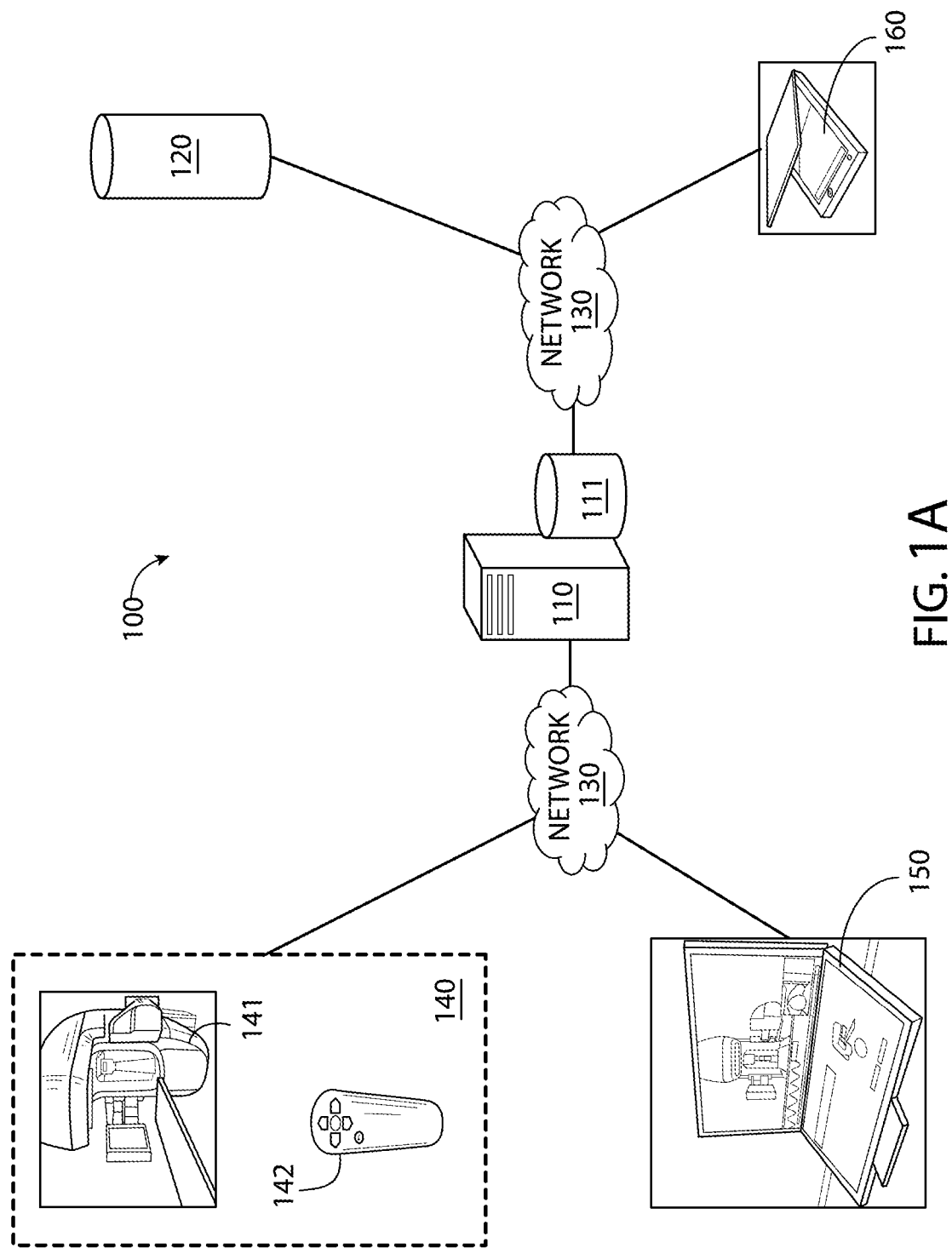

| SRS, Susan CLTST_503C | | | | ☒ Field | KV-KV Setup Pair | |
|---|---|---|---|---|---|---|
| | Plan | Actual | | Plan | | Actual Go To/Resume |
| Int Mount | No Accy | No Accy | Gantry Rtn | 0.0 ▽ | | 3.4 |
| Acc Mount | No Accy | No Accy | | | | |
| e-Aperture | No Accy | No Accy | Coll Rtn | 0.0 | | 0.0 |
| Comp Mount | No Accy | No Accy | Y | 4.2 | | 4.2 |
| Bolus | None | | Y1 | -2.1 | | -2.1 |
| EDW | None | | Y2 | +2.1 | | +2.1 |
| | | | X | 10.0 | | 10.0 |
| Imager | Plan | Actual Go To | X1 | -10.0 ▽ | | -11.5 |
| MV Vrt | Mid | Mid | X2 | +10.0 ▽ | | +11.5 |
| Lng | Mid | Mid | Couch | | | |
| Lat | Mid | Mid | Vrt | -0.00 ▽ | | +0.02 |
| kV Vrt | -50.0 | -50.0 | Lng | +60.00 | | +55.08 |
| Lng | 0.0 | +0.0 | Lat | -0.00 | | +0.00 |
| Lat | 0.0 | 0.0 | Rtn | 0.0 ▽ | | 357.3 |
| kV Blade Y1 | Tracking | -10.3 | Pitch | )0.0 | | 0.0 |
| Y2 | Tracking | +10.3 | Roll | )0.0 | | 0.0 |
| X1 | Tracking | -13.3 | SSD | | | |
| X2 | Tracking | +13.3 | | | | |
| Source | +100.0 | +100.0 | Display scale: IEC 61217 (Units shown are centimeters or degrees) | | | |

02:11 PM
01-May-2013

PRIOR ART

FIG. 1C

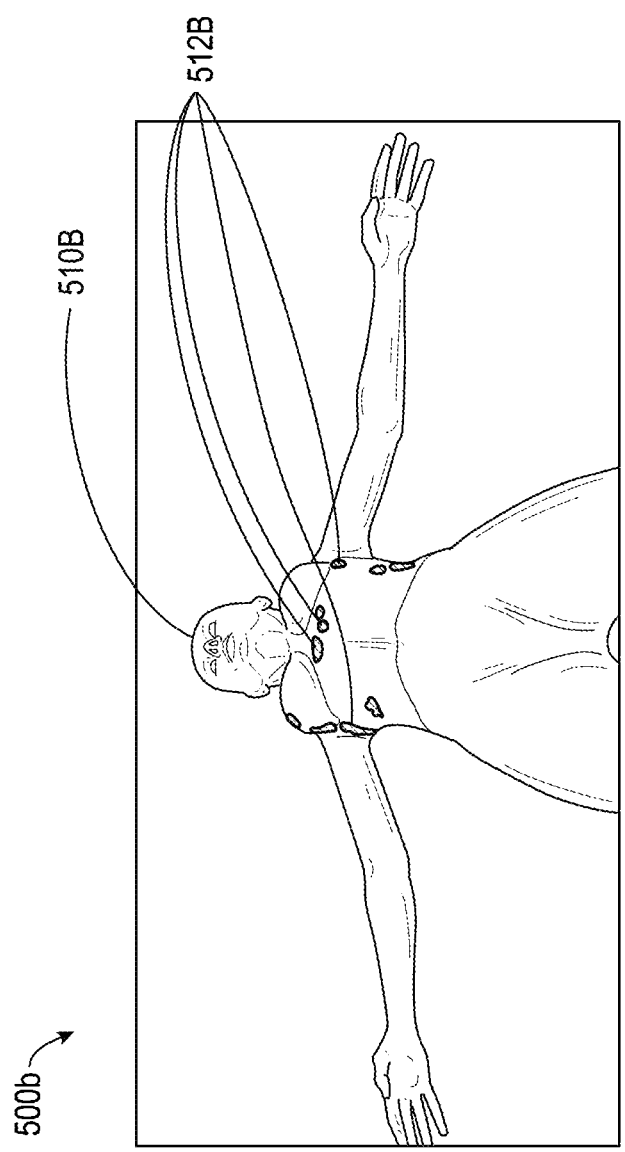

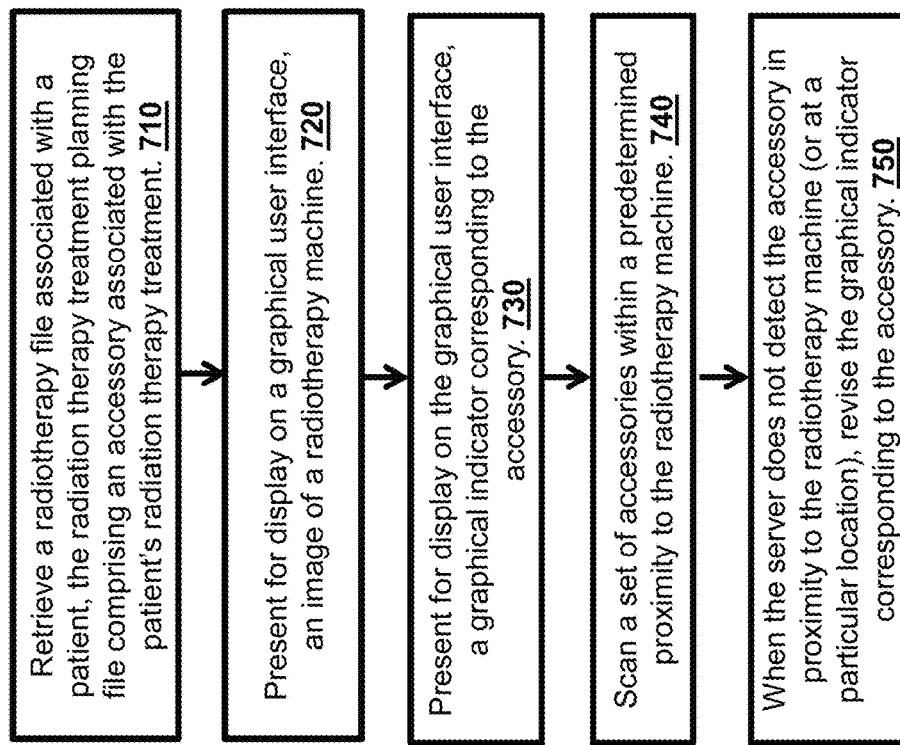

RADIOTHERAPY METHODS, SYSTEMS, AND WORKFLOW-ORIENTED GRAPHICAL USER INTERFACES

TECHNICAL FIELD

This application relates generally to graphical user interfaces and software for radiotherapy treatments and machines.

BACKGROUND

Radiation therapy, which is the use of ionizing radiation, is a localized treatment for a specific target tissue, such as a cancerous tumor. Ideally, radiation therapy is performed on target tissue (also referred to as the planning target volume or the target organ) that spares the surrounding normal tissue from receiving doses above specified tolerances, thereby minimizing risk of damage to healthy tissue. So that the prescribed dose is correctly supplied to the planning target volume during radiation therapy, the patient should be precisely positioned relative to the linear accelerator that provides the radiation therapy, typically using a movable treatment couch mounted on a turntable assembly.

Therefore, implementing the radiation therapy is a complex process that contains specific guidelines, protocols and instructions adopted and observed by different medical professionals, such as the clinicians/technicians, the manufacturers of the medical device, the treating physicians, and the like. Due to the above-described hazards associated with radiation emitted from the radiotherapy (also referred to as radiation therapy) machine, it is imperative that all the instructions are precisely followed.

Conventional radiation therapy systems can be complex to operate, and users generally require extensive training to perform the various workflows on the system efficiently. For instance, patient positioning, system calibration, and other adjustments of the machine and/or accessories typically involve various interactions with and adjustments of the patient and the radiotherapy machine. Because data needed to set up the machine and/or the patient is voluminous and complicated, conventional methods typically display the data on a screen within the treatment room. However, conventional methods/system can be inefficient, ineffective, or even dangerous.

As depicted in FIG. 1B, the information needed by an operator (e.g., radiotherapy technician) is typically displayed on a screen that is usually placed on a wall near the radiotherapy machine or on another monitor within the treatment room. As a result, when the operator focuses on the display screen, the operator must turn away from the patient and the radiotherapy machine. The process of adjusting the radiotherapy machine and/or the patient is interrupted by shifting the focus away from the radiotherapy machine and/or the patient. The inconvenient placement of the display screen has been proven to be ineffective and time-consuming.

Furthermore, conventional radiotherapy systems do not provide an efficient manner of displaying the data needed for the operator to set up the patient and/or the radiotherapy machine. For instance, conventional radiotherapy systems display all the information needed to implement a patient's radiotherapy treatment on a screen at one time. Referring to FIGS. 1C-D, two examples of conventional graphical user interfaces (GUIs) displaying radiation therapy data is presented. As depicted, these GUIs are static and difficult to understand and follow. Furthermore, these GUIs display data that is not necessarily needed at a particular stage of the machine or patient set up. Therefore, by displaying all radiotherapy data at once, these GUIs have created inefficiencies. As a result, unless an operator is very experienced with a particular radiation therapy system, utilization of the system will not be maximized, which slows set up of the system and degrades the radiation therapy experience of the patient.

Furthermore, a typical radiation therapy system usually involves a specific sequence of user inputs selected from this multiplicity of input mechanisms. Consequently, when performing a radiation therapy workflow, selecting the correct input button or switch from among the dozens of possible input mechanisms available can be problematic and time-consuming. Conventional methods also allow operators to interact with the radiotherapy system (e.g., adjust the radiotherapy machine) using a controller (sometimes referred to as a pendant) connected to the radiotherapy machine. Referring now to FIG. 1E, an example of a conventional pendant is presented. As depicted, the pendant depicted in FIG. 1E has many input mechanisms (e.g., buttons and switches) where each input mechanism is specific to different parameters and attributes of the radiotherapy system. Therefore, conventional pendants are complicated and require the operators to be familiar with many input mechanisms, resulting in errors and inefficiencies.

Finally, most radiotherapy systems require a secondary operator to monitor the radiotherapy machine and patient set up from a different room other than the treatment room using console monitor(s). In some configurations, the same operator (from the treatment room) may need to monitor the radiotherapy machine and patient set up from a different room. Typically, the operator leaves the treatment room before the patient's treatment begins to avoid exposure to radiation. Therefore, there is a need to monitor the patient and/or the radiotherapy machine from a secondary location that shields the operator from radiation (also referred to as a console room). FIG. 1F is an example of a monitoring station in a secondary location. Conventional console monitor(s) provide radiotherapy machine and patient data. Because the data being monitored is voluminous, conventional console monitor(s) display the data on multiple display screens. For instance, one monitor may display parameters and one monitor may display a view of the patient. As depicted, multiple monitors display information about the radiotherapy machine and/or patient. The operator may focus on several screens to safely and effectively monitor the patient in the treatment room. Monitoring data simultaneously displayed on multiple screens is difficult and has led to inefficiencies. Further, the operator may have several input mechanisms (e.g., buttons, switches, mouse, and keyboard) where each input mechanism is specific to different parameters and attributes of the radiotherapy machine. Therefore, the monitoring station may require one or more experienced operators familiar with the input mechanisms and the location of relevant information on the various console monitors.

SUMMARY

For the aforementioned reasons, there is a desire for a workflow-oriented graphical user interface(s) that displays the treatment data (e.g., machine parameters, patient alignment data, and accessories needed) in an efficient way. The methods and systems described herein provide graphical user interface having a series of interconnected pages that segment the data based on different treatment stages and only show data relevant to a particular stage and relevant to the patient's treatment. A central server can control the workflow-oriented series of pages based on inputs received from the technician. The pages can be displayed on one or more electronic devices described herein (e.g., directly on a gantry), allowing the technician to operate the radiotherapy machine without diverting attention away from the patient.

Moreover, there is a desire to control a workflow-oriented graphical user interface using a pendant that is easy to use. Described herein are different embodiments of a pendant that can be used in conjunction with the workflow-oriented series of pages where the pendant can control the radiotherapy machine and navigate various pages described herein.

Furthermore, there is a desire for a console monitoring system that uses a series of interconnected pages that segment the data based on different treatment stages and/or the actions performed within the treatment room.

In an embodiment, a method comprises presenting, by a server, a graphical user interface for display on a screen associated with a radiotherapy machine, wherein the graphical user interface contains a page corresponding to one or more stages of radiotherapy treatment for the patient, and transitioning, by the server, the graphical user interface from a first page representing a first stage to a second page representing a second stage provided that at least a predetermined portion of tasks associated with the first stage has been satisfied.

In another embodiment, a system comprises: a server comprising a processor and a non-transitory computer-readable medium containing instructions that when executed by the processor causes the processor to perform operations comprising: present a graphical user interface for display on a screen associated with a radiotherapy machine, wherein the graphical user interface contains a page corresponding to one or more stages of radiotherapy treatment for the patient, and transition the graphical user interface from a first page representing a first stage to a second page representing a second stage provided that at least a predetermined portion of tasks associated with the first stage has been satisfied.

In another embodiment, a method comprises retrieving, by a server, information from a radiotherapy file associated with a patient, the information comprising an alignment data of at least a treatment region of the patient; presenting, by the server, for display on a graphical user interface, an image corresponding to the patient positioned on a couch of a radiotherapy machine, the image comprising an overlay on a surface of the patient in the treatment region; and presenting, by the server, for display, a visually distinct revised overlay for at least a portion of the surface of the patient in the treatment region that matches, within a predetermined margin of error, the alignment data.

In another embodiment, a system comprises a server comprising a processor and a non-transitory computer-readable medium containing instructions that when executed by the processor causes the processor to perform operations comprising: retrieve information from a radiotherapy file associated with a patient, the information comprising an alignment data of a treatment region of the patient; present for display on a graphical user interface, an image corresponding to the patient positioned on a couch of a radiotherapy machine, the image comprising an overlay on a surface of the patient in the treatment region; and present for display a visually distinct revised overlay for at least a portion of the surface of the patient in the treatment region that matches, within a predetermined margin of error, the alignment data.

In another embodiment, a method comprises presenting, by a server, for display on a graphical user interface, an image of a position of a patient on a couch of a radiotherapy machine, whereby at least a gantry of the radiotherapy machine is configured to rotate around the patient; calculating, by the server, one or more predicted collisions between a part of the radiotherapy machine and at least one of (a) the patient or (b) another part of the radiotherapy machine; and when a portion of the patient is calculated to be in a collision with the part of the radiotherapy machine, revising, by the server, the graphical user interface such that the portion of the patient calculated to be in the collision is visually distinct in the image.

In another embodiment, a system comprises a server comprising a processor and a non-transitory computer-readable medium containing instructions that when executed by the processor causes the processor to perform operations comprising: present for display on a graphical user interface an image of a position of a patient on a couch of a radiotherapy machine, whereby at least a gantry of the radiotherapy machine is configured to rotate around the patient; calculate one or more predicted collisions between a part of the radiotherapy machine and at least one of (a) the patient or (b) another part of the radiotherapy machine; and when a portion of the patient is calculated to be in a collision with the part of the radiotherapy machine, revise, the graphical user interface such that the portion of the patient calculated to be in the collision is visually distinct in the image.

In another embodiment, a method comprises retrieving, by one or more servers, a radiotherapy file associated with a patient, the radiotherapy file comprising information associated with one or more accessories associated with the patient's radiation therapy treatment; presenting, by one or more servers, for display on the graphical user interface, a graphical indicator corresponding to each of the one or more accessories; scanning, by one or more servers, a set of accessories within a predetermined proximity to the radiotherapy machine; and when the server does not detect one or more of the one or more accessories in proximity to the radiotherapy machine or when one or more of the one or more accessories is not within a predetermined location, revising, by one or more servers, the graphical indicator corresponding to that accessory.

In another embodiment, a system comprises one or more servers comprising a processor and a non-transitory computer-readable medium containing instructions that when executed by the processor causes the processor to perform operations comprising: retrieve a radiotherapy file associated with a patient, the radiotherapy file comprising information associated with one or more accessories associated with the patient's radiation therapy treatment; present for display on the graphical user interface, a graphical indicator corresponding to the each of the one or more accessories; scan a set of accessories within a predetermined proximity to the radiotherapy machine; and when the server does not detect one or more of the one or more accessories in proximity to the radiotherapy machine or when one or more of the one or more accessories is not within a predetermined location, revise the graphical indicator corresponding to that accessory.

In another embodiment, a method comprises presenting, by a server, a graphical user interface for display on a screen positioned on a gantry of a radiotherapy machine, wherein the graphical user interface comprises a page corresponding to radiotherapy treatment of a patient, wherein the page comprises a first graphical element indicating at least one attribute of the alignment data corresponding to the radiotherapy treatment of the patient.

In another embodiment, a system comprises a server comprising a processor and a non-transitory computer-readable medium containing instructions that when executed by the processor causes the processor to perform operations comprising: present a graphical user interface for display on a screen associated with a radiotherapy machine, wherein the graphical user interface comprises a page corresponding to radiotherapy treatment of a patient, wherein the page comprises a first graphical element indicating at least one attribute of the alignment data corresponding to the radiotherapy treatment of the patient.

In another embodiment, a method comprises presenting, by server for display on a screen associated with a radiotherapy machine, a series of consecutive graphical user interfaces, wherein a first graphical user interface within the series of consecutive graphical user interfaces comprises: a first graphical indicator corresponding to a first attribute associated with configuration of the radiotherapy machine, and a second graphical indicator corresponding to a second attribute associated with the patient; when the server receives an indication that a user interacting with a pendant having a processor in communication with the server has inputted a first input corresponding to a first direction towards the first graphical indicator, displaying, by the server on the gantry, a second graphical user interface comprising data associated with the first attribute; and when the server receives an indication that a user interacting with the pendant has inputted a second input corresponding to a second direction towards the second graphical indicator, displaying, by the server on the gantry, a third graphical user interface comprising data associated with the second attribute.

In another embodiment, a system comprises a server comprising a processor and a non-transitory computer-readable medium containing instructions that when executed by the processor causes the processor to perform operations comprising: present for display on a screen associated with a radiotherapy machine, a series of consecutive graphical user interfaces, wherein a first graphical user interface within the series of consecutive graphical user interfaces comprises: a first graphical indicator corresponding to a first attribute associated with configuration of the radiotherapy machine, and a second graphical indicator corresponding to a second attribute associated with the patient; wherein when the server receives an indication that a user interacting with a pendant having a processor in communication with the server has inputted a first input corresponding to a first direction towards the first graphical indicator, display on the gantry, a second graphical user interface comprising data associated with the first attribute; and wherein when the server receives an indication that a user interacting with the pendant has inputted a second input corresponding to a second direction towards the second graphical indicator, display a third graphical user interface comprising data associated with the second attribute.

In another embodiment, a pendant having a processor in communication with a radiotherapy machine and a computer, the pendant comprises a first controller configured to adjust at least one configuration of the radiotherapy machine; and a second controller configured to receive an input from a user, whereby when the computer receives the input, the computer revises a graphical user interface displayed on a gantry of the radiotherapy machine.

In another embodiment, a method comprises presenting, by the server for display on a screen associated with a radiotherapy machine, a series of consecutive graphical user interfaces, wherein each graphical user interface displays one or more graphical components corresponding to one or more tasks of one or more stages of a patient's radiotherapy treatment; and when a user operating the pendant interacts with a first controller of the pendant, the radiotherapy machine adjusts at least one of its configurations; and when the user interacts with a second controller of the pendant, the server revises the graphical user interface corresponding to the user's input.

In another embodiment, a system comprises a server comprising a processor and a non-transitory computer-readable medium containing instructions that when executed by the processor causes the processor to perform operations comprising: display on a screen associated with a radiotherapy machine, a series of consecutive graphical user interfaces, wherein each graphical user interface displays one or more graphical components corresponding to one or more tasks of one or more stages of a patient's radiotherapy treatment; and when a user actuates a first controller of the pendant, the radiotherapy machine adjusts at least one of its couch or gantry; and when the user actuates a second controller of the pendant, the server revises the graphical user interface corresponding to the user's input.

In another embodiment, a system comprises a radiotherapy machine comprising: a couch; and a gantry having a camera in communication with a server, wherein the server is configured to: present for display, in real time on a screen associated with the radiotherapy machine, images received from the camera, wherein when the gantry changes its orientation, the camera revises at least one of its orientations, such that images transmitted to the server maintain an original orientation.

In another embodiment, a method comprises presenting, by a server, for display a graphical user interface on a screen associated with a radiotherapy machine, presenting, by the server, for display real time images received from a camera positioned on a gantry of the radiotherapy machine; when the gantry changes its orientation, revising, by the server, in real time, at least one orientation of an image received from the camera, such that images displayed on the graphical user interface maintain an original orientation.

In another embodiment, a method for displaying on a radiotherapy console, the method comprises presenting, by a server, a first page of a first graphical user interface on the radiotherapy console associated with a radiotherapy machine in a treatment room, wherein the first graphical user interface contains a plurality of pages, each page corresponding to a stage of treatment implemented by the radiotherapy machine, and the first page corresponds to a first stage; and transitioning, by the server, the first page of the first graphical user interface to a second page of the first graphical user interface corresponding to a second stage responsive to an input of a user interacting with a second graphical interface presented on a display in the treatment room indicating that at least a predetermined portion of tasks associated with the first stage has been satisfied.

In another embodiment, a radiotherapy system comprises a radiotherapy machine in a treatment room having a display; a radiotherapy console display outside the treatment room; and a server communicable with the radiotherapy machine and the radiotherapy console display, the server configured to present a first graphical user interface associated with the radiotherapy machine on the radiotherapy console display, wherein the first graphical user interface contains a plurality of pages, each page corresponding to a stage of treatment implemented by the radiotherapy machine, a first page corresponds to a first stage, and wherein the first graphical user interface transitions the first page of the first graphical user interface to a second page of the first graphical user interface corresponding to a second stage responsive to an input of a user interacting with a second graphical interface presented on the display in the treatment room indicating that at least a predetermined portion of tasks associated with the first stage has been satisfied.

In another embodiment, a method comprises presenting, by a server, a plurality of pages for display, each page corresponding to a stage of a radiotherapy treatment for a patient; in response to receiving an indication that a surface of a patient is aligned, retrieving, by the server, from a radiotherapy file of a patient a first image of an internal target of the patient aligned in accordance with one or more treatment attributes; receiving, by the server, a second image of the internal target of the patient on a couch of a radiotherapy machine; overlaying, by the server, on a first page of the plurality of pages, the first image and the second image, wherein the first page displays a direction to position the internal target in the second image to align with the internal target in the first image; and when the internal target is aligned, presenting, by the server, a second page of the plurality of pages corresponding to a subsequent stage of the radiotherapy treatment for the patient.

In another embodiment, a system comprises a server comprising a processor and a non-transitory computer-readable medium containing instructions that when executed by the processor causes the processor to perform operations comprising: presenting a plurality of pages for display, each page corresponding to a stage of a radiotherapy treatment for a patient; in response to receiving an indication that a surface of a patient is aligned, retrieve from a radiotherapy file of a patient a first image of an internal target of the patient aligned in accordance with one or more treatment attributes; receive a second image of the internal target of the patient on a couch of a radiotherapy machine; overlay on a first page of the plurality of pages, the first image and the second image, wherein the first page displays a direction to position the internal target in the second image to align with the internal target in the first image; and when the internal target is aligned, present a second page of the plurality of pages corresponding to a subsequent stage of the radiotherapy treatment for the patient.

In another embodiment, a system comprises a first display in communication with a server, the first display configured to display a first graphical user interface; a second display in communication with the server, the second display configured to display a second graphical user interface, wherein the server is configured to: present the first graphical user interface for displaying on the first display, wherein the first graphical user interface contains one or more pages corresponding to one or more stages of a radiotherapy treatment, wherein the server transitions from a first page of the one or more pages representing a first stage to a second page of the one or more pages representing a second stage responsive to an indication that at least a predetermined portion of tasks associated with the first stage has been satisfied.

In another embodiment, a method comprises displaying, by a server, a first graphical user interface on a first display; displaying, by the server, a second graphical user interface on a second display; presenting, by the server, the first graphical user interface for display on the first display, wherein the first graphical user interface contains one or more pages corresponding to one or more stages of a radiotherapy treatment, and wherein the server transitions from a first page of the one or more pages representing a first stage to a second page of the one or more pages representing a second stage responsive to an indication that at least a predetermined portion of tasks associated with the first stage has been satisfied.

In another embodiment, a system comprises a radiotherapy machine comprising: a gantry having a screen in communication with a server, the screen configured to display a graphical user interface; and at least one camera, wherein the server is configured to: present, in real time, images received from the at least one camera for display on a graphical user interface displayed on the screen.

In another embodiment, a method comprises presenting, by a server, a graphical user interface for display on a screen on a gantry of a radiotherapy machine; and presenting, by the server, in real time, images received from at least one camera for display on a graphical user interface displayed on the screen of the gantry.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIG. 1A illustrates components of a workflow-oriented radiotherapy system, according to an embodiment.

FIGS. 1C-D illustrate conventional methods of displaying data needed to implement a patient's radiotherapy, according to an embodiment.

FIGS. 5B-5C illustrate pages displayed in a workflow-oriented radiotherapy system, according to an embodiment.

FIG. 7A illustrates a flow diagram executed in a workflow-oriented radiotherapy system, according to an embodiment.

DETAILED DESCRIPTION

Figure 1B:
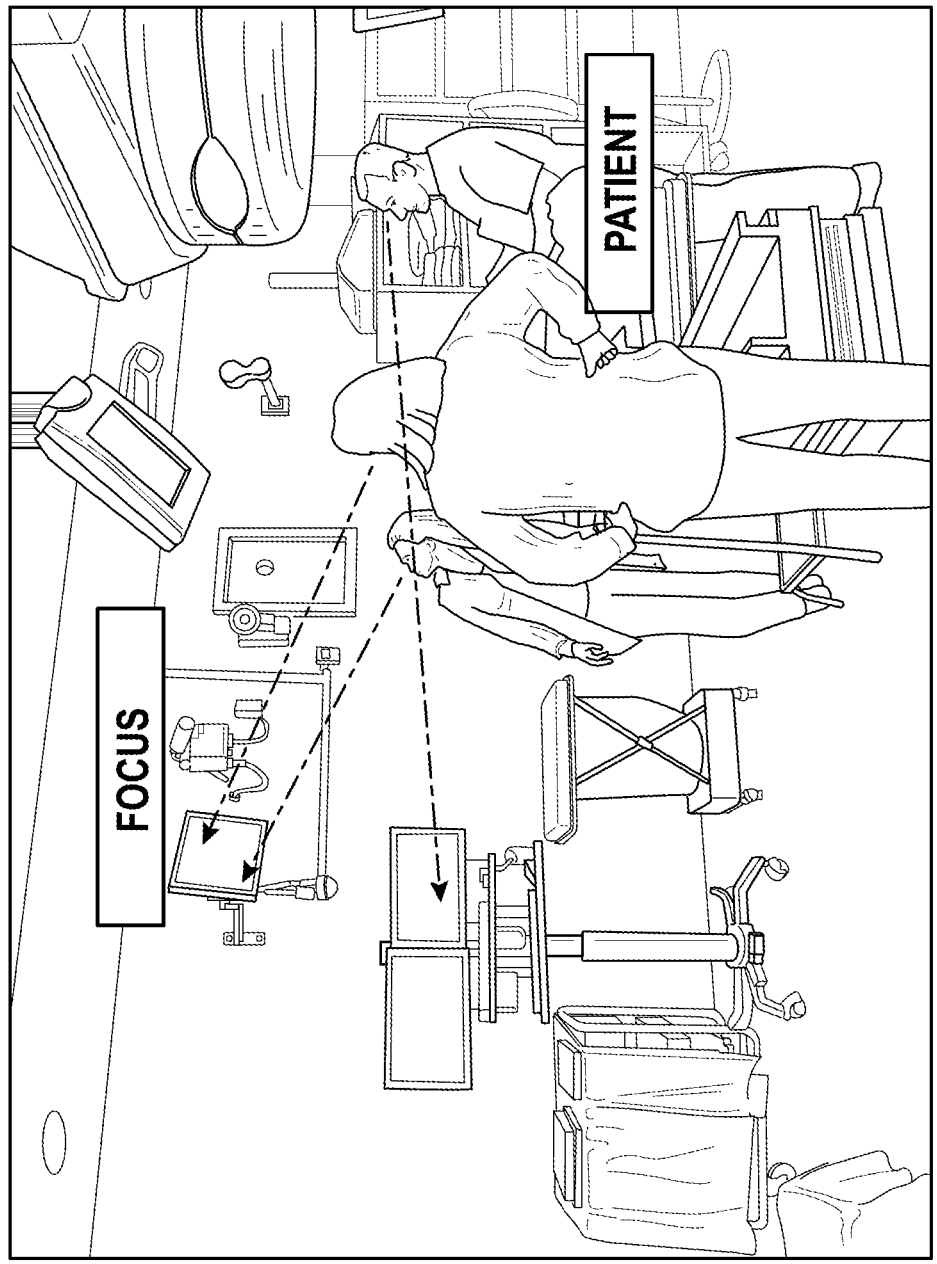
FIG. 1B illustrates conventional methods of displaying radiotherapy data, according to an embodiment.
Figure 1D:
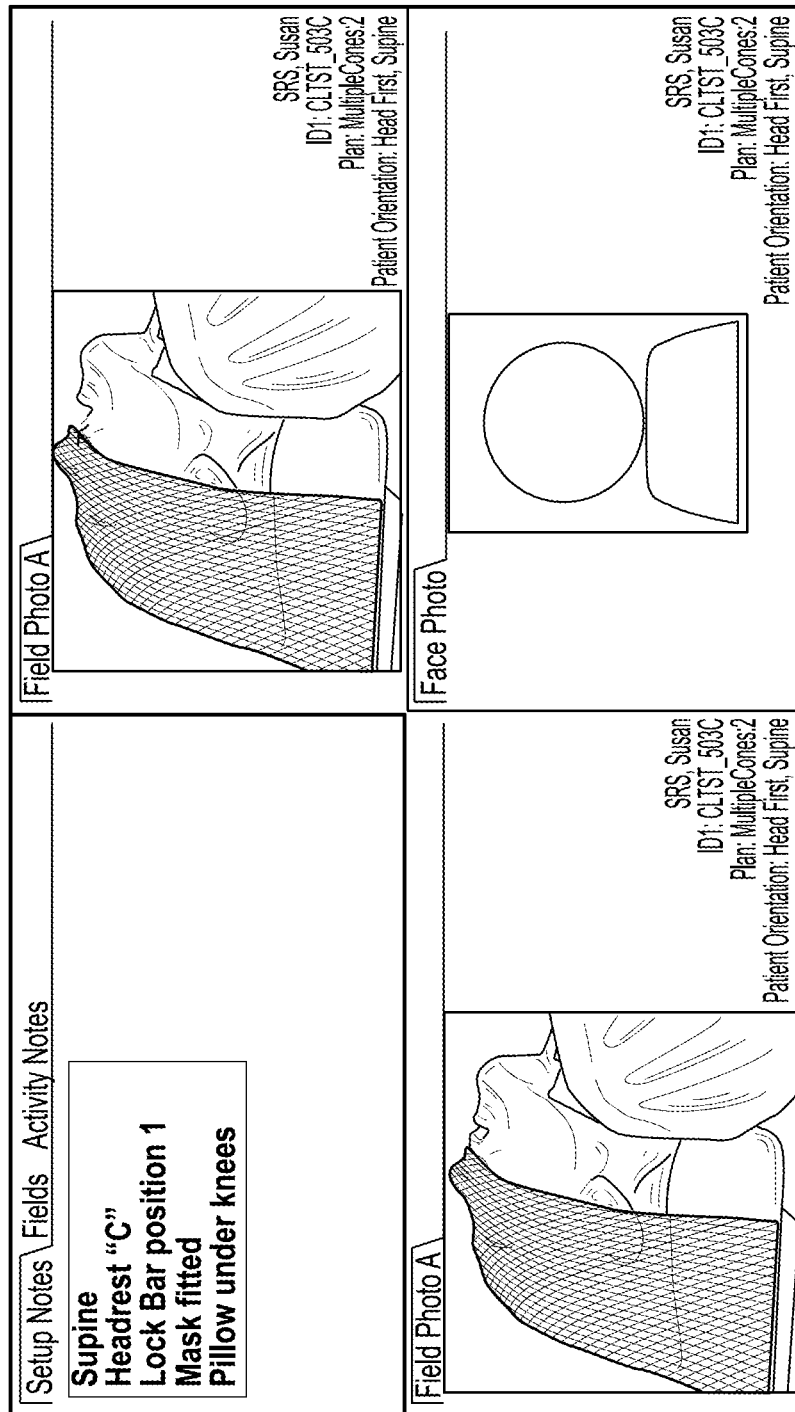
Figure 1E:
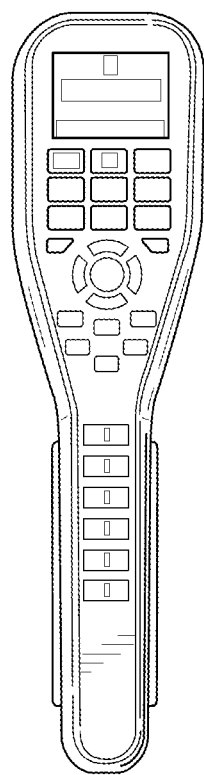
FIG. 1E illustrates a conventional pendant for a radiotherapy system, according to an embodiment.
Figure 1F:
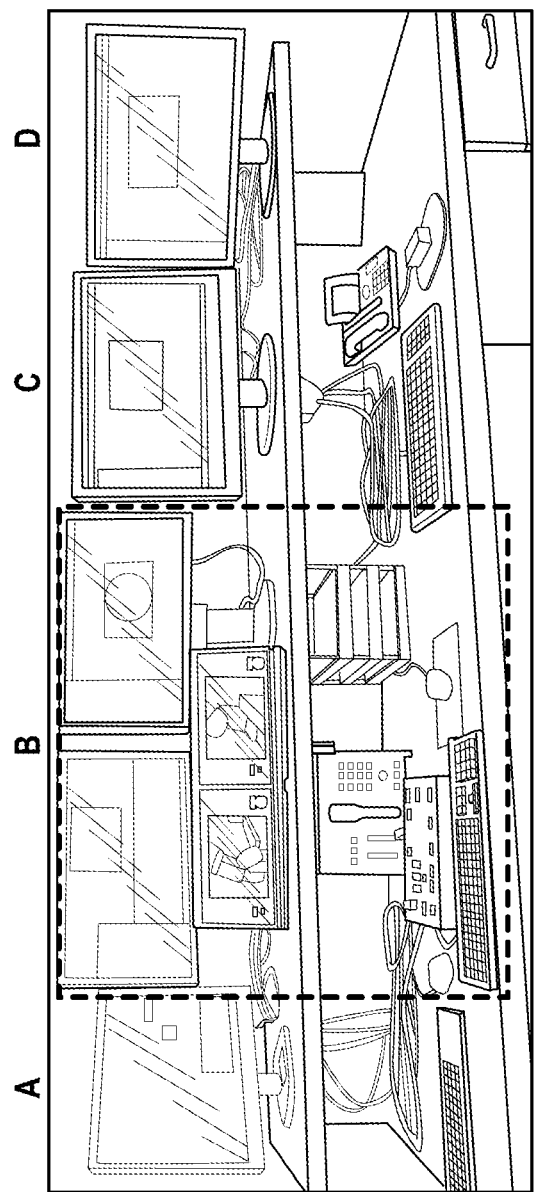
FIG. 1F illustrates conventional console monitors, according to an embodiment.

Reference will now be made to some embodiments illustrated in the drawings, and specific language will be used here to describe the same. It will nevertheless be understood that no limitation of the scope of the embodiments of the methods and systems described herein is thereby intended. Alterations and further modifications of the features illustrated here, and additional applications of the principles of the embodiments of the methods and systems described herein as illustrated here, which would occur to a person skilled in the relevant art and having possession of this disclosure, are to be considered within the scope of the embodiments, methods, and/or systems described herein.

System Architecture

The methods described herein can be implemented using various computing devices/features described in FIG. 1A. Therefore, FIG. 1A describes a non-limiting example of a computer environment where a server can perform the processes/methods described herein, such as retrieving, processing, and presenting treatment data, and presenting data for a graphical user interface (GUI) having workflow-oriented pages (or instances) on different displays screens.

FIG. 1A illustrates various components of a system 100 for presenting various pages related to operation of a radiotherapy treatment, in accordance with an embodiment. The system 100 may include an analytics server 110, a medical records database 120, a radiotherapy system 140, console monitor(s) 150 (shown in the example embodiment as two monitors), and a system administrator computer or workstation 160. These features may communicate with each other over a network 130. For example, the system 100 may present, via the analytics server 110, a series of workflow-oriented pages on the radiotherapy machine 141 and/or console monitors 150. In another example, the system 100 may present, via the analytics server 110, a page overlaid on a live feed of a patient to the radiotherapy machine 141 and/or console monitors 150.

The network 130 may include wired and/or wireless communications according to one or more standards via one or more transport mediums. Communication over the network 130 may be in accordance with various communication protocols, such as transmission control protocol and internet protocol (TCP/IP), user datagram protocol (UDP), and Institute of Electrical and Electronics Engineers (IEEE) communication protocols. The network 130 may further include wireless communications according to Bluetooth specification sets, or another standard or proprietary wireless communication protocol. The network 130 may further include communications over a cellular network, including, for example, a global system for mobile (GSM) communications, code division multiple access (CDMA), and enhanced data for global evolution network (EDGE). The examples of the network 130 may include, but are not limited to, private or public local area network (LAN), wireless LAN (WLAN), metropolitan area network (MAN), wide area network (WAN), and the Internet.

The analytics server 110 may be any computing device capable of performing the actions described herein. For instance, the analytics server 110 includes a processing unit and a non-transitory machine-readable storage medium. The processing unit includes a processor with a computer-readable medium, such as a random access memory coupled to the processor. The analytics server 110 executes algorithms or computer executable program instructions, which may be executed by a single processor or multiple processors in a distributed configuration. The instructions allow the processor to implement the functionality described herein. The analytics server 110 may be configured to interact with one or more software modules of a same or a different type operating within the system 100.

Non-limiting examples of the processor may include a microprocessor, an application specific integrated circuit, and a field programmable object array, among others. The analytics server 110 may be capable of executing data processing tasks, data analysis tasks, and valuation tasks. Non-limiting examples of the analytics server 110 may include a desktop computer, a server computer, a laptop computer, a tablet computer, and the like. For simplicity, the FIG. 1A depicts a single-server computing device functioning as the analytics server 110. However, some embodiments may include a plurality of server computing devices capable of performing various tasks described herein.

Implementation of the methods described herein is not limited to the system architecture depicted in FIG. 1A. In alternative embodiments, the analytics server 110 may be an embedded computing device disposed within the radiotherapy machine 141. In some embodiments, the analytics server 110 may be an embedded computing device disposed within the console monitors 150 or disposed within the system administrator computer 160. In some embodiments, the analytics server 110 may be a plurality of computing devices operated locally and/or remotely. In various embodiments, the analytics server 110 may be operated through a cloud service (e.g., network, internet). The cloud service may be performed in accordance with various communication protocols such as TCP/IP, UDP, and IEEE communication protocols.

The analytics server 110 may utilize a database, such as a local database 111, to store and/or retrieve various data described herein. For instance, the analytics server 110 may store different data corresponding to the different pages within the local database 111. The page may be displayed on a display screen associated with the radiotherapy system 140 and/or the console monitors 150.

For instance, the analytics server 110 may display a page having a live feed of the patient before the treatment has begun or may display various pages describing how to position the patient on the couch and/or how to adjust the radiotherapy machine 141. Even though some embodiments describe the analytics server 110 displaying various pages on a display screen attached to the radiotherapy machine 141 (e.g., located on the gantry of the radiotherapy machine 141), it is expressly understood that the analytics server 110 may display different pages described herein on a display screen located anywhere within the treatment room, such as located on the wall of the treatment room or on any electronic device within the treatment room. In some configurations, the analytics server 110 may display the pages on the system administrator computer or workstation 160.

The local database 111 may also store data corresponding to the radiotherapy machine 141 (e.g., default position of the radiotherapy machine 141, current position of the radiotherapy machine 141, such as the orientation of the bed/couch and gantry).

If the analytics server 110 receives a request from the radiotherapy system 140 and/or the console monitors 150 to provide the current position/orientation of the radiotherapy machine 141, the analytics server 110 may query the local database 111 and may be retrieve the corresponding data. Additionally, or alternatively, the analytics server 111 may also communicate with various sensors associated with the radiotherapy system 140 to retrieve machine data and parameters. The analytics server 110 may then use the methods/systems described herein to instruct the radiotherapy machine 141 to adjust the positioning of the radiotherapy machine 141 to the default positon of the radiotherapy machine 141 or another position of the radiotherapy machine, or to display one or more pages instructing a technician to adjust the radiotherapy machine 141 and/or the patient.

The local database 111 may also store data associated with different users of the radiotherapy system 140. In a non-limiting example, the user data may include the user's login (e.g., sign-in, credentials) information and authorization levels. For example, the analytics server 110 may store, using the local database 111 may store, the user's name and password. The analytics server 110 may allow the user to log in to the radiotherapy machine 141, the console monitors 150, and/or the system administrator computer 160. If the user logs-in into the system, the analytics server 110 may adjust what the user is able to view, adjust, and control based on the user's authorization level. For example, if a medical technician were to sign-in to the console monitors 150 the analytics server 110 may only allow the medical technician to see the treatment plan. The analytics server 110 may conceal the patient's medical information that is not relevant to the radiation treatment from the medical technician. In another example, the analytics server 110 may conceal all of the patient's medical information if a machine technician signs-in.

The analytics server 110 may also utilize one or more other databases, such as the medical records database 120, to store and/or retrieve various data described herein. The databases herein can be configured as one or more databases storing the data, and the disclosure is not intended to be limited to a particular number or location of databases. The analytics server 110 may instruct the medical records database 120 to store patient data (e.g., patient name, patient machine alignment information) associated with a patient identifier (e.g., patient's name, patient's profile image). The analytics server 110 may then instruct the medical records database 120 to populate a dataset corresponding to a patient and display the profile image of the patient. If the analytics server 110 receives a request from the console monitors 150 and/or the radiotherapy system 140 to display the data associated with the patient identifier, the analytics server 110 may query the medical records database 120 and may retrieve the corresponding dataset. The analytics server 110 may then use the methods/systems described herein to dynamically display the patient data in accordance with the patient identifier.

The medical records database 120 may also include a radiotherapy treatment (RT) file associated with the patient identifier. As used herein, the RT file refers to all data associated with a patient's radiation therapy treatment and is not limited to a particular step or information. The RT file may also be retrieved from the radiotherapy system 140, the console monitors 150, the database 120, and/or the system administrator computer 160. The RT file may include the treatment data associated with a patient. The RT file may be associated with a patient identifier and may also be updated after a patient has completed treatment. For example, after the patient has completed a treatment session, the medical records database 120 may retrieve the duration of the treatment session from the radiotherapy system 140 and update the radiotherapy file to include the duration of the treatment session. Even though aspects of the embodiments descried herein discuss RT as a file, the RT file represents a collection of the patient's medical and treatment data, which may be stored in different files. For brevity, the present disclosure refers to the patient's data as a RT file.

The RT file may include data for treatment plans for one or more patients where each treatment plan is specific to a single patient. For instance, each treatment plan is uniquely created for each patient and corresponds to the patient's unique attributes (e.g., physical attributes of the patient and the patient's unique condition to be treated). In some configurations, each treatment plan for each patient may itself include multiple files.

The analytics server 110 may retrieve treatment data associated with a patient that is stored within the patient's RT file(s). As described herein, the analytics server 110 may analyze the treatment data and may display various features and graphical components described herein. While the medical record database 120 may contain treatment data (RT files) associated with multiple patients, the methods described herein are implemented such that various pages and graphical features described herein are specific to the particular patient being treated.

In some configurations, the analytics server 110 may retrieve RT files associated with multiple patients. The analytics server 110 may then receive a selection by an operator (e.g., technician) of a patient to be treated. As a result, the analytics server 110 identifies the RT file associated with the selected patient and customizes the graphical components described herein for the selected patient.

The analytics server 110 may also retrieve and instruct the medical records database 120 to store patient data associated with the patient from the medical records database 120, the radiotherapy system 140, the console monitors 150, and/or the system administrator computer 160. For instance, the medical records database 120 may include patient data (e.g., previously populated by the analytics server 110 and/or periodically retrieved from a third-party data source). If a patient is selected, the analytics server 110 may query and retrieve patient data from the medical records database 120 and provide the retrieved patient data to the console monitors 150. For instance, the analytics server 110 may display the patient's profile image when the patient is selected, providing an opportunity to verify the correct patient was selected. A non-limiting example of the analytics server 110 illustrating example patient identifiers is depicted in FIG. 4C.

The analytics server 110 may receive treatment data associated with a patient from the medical records database 120, the treatment data may further include at least a patient identifier. The analytics server may receive RT file associated with one or more patients from the medical records database 120. The RT file may refer to a file having data associated with a process in which a medical team (e.g., radiation oncologists, radiation therapist, medical physicists, and/or medical dosimetrists) plan the appropriate external beam radiotherapy or internal brachytherapy treatment techniques for a patient. The data within the RT file is not limited to the external radiation therapy as other treatments may impact the radiation therapy, such as medical oncology treatment (chemotherapy), interventional oncology treatment (e.g. cryotherapy, microwave therapy, or embolic therapy) or other non-treatment procedures, such as labs and appointments with other medical professionals. The RT file may include data specific to one or more patient's radiotherapy treatment. In some configurations, the analytics server 110 may receive treatment data associated with a patient from the console monitors 150, treatment machine 140, or system administrator computer 160.

The RT file may include a patient identifier, patient's electronic health data records, medical images (e.g., CT scans, 4D CT Scans, Mills, and x-ray images), treatment-specific data (e.g., arc information or treatment type), target organ (e.g., specification and location data to identify the tumor to be eradicated), treatment plan, etc. Additional examples may include non-target organs, dosage-related calculations (e.g., radiation dose distribution within an anatomical region of the patient), and radiotherapy machine specific information (e.g., couch-gantry orientations, machine trajectory, control points, dose distributions, and/or arc information).

The analytics server 110 may use the patient identifier within the RT file to identify a particular patient and retrieve additional information regarding said patient. For instance, the analytics server 110 may query the medical records database 120 to identify medical data associated with the patient. For instance, the analytics server may query data associated with the patient's anatomy, such as physical data (e.g., height, weight, and/or body mass index) and/or other health-related data (e.g., blood pressure or other data relevant to the patient receiving radiotherapy treatment). The analytics server 110 may also retrieve data associated with current and/or previous medical treatments received by the patient (e.g., prior treatment fractions, or data associated with the patient's previous surgeries).

The analytics server 110 may analyze the data received and generate additional queries accordingly. For instance, the analytics server 110 may retrieve data associated with one or more medical (or other) devices needed for the patient. The analytics server may retrieve data indicating that the patient suffers from a respiratory medical condition. As a result, the analytics server 110 may generate and transmit a query to the radiotherapy machine 141, the console monitors 150, or the system administrator computer 160 to identify whether the patient uses/needs a ventilator.

If necessary, the analytics server 110 may also analyze the patient's medical data records to identify the needed patient attributes. For instance, the analytics server 110 may query a database to identify the patient's BMI. However, because many medical records are not digitalized, the analytics server 110 may not receive the patient's BMI value using simple query techniques. As a result, the analytics server 110 may retrieve the patient's electronic health data and may execute one or more analytical protocols (e.g., natural language processing) to identify the patient's body mass index. In another example, if the analytics server 110 does not receive tumor data (e.g., end-points) the analytics server 110 may execute various image recognition protocols and identify the tumor data.

Another example of a patient attribute may include specific tumor locations. More specifically, this data may indicate the primary tumor location with respect to the patient's centerline. This data may be inputted by the treating oncologist or may be analyzed using various image recognition or segmentation methods executed on the patient's medical images.

Another example of a patient attribute may include whether the patient uses prosthesis (e.g., hip or femoral head prosthesis). This attribute may result in a change of the patient's treatment (e.g., patients with these conditions might require a special treatment).

The analytics server 110 may use various application-programming interfaces (APIs) to communicate with different features described herein. As used herein, an API refers to a computing interface that uses connector programming code to act as a software intermediary between at least two computing components/features described herein. The API may automatically and/or periodically transfer various calls, instructions, and/or requests among different features of the system 100. Using different APIs, the analytics server 110 may automatically transmit and/or receive calls and instructions. For instance, the analytics server 110 may use an API to communicate with the network 130 such that when an end user (e.g., system administrator or technician) operating the console monitors 150 requests a particular patient information, the API automatically transmits an instruction to the radiotherapy system 140. The instruction may include data needed for the analytics server 110 to generate and display the pages described herein. The analytics server 110 may also use the API to communicate with the local database 111 (e.g., retrieve the set of prompts).

The analytics server 110 may also use the API to transmit a second call to the network 130. The second call may include instructions to display the generated pages (e.g., software code defining the pages and instructing the network 130 to embed the pages within the radiotherapy system 140). As the network 130 displays the pages, the analytics server 110 may use the API to receive inputs from the technician. The analytics server 110 may then aggregate the inputs and use the API to transmit the aggregated responses to the radiotherapy system 140. The analytics server may similarly use a two-way API to communicate with the medical records database 120.

Additionally, or alternatively, the analytics server 110 may use a content delivery network (CDN) to ensure data integrity when communicating with different features described in the system 100. As described herein, a CDN refers to a distributed delivery network of proxy servers/nodes that uses multi-layered delivery methods/systems to transmit data (e.g., Akamai). The analytics server 110 may use a CDN when communicating various calls/instructions with the network 130 and/or the local database 111.

The radiotherapy system 140 may include a radiotherapy machine 141 and a pendant 142. The radiotherapy machine 141 may be located in the treatment room. As discussed in greater detail herein, the radiotherapy machine 141 may be controlled locally using a computer/processor associated with the radiotherapy machine and/or by the pendant 142. The radiotherapy machine 141 may also be instructed by the analytics server 110 outside of the treatment room, by the console monitors 150, and/or the system administrator computer 160. For example, the technician may power on the radiotherapy machine 141 using a page located on the console monitors 150. The radiotherapy machine 141 may also communicate with the medical records database 120 to retrieve and/or store patient data.

The radiotherapy machine 141 may also include a couch to align the patient in a designated position before the treatment begins. The designated position may be identified, calculated, and/or retrieved by the analytics server 110. For example, the analytics server 110 may retrieve patient data from the medical records database 120, analyze the data, and utilize the analyzed data to position the patient on the couch. In some embodiments, the doctor identifies how to align the patient on the couch to optimize the treatment therapy. The radiotherapy machine 141 directs radiation at specified locations of the patient resting on the couch during treatment. The specified locations may be selected by the technician operating the radiotherapy machine 141, the pendant 142, the console monitors 150, and/or the system administrator computer 160. The analytics server 110 may also specify the locations on the patient to direct the radiation.

The radiotherapy machine 141 may also include an x-ray emitter and an x-ray receiver. The x-ray emitter may be disposed on a gantry of the radiotherapy machine 141 and may be configured to provide x-ray (e.g., a penetrating form of high-energy electromagnetic radiation) waves. The x-ray emitter emits x-ray waves to the patient who is positioned on the couch. The x-ray receiver may be disposed opposed to the x-ray emitter. The x-ray waves received by the x-ray receiver generate an imprint (e.g., image) of the patient's internal anatomy. Although the example embodiment recites the use of x-ray imaging, an alternative configuration for the radiotherapy machine may include an additional or other medical imaging apparatus (e.g., fluoroscopy apparatus, MIll, etc.).

The radiotherapy machine 141 may also include a set of cameras (e.g., camera on an end of the couch, gantry camera, ceiling camera, or other cameras placed within the radiotherapy room). The analytics server 110 may retrieve a live feed of the couch (e.g., with or without the patient) from the set of cameras and provide it to a display screen disposed on the radiotherapy machine 141 and/or the console monitors 150. The set of cameras may also directly communicate with the radiotherapy system 140.

The radiotherapy machine 141 may also include a gantry that may be in communication with the analytics server 110. If the radiotherapy machine 141 is in operation, the gantry may rotate relative to the radiotherapy machine 141 to begin the treatment of the patient. The analytics server 110 may use the live feed of the set of cameras to control and/or stop the movement of the gantry. During operation, the analytics server 110 may instruct the display screen of the radiotherapy machine 141 to display the live feed of the set of cameras and/or a designated page to the display screen of the radiotherapy machine 141. In various embodiments, the analytics server 110 may not instruct the display screen of the radiotherapy machine 141 to activate the display screen of the radiotherapy machine 141 during operation. In some embodiments, the display screen of the radiotherapy machine 141 may be a touch screen and may control the pages generated by the analytics server 110 through the display screen of the radiotherapy machine 141.

The radiotherapy machine 141 may have a default home position. Before the patient receives treatment, the radiotherapy machine 141 may be reset to a position that is ergonomically desirable for the patient. The default home position may also be optimized to receive a new patient or allow the patient to more easily get off the couch.

As discussed in greater detail herein, the radiotherapy machine 141 may also be controlled by the pendant 142. The pendant 142 may be connected to the radiotherapy machine 141 through wired or wireless communications according to, for example, Bluetooth specification sets or another standard or proprietary wireless communication protocol. In various embodiments, the pendant 142 may be connected to the radiotherapy machine 141 through a wired connection or be integrated into the radiotherapy machine 141. The pendant 142 may also be in communication with the analytics server 110. The pendant 142 may adjust the positioning of the radiotherapy machine 141 through a selection of buttons that axially actuates the radiotherapy machine 141 (e.g., couch) towards a desired direction. The technician may also use the pendant 142 to initialize the radiotherapy machine 141, and/or to have the radiotherapy machine 141 return to its home position.

The pendant 142 may also allow the technician to input patient information, which may be then communicated to the radiotherapy machine 141, the analytics server 110, the console monitors 150, and/or the medical records database 120. The pendant 142 may be used to control one or more of the steps of the setup and treatment of the patient.

The pendant 142 may also include a touch pad (e.g., tactile sensor). The touch pad may be used to control various pages generated by the analytics server 110. For example, the user may use the touch pad of the pendant 142 to control a page, generated by the analytics server 110, to proceed through the workflow steps of the radiotherapy treatment. In some embodiments, the page may be controlled through a touch screen on the radiotherapy machine 141 or elsewhere in the treatment room.

As discussed in greater detail herein, the radiotherapy system 140 may further include accessories that assist in the treatment of the patient. The analytics server 110 may communicate with the radiotherapy system 140 to select which accessories are required. The analytics server 110 may also communicate with the medical records database 120, the console monitors 150, and/or the system administrator computer 160 to determine which accessories are required. For example, a patient may require a specific accessory for their treatment. The analytics server 110 may retrieve that the patient requires a specific accessory by accessing the medical records database 120 and communicate that information to the radiotherapy system 140. The accessories may in communication with the radiotherapy system 140. For instance, as will be described below, the analytics server may use RFID tags to scan and identify the location and/or presence of various accessories. In some embodiments, the accessories are wired or otherwise integrated into the radiotherapy machine 141.

As discussed in greater detail herein, the console monitors 150 may be a computing device including a processing unit. The processing unit may execute a software that accesses or receives data records from the medical records database 120 and/or the local database 111. The processing unit may include a processor with computer-readable medium, such as a random access memory coupled to the processor. The console monitors 150 may be running algorithms or computer executable program instructions, which may be executed by a single processor or multiple processors in a distributed configuration. The console monitors 150 may interact with one or more software modules of a same or a different type operating within the system 100.

Non-limiting examples of the processor may include a microprocessor, an application specific integrated circuit, and a field programmable object array, among others. Non-limiting examples of the console monitors 150 may include a server computer, a workstation computer, a tablet device, and a mobile device (e.g., smartphone, PDA). The technician may operate the console monitors 150 (e.g., by inputting the patient data or adjusting the radiotherapy machine 141). For simplicity, FIG. 1A illustrates a single computing device functioning as the console monitors 150. However, some embodiments may include a plurality of computing devices capable of performing the tasks described herein. In some embodiments, the console monitors 150 may be located outside of the treatment room.

The local database 111 associated with the analytics server 110, the medical records database 120, the radiotherapy machine 141, and the console monitors 150 are capable of storing information in various formats and/or encrypted versions. The information may include data records associated with various patient information, user preferences, a set of prompts (e.g., question, query, and inquiry), attributes associated with various pages to be generated by the analytics server 110, and the like. The medical records database 120, may have a logical construct of data files, which are stored in non-transitory machine-readable storage media, such as a hard disk or memory, controlled by software modules of a database program (e.g., structured query language (SQL)), and a database management system that executes the code modules (e.g., SQL scripts) for various data queries and management functions.

The system administrator computer 160 may represent a computing device operated by a system administrator. The system administrator computer 160 may communicate with the analytics server 110. The system administrator computer 160 may be configured to display various analytic metrics where the system administrator can monitor gantry movement, patient information, and modify various thresholds/rules described herein. The system administrator computer 160 may be configurable to display certain analytics metrics when specific thresholds/rules have been exceeded. For example, the system administrator computer 160 may be alerted if a patient has moved a specified amount during treatment. The analytics server 110 may allow the system administrator computer 160 to also control and/or override the settings of the radiotherapy machine 141, the pendant 142, and/or the console monitors 150. For instance, an administrator may revise the minimum distance threshold and/or customize any feature on the pages described herein (e.g., move features within the page, color, font, shape, size, or the order of display for one or more pages).

The analytics server 110 may configure the system administrator computer 160 to review any and/or all commands made through the radiotherapy system 140 and/or the console monitors 150 at specified process steps. The system administrator computer 160 may then allow or reject the commands made through the radiotherapy system 140 and/or the console monitors 150. For example, before the technician starts the patient treatment using the radiotherapy machine 141, the analytics server 110 may first prompt the system administrator computer 160 to review the radiotherapy machine 141 parameters for approval. Once approved, the technician may then control the radiotherapy machine 141 by the console monitor.

The analytics server 110 may configure the system administrator computer 160 to review any and/or all reading and/or (over)writing of patient data to and/or from the medical records database 120. For example, before the technician may (over)write patient information collected by the radiotherapy machine 141, the analytics server 110 may first prompt the system administrator computer 160 to review the patient information before it is stored in the medical records database 120.

As discussed in greater detail herein, the analytics server 110 may generate various pages that are designed to interact with the individual operating the radiotherapy machine 141, the console monitors 150, and/or the system administrator computer 160. The analytics server 110 may then generate various interactive pages and may instruct the network 130 to incorporate the generated pages displayed on the radiotherapy machine 141 and/or the console monitors 150.

The analytics server 110 may generate the various pages for the radiotherapy machine 141, the console monitors 150, and/or the system administrator computer 160 synchronously (e.g., simultaneously, contemporaneous). The analytics server 110 may also generate the various pages for the radiotherapy machine 141, the console monitors 150, and/or the system administrator computer 160 asynchronously (e.g., non-simultaneously). The analytics server 110 generates the various pages by first receiving data from the radiotherapy system 140, the medical records database 120, the console monitors 150, and/or the system administrator computer 160. The analytics server 110 analyzes the data received, and generates the respective page based on the analyzed data. For example, the analytics server 110 uses the live feed provided by the set of cameras to instruct the console monitors 150 to display the live feed and then overlay a page over the live feed to the console monitors 150.

In operation, the analytics server 110 may receive a patient identifier from a technician operating the pendant 142 connected to the radiotherapy machine 141. The analytics server 110 may then retrieve treatment data from the medical records database 120 and/or the system administrator computer 160. Upon analyzing the treatment data, the analytics server 110 may identify/calculate various treatment attributes associated with the patient's treatment. Non-limiting examples of treatment attributes may include alignment angles (e.g., angles in which the patient must be positioned to receive optimum treatment), accessories needed, machine parameters, and the like.

The analytics server may then instruct a display screen associated with the radiotherapy system 140 to display a series of pages on the display screen associated with the radiotherapy system 140, such as a display screen position on the throat of the gantry. As will be described below, the series of pages may correspond to a workflow-oriented progression of treatment stages where each page corresponds to a particular stage of the patient's treatment and only displays information relevant to that particular stage. Using the information provided by the analytics server 110, the technician may gather necessary accessories, align the patient in accordance with treatment data, and set up the radiotherapy machine 141 accordingly.

After the patient and/or the radiotherapy machine 141 have been properly set up, the technician may leave the treatment room to allow the radiation treatment to begin. The analytics server 110 may also instruct the console monitors 150 to display a second workflow-oriented series of pages on the console monitors 150. For instance, the technician or other authorized medical professionals (e.g., radiation therapy technicians) may monitor the patient/machine set up before the treatment has begun. The console monitors 150 may also provide patient/machine information during the treatment and may allow a medical professional to monitor the patient's treatment.

Set of Cameras Associated with the Radiotherapy Machine

Figure 2A:
FIG. 2A illustrates a diagram of a radiotherapy machine used in a workflow-oriented radiotherapy system, according to an embodiment.
Figure 2B:
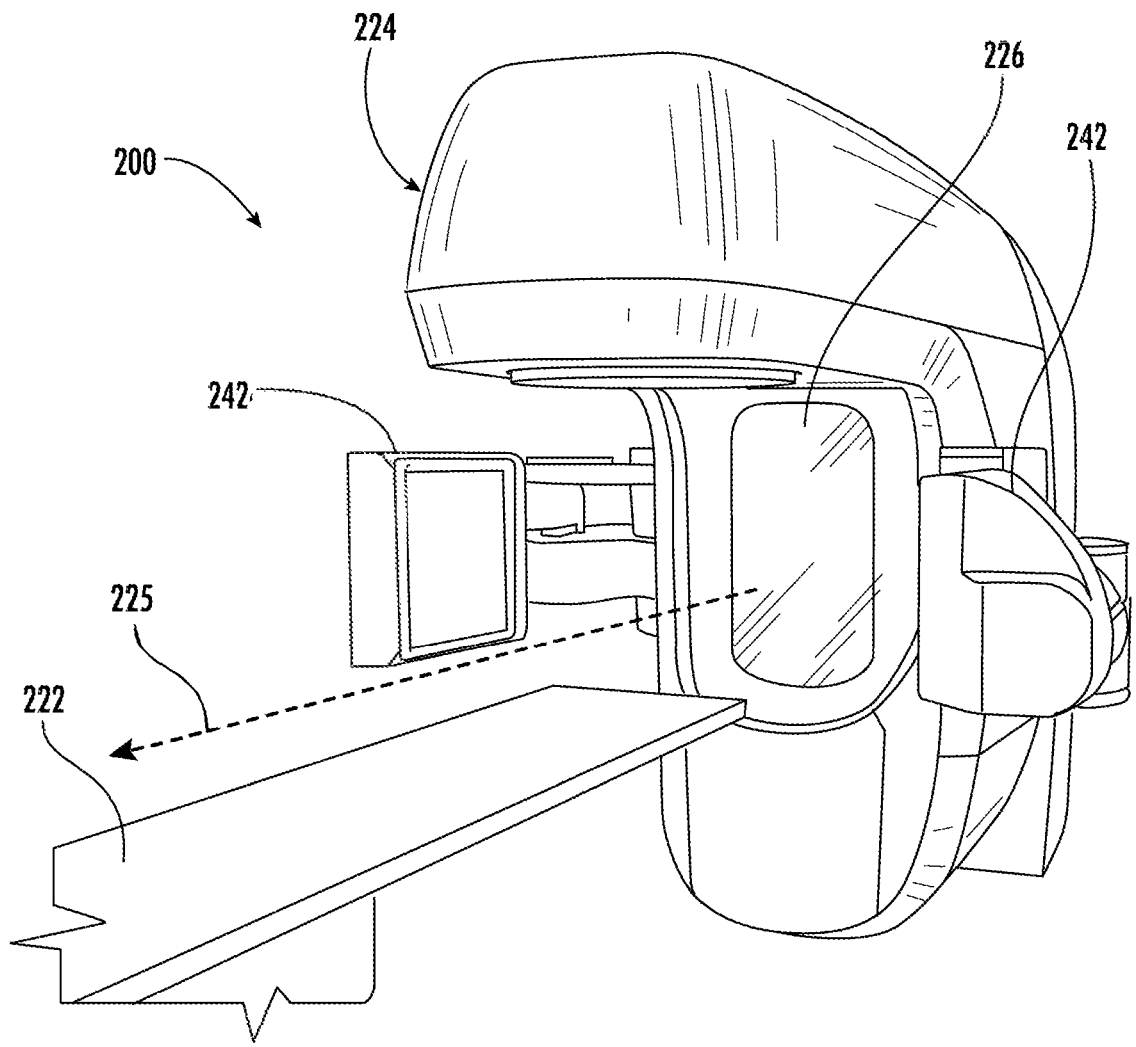
FIGS. 2B-2G illustrate a radiotherapy machine used in a workflow-oriented radiotherapy system, according to an embodiment.

FIG. 2A illustrates a radiotherapy system 200. The radiotherapy system 200 may be similar to the radiotherapy system depicted in FIG. 1A. The radiotherapy system 200 may include a radiotherapy machine 210. The radiotherapy machine 210 may be in communication with an analytics server 240, such as the analytics server depicted in FIG. 1A, which communicates with the radiotherapy machine 210. For example, the analytics server 240 may retrieve the patient's RT file from a medical database. The analytics server 240 may then display various pages on the radiotherapy machine 210, as described herein.

The methods and systems described herein are not limited to the particular radiotherapy system described and depicted herein (e.g., radiotherapy system depicted in FIGS. 2A-2G) and may also apply to ring-shaped radiotherapy systems, robotic arms, proton radiotherapy machines, FLASH radiotherapy machines, and the like.

The analytics server 240 may also communicate with one or more cameras 230a, 230b connected or otherwise associated with the radiotherapy machine 210, such as a camera on a couch or walls or ceiling 230a and/or a camera positioned proximate to a screen on a gantry, or on a gantry and not proximate to a screen 230b. Accordingly, the analytics server may use the images captured by the cameras 230a, 230b to display various information (e.g., alignment of the patient's body, machine parameters, and/or accessories) on one or more pages described herein.

As described herein, the analytics server 240 may receive treatment data associated with a patient from the radiotherapy machine 210. The analytics server 240 may use the treatment data in conjunction with data received from the set of cameras to display one or more pages described herein.

FIG. 2A, in conjunction with FIGS. 2B-2F, illustrate various features of an example radiotherapy machine 210. Even though the display screen 226 is depicted as being located on the gantry 224, it is expressly understood that, in alternative embodiments, the display screen 226 may be located on other parts of the radiotherapy machine or any other location within the treatment room (e.g., on a workstation computer and/or mounted on the wall/ceiling of the treatment room).

The radiotherapy machine 210 may include a couch 222 where the patient is placed to receive radiation therapy treatment. The couch 222 may be configured to align the patient in a designated position during treatment. For example, the analytics server may retrieve patient data from the patient's RT file, analyze the data, and utilize the analyzed data to position the patient. In some embodiments, a doctor identifies how to align the patient on the couch 222 to optimize the treatment therapy. The couch 222 may be adjusted based on the location at which the patient will be receiving therapy. For example, if the patient's tumor is located on their left pectoral, the couch 222 may be then configured so that the radiation targets the patient's left pectoral. In some embodiments the couch 222 may be adjusted in any axial direction. For example, the couch may be elevated or lowered, it may be adjusted to move towards or away from the radiotherapy machine 210. The couch 222 can also be adjusted for rotation, pitch, and roll around an isocenter point. In other embodiments the couch may have fewer degrees of freedom/axes of movement. Segments of the couch 222 may also be adjusted to elevate or lower a segment of the couch 222.

The technician may manually adjust the couch 222 through the radiotherapy system 200. The technician may adjust the positioning of the couch 222 using data displayed by the analytics server. The analytics server may track the positioning of the couch 222 through sensors disposed on the radiotherapy machine 210. The analytics server may automatically adjust the couch 222 when the patient's RT file is selected by the technician. In some configurations, the analytics server may transmit a notification (to the technician) that adjustment of the couch may be needed.

The analytics server may also record any changes to the positioning of the couch 222 in the patient's RT file and update the medical database to include the positioning of the couch 222. For example, after a patient has completed their treatment, the final positioning of the couch 222 may be recorded by the radiotherapy machine 210. The analytics server may then store the final positioning of the couch 222 in that patient's RT file. Accordingly, the analytics server will automatically adjust the couch 222 to that position for the next treatment of the same patient. The couch 222 may also be adjusted manually.

The radiotherapy system 200 may further include a pendant. As discussed in greater detail herein, the radiotherapy machine 210 may also be controlled by a pendant, such as the pendant 142 described in FIG. 1A. The pendant may adjust the positioning of the radiotherapy machine 210 through a selection of buttons that axially actuates the radiotherapy machine 210 towards a desired direction. The technician may also use the pendant to perform other tasks such as to initialize the radiotherapy machine 210, and/or to have the radiotherapy machine 210 return to its home position.

Figure 2C:
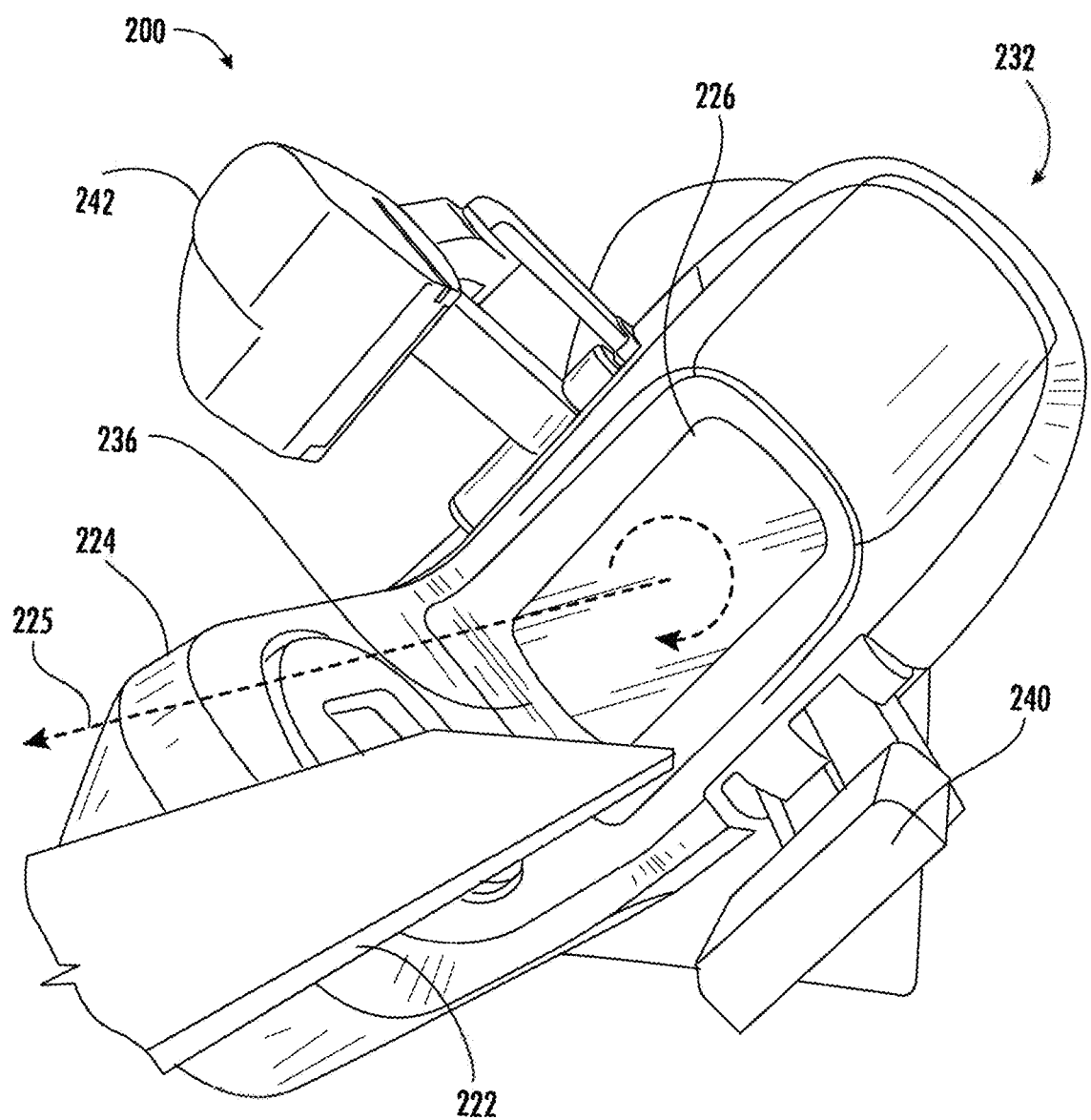

The radiotherapy machine 210 may also include a gantry 224. The gantry 224 may be disposed on a center axis 225 and is configured to rotate about the center axis 225. The gantry 224 may be positioned relative to a proximate end of the couch 222. During rotation, the gantry 224 may be configured to emit radiation towards the couch 222 while the patient is resting on the couch 222. A non-limiting example of gantry 224 in rotation is depicted in FIG. 2C. In some configurations, the display screen 226 is configured to rotate when the gantry 224 is rotating. The rotation of the display screen 226 may be such that the display screen 226 maintains its orientation. For instance, the rotation of the gantry 224 may be such that it counteracts the rotation of the gantry 224.

The gantry 224 may also include a display screen 226. The display screen 226 may be disposed on an external surface of the radiotherapy machine 210 adjacent to the proximate end of the couch 224. The display screen 226 may further be disposed on a throat of the gantry 224. The display screen 226 may be in communication with the analytics server. The analytics server may communicate with the display screen 226 to display various pages described herein. For instance, the analytics server may instruct the display screen 226 to display a page on the display screen 226 that informs the technician of the next step/stage in the treatment process. In various other embodiments, the analytics server deactivates the display screen 226 during the radiotherapy to protect the display screen 226. For instance, the analytics server may display the workflow-oriented series of pages described herein allowing the technician to set up the patient and prepare the patient for his/her treatment. When the treatment starts, the analytics server may deactivate the display screen 226.

The display screen 226 may display a live feed of the patient. A non-limiting example of this configuration depicted in FIG. 2B. The display screen 226 may be a touchscreen and may control the pages generated by the analytics server displayed on the display screen 226. In some embodiments, the display screen 226 may be controlled by the pendant.

The radiotherapy system 200 may also include an imager 242 that is configured to captured medical images, such as medical images of the patient resting on the couch 222.

The radiotherapy machine 210 may also include a set of cameras 230a, 230b (collectively 230). The set of cameras may provide a live feed of various perspectives of the radiotherapy machine 210. The set of cameras are in communication with the analytics server. The analytics server retrieves the various live streams from the set of cameras. Referring now to FIG. 2C, the analytics server may use the various live streams to analyze and display the patient's position and alignment data. In some configurations, the analytics server may also use the images captured by the cameras 234, 238 depicted in FIG. 2G to analyze the patient's position on the couch in addition to the cameras 230 (not shown in FIG. 2G). The analytics server may instruct the display screen 226 to display (e.g., present the page to a processor for displaying) a page onto the display screen 226. The analytics server may provide instructions to display various pages on the display screen 226, a console monitor (e.g., a console monitor as depicted in FIG. 1A), and/or a system administrator computer (e.g., a system administrator computer as depicted in FIG. 1A).

The analytics server may utilize the various live streams to control the radiotherapy machine 210. For example, the set of cameras may provide a view of the gantry 224 while in rotation. The analytics server may use the live feed to measure and monitor the distance between the gantry 224 and the patient to avoid a collision. Specifically, the analytics server may use the images captured by the cameras 234 and/or 238 (depicted in FIG. 2G) and combine that information with a mathematical machine model to identity the patient's position on the couch 222.

The set of cameras may include a first camera 234. The first camera 234 may be positioned at a distal end of the couch 222. The distal end of the couch 222 may be diametrically opposed to the proximate end of the couch 222. The distal end of the couch 222 may also be diametrically opposed to the display screen 226. The first camera 234 may be disposed on a standalone mount. In various embodiments, the first camera 234 may be disposed on an axillary component of the radiotherapy machine 210.

Figure 2D:
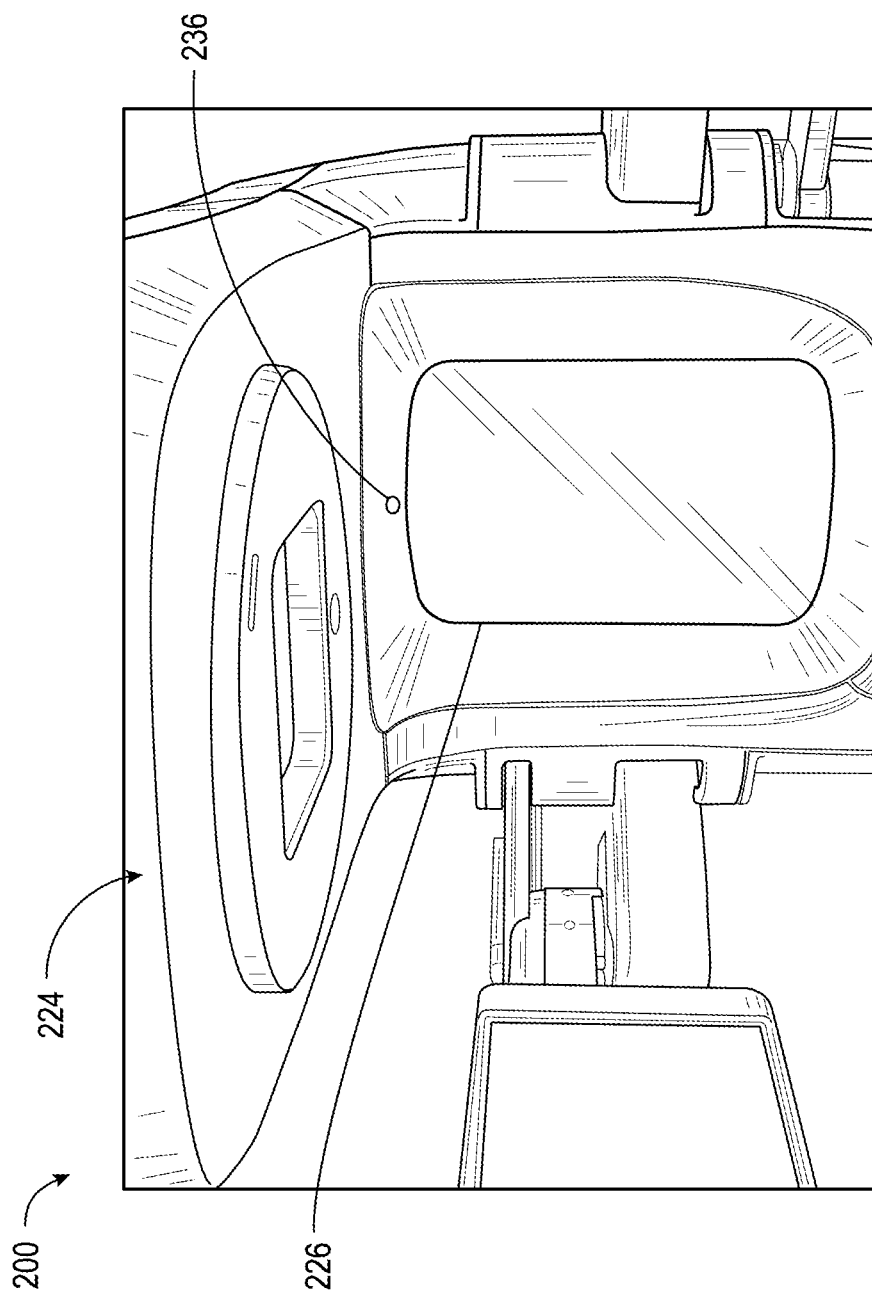
Figure 2E:
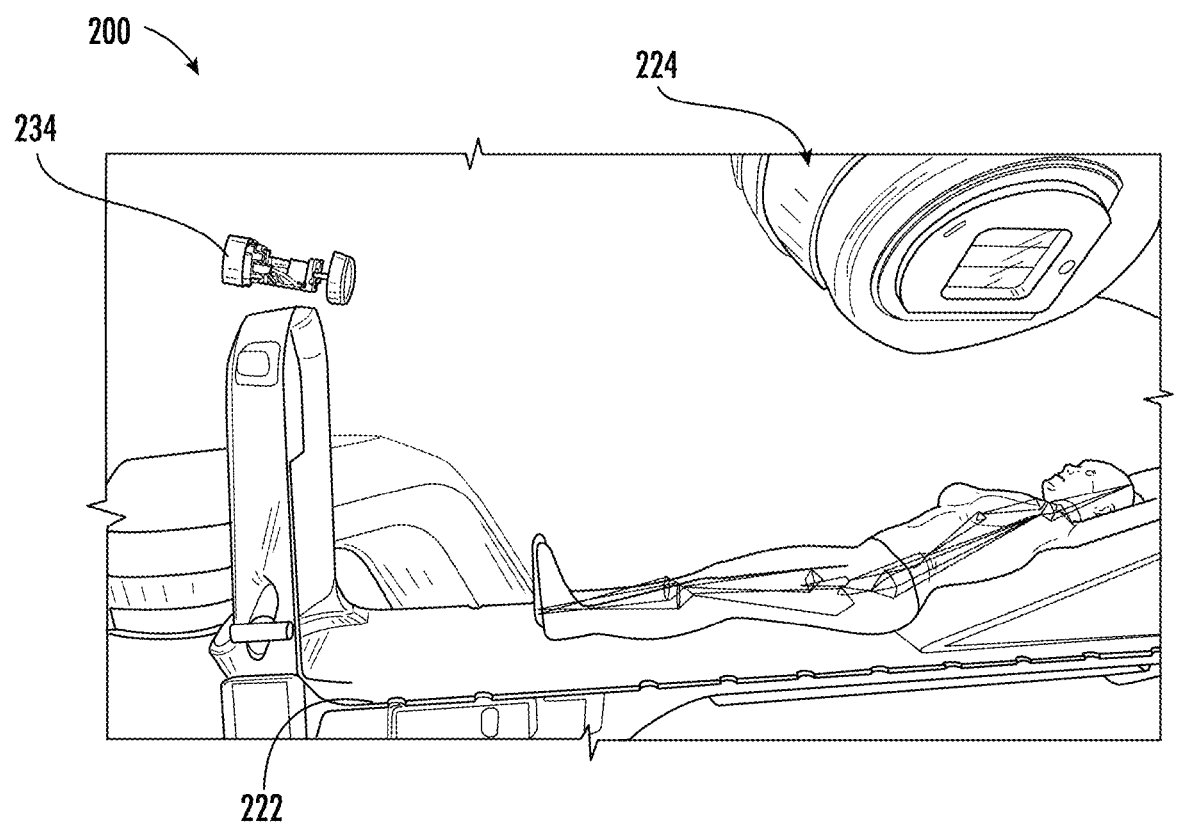

As illustrated in FIG. 2E, the first camera 234 may provide a live feed of the couch 222 (e.g., with or without the patient). The first camera 234 provides the live feed to the analytics server. The analytics server may receive the live feed from the first camera 234 and provide it to display screen 226. As discussed in greater detail herein, the analytics server may overlay pages onto the display screen 226. The analytics server may also provide the live feed of one or more cameras discussed herein and the page overlay to the console monitors 150 and/or the system administrator 160.

As illustrated in FIG. 2D, the set of cameras may include a second camera 236. The second camera 236 may be disposed at the proximate end of the couch 222. The proximate end of the couch 222 may be proximate to the display screen 226. The second camera 234 may be a 360 degree. A 360 degree camera, as used herein, refers to a camera with a spherical field of view. In some configurations, the camera 234 may be a 360 camera while in other embodiments the camera 236 is a wide-angle camera (180 degree camera). The second camera 236 may also provide a live feed of the couch 222 (e.g., with or without the patient). The second camera 236 provides the live feed to the analytics server. Due to the rotation of the gantry 224, the second camera may 236 also rotates. The second camera 236 may be configured to counter-rotate with respect to the rotation of the gantry 224. For example, if the gantry 224 rotates 20° the second camera rotates −20°. This allows the second camera to maintain the same orientation during rotation of the gantry 224.

The second camera 236 may not counter rotate, but instead, may rotate the live feed relative to the rotation of the gantry 224 to maintain the orientation. For example, the second camera 236 may rotate with the gantry so that if the gantry 224 rotates 20° the second camera may also rotate 20°. In this configuration, the second camera 236 may rotate the live feed −20° before providing the live feed to the analytics server. Therefore, the camera 236 may utilize software to rotate the transmitted images instead of (or in conjunction with) physically rotating the camera itself. The software and the analytical protocols described herein may be implemented either in the camera (e.g., before the analytics server receives the feed) or implemented in the analytics server (e.g., as part of the image feed post-processing). The display screen 226 may be rigidly attached to the gantry. However, in some implementations, the display screen 226 may feature a physical counter-rotation of the screen without necessarily rotating the content displayed on the display screen 226.

In some embodiments, the content of the display screen 226 may also rotate in a similar fashion as described within the context of the second camera 236. For instance, if the gantry 224 rotates 20° in a clockwise orientation, the content of the display screen 226 may also rotate (e.g., 20° in a counterclockwise orientation). This rotation allows the patient and/or technician to easily view various pages described herein when the gantry changes its orientation. Moreover, even though the display screen is shown as having a rectangular shape, it is expressly understood that the display screen may be in other shapes (e.g., circular or oval).

In some configurations, the analytics server may manipulate the live feed (e.g., crop and/or rotate the images received from any of the cameras discussed herein. For instance, the analytics server may rotate the images received from a camera that it itself rotating, such that counter rotation of the camera itself is no longer necessary.

The analytics server may receive the live feed from the second camera 236 and provide it to display screen 226. As discussed in greater detail herein, the analytics server may instruct the display screen 226 to display various pages onto the display screen 226. The analytics server may also provide the live feed of the second camera 236 and the page overlay to the console monitors 150 and/or the system administrator 160.

The analytics server may display the live feed of the first camera 234 and the second camera 236 simultaneously (e.g., at the same time). The analytics server may display the live feed of the first camera 234 and the second camera 236 near-simultaneously (e.g., a delay). The analytics server may display the live feed of the first camera 234 and overlays the live feed of the second camera 236 at a corner. A non-limiting example of this configuration is depicted in FIG. 10C. In some embodiments, the analytics server instructs the console monitors 150 to display the live feed of the first camera 234 on a first half of the console monitors 150 and displays the live feed of the second camera 236 at a second half of the console monitors 150.

In some configurations, the analytics server may display the feed received from the camera 234 simultaneously with a zoomed crop (e.g., zoomed portion of the same feed) received from the camera 234 as a picture-in-picture overlay. Therefore, the analytics server may display two feeds (different sizes) from the same camera.

The set of cameras may include a plurality of cameras disposed within the treatment room. In some embodiments, the plurality of cameras are disposed above the radiotherapy machine 210. The plurality of cameras may provide a top-down view (e.g., bird's eye view) of the radiotherapy machine 210. The plurality of cameras may provide a perspective view (e.g., angled view) of the radiotherapy machine 210. For example, the plurality of cameras may provide a live feed of the rotation of the gantry 224. The plurality of cameras may be positioned to also provide a live feed of the couch 222 (e.g., with or without the patient).

Figure 2F:
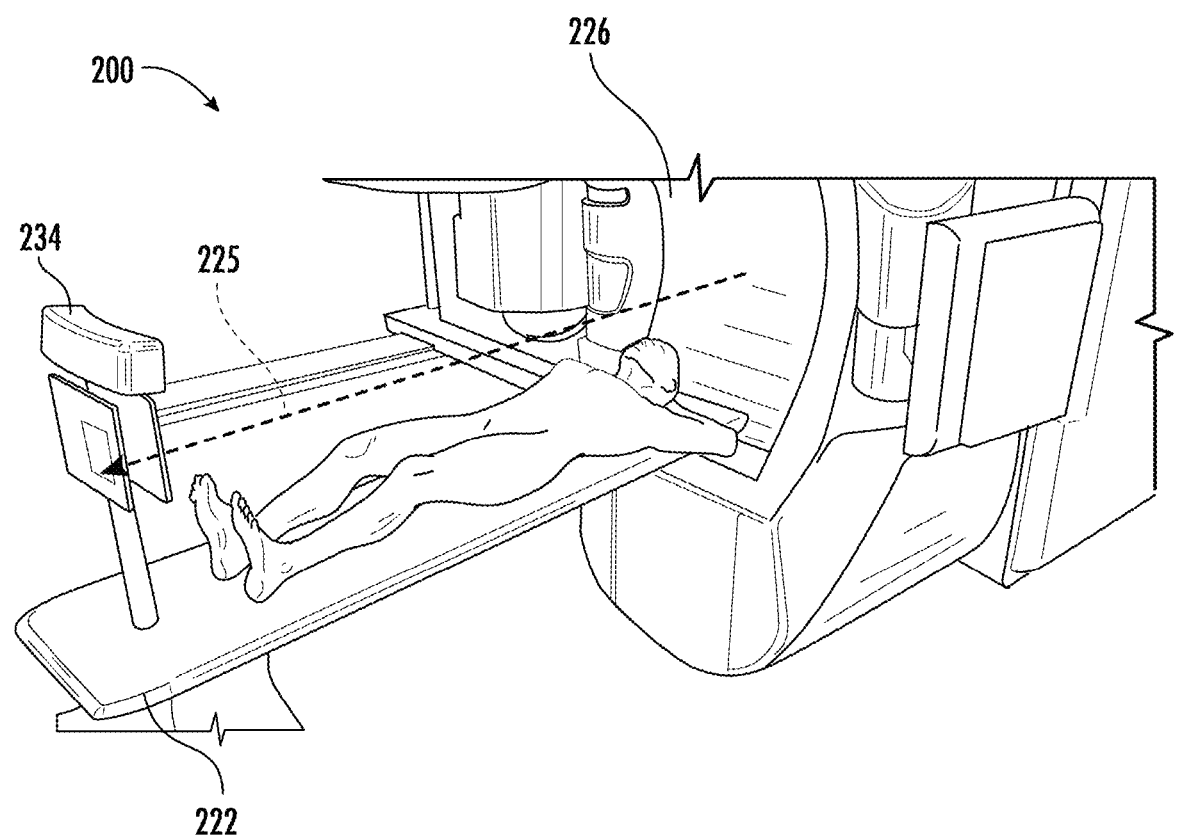
Figure 2G:
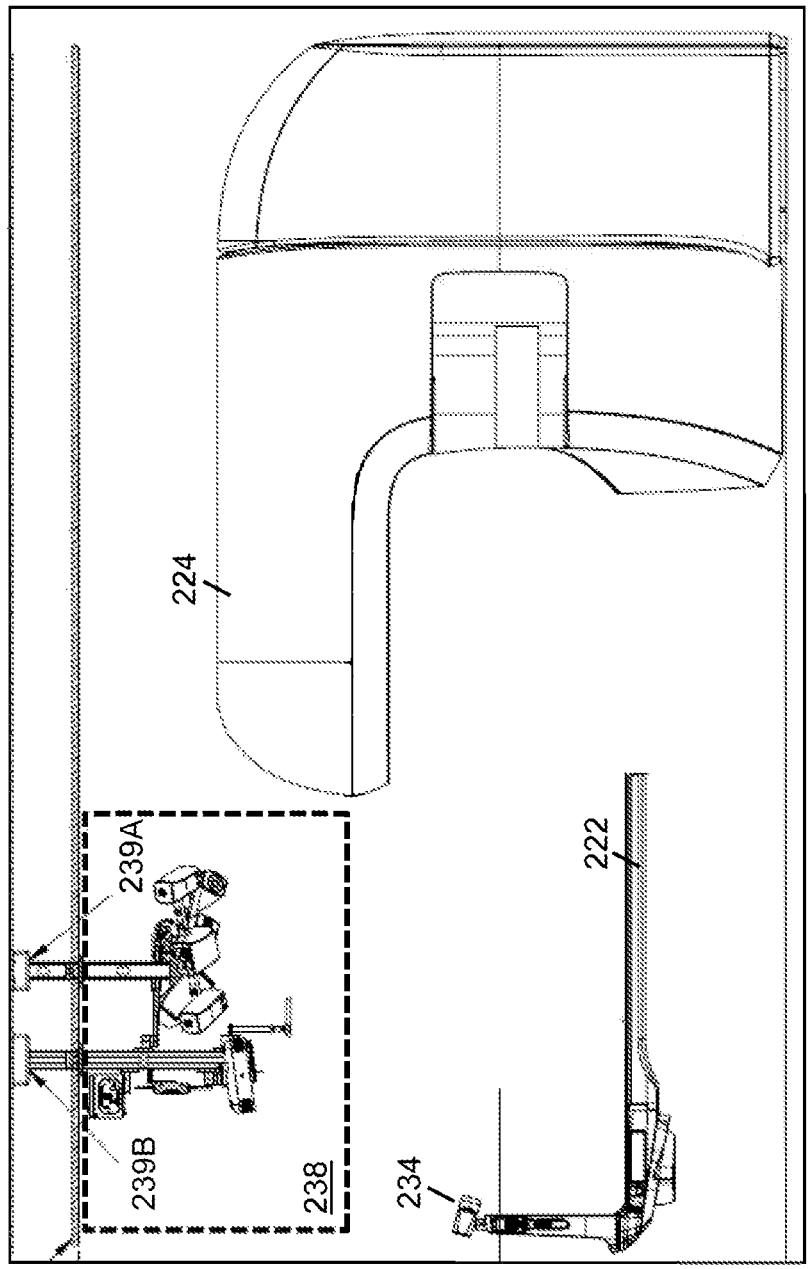

Referring now to FIG. 2G, a non-limiting example of cameras placed within the treatment room is illustrated. For instance, the treatment room 201 may include a radiotherapy machine (gantry 234 and couch 222) along with the camera 234 described herein. The treatment room 201 may also include cameras 238 placed on the ceiling that can monitor various attributes described herein. For instance, the cameras 238 may be pointed towards the patient where a live feed of the patient is transmitted to the analytics server. As a result, the analytics server may use various methods described herein (e.g., triangulation from multiple cameras) to identify the patient's position on the couch or the couch or the gantry's position itself. The analytics server may adjust the cameras 238 and point the cameras 238 towards a desired location, for instance by swiveling the cameras 238 at the mounts 239A-B. In another configuration (not shown), the cameras 238 can move along tracks in one or more directions. In yet another configuration (not shown), the cameras 238 can swivel and rotate from the posts connected to the mounts 239A-B.

The cameras may provide the live feed to the analytics server. The analytics server may receive the live feed from the plurality of cameras and provide it to the display screen 226. As discussed in greater detail herein, the analytics server may overlay pages onto the display screen 226. The analytics server may also provide the live feed of the plurality of cameras and the page overlay to the console monitors 150 and/or the system administrator 160.

In some embodiments one or more of the cameras discussed herein may be capable of determining three dimensional (3D) surface, shape, and positional information, for example by the use of time of flight cameras, structured light cameras, or any other 3D camera known in the art.

The plurality of cameras may be rearranged at various points within the treatment room. The plurality of cameras may be disposed on the ceiling of the treatment room or disposed at eye-level. The plurality of cameras may be disposed to provide a vertical view of the treatment room, a horizontal view of the treatment room or a perspective view of the treatment room. In some embodiments, each of the plurality of cameras may be manually adjusted to provide a desired view of the treatment room.

The analytics server may also be configured to execute a triangulation protocol using the live stream of the plurality of cameras. In some embodiments, each of the plurality of cameras are time-of-flight cameras (e.g., range sensing, distance measuring). In an example, the analytics server may execute photogrammetry to extract three-dimensional measurements from the captured two-dimensional subsequent images. The scale of the subsequent images may be determined, for instance by measuring various distance of the patient (e.g., length of arms, length of legs, and the like) and associating the measured distances of the gantry and/or couch with an image of patient (e.g., the subsequent images), the analytics server may determine the current position of the patient using the distances measured and the subsequent images.

Additionally, or alternatively, the analytics server may use triangulation to generate a three-dimensional model of the patient based on images from various perspectives (e.g., the set of cameras in the treatment room). As an example, the analytics server may associate a two-dimensional pixel in the subsequent images with a ray in three-dimensional space. Given multiple perspectives of the image (e.g., at least two sets of subsequent images capturing the position of the patient from at least two different perspectives), a three-dimensional point can be obtained as the intersection of at least two rays from pixels of the subsequent images.

The analytics server may execute various consistency functions to determine that the rays from the subsequent images are associated with consistent pixels. For instance, the analytics server may determine from the consistency functions, whether the pixels used to determine the three-dimensional point are similar colors and whether the pixels used to determine the three-dimensional point are similar textures.

The analytics server may compare the subsequent images or generated three-dimensional model to the reference image and/or model. For example, the analytics server may determine a position vector based on the comparison of the subsequent image or generated three-dimensional model and the reference image and/or model, indicating the difference in position of the gantry, couch, and/or patient in the subsequent image or generated three-dimensional model to the compared reference image and/or model.

The analytics server may measure the distance of the patient relative to the motion path of the gantry 224 or other machine parts (e.g., the imagers attached to the radiotherapy machine). The analytics server may then monitor patient movement during treatment. The patient may be monitored such that the patient adjustments exceeding a threshold may be revealed (and an operator may be informed of the movement), while the analytics server may determine that patient adjusts within a threshold may be a result of patient breathing. If the patient at any point may be within proximity of the movement path of the gantry 224, the analytics server may then send a call to the radiotherapy machine 210 to immediately stop rotating the gantry 224 and/or the beam delivery. The analytics server may also be configured to provide a prompt to the console monitors 150 and the system administrator 160 of the potential collision between the radiotherapy machine 210 and the patient. The analytics server may then resume rotation of the gantry 224 after user intervention. For instance, a clinician or a medical professional may realign the patient, such that the patient is no longer at risk of colliding with the radiotherapy machine. Upon the realignment, the treatment may continue. For instance, the radiotherapy treatment technician may continue with the workflow described herein.

The analytics server may also be configured to provide the console monitors 150 and the system administrator 160 a warning prompt if the patient may be within a specified margin of the motion path of the gantry 224. The analytics server may reduce the velocity of the gantry 224 when the patient may be within the specified margin of the motion path of the gantry 224 or other parts of the radiation therapy machine.

The analytics server may assign a position to any item that may be within the radial path of the gantry 224. For example, if the patient is connected to a ventilator during treatment, the analytics server may assign a position to the ventilator through the live feed of the plurality of cameras. The analytics server may then monitor the position of the ventilator during treatment.

Pendant Configuration

Figure 3A:
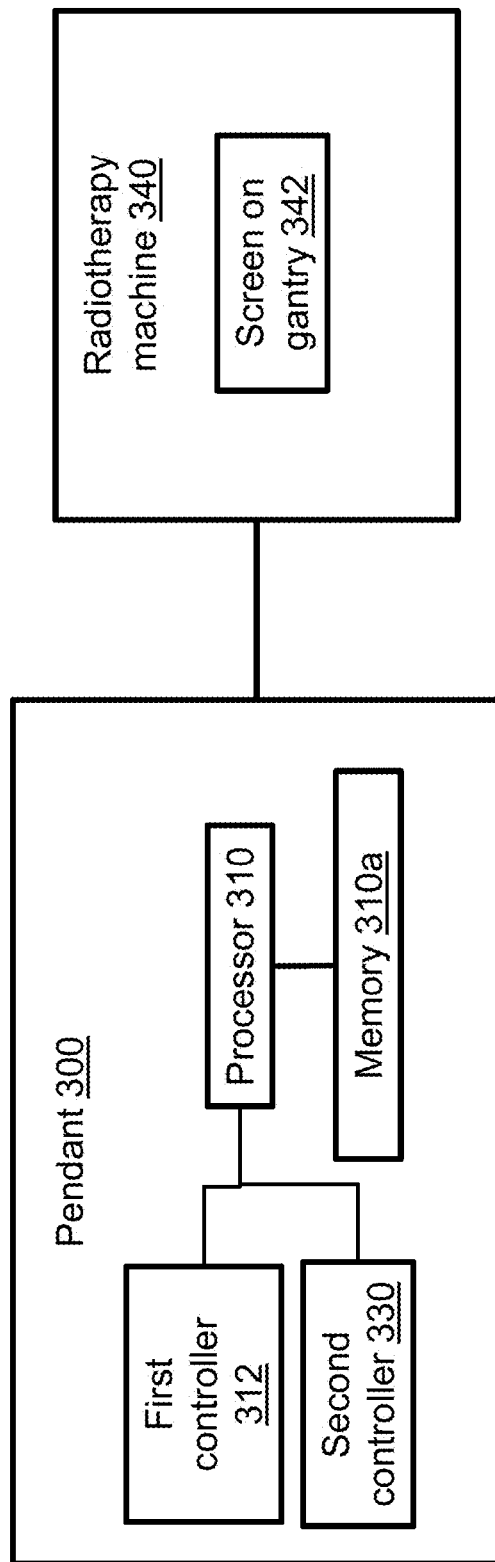
FIG. 3A illustrates a diagram of a pendant used in a workflow-oriented radiotherapy system, according to an embodiment.
Figure 3B:
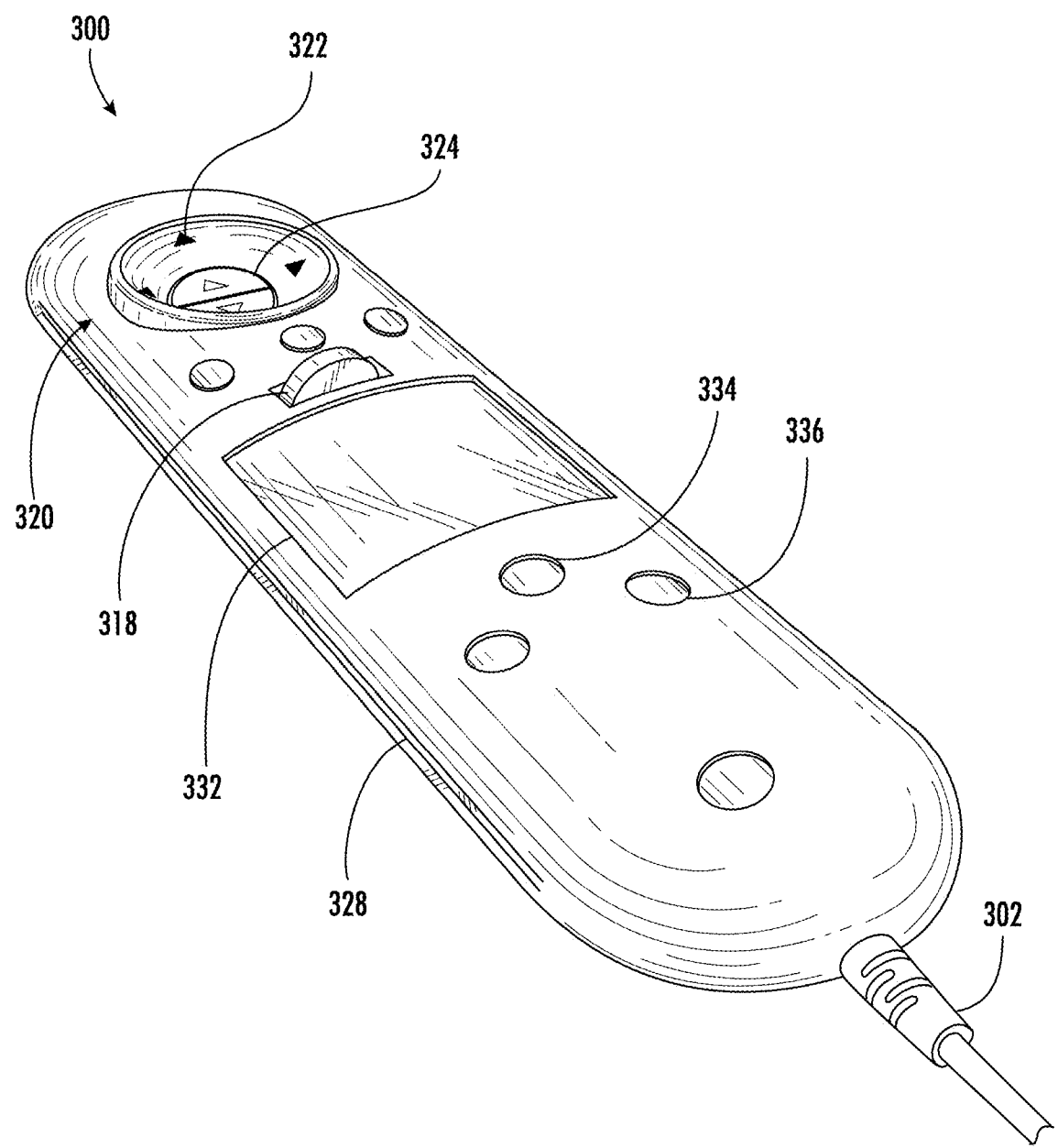
FIG. 3B illustrates a pendant used in a workflow-oriented radiotherapy system, according to an embodiment.

FIGS. 3A-3B illustrate various components of a pendant 300. The pendant 300 may be similar to the pendant depicted in FIG. 1A. The pendant 300 may be communicatively coupled to a radiotherapy machine, such that the pendant can transmit instructions to the radiotherapy machine. The radiotherapy machine may be similar to the radiotherapy machine depicted in FIG. 1A. The pendant 300 may be connected to the radiotherapy machine through wireless communications according to, for example, Bluetooth specification sets or another standard or proprietary wireless communication protocol. In various embodiments, the pendant 300 may be connected to the radiotherapy machine through a wired connection 302 or be integrated into the radiotherapy machine. The pendant 300 may also be in communication with a computer and/or server (e.g., such as the analytics server depicted in FIG. 1A).

The pendant 300 may be used to navigate the workflow-oriented series of pages described herein. Additionally, or alternatively, the various pages associated may be stand-alone pages that can be separately displayed (e.g., not as a part of the workflow-oriented series of pages). The workflow-oriented series of pages may be modified (e.g., with respect to content, with respect to order, with respect to the number of stages) by the pendant 300. Therefore, the pendant 300 can also navigate (can be used to navigate each page individually).

The pendant 300 may also be used to adjust the positioning of the radiotherapy machine through a selection of buttons that position the radiotherapy machine (axially or otherwise) in a desired direction. A technician may use the pendant 300 to initialize the radiotherapy machine 141, to have the radiotherapy machine 141 return to its home position. The radiotherapy machine may include a couch (e.g., such as the couch depicted in FIG. 1A). The couch may be configured to align the patient in a designated position during treatment. The pendant 300 may be configured to position the couch. The designated position may be identified by the analytics server or calculated by the technician (or any other medical professional). In some embodiments, a doctor identifies how to align the patient on the couch to optimize the treatment therapy. The technician may use the pendant 300 to move the couch and align the patient to receive optimum radiotherapy treatment.

The pendant 300 may include a processor in communication with a radiotherapy machine 340, a console monitor (e.g., such as the console monitor depicted in FIG. 1A) and/or a system administrator computer (e.g., such as the system administrator computer depicted in FIG. 1A). The processor may include a computer-readable medium 310a, such as a random access memory coupled to the processor (310). The pendant 300 may be executing algorithms or computer executable program instructions, which may be executed by a single processor or multiple processors in a distributed configuration. The pendant 300 may be configured to interact with one or more software modules of a same or a different type operating within the pendant 300. Non-limiting examples of the processor may include a microprocessor, an application specific integrated circuit, and a field programmable object array, among others. The pendant 300 may be capable of executing data processing tasks, data analysis tasks, and valuation tasks.

The pendant 300 may include a first controller 312 configured to adjust at least one configuration of the radiotherapy machine 340. In particular, the first controller that may adjust the positioning of the couch (312). The first controller that may include a button or a plurality of buttons (e.g., switches, toggle, and/or knob) disposed on the pendant 300. As depicted in FIG. 3B, the plurality of buttons may include a rotating wheel 318. The pendant 300 may also include a separate rotating controller (not shown here) for each rotational access. For instance, the clinician may use this rotating controller to toggle among axes (e.g., toggle to control different axes).

The rotating wheel 318 may facilitate movements of the couch or other rotational motions. In some embodiments, the rotating wheel 318 facilitates fine-tune movement of the couch. The plurality of buttons may also include a set of buttons 320 configured to position the couch towards specific axial directions. The set of buttons 320 may be disposed at an end of the pendant 300. In some embodiments, the set of buttons 320 are disposed in the center of the pendant 300. The set of buttons 320 may include a first group of buttons 322 configured to facilitate the axial movement of the couch in the X-axis and Y-axis. The X-axis and Y-axis may be on the same plane as the resting surface of the couch.

Various features described in the pendant 300 may be customized based on different user's preferences. For instance, a medical professional may customize the functionality of one or more features (e.g., buttons, touch pad, or any other feature of the pendant 300) such that said feature can adjust the radiotherapy machine accordingly. In some configurations, the medical professional may use the wheel 318 to determine which attribute of the radiotherapy machine to adjust. For instance, the medical professional may use the wheel 318 such that the buttons 322 only adjust the couch, collimator, or the gantry. Therefore, the wheel 318 may be used as a toggle and reconfigured the functionality of other buttons described herein. The wheel 318 may be spring-loaded to avoid accidental actuation by the medical professional.

The set of buttons 320 may also include a second group of buttons 324 configured to facilitate the axial movement of the couch in the Z-axis. The Z-axis may be orthogonal to both the X-axis and the Y-axis.

The plurality of buttons may also include a safety button 328. The safety button 328 may need to be depressed (or otherwise interacted with) before repositioning the couch. The pendant 300 may be configured, such that interactions with the safety button 328 may be required for any external machine motion. The safety button 328 may prevent the accidental repositioning of the couch if the set of buttons 320 are unintentionally pressed by a user. The safety button 328 may be disposed on the side of the pendant 300. In some embodiments, the safety button 328 may be disposed on the front or back of the pendant 300. The safety button 328 may also be embedded in the individual axis controls and may use separate circuitry as the rest of the features described herein. In some embodiments, the safety button 328 may be disposed on an auxiliary component. For instance, the safety button 328 may be actuated or de-actuated to interrupt the motion should one of the controls fail (e.g., when a feature of the pendant 300 is stuck in the engaged position). Various alternative features of the safety mechanism described above are also described in U.S. patent application Ser. No. 15/957,727, which is incorporated by reference herein in its entirety.

It may be desirable for the pendant 300 to have a control separate from the radiotherapy machine controller (first controller 312) to avoid accidental commands on the radiotherapy machine controller that are intended to control the GUI. In this embodiment, the pendant 300 includes a second controller 330. The second controller 330 may be configured to receive an input from a user to be received by a computer (e.g., such as the analytics server depicted in FIG. 1A). The computer revises a page displayed on a gantry 342 of the radiotherapy machine 340. The second controller 330 may include a touch pad 332 (e.g., touch-sensitive). The touch pad 332 may utilize capacitive sensing or resistive sensing. The touch pad 332 may be disposed at the center of the pendant 300. In some embodiments, the touch pad 332 may be disposed on an end of the pendant. The touch pad 332 may be configured to allow a user to register movements through touch. For example, the user can swipe from the center of the touch pad 332 to a first side of the pendant 300. The computer may then revise the page to provide additional patient information.

Different movements performed on the touch pad 332 may result in different input types used to navigate and/or otherwise interact with the pages described herein. For example, if the user swipes the touch pad 332 in a first direction, it may cause the workflow to continue to the next step. If the user swipes the touch pad 332 in an opposite direction, it may cause the workflow to return to the last step. These movements (and the corresponding action performed by the analytics server) may be customized by the users. For instance, a user can set up the system, such that a circular motion on the touch pad causes the analytics server to move backwards or forward within the workflow-oriented series of pages.

The touch pad 332 may also be configured to register several points of contact, which would generate additional input types. For example, if the user uses two figures to swipe the touch pad 332, the touch pad 332 may be configured to hide a page. In another example, if the user uses a single figure to swipe the touch pad 332, the touch pad 332 may be configured to alternate between different pages.

The touch pad 332 may be clickable (e.g., depressible) so that it provides an additional input type. For example, if the user clicks the touch pad 332, the workflow may register that as an input that the current step has been completed. In some configurations, functionality associated with the touch pad 332 may be performed using other input elements, such as buttons, wheels, and the like. For instance, instead of interacting with the touch pad 332 to navigate through the GUIs described herein, the user may interact with physical buttons (e.g., next, previous). Therefore functionality attributed to the touch pad 332 is not limited to touch pad technology.

The second controller 330 may also include a return button 334 (e.g., back button). The return button 334 may also be used to register an input for the pages. The return button 334 may be disposed adjacent to the touch pad 332. The return button 334 may cause the workflow to return back a step. For example, if the technician would like to return to a prior step of the workflow, the technician may press the return button 334.

The second controller 330 may also include a "home" button 336. "Home," as used herein, may refer to a machine home/unload position. Therefore, interacting with the home button 336 may cause the workflow to go to an unload step.

The pendant may also include an "enter" button. The enter button may also be used to register an input for the pages. The enter button may be disposed adjacent to the touch pad 332. The enter button may be used to navigate the workflow. The enter button may navigate the workflow to go to a home page. The home page may be the first page of the workflow. For example, if the technician would like to return to a first page, the technician may press the enter button. In some embodiments, the home page may be the first page of the stage of the workflow the user is currently in.

The pendant 300 may be a handheld device that may be operated by the technician, e.g. while preparing the patient and/or the radiotherapy machine, or while unloading the patient after radiotherapy treatment. In some configurations, the pendant 300 may be connected to the radiotherapy machine (using a wire or wirelessly) where the pendant 300 can be freely moved by the technician. In some configurations, the pendant 300 may be mounted to the radiotherapy machine, such that the pendant's movements are restricted. For instance, the pendant 300 can be mounted (removably or irremovably) to the couch, gantry, display screen, or any other part of the radiotherapy machine.

The pendant 300 may be designed to be operated by the technician's foot. For instance, the pendant 300 may be placed/mounted on the couch such that the technician can interact with pages described herein using the technician's foot. For instance, the size and shape of various buttons, rotating wheel 318, touch pad 332 or other features may be revised accordingly.

In some configurations, the pendant 300 may include a lighting feature where one or more of the input elements described herein (rotating wheel 318, touch pad 332, return button 334, home button 336, safety button 328, and/or buttons 320) can be highlighted for easier access. In some configurations, the lighting feature may emit white light. However, the color and intensity of the light may be customized by the technician and/or the system administrator. In some configurations, color/intensity could also be used to communicate different states of the controls or guide the user through the workflow described herein.

In some configurations, various input elements described herein may be depressed/recessed (e.g., flushed with the surface of the pendant) to avoid accidental actuation by the technician.

The pendant 300 may also include a "back" button. The back button may allow the user to navigate one step back in the workflow. For instance, the user may interact with the back button to navigate to a previous page or stage. The back button may also be customized to navigate the user to the main screen from any of the secondary screens. Additionally, the pendant 300 may include a "menu button" that may provide additional options to the user. Therefore, the menu button may behave similar to the common use of the right mouse click in current desktop or laptop computers, such that its function is context sensitive e.g. brings up the position presets when used in the machine parameter screen but shows secondary screen navigation on the main screen. Even though the back button and the menu buttons are described in the context of "buttons," a skilled artisan will recognize that "button" refers to any input element implemented on the pendant 300.

Figure 4A:
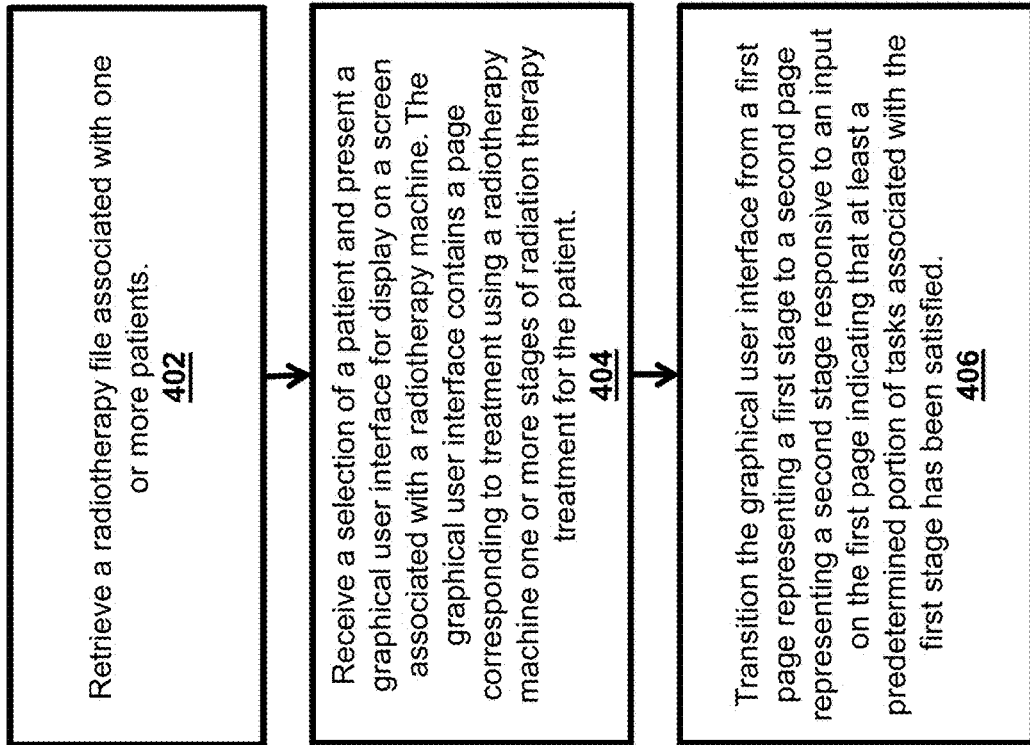
FIG. 4A illustrates a flow diagram executed in a workflow-oriented radiotherapy system, according to an embodiment.

Treatment Room GUI:

FIG. 4A illustrates a flowchart depicting operational steps performed by the analytics server in accordance with an embodiment. The method 400a describes how a server, such as the analytics server described in FIG. 1A, displays various interactive pages configured to display various stages of performing radiotherapy on a patient (e.g., a person to be treated by the radiotherapy machine). Even though the method 400a is described as being executed by the analytics server, the method 400a can be executed by any server(s) and/or performed locally using a computer/processor associated with the radiotherapy machine and/or the console (as discussed in FIGS. 10A-10D). Other configurations of the method 400a may comprise additional or alternative steps, or may omit and/or mix one or more steps altogether.

At step 402, the analytics server retrieves an RT file associated with one or more patients. The RT file may be retrieved from one or more medical databases (such as the medical database in FIG. 1A), servers, files, and the like.

The RT file may comprise a patient identifier. The patient identifier may be a series of numbers and/or letters to identify patients. A user (e.g., technician, doctor, nurse, or other professional) and/or system administrator may determine the patient identifiers and map the patient identifiers with particular patients. The analytics server may update the RT file such that the RT file contains the mapped patient identifiers and associated patients. Additionally, or alternatively, the analytics server may store the mapped patient identifiers and associated patients.

The RT file may further include various treatment details associated with the patient's treatment. For instance, the RT file may include various couch/gantry attributes, such as couch angles, gantry rotation attributes (e.g., full or partial arcs), the number of partial arcs (if applicable), machine trajectories, control points, and the like associated with each patient. In an example, the treatment data (e.g., RT file) may include the amount of dose delivered to the patient at each determined control point of the planned machine position.

In addition, the RT file may contain patient information, including personal identifying information (PII) such as the diagnoses of the patients, the name of the patient, nicknames of the patient, the birthdate of the patient, one or more photos of the patient, and the like. The RT file may also contain notes from one or more doctors regarding the patient and/or the diagnoses of the patient, and medical diagnoses tools such as x-ray scans, including computed tomography (CT) scans, MRI images, SPECT images, PET images, ultrasound images, and the like. The RT file may also include whether the treatment is a volumetric modulated arc therapy (VMAT) treatment, intensity-modulated radiation therapy (IMRT) treatment, or high dose rate (FLASH) treatment.

Additionally, or alternatively, the RT file may contain a list of patients (or patient identifiers) and a corresponding time associated with each patient. In some embodiments, the corresponding time may indicate the time at which the patient is expected to arrive at the treatment room for a treatment appointment. In other embodiments, the corresponding time may indicate the time at which the patient is expected to begin an appointment with the radiotherapy machine. In other embodiments, the corresponding time may indicate the time at which the patient is expected to arrive at the treatment center (e.g., a clinic, hospital).

The RT file may also contain various patient attributes. Patient attributes may include the height of the patient, the length of the patient's arms, the length of the patient's legs, the width of the patient's torso and other bodily measurements. The analytics server may determine the measurements of the patient's body based on one or more cameras or other devices feeding the analytics server images and/or live video data. Additionally, or alternatively, a user may input patient measurements such that the analytics server receives measurements of the patient's body. The analytics server may also retrieve measurements of the patient's body from the RT file or other one or more servers, files and/or databases.

Additionally, or alternatively, the analytics server may retrieve information contained within the RT file from one or more source. For instance, the patient identifier may be retrieved by the analytics server from a medical database (such as the medical database in FIG. 1A), the treatment details associated with the patient's treatment may be retrieved from a doctor's file. Additionally, or alternatively, the analytics server may retrieve various portions of information from various source. For instance, patient identifiers and treatment details associated with the patient's treatment may be retrieved by the analytics server from a medical database (such as the medical database in FIG. 1A). Further, some PII may be retrieved by the analytics server from a patient file, while other PII may be retrieved by the analytics server from a library.

At step 404, the analytics server presents, in response to receiving a selection of a patient from the one or more patients in the RT file, a page associated with the selected patient. The response by the server may be generated by a user input (e.g., an input from a pendant as discussed in FIGS. 3A-3B, an input from a console as discussed in FIGS. 10A-10D), an input from the screen displayed on the radiotherapy machine, and the like. Additionally, or alternatively, the response by the server may be in response to a timing trigger (e.g., the time at which the patient is expected to begin an appointment with the radiotherapy machine).

Steps 402 or 404 describe an embodiment where the analytics server retrieves RT files associated with multiple patients and then receives a selection from an operator of the radiotherapy machine (e.g., technician in the treatment room) for a particular patient. Upon receiving the selection, the analytics server identifies treatment data (RT file(s)) associated with the selected patient and displays the GUIs described herein. Therefore, the method 400 is specific to the patient who is being treated.

The analytics server presents the GUI on a display of a screen associated with the radiotherapy machine (e.g., the screen positioned on the gantry as described in FIGS. 2A-2F) or alternatively, on a screen located elsewhere within the treatment room. The screen may be placed onto (other otherwise connected to) the radiotherapy machine itself, such as by placing the screen on the throat (or any other part) of the gantry. The screen may also be placed communicatively coupled to the radiotherapy machine and positioned in the treatment room (e.g., the same room as the radiotherapy machine). Various other screens may display the GUIs presenting information from the analytics server. For instance, screens in rooms outside of the treatment room (such as a console screen in a room monitoring the treatment room) may also display the GUIs presenting information from the analytics server. Additionally, or alternatively, the GUI may be displayed on various platforms. For instance, a user may view the GUIs displayed by the analytics server on the various platforms by executing an application such as a browser application.

Various pages of the GUI associated with the method 400 may be a part of a workflow-oriented series of pages described herein. Additionally, or alternatively, the various pages associated with the method 400 may be standalone pages that can be separately displayed as a GUI (e.g., not as a part of the workflow-oriented series of pages). The workflow-oriented series of pages of the GUI associated with the method 400 can be modified (e.g., with respect to content, with respect to order, with respect to the number of stages) by a system administrator and/or user.

The GUI(s) described herein may be displayed on multiple screens (and on various platforms) in a synchronous or asynchronous manner. For instance, the analytics server may display the GUI(s) on the throat of the gantry, radiotherapy room screen, console monitors, and/or a physician device in a simultaneous or near simultaneous manner, such that one or more users can monitor the actions of the user in the treatment room. Additionally, or alternatively, the analytics server may receive one or more inputs that may raise an alert and/or indicator on the GUI displayed to the user in the treatment room. The alert and/or indicator may be visual and/or audible. For instance, a user in a different room (e.g., console room) may notify the user in the treatment room that the user in the treatment room is missing something and/or did not complete a task. The analytics server may also receive one or more inputs that cause a change in the displayed page of the GUI in the treatment room (or the console room). For instance, the displayed page may change to display a different page.

The analytics server may display an image of the radiotherapy machine (e.g., couch) on the GUI. As described in FIGS. 2A-2F, the analytics server may be in communication with one or more cameras (e.g., camera on the couch, gantry camera, or other cameras places within the radiotherapy room). Additionally, or alternatively, the analytics server may present for display a live feed of the radiotherapy machine (e.g., live feed of the couch with or without the patient) on the GUI.

Figure 4B:
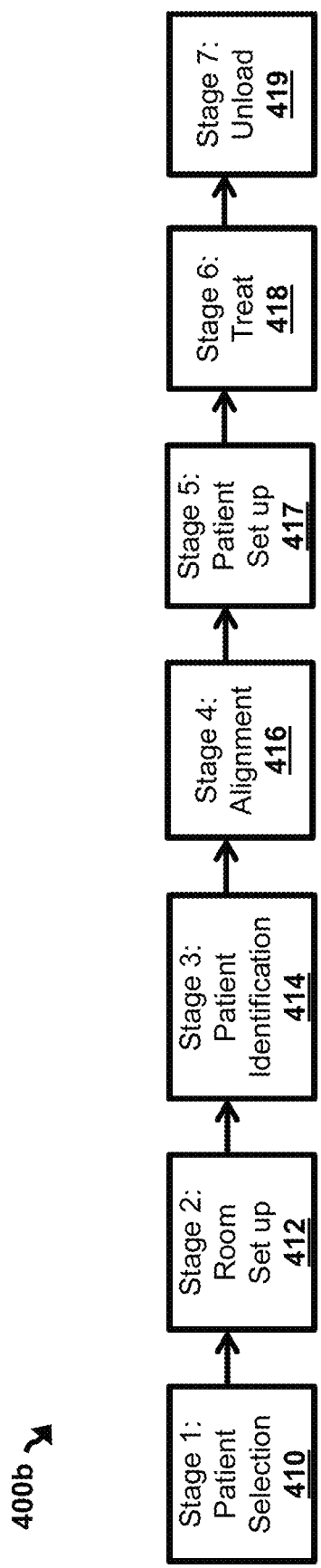
FIGS. 4B-4P illustrate pages displayed in a workflow-oriented radiotherapy system, according to an embodiment.
Figure 4C:
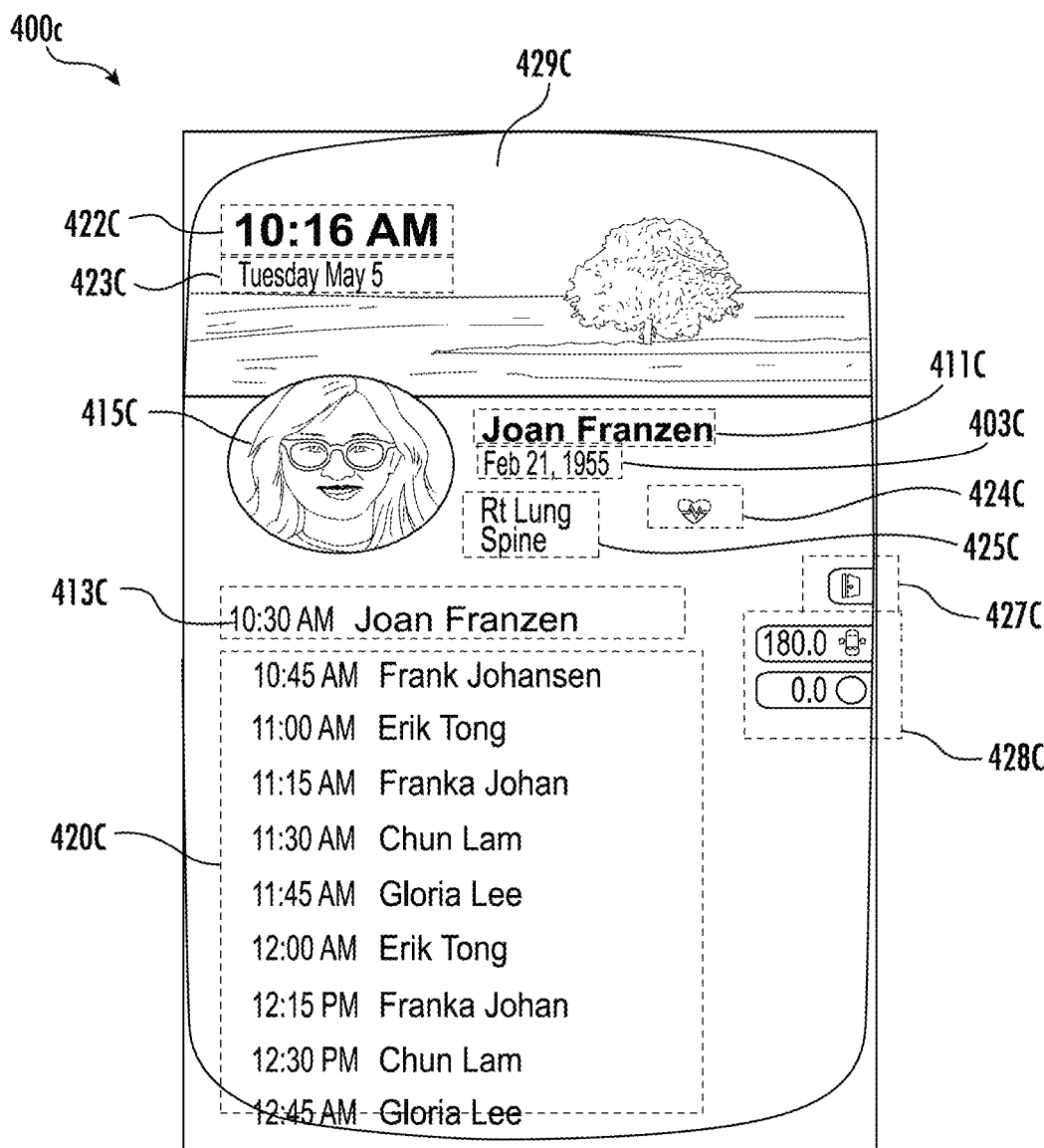

The analytics server instructs the screen associated with the radiotherapy machine (e.g., positioned on the gantry of the radiotherapy machine) to present pages of the GUI on the screen in step 404 where the pages correspond to stages of a treatment workflow using the radiotherapy machine (e.g., stages of treatment shown in FIG. 4B). The workflow described herein may be preconfigured, such that it cannot be revised by different unauthorized parties However, in some configurations, a user and/or system administrator may determine the number of stages and the content associated with each of the stages. In some embodiments the analytics server may present each of the seven predetermined stages on one or more pages of the GUI, in addition to supplemental pages with supplemental information. One or more pages may be used to describe the workflow stages to treat a patient using a radiotherapy machine. The workflow on the GUI (presented by the analytics server) describes the work performed by a user to treat a patient using the radiotherapy machine.

The analytics server displays only relevant information on the GUI during each stage. Relevant information, as used herein, may refer to information that facilitates a user advancing to the next stage. Relevant information, as used herein, may refer to a subset of all information used to treat the patient at a given stage in the workflow. The relevant information is consumed by the user while the user performs tasks at a given stage of workflow. The analytics server displays the relevant information for the current stage of workflow on a page. A user and/or system administrator may determine what is considered relevant information. Further, the user and/or system administrator may determine whether information is relevant for various stages of the workflow. The analytics server may not display information that is not relevant, which may include information that a user will have to remember for succeeding stages in the workflow or information that is not pertinent to completing the particular stage because it involves a future stage or an already-completed stage. The relevant information may be visually organized in different areas of the displayed page using various types of graphical elements, as described below.

The GUI may display various graphical indicators. A graphical indicator, as used herein, may correspond to any graphical component (e.g., graphical icon) displayed on a page. Non-limiting examples of a graphical indicator may include icons in different shapes (e.g., rectangular, square, and circle) and/or in different colors (e.g., black, white, red, orange, or translucent), and the graphical indicator may optionally include text (any alphanumeric characters). Graphical indicators may be used to represent information, such as adjustments to be made to the configuration of the radiotherapy machine, aligning a patient with a predetermined angle, accessories for treatment, and the like. Example pages having graphical indicators include pages 400c-400p shown in FIGS. 4C-4P (as well as FIGS. 11C-N).

On some of the pages, the analytics server may display a progress indicator. The progress indicator may be comprised of various graphical indicators and/or text (or some combination). The progress indicator displayed on the pages indicates a progression of the stages (e.g., highlighting the workflow step). In some embodiments, names corresponding to each of the stages may be displayed on the progress indicator. In other embodiments, numbers corresponding to each of the stages may be displayed on the progress indicator. Example pages having graphical indicators may include pages 400c-400p shown in FIGS. 4C-4P (as well as FIGS. 11C-N).

In some configurations, the GUI may emphasize the name of the stage on the process indicator. In an example, the GUI may emphasize the name of the currently displayed stage by highlighting the currently displayed stage name (e.g., using a color such as white, red, or yellow). The GUI may display the preceding and succeeding stages using contrasting colors as such as grey, black, or translucent. In another example, the GUI may emphasize the name of the current displayed stage by using shapes. For instance, the name of the currently displayed stage on the page may correspond (partially or fully) by a shape. The GUI may display the preceding and succeeding stages using shapes that are different from the shape containing the name of the currently displayed stage. For example, the current stage name may be contained within a circle, while the preceding and succeeding stages may be in a square.

Additionally, or alternatively, the name of the stage currently displaying on the page may be bordered in a way that is visibly distinct from the border for the preceding and succeeding stages. For instance, the name of the currently displaying stage may be enclosed in a dashed shape, while the preceding and succeeding stages may be enclosed in a solid shape. Further, the current stage name may be enclosed in a border, while the preceding and succeeding stages may not be enclosed in a border.

In some configurations, all of the stages of workflow may be displayed on the progress indicator (e.g., using numbers or text or the like) of the GUI. Additionally, or alternatively, a portion of all of the stages may be displayed on the GUI. Additionally, or alternatively, the analytics server may display only the current stage of the workflow on the GUI. Additionally, or alternatively, the analytics server may only display on the GUI the stages of the workflow that have been completed (in addition to the current stage of the workflow). Additionally, or alternatively, the analytics server may only display on the GUI the stages of the workflow that have not been completed (in addition to the current stage of the workflow). The stage indicated on the progress indicator on the GUI allow the system administrator and/or user to more easily determine the current stage.

The GUI may display the progress indicator anywhere on the page including horizontally along the bottom of the page, horizontally along the top of the page, horizontally along a side of the page (e.g., as if in a column a side of the page), vertically along a side of the page (e.g., rotated vertically along a side of the page), in the middle of the page, some position offset from the middle of the page, and the like. A system administrator and/or user may determine the position of the progress indicator on the page.

On some of the pages, the analytics server may display treatment related images. The treatment related image may be an image taken by a doctor, technician, or a user related to treatment. For example, treatment related images might convey positions the patient should lie in for optimal treatment, positions of accessories with respect to the patient and/or radiotherapy machine, x-rays, CT scans, ultrasounds and the like. In some instances, the treatment related image might be a two-dimensional or three-dimensional representation (e.g., animation and/or four-dimensional CT scan imaging). Pages including treatment related images may include pages 400c-400p shown in FIGS. 4C-4P (as well as FIGS. 11D-M).

The GUI may display the treatment related image anywhere on the page including horizontally along the bottom of the page, horizontally along the top of the page, horizontally along a side of the page, vertically along a side of the page (e.g., treatment related image is rotated vertically), across the whole page (e.g., a background), in the middle of the page, some position offset from the middle of the page, and the like.

On some of the pages, the analytics server may display one or more non-treatment related images. The non-treatment related images may be elected by the patient based on the patient's preferences. In other circumstances, the non-treatment related image might be selected by a person other than the patient (e.g., the non-treatment related image might be a logo of the clinic in which the treatment is occurring). Pages including non-treatment related images may include pages 400c-400p shown in FIGS. 4C, 4K, and 4P.

The GUI may display the non-treatment-related image anywhere on the page including horizontally along the bottom of the page, horizontally along the top of the page, horizontally along a side of the page, vertically along a side of the page (e.g., non-treatment related image is rotated vertically), across the whole page (e.g., a background), in the middle of the page, some position offset from the middle of the page, and the like.

Some of the pages may display a background. The GUI can display for the background a solid color, a pattern, a treatment related image, a non-treatment related image, and the like. Additionally, or alternatively, the background may be a live view of the couch using a three-dimensional representation (e.g., animation) of the couch. Additionally, or alternatively, the GUI may display a live feed view of the couch (including the user and/or patient captured by a camera live feed) based on a received live stream of data from one or more cameras. As discussed herein, the cameras placed on the gantry, at an end of the couch, on the ceiling, or generally within the room comprising the radiotherapy machine (e.g., as discussed in FIGS. 2A-2F). Further, the background of the page may be in focus (clear) or out of focus (blurry). Pages including a background may include pages 400c-400p shown in FIGS. 4C-4P.

The GUI may display a live feed of the radiotherapy machine, for instance, a live feed of the couch based on a received live stream of data from the one or more cameras on the radiotherapy machine and/or in the treatment room. The displayed live feed of the radiotherapy machine may be an actual image (revised in real time or near real time as the patient enters into view of the camera or as the radiotherapy machines moves) and/or a two-dimensional or three-dimensional representation (e.g., animation) representing the radiotherapy machine. Pages including the live feed of the radiotherapy machine may include pages 400c-400p in FIGS. 4C-4P.

Non-limiting examples of camera placements that provide the analytics server the live feed of the radiotherapy machine include cameras placed on the gantry, on the couch, on the ceiling, or generally within the room comprising the radiotherapy machine (e.g., as discussed in FIGS. 2A-2F). In the event the patient enters into a view of a camera, the analytics server may display a live feed of the patient and the radiotherapy machine (e.g., a live feed of the patient positioned on the couch). The displayed live feed of the patient (or portion of the patient) may be an actual image (revised in real time or near real time as the patient enters moves on the couch) and/or a two-dimensional or three-dimensional representation (e.g., animation) representing the patient.

The analytics server may continuously receive the live feed of the radiotherapy machine from the cameras (or other devices capable of capturing images in real time or near real time). The analytics server may continuously analyze the live feed of the radiotherapy machine according to the methods described herein, even in the event that the analytics server does not display the live feed of the patient and/or radiotherapy machine. In the event that the analytics server is not displaying the live feed of the radiotherapy machine, the analytics server may be triggered to display the live feed of the radiotherapy machine. The analytics server may be triggered to display the live feed of the radiotherapy machine in the event that the analytics server receives an input from a user to display the live feed of the radiotherapy machine. For instance, the user in the treatment room may provide an input to the analytics server using a pendant and/or interacting with the screen on the gantry. Additionally, or alternatively, a user in a different room (who may be viewing the same page or other screen corresponding to the same stage on a different screen) may provide an input to the analytics server to display the live feed of the radiotherapy machine. Additionally, or alternatively, the analytics server may present the live screen, for instance, in the event a certain amount of time has elapsed or a problem is detected or anticipated.

The GUI may display notes. In some embodiments, the GUI displays notes based on a received stream of data from a console (e.g., as discussed in FIGS. 10A-10D). The console may be used to update the analytics server and provide information to the analytics server in real time. In addition, the analytics server may be used to update the console and provide information to the console in real time. In other embodiments, the analytics server displays notes that have been previously stored by the analytics server (e.g., setup notes, notes of patient preferences, notes of accessory placement). The notes may also include content retrieved from any of the data sources described in FIG. 1A, such as treatment notes inputted by a treating oncologist.

The GUI may display the display notes anywhere on the page including horizontally along the bottom of the page, horizontally along the top of the page, horizontally along a side of the page (e.g., the analytics server displays the display notes on the page such that the display notes appear below/above each other as if in a column on a side of the page), vertically along a side of the page (e.g., display notes are rotated vertically), in the middle of the page, some position offset from the middle of the page, and the like.

The analytics server may display a graphical indicator corresponding to one or more accessories. The identification of the accessories necessary for the patient treatment is described herein (e.g., FIGS. 7A-7C). The graphical indicator corresponding to one or more accessories may be displayed by the analytics server in conjunction with a status indicator to convey/identify whether the analytics server has identified necessary predetermined accessories to be present within a predetermined proximity. For example, the status of the accessories may be provided in various ways including a color scheme where different colors represent different statuses. For instance, a red graphical indicator represents a missing or incorrect accessory, an orange graphical indicator represents the placement of the accessory must be fixed before treatment begins, and a grey graphical indicator represents the accessory is present and in a proper location. A graphical indicator may also be shown as partially orange, whereby the extent of the orange portion represents an amount of adjustment, alignment, or other action needed. Likewise, a graphical indicator may be shown as partially grey, whereby the extent of the grey portion represents an amount that is already in a satisfactory position, stage, or completion.

The status of the accessory may be provided using different shapes representing different statuses. For instance, an octagon associated with an accessory represents a missing or incorrect accessory, a rectangle associated with an accessory represents the placement of the accessory must be fixed before treatment begins, and a circle associated with an accessory represents that the accessory is present and in a proper location. Additionally, or alternatively, the status of the accessory may be provided using different borders representing different statuses. For instance, a solid border around a shape represents a missing or incorrect accessory, a dashed border around a shape represents the placement of the accessory must be fixed before treatment begins, and no border represents that the accessory is present and in a proper location. The statuses used in the status indicator makes the various statuses visually distinct. These status indicator statuses such as the color, shape, and border can be revised based on user preferences and/or system administrator. The analytics server may display status indicators in conjunction with other graphical indicators.

The GUI may display the accessory graphical indicator anywhere on the page including horizontally along the bottom of the page, horizontally along the top of the page, horizontally along a side of the page (e.g., the analytics server displays the accessories on the page such that the accessories appear below/above each other as if in a column on a side of the page), vertically along a side of the page (e.g., the accessories are rotated vertically), in the middle of the page, some position offset from the middle of the page, and the like.

As depicted, the accessory indicators may be placed on the left side of the GUIs described herein to indicate the left side pullout panel contains more information related to the accessories. As a result, the user may indicate a desire to view more information by interacting with the GUIs depicted in FIGS. 7B-C. For instance, the user may click left and the analytics server may display more detailed information regarding the accessories. The same principle may be applied to the patient info displayed within the top portion of many of the GUIs described herein and/or the machine info depicted on the right side. While the location of these panels could be an arbitrary decision that is revisable by the end users, the proximity of the indicator to these panels is deliberate and consistent with the way the analytics server displays the information. Therefore, the placement of the indicators corresponds to the workflow.

The analytics server may also indicate the status of the workflow stage using ambient light. The analytics server may also indicate a status of the machine, e.g., a collision detected, fault/error, progress of the treatment, etc., or even reflect the patient's mood or biological functions relevant to the treatment, such as the patient's breathing.

The analytics server may control the color of ambient light in the treatment room, ambient light originating from under the couch, ambient light originating from one or more portions of the radiotherapy machine (e.g., a bezel on the machine), and the like. The ambient light may be controlled by the server to convey information. In some instances, the ambient light may convey binary information to the user (e.g., the workflow stage is complete or the workflow stage is incomplete). For example, while the user is performing the tasks on the page related to a particular stage of workflow, the ambient light may be orange. When the user finishes a predetermined number of tasks (e.g., all of the tasks) related to the displayed stage on the page, the analytics server may change the ambient light to blue, indicating that the workflow stage has been completed.

The analytics server presents a GUI on the screen associated with the radiotherapy machine (e.g., positioned on the gantry) in step 404 for the selected patient from the one or more patients. The GUI transitions from a first page to a second page based on an input received by the server, as shown in step 406.

The second page may contain information corresponding to a stage on the first page. For example, the second page may contain additional information about the stage on the first page. For instance, during the Room Setup stage (e.g., Stage Two), as discussed herein, the server may display, on a first page of the page, a live feed of the patient on the couch. The analytics server may use graphical indicators on the first page to provide information about certain tasks. For instance, a graphical indicator coupled with a status indicator may provide some information as to the accessories that the analytics server is detecting. A user may use the pendant and switch the displayed page from the live feed of the patient on the couch having accessory information provided in the form of graphical indicators and/or status indicators to a second page containing information that describes the accessories requirements in more detail.

Additionally, or alternatively, the second page may not contain at least some information belonging to the stage on the first page. In a non-limiting example, the first page may display information related to a particular stage of the workflow and the second page may contain information related to the subsequent stage of the workflow. In this circumstance, the second page is used to display information facilitating the user's progression through the stages of the workflow, not to provide more information about the first page.

A user using a pendant may generate an input to the analytics server using a pendant, as discussed herein (e.g., FIGS. 3A-3B). The user may activate, press, touch, spin, swipe, actuate, or otherwise interact with the pendant to generate the input for the analytics server.

Additionally, or alternatively, the input received by the analytics server may be a flag or other notification signaling the completion of particular one or more tasks (or the completion of a predetermined portion of tasks) displayed on the GUI. A user and/or system administrator may determine the predetermined portion of tasks that trigger the flag or other notification signaling the completion of the particular one or more tasks. For instance, a user may be viewing a page and adjust the patient and/or perform the steps as recommended on the page. In the event the analytics server determines that a task has been performed, the analytics server may generate the flag or other notification. The analytics server may use a flag threshold to determine whether a predetermined portion of tasks has been performed. For example, if the flag threshold is two, but only one flag has been generated (representing that only one task has been completed), then the analytics server can determine that a predetermined portion of tasks have not been completed. In some embodiments, when the analytics server determines that the predetermined portion of tasks has been completed (e.g., the flags generated by the analytics server meets and/or exceeds the flag threshold), the analytics server may display an interactive button (e.g., a graphical indicator configured to receive an input). To progress from the current stage of the workflow to a subsequent stage of the workflow, the user may need to interact with the interactive button, indicating that the user is ready to progress. For example, the interactive button may have an indicator (such as an arrow to the next stage) or text (e.g., "next," "continue," "proceed," "done")

Figure 4D:
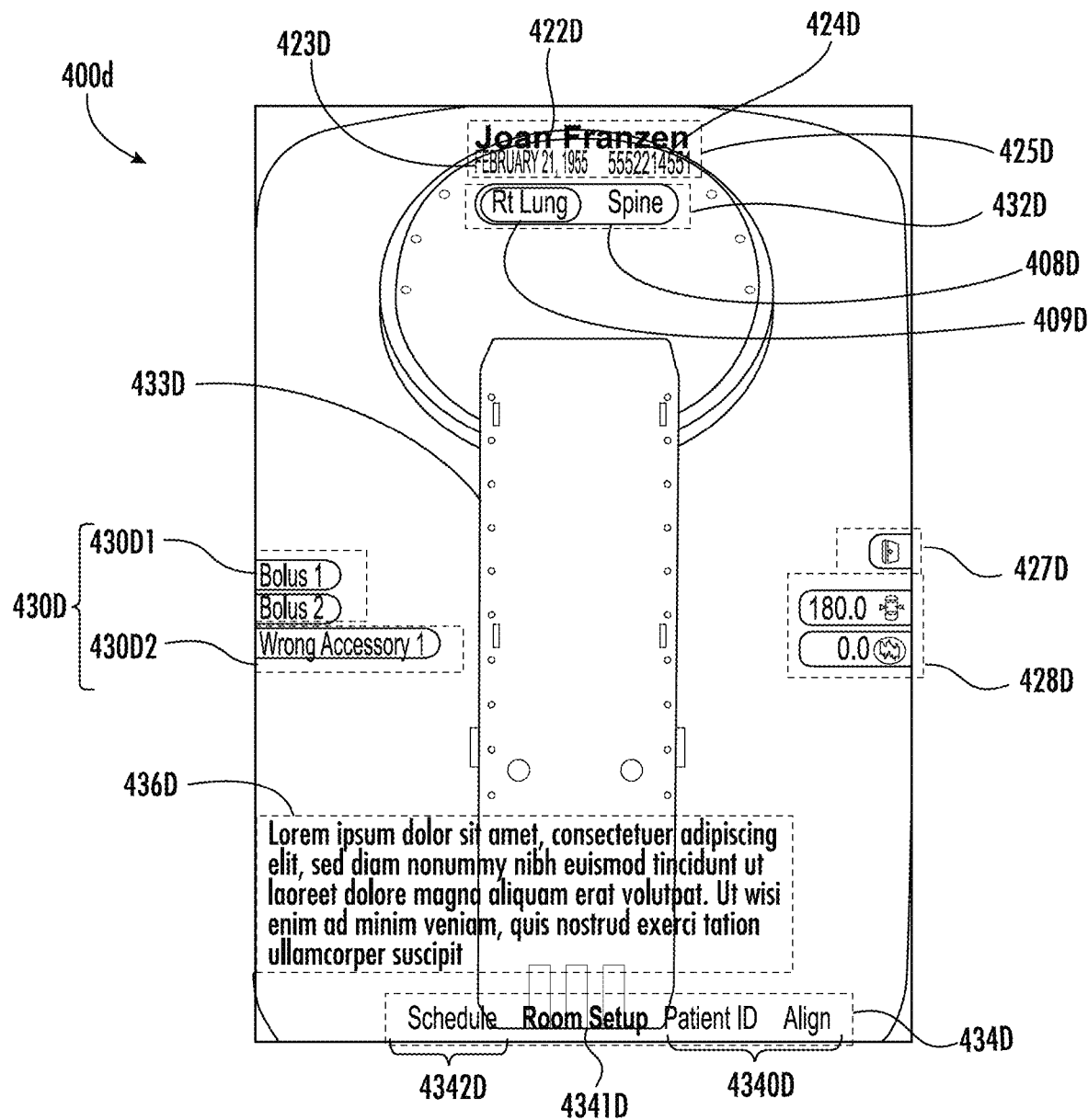

In a non-limiting example, the analytics server receives a live feed of the couch from a camera placed on the gantry (or other position such as the cluster of cameras placed within the ceiling and/or walls of the treatment room). The analytics server continuously/periodically scans the live feed to identify information related to the information being displayed on the page. For example, the analytics server may display graphical indicators corresponding to required and/or detected accessories on the Patient Alignment page (e.g., Stage Four, as indicated by FIGS. 4L-4M). Further, the analytics server may display graphical indicators corresponding to amounts and/or directions of adjustments to be performed by the technician/clinician on the patient (e.g., making sure the patient's arms are in the right place such that the exposure of the radiation to non-intended parts of the body is limited). Based on the information on the page, the accessories and adjustments to the patient's body may be made before the radiotherapy treatment begins.

Figure 7B:
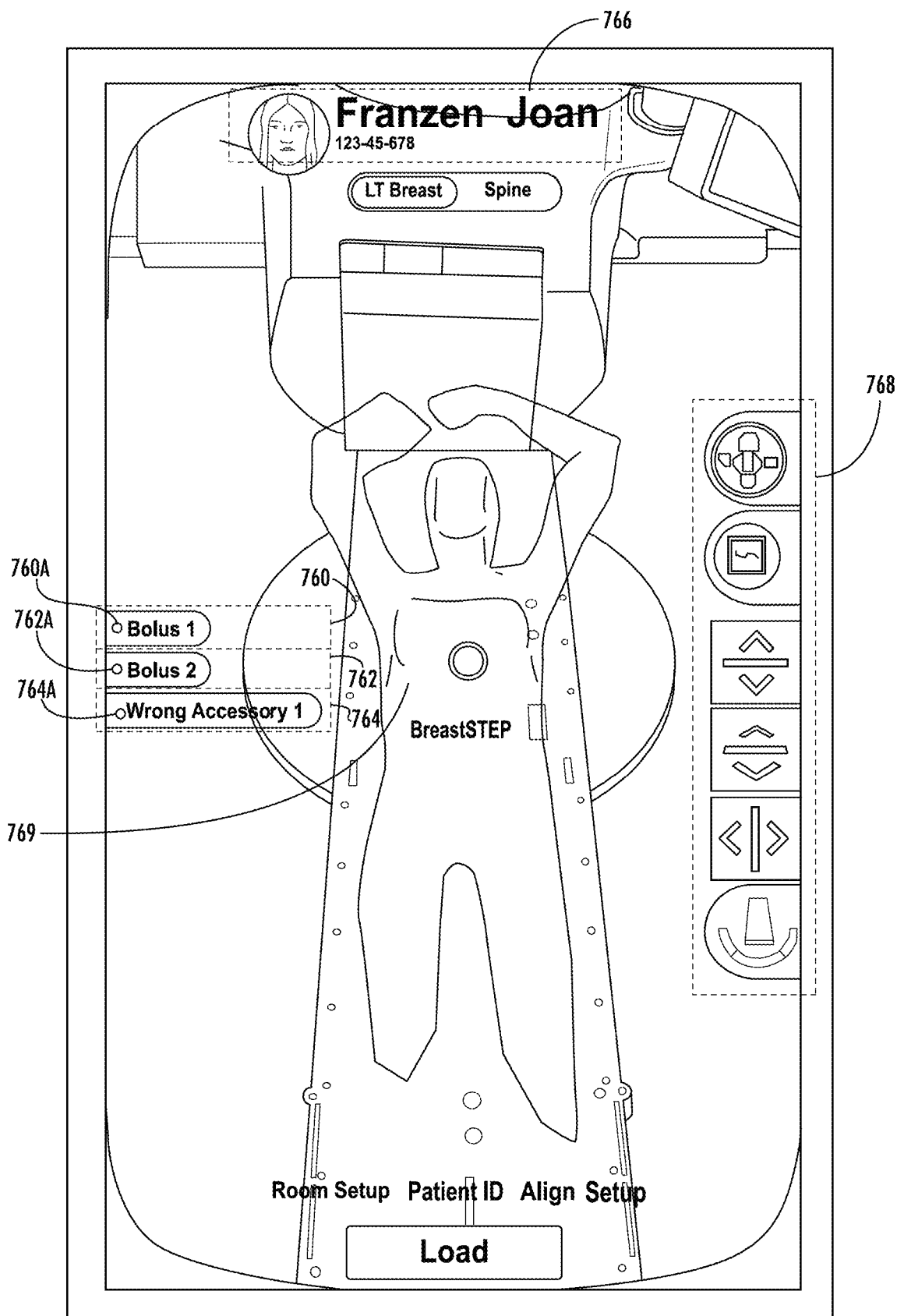
FIGS. 7B-7C illustrate pages displayed in a workflow-oriented radiotherapy system, according to an embodiment.
Figure 7C:
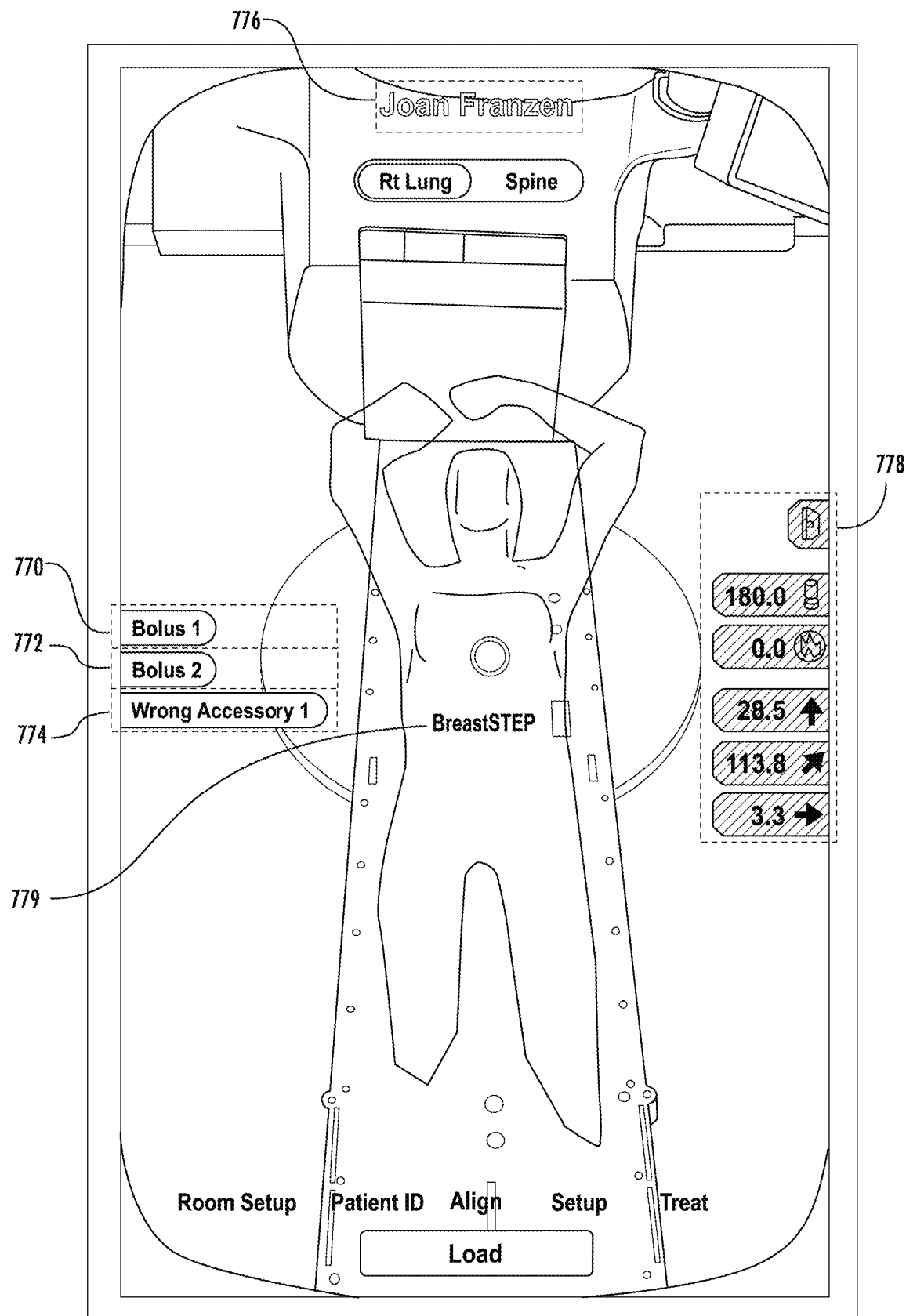

As discussed with respect to FIGS. 7A-7C, the analytics server may use radio-frequency identification (RFID) technology, in addition to other technology, to identify the locations of one or more accessories within a predetermined proximity to the radiotherapy machine. In addition, or alternatively, the system may use any known identification technology to identify locations of one or more accessories within a predetermined proximity to the radiotherapy machine, such as but not limited to QR tags, image reconstruction, segmentation, trained AI/machine learning algorithms, bar codes, Bluetooth, Bluetooth low energy, etc. The analytics server may be in communication with one or more nearby RFID readers, which can in turn communicate with one or more RFID tags placed onto each accessory devices. In a non-limiting example, the analytics server queries/activates an RFID reader placed on the couch. As a result, the RFID reader communicates with all RFID tags within the RFID reader's range and transmits RFID tag numbers/identifiers to the analytics server. The analytics server then queries a data table to identify an accessory associated with each received RFID number to identify the corresponding accessory.

The proximity, as used herein may indicate an amount of distance away from the radiotherapy machine or an exact location on the couch, in the room, or any other predetermined location (e.g., indicated by the user and/or a system administrator).

The analytics server may have a threshold that determines how many flags must be obtained before moving to the next stage. In one embodiment, the analytics server may require only a subset of the flags to progress to the next stage. However, the analytics server could alternatively require all flags before moving to the next stage. For example, in the event that the flag threshold to progress to the next stage is two flags, then the singular flag would not be enough to progress the stage to any subsequent stages. Subsequently, the GUI would continue displaying the current stage until the user addresses the other task on the page (e.g., adjusting the patient for a satisfactory position for treatment).

In some embodiments, the analytics server may continue periodically/continuously query the RFID reader to determine whether the accessories (or predetermined number of accessories) are still within the predetermined proximity to the radiotherapy machine. In the event the accessories are moved out of the predetermined proximity, the analytics server may remove the raised flag or other indicator associated with the completion of the accessory task.

The analytics server may track the movement of the patient using any suitable tracking mechanism and determine, based on the tracked movement, that the patient's position is satisfactory for treatment. For instance, the analytics server may use time of flight generated point cloud or structured light technology to obtain object information. In other examples, the analytics server may use Simple Online Real-Time Tracking (SORT) technology to track the patient's movement. More specifically, the analytics server may perform object detection to determine what an object is and where the object is within a frame of live data. A frame can be considered a window of live video data for a fixed duration of time. In a non-limiting example, object detection may be performed by the analytics server dividing the frame into regions and creating boundary boxes around the objects within each region.

In some instances, the analytics server may apply boundary boxes to objects using a computer model (e.g., an object recognition neural network trained to detect objects). In some instances, the analytics server may apply classification approaches to determine the boundary boxes by utilizing Support Vector Machines, K-means clustering, and the like. Each boundary box around the object may have an associated class and a probability of that boundary box belonging to the class (e.g., whether the object in the frame corresponds to trained classes of objects such as a portion of the couch, a portion of the accessory, or a portion of the patient). The objects in each of the boundary boxes in the regions comprise a total object. For instance, a finger may be classified in one boundary box of a region, where the finger is associated with the patient's finger because the finger belongs to the class of the patient.

The analytics server propagates the detected object from the current frame to a subsequent frame. Specifically, the analytics server may apply the Kalman Filter to estimate the next position of the boundary boxes and/or object based on the boundary box and/or object estimated velocity and position within the current frame. The analytics server may compare the estimated positions of the boundary box and/or object to the actual location of the boundary box and/or object in the latest frame. The estimated prediction of the boundary box and/or object can be optimized using, for instance, the intersection over union metric to measure the accuracy of estimated boundary box and/or object. The intersection over union metric considers the area of overlap between the estimated boundary box and/or object and actual boundary box and/or object and the area of union of the estimated boundary box and/or object and actual boundary box and/or object.

The objects may be labeled with identifiers. Identifiers can be used to distinguish between the objects and/or classes. For example, a patient may be labeled with a certain identifier to distinguish the patient from the user. Similarly, the user may be labeled with a certain identifier. In an example, the analytics server may determine to create an identifier to be tracked in the event that the predicted area of overlap (with respect to the estimated boundary box and/or object and actual boundary box and/or object) is less than a predetermined acceptable intersection over union metric. In some cases, the identifiers of the object correspond with the class.

The analytics server may determine that the patient is in a satisfactory position for treatment by comparing a position of patient in a frame from the live stream of data to frames in a stored acceptable position of a patient. The analytics server may determine that the position of the patient from the live stream of data is acceptable when the position of the patient is within a predetermined margin of error from a stored satisfactory position for treatment. When the analytics server determines that the patient is in an acceptable position (or within the predetermined acceptable margin of error), the server may raise a flag (and/or receive a flag as an input) or other notification of the acceptable position.

The server may continuously monitor the patient to track any further movement because the patient may move into an unsatisfactory position (e.g., out of the acceptable margin of error) over time. In the event the patient moves to an unsatisfactory position, (or exceeds one or more thresholds that take into the patient breathing) if the analytics server is still displaying the Patient Alignment stage (as shown in FIGS. 4L-4M), the flag that was raised that indicated the patient's acceptable position will be removed and the patient will have to get into an acceptable position again. The analytics server may display an alert such that the user is notified that the patient is not in an acceptable position for treatment. Such flagging may also be used to stop the treatment delivery or even be used to guide an auto-correction of the patient position.

The analytics server may communicate with one or more cameras to capture the position of the patient. In some instances, the captured position of the patient may be two-dimensional (e.g., an image) or three-dimensional (e.g., a model). In some instances, the captured image of the patient in a satisfactory position for treatment may be converted into a three-dimensional model. In other instances, the server may retrieve a three-dimensional model, three-dimensional image, or two-dimensional image stored in memory of the analytics server, from a database, or contained within the RT file. The analytics server may label and/or identify the captured position of the patient in the satisfactory position for treatment according to an identifier (e.g., a reference satisfactory position image and/or model). The reference satisfactory position image and/or model may be used as a reference image and/or model.

The analytics server may communicate with one or more cameras to capture subsequent images of the position of the patient. The captured position of the patient may be received by the analytics server as a series of two-dimensional continuous timeframes (e.g., subsequent images). In an example, the analytics server may execute photogrammetry to extract three-dimensional measurements from the captured two-dimensional subsequent images. The scale of the subsequent images may be determined, for instance by measuring various distance of the patient (e.g., length of arms, length of legs, length of a limb, position of a joint such as a knee or elbow) and associating the measured distances of the gantry and/or couch with an image of patient (e.g., the subsequent images), the analytics server may determine the current position of the patient using the distances measured and the subsequent images.

Additionally, or alternatively, the analytics server may use triangulation to generate a three-dimensional model of the patient based on images from various perspectives (e.g., the one or more cameras in the treatment room). As an example, the analytics server may associate a two-dimensional pixel in the subsequent images with a ray in three-dimensional space. Given multiple perspectives of the image (e.g., at least two set of subsequent images capture the position of the patient from at least two different perspectives), a three-dimensional point can be obtained as the intersection of at least two rays from pixels of the subsequent images.

The analytics server may determine that the rays from the subsequent images are associated with consistent pixels. For instance, a pixel from a first perspective of an image, mapped to a three-dimensional point using a ray based on the first perspective of the image, is consistent with a pixel from a second perspective of an image mapped to the same three-dimensional point using a ray from the second perspective of the image. The analytics server may determine from the consistency functions, whether the pixels used to determine the three-dimensional point are similar colors, whether the pixels used to determine the three-dimensional point are similar textures the textures, and the like.

The analytics server may compare the subsequent images or generated three-dimensional model to the reference image and/or model. For example, the analytics server may determine a position vector based on the comparison of the subsequent image or generated three-dimensional model and the reference image and/or model, indicating the difference in position of the gantry, couch, and/or patient in the subsequent image or generated three-dimensional model to the compared reference image and/or model.

The analytics server may present on the GUI the content associated with the position vector to the user and/or patient. For example, the GUI may present a numerical and/or graphical representation of the magnitude and direction of the position vector. For example, the direction of the position vector may indicate the adjustments that the patient should be moved using directions such as up, down, left, right to return the patient to the satisfactory position for treatment. The magnitude of the position vector may indicate the extent of the difference between the subsequent images or generated three-dimensional model and the compared reference image and/or model to return the patient to the satisfactory position for treatment. In another example, the analytics server may display graphical indicators to convey the direction (e.g., arrows represented by the graphical indicators). Additionally, or alternatively, the analytics server may display the extent of difference between the subsequent image captured and the compared reference image using colors. For instance the color red may indicate a difference greater than 10 mm, the color orange may indicate a difference between the subsequent image and reference image from 5-10 mm, and the color grey may indicate a difference between the subsequent image and reference image from 0-5 mm. The colors and associated differences between the subsequent image and reference image may be determined by a user and/or system administrator.

The analytics server might employ the described methods herein to determine satisfactory positions for treatment of the couch and/or gantry. However, the analytics server's monitoring of the patient's position when loaded onto the couch is not limited to the methods and systems described herein. The analytics server may use other image recognition protocols to identify whether the patient's position is consistent with the alignment data indicated by the reference surface and/or image (e.g., is the patient aligned with the predetermined angles optimizing the patient's position to receive radiation treatment).

In the event that the analytics server receives an input generated by the user, the analytics server may determine whether one or more flags representing one or more completed tasks satisfy a flag threshold. If the analytics server determines that the predetermined portion of tasks have been completed (e.g., the flags generated by the analytics server exceeds and/or meets the flag threshold), then the analytics server may transition the displayed first page associated with information related to a particular stage of the workflow to a second page containing information related to the subsequent stage of the workflow. If the analytics server determines that the predetermined portion of tasks have not been completed (e.g., the flags generated by the analytics server does not exceed and/or meet the flag threshold), then the analytics server may conditionally transition the displayed first page associated with information related to a particular stage of the workflow to a second page containing information related to the subsequent stage of the workflow.

The analytics server may conditionally transition such that preceding or succeeding pages may be displayed, but the analytics server may refrain from registering any tasks on the preceding or succeeding pages. For instance, the tasks completed on the second page may not be registered by the analytics server until the tasks on the first page are completed.

Additionally, or alternatively, in the event the analytics server receives an input to transition the second page to a third page, the analytics server will conditionally transition to the third stage. For instance, the analytics server displays the content associated with the third page but does not register the completion of any tasks associated with the third page. In some circumstances, the third page is related to the second page (e.g., a page that provides more details about the second page). In other circumstances, the third page is associated with a third stage of the workflow (e.g., the user is able to view the workflow tasks associated with the third page displayed by the analytics server).

The analytics server may display a graphical indicator and/or text indicating that the pages displayed have been conditionally transitioned. For instance, the graphical indicator may indicate that the user is viewing the pages in a "view only" mode, thereby limiting the tasks recognized by the analytics server. For example, a graphical indicator may appear on a page informing that the user that any tasks performed by the user in response to the displayed tasks on the page may not be registered by the analytics server. The analytics server may also display the conditionally transitioned pages such that the pages appear visibly distinct. For example, the page that the server has conditionally transitioned to may appear faded with less contrast, brightness, or color.

Additionally, or alternatively, if the analytics server determines that the predetermined portion of tasks have not been completed (e.g., the flags generated by the analytics server does not exceed and/or meet the flag threshold), then the analytics server may deny the user from transitioning to a subsequent page associated with a next stage in the workflow. Additionally, or alternatively, the analytics server may determine not to transition from the first page (showing the first page) to the second page (showing the second page) based on an input received from an additional user and/or third party (including a system administrator or supervisor). For instance, a user and/or third party viewing the page displayed by the analytics server may effectively "pause" a user in the treatment room from progressing to a subsequent page associated with a next stage in the workflow. The "pause" of the workflow may be for a predetermined period of time or until the analytics server receives additional one or more inputs from the same user and/or third party (or a different user and/or third party). The "pause" of the workflow for the predetermined period of time may be determined by a user and/or system administrator. The user, system administrator, supervisor or the like may "un-pause" the "paused" workflow progression (even in the event the "pause" of the workflow is for a predetermined period of time) by inputting one or more inputs to the analytics server.

Additionally, or alternatively, the analytics server may transition to a second page associated with the next stage in the workflow even if the analytics server has determined that the predetermined portion of tasks have not been completed (e.g., by comparing the one or more received flags generated upon the completion of the one or more tasks to the flag threshold). In the event the analytics server transitions to the second page associated with the next stage in the workflow even though the analytics server has determined that the predetermined portion of tasks have not been completed, the analytics server may display an indication that the predetermined portion of tasks from the first page have not been completed. The indication may be visually distinguishable from the content on the page. For instance, the indication may have contrasting colors from the content, different shapes than those used in the content, different borders than those used in the content, contrasting shine or translucence from the content, contrasting texture from the content, contrasting pattern from the content, and the like.

In one embodiment, another user or GUI (e.g., GUI displayed on a console) can receive an input to halt progress on another GUI (e.g., GUI displayed in a treatment room). In response to receiving an input generated by the user in the treatment room, a user outside of the treatment room, a system administrator or other third party, the analytics server displays an alert on the GUI that one or more tasks have not been completed on the first page. For instance, the GUIs displaying different stages of the workflow for the console monitors cannot progress to the next stage until one or tasks within the treatment room are completed.

FIG. 4B illustrates seven stages of workflow to be performed in a treatment room for a successful execution of treating a patient with radiation using a radiotherapy machine, in accordance to an embodiment. Although seven stages are shown, it is intended that the workflow can comprise any number of stages and/or sub-stages. The method 400b describes the workflow stages of performing radiotherapy on a patient displayed on a GUI by a server, such as the analytics server described in FIG. 1A. The workflow stages displayed by the analytics server are displayed on various interactive workflow-oriented series of pages configured to display the various stages. Even though the method 400b is described as being executed by the analytics server, the method 400b can be executed by any server(s) and/or performed locally using a computer/processor associated with the radiotherapy machine and/or the console. Other configurations of the method 400b may comprise additional or alternative stages, or may omit and/or mix one or more stages altogether. Further, each of the seven stages of workflow represented in method 400b may be standalone stages displayed by the analytics server on standalone pages.

Figure 4E:
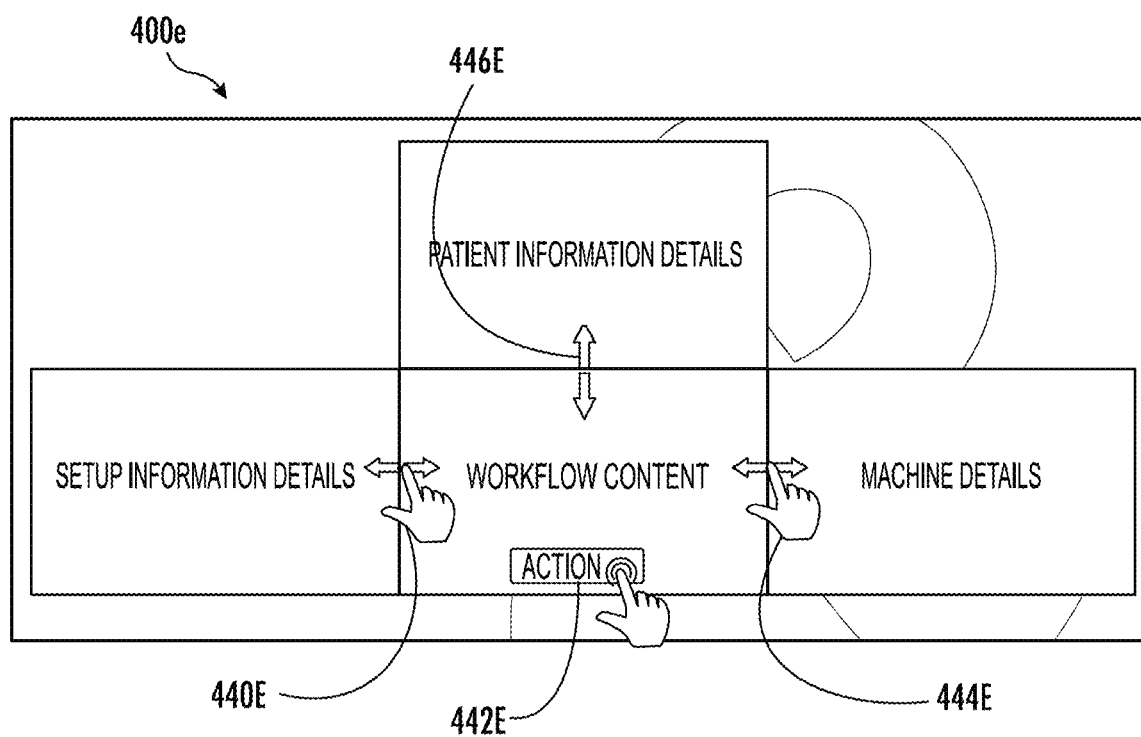
Figure 4G:
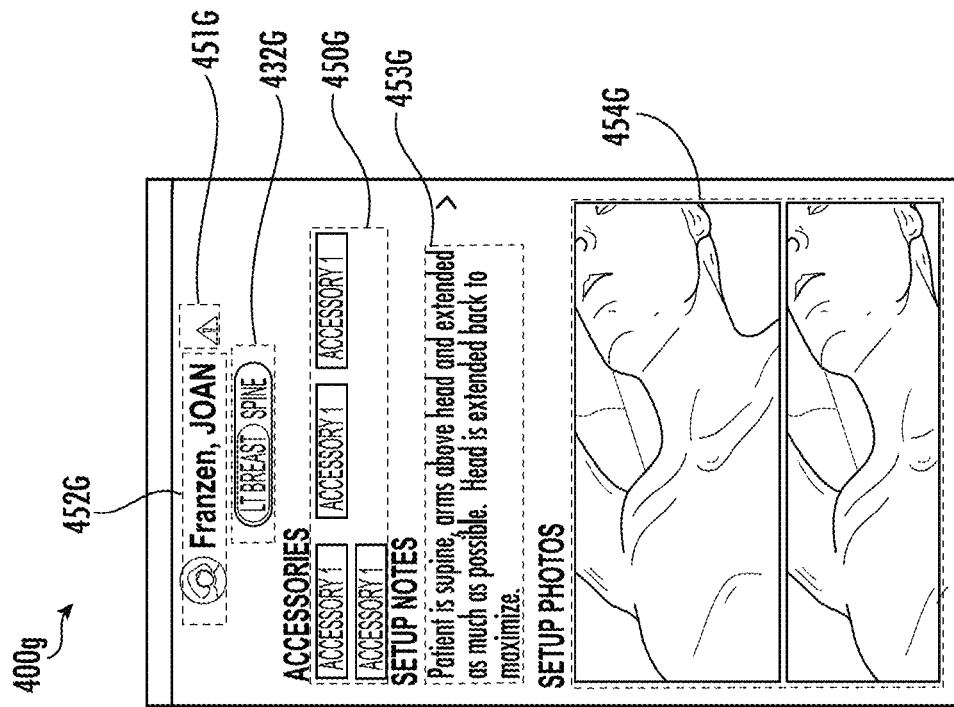
Figure 4F:
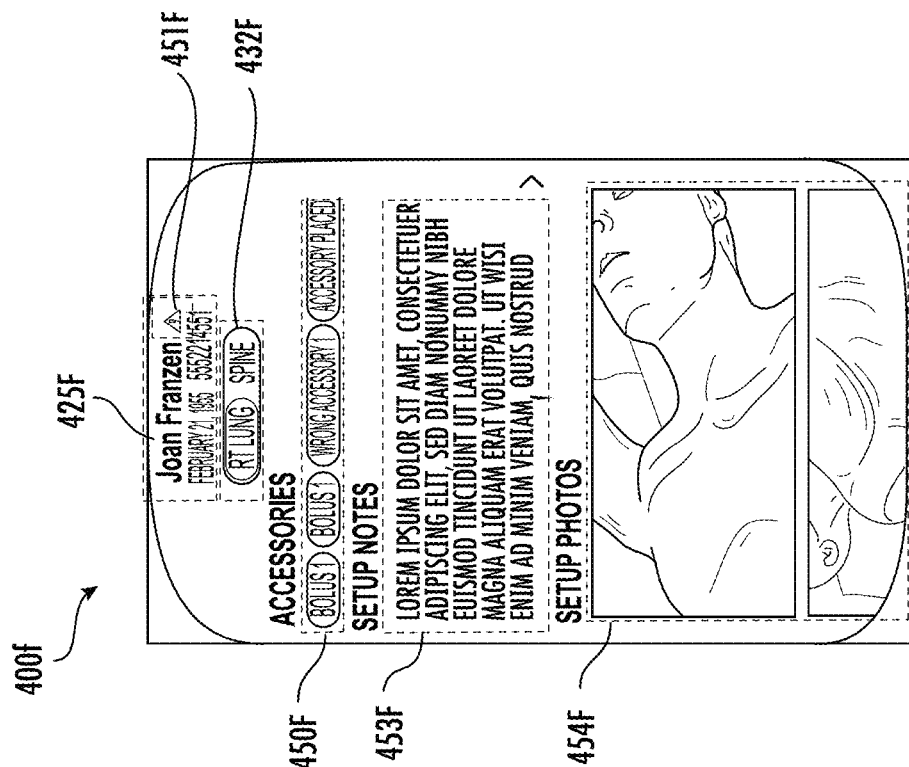
Figure 4H:
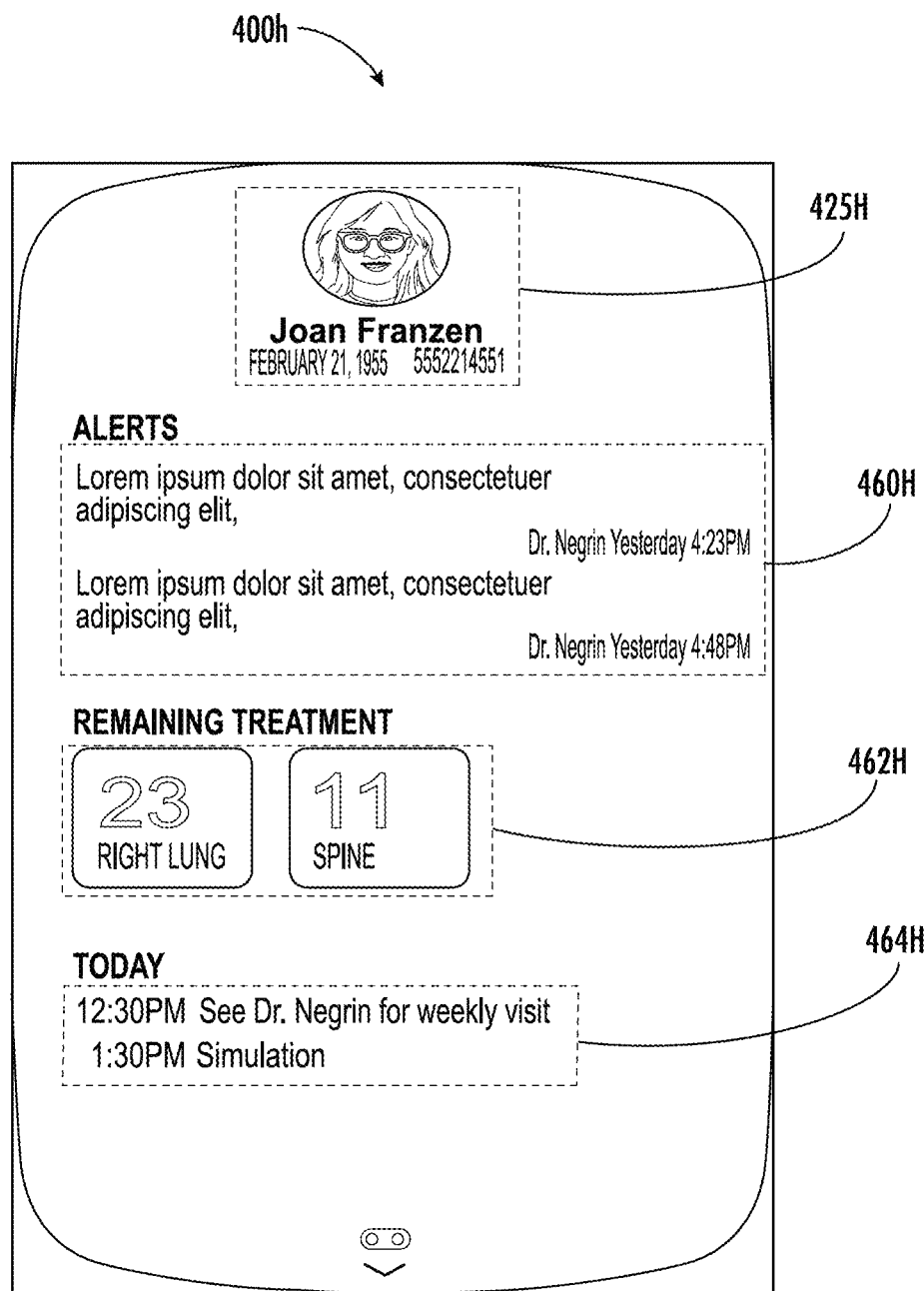
Figure 4I:
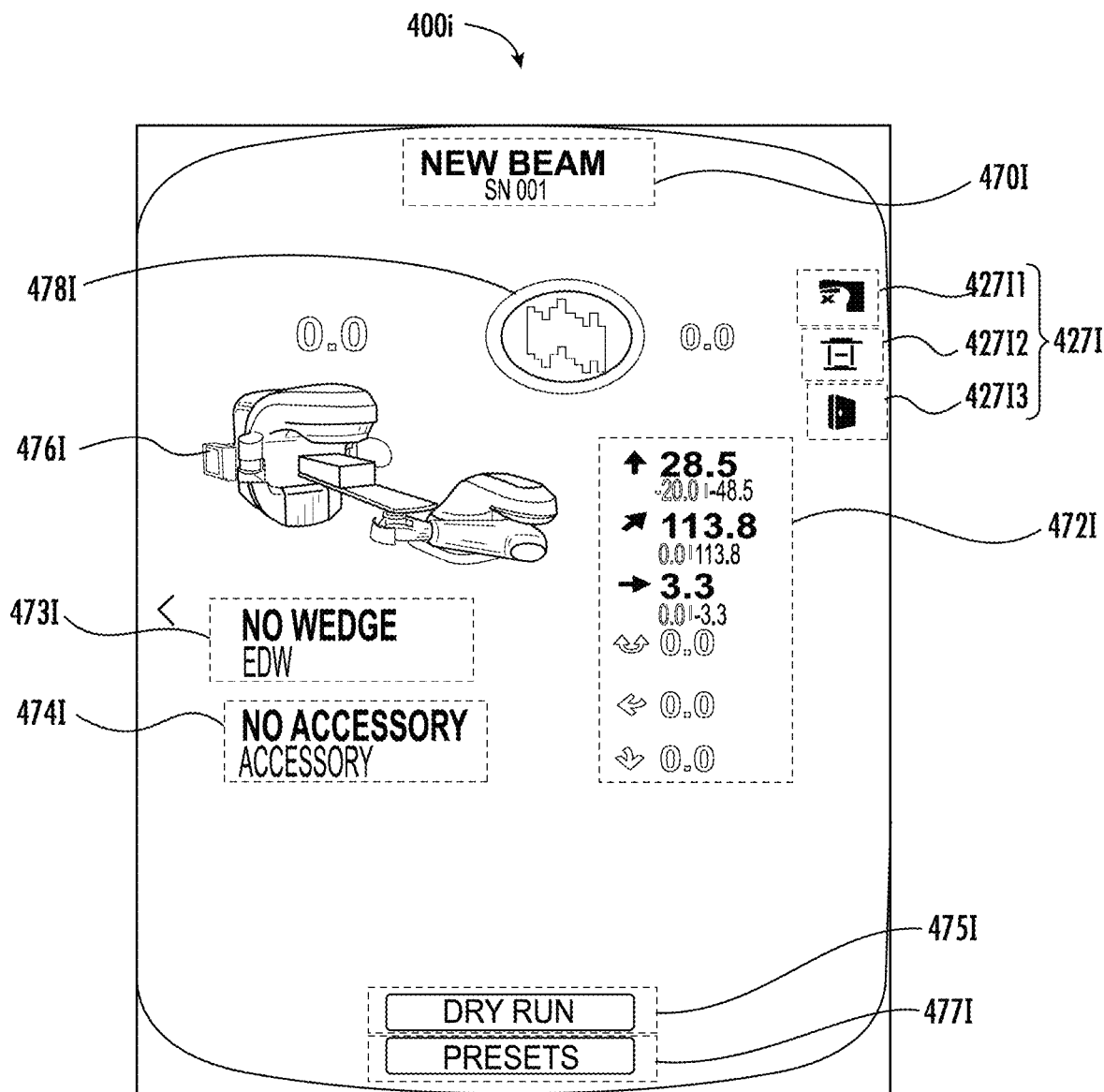
Figure 4J:
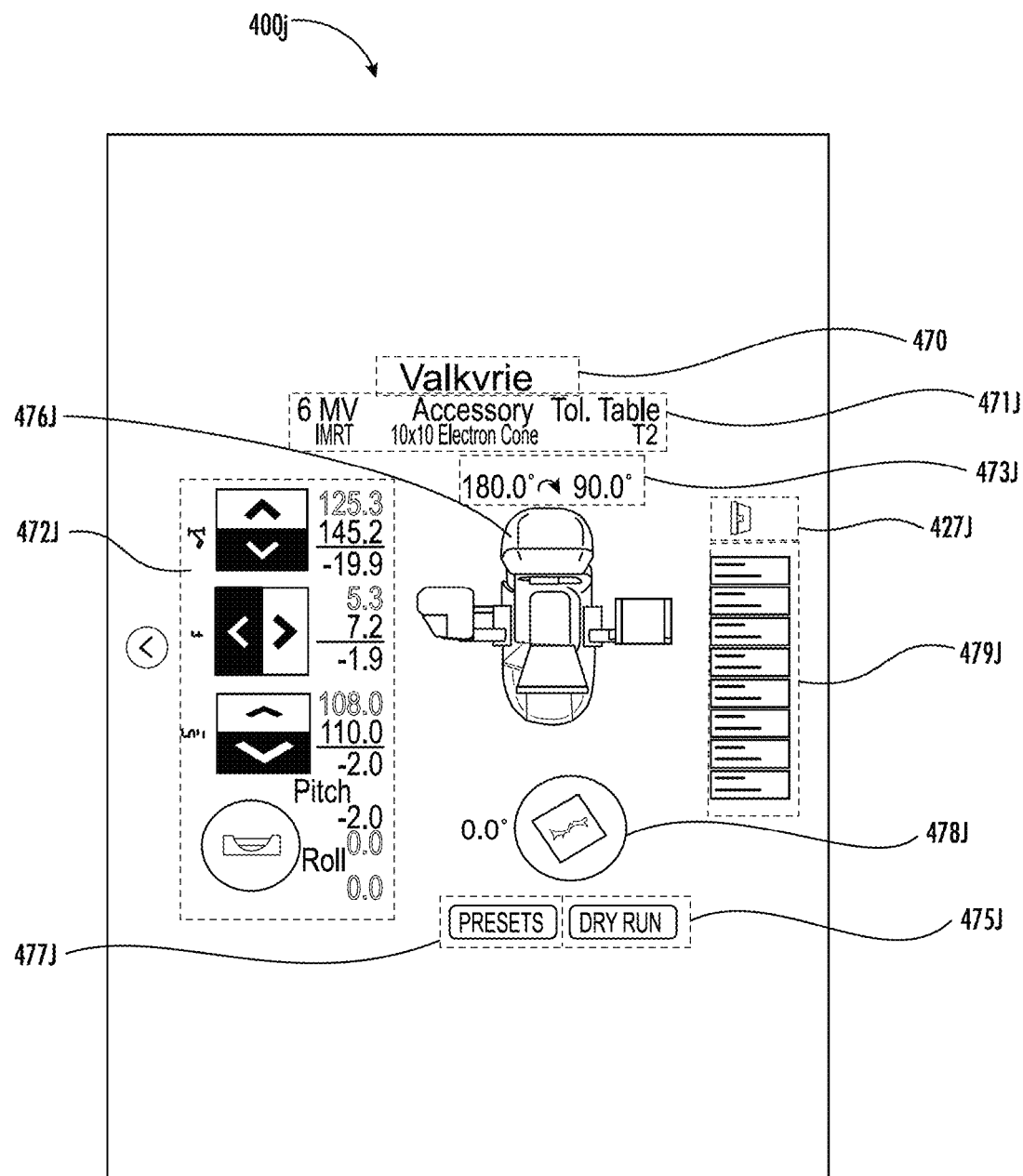
Figure 4K:
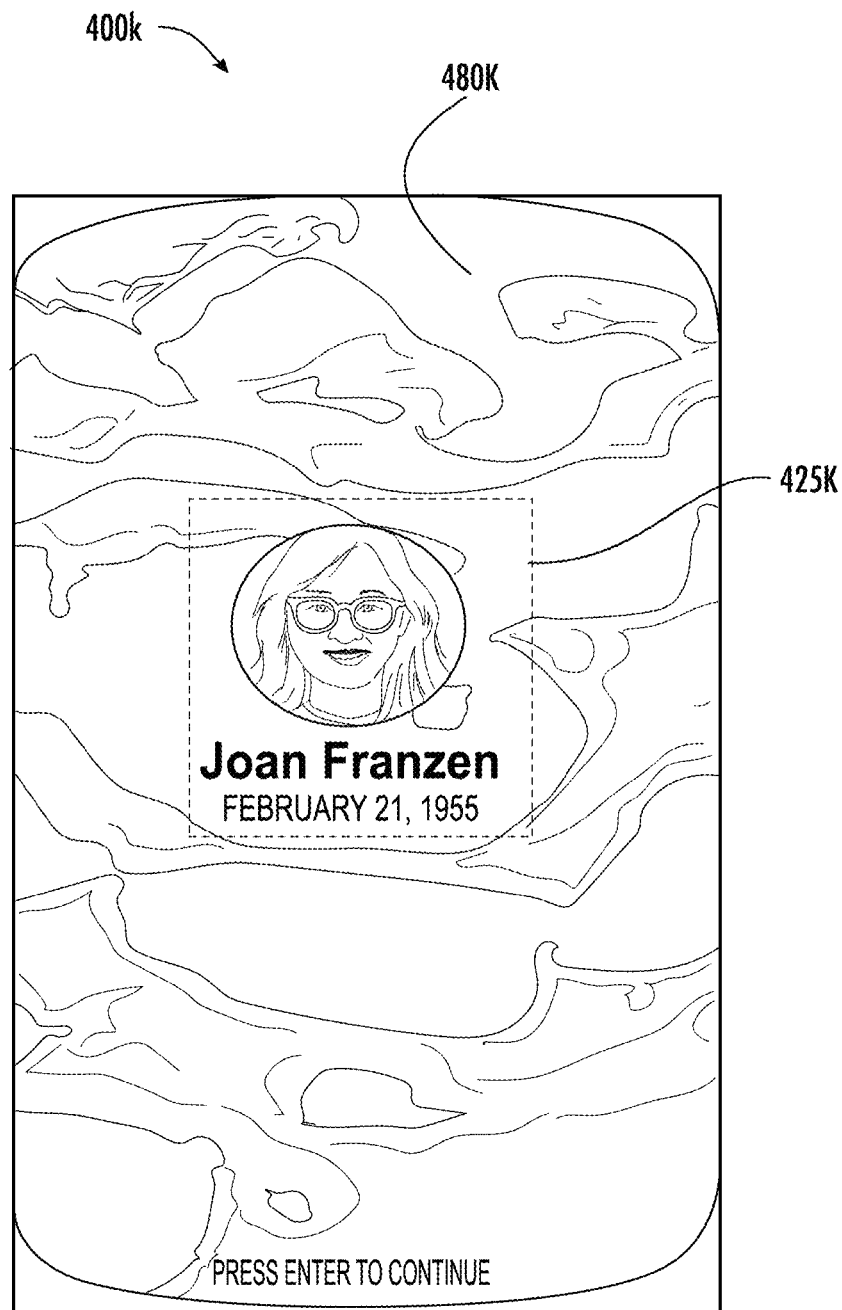
Figure 4L:
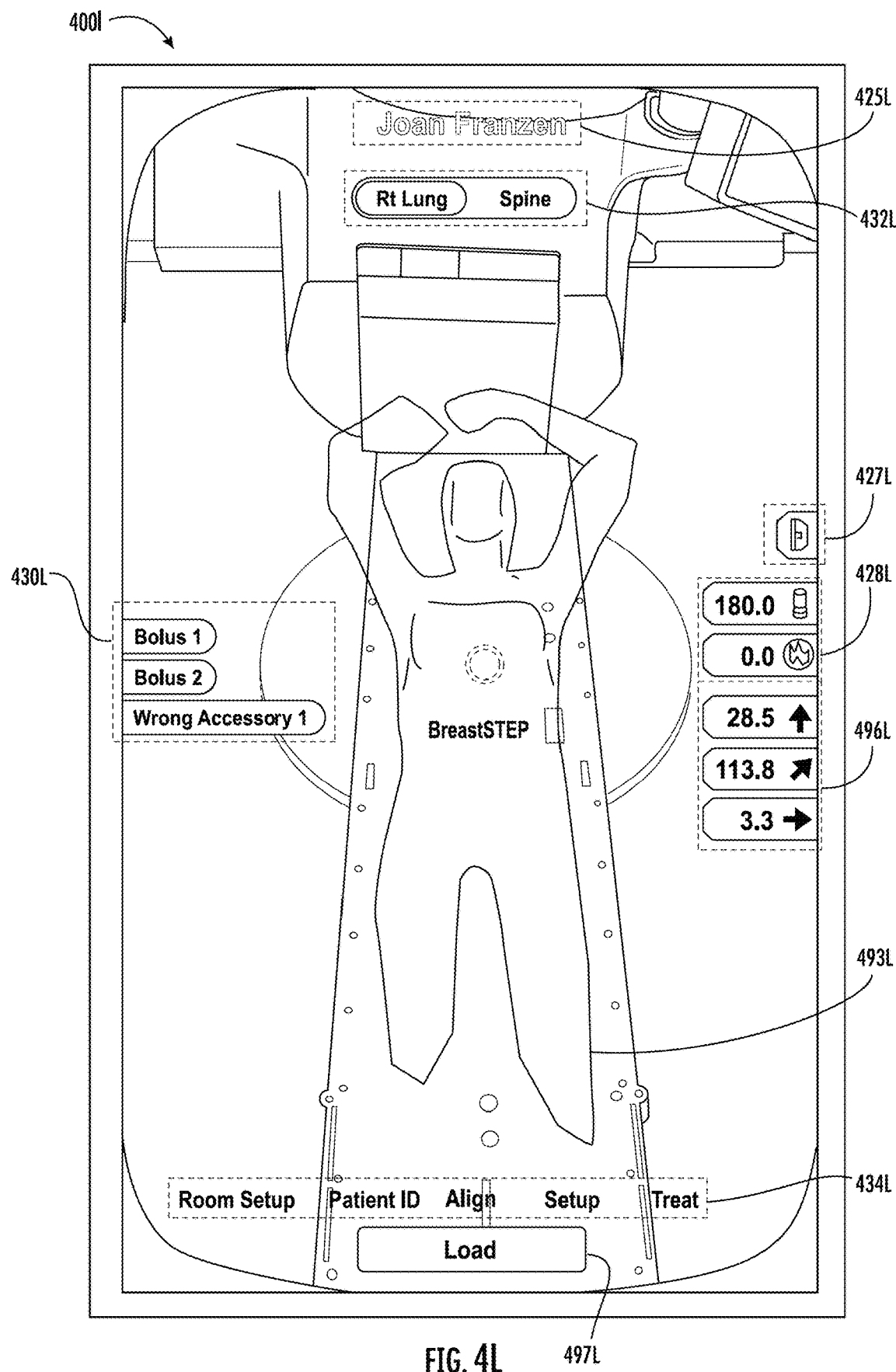
Figure 4M:
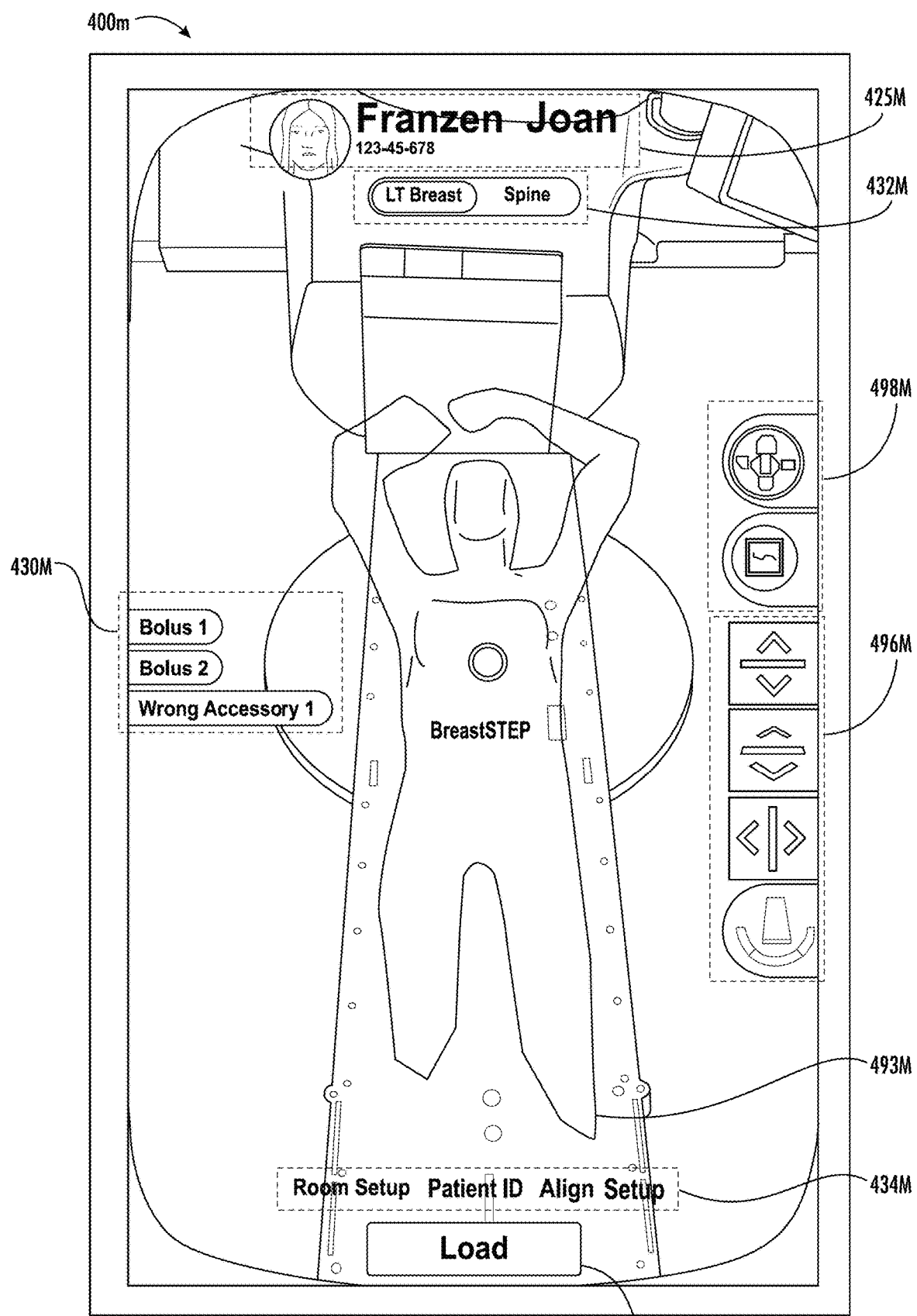
Figure 4N:
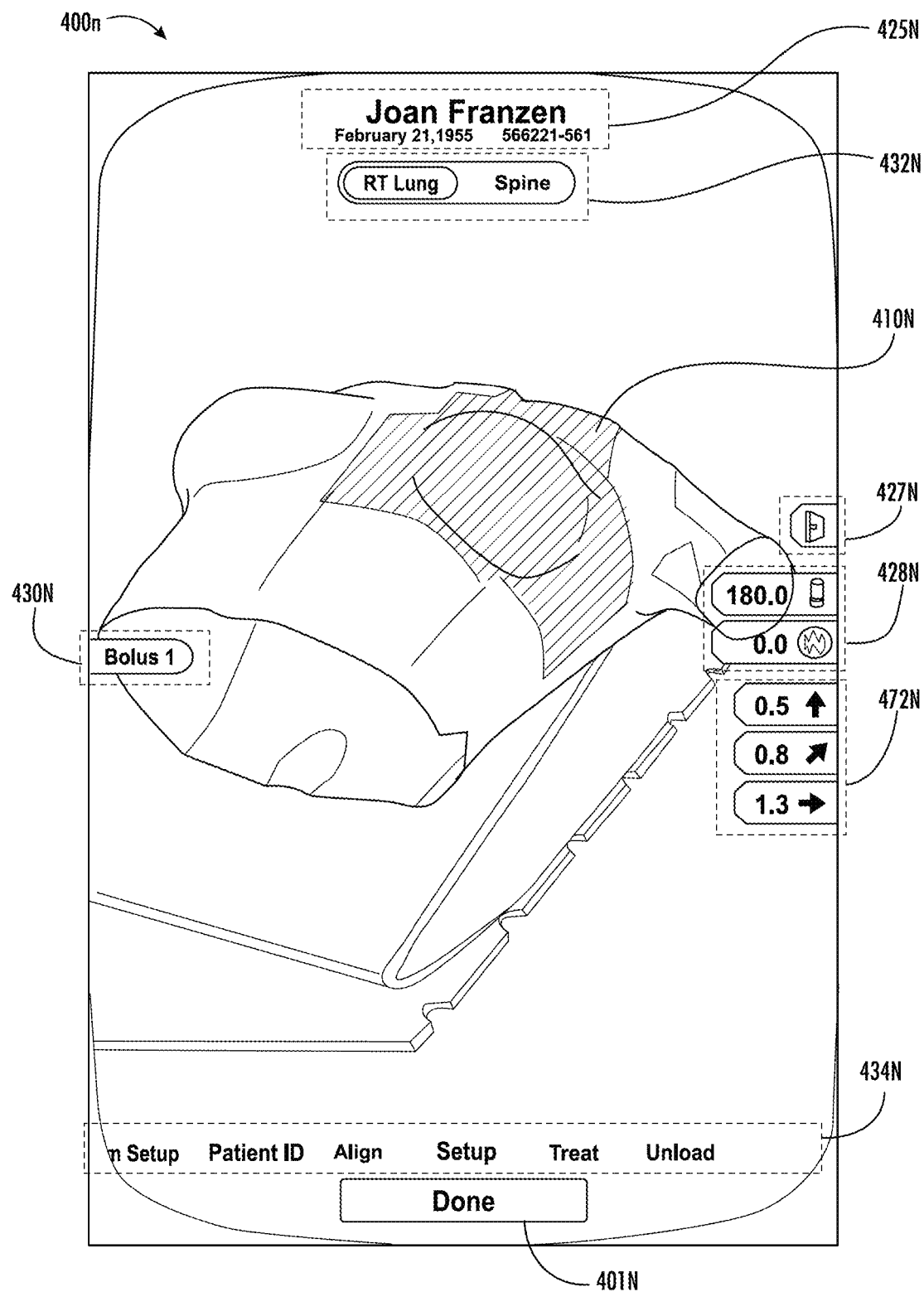
Figure 4O:
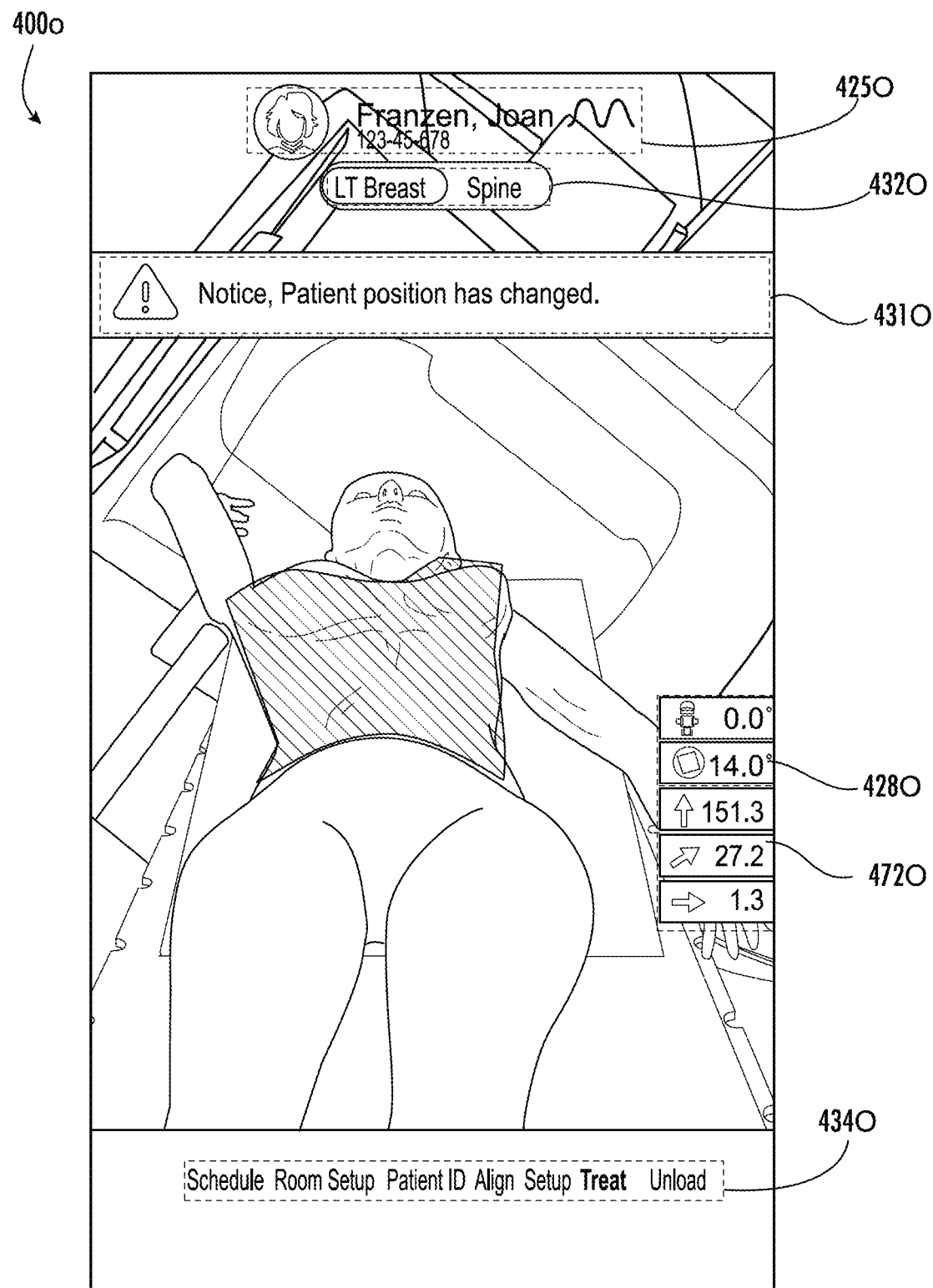
Figure 4P:
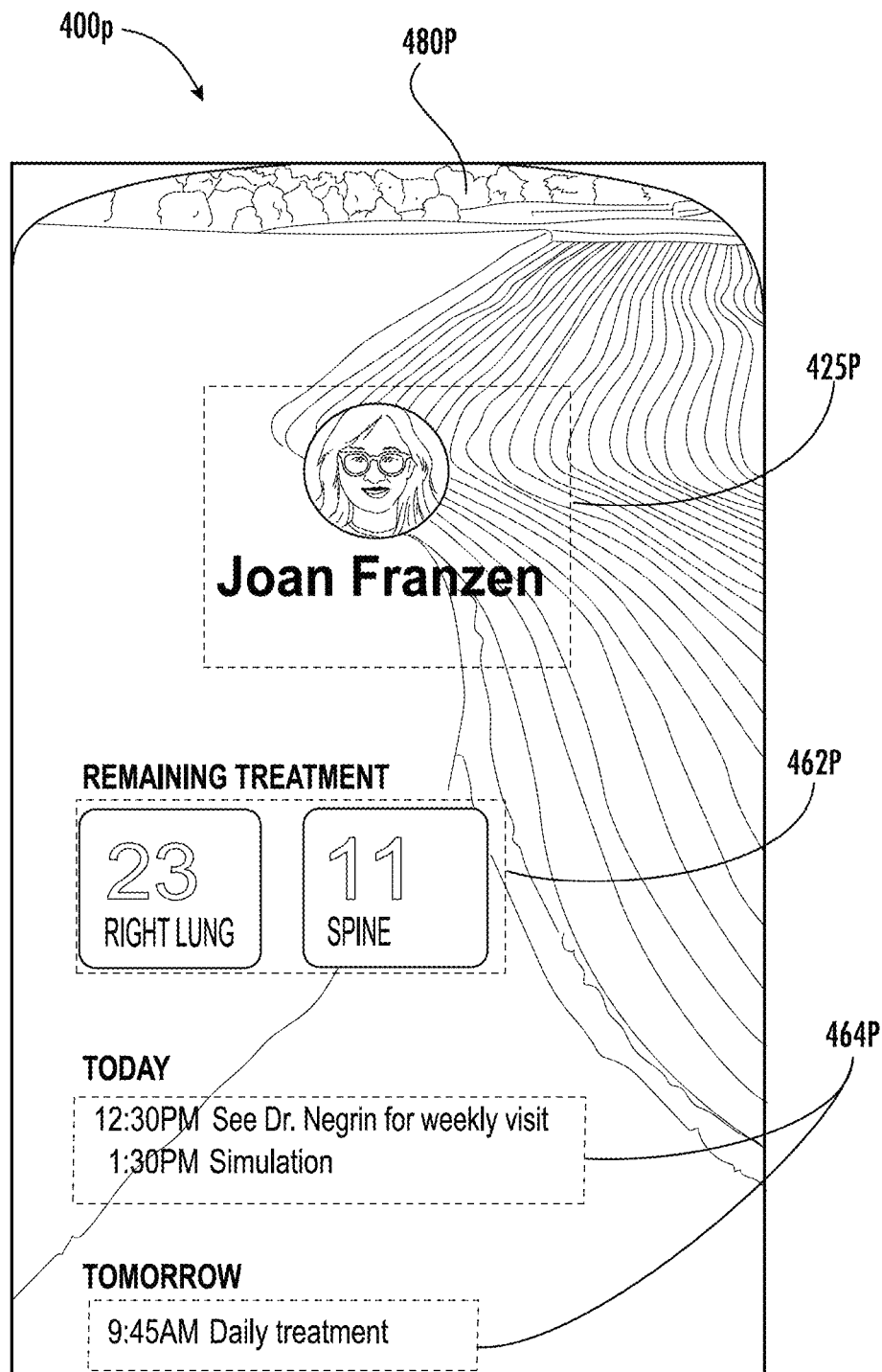

In describing the various stages of workflow, references is also made to FIGS. 4C-4P, non-limiting examples of the analytics server displaying pages of a GUI based on a user's progression through the stages of the workflow. Even though FIGS. 4C-4P illustrate a progression in sequential pages, in some configurations the analytics server may display the depicted pages in another order. Moreover, the analytics server may not display one or more of the pages described herein. The analytics server may display various combinations and configurations of the pages depicted herein. In particular, the pages depicted in FIGS. 4C-4P illustrate one or more pages displayed by the analytics server through a display on a gantry, as described in FIG. 1A. The analytics server may use the methods and systems described herein to display workflow-oriented series of pages (e.g., page 400c-400p in FIGS. 4C-4P respectively) such that a user progresses through the workflow to successfully treat a patient using a radiotherapy machine.

At step 410, the analytics server displays a page on a GUI representing Stage One. In this example, Stage One relates to patient selection. A user using a patient identifier (e.g., name, social security number, other identifier) selects a patient for treatment using the display on the radiotherapy machine. In other embodiments, the analytics server may automatically select a patient according to a schedule. For instance, the analytics server may store the schedule of patients and the associated patient identifiers (or other patient name) for the day, week, month, and the like. The analytics server may retrieve treatment data associated with the selected patient based on the patient identifier from a database, the RT file, the analytics server's memory, and the like.

As will be described below, the console monitors will also provide the users the option to select the patient. However, in some embodiments, when a patient is selected in the treatment room, the analytics server syncs the information displayed on the console monitors, such that they are consistent and correspond to the same patient, or visa-versa.

The analytics server and/or the RT file may associate treatment information with the selected patient. For example, the treatment information associated with the patient may include various patient-preferred and/or treatment-necessitated couch/gantry attributes, such as couch angles, gantry rotation attributes (e.g., full or partial arcs), the number of partial arcs (if applicable), personally identifiable patient information (e.g., name, nickname, birthdate, photos), diagnoses of the patients, notes from one or more doctors regarding the patient and/or the diagnoses of the patient, and medical diagnoses tools (e.g., x-ray scans, including computed tomography ("CT") scans, MM, PET, SPECT, or ultrasound images).

As depicted in FIG. 4C, the analytics server may display a page on a screen, the page indicating information associated with Stage One of the workflow. The analytics server may display Stage One of the workflow on the page before a patient arrives at the treatment room and/or clinic.

The page 400c (Stage One, Patient Selection) displayed in FIG. 4C illustrates an initial page displayed by the analytics server on a screen. The analytics server may display text 420C indicating the patients scheduled to be treated using a particular radiotherapy machine. The schedule of patients to be treated using a particular radiotherapy machine displayed by the analytics server may include the patient's name associated with a time. In some instances, the time may be the time the patient is expected to arrive at the clinic (or other treatment area). In other instances, the time may be the time the patient is expected to begin treatment (e.g., the patient enters a treatment room). In some instances, the time may be the time the patient is expected to check-in at a waiting area (e.g., the user may begin prepping a treatment room). In some instances, the analytics server may display a wait time, or the time that has elapsed since the patient has checked in. The patient's name may be the patient's full name (or a portion of the full name, such as a last name) and/or a nickname.

The analytics server displays text 413C, conveying (and in some instances emphasizing) the patient scheduled for upcoming treatment. The text 413C may emphasize the patient scheduled for upcoming treatment by indicating the patient schedule for upcoming treatment with a color different from the colors (if any) from the patient scheduled to be treated using the particular radiotherapy machine. In other circumstances, the emphasis of the patient scheduled for upcoming treatment may be indicated by containing the patient scheduled for upcoming treatment within a shape (e.g., within a rectangle or circle or the like). The shape may be a different shape than shapes containing each of the other patients scheduled to be treated using the particular radiotherapy machine. In an example, the shape may indicate that the patient is present (e.g., in the waiting room).

Additionally, or alternatively, the patients scheduled to be treated using the particular radiotherapy machine may not be contained in any shape. In other circumstances, the emphasis of the patient scheduled for upcoming treatment may be indicated by bordering the patient scheduled for upcoming treatment within a particular border (e.g., a dashed line). The patients scheduled to be treated using the particular radiotherapy machine may be indicated by a border different than the border used to indicate the patient scheduled for upcoming treatment (e.g., no border, a solid border).

The analytics server may display PII using text and/or graphical indicators. The analytics server may display the image 415C depicting an image of the patient scheduled for upcoming treatment. The image of the patient may be used by the user to identify the patient as the patient enters the treatment room. The analytics server may display text 411C indicating an identity of the patient. In some circumstances, the identity of the patient may be patient's name may be the patient's full name (or a portion of the full name, such as a last name) and/or a nickname. Additionally, or alternatively, the analytics server may display 403C indicating a patient identifier. The patient identifier may be used to identify a patient stored in the memory of the analytics server and/or contained within RT file. The patient identifier may also include date of birth, age, gender, or any other PII.

The analytics server may display text 422C indicating the current time. In some circumstances, a digital or analog clock may be displayed by the analytics server to represent the time. The analytics server may display 423C displayed by the analytics server indicates the current date and day of the week. In some circumstances, a calendar (e.g., month view, week view) may be displayed by the analytics server to represent the date and/or day of the week. The analytics server may display non-treatment related image 429C. The non-treatment related image 429C may be any image that is used to create a more astatically pleasing GUI, identify the treatment center, etc. The analytics server may display text 425C indicating one or more areas of the patient requiring treatment.

The analytics server may also display the graphical indicator 424C indicating to the user that a motion management strategy should be employed for the patient in order to mitigate or compensate for the patient's minor movements resulting from the patient's breathing. Such motion mitigation strategies may include, but are not limited to, gating, tracking, breath-hold, deep inspiration breath hold, coached breath hold, etc. The graphical indicator 424C may indicate which motion management strategy is to be employed for the current patient. As will be described below, the analytics server may use the methods and systems described herein to align the patient's target organs (e.g., the organ receiving radiation) with various predetermined angles, such that the treatment is optimized. Moreover, as described herein, the analytics server may align the patient's body using various alignment data. However, the patient's minor movements due to breathing may impede the alignment efforts. Thus a motion management strategy may be required or prescribed.

The analytics server may use various methods to determine whether the patient is causing relevant movement. For instance, the analytics server may use one or more of the cameras described herein to monitor the patient's body (e.g., stomach or chest) to detect movements caused by the patient breathing. The analytics server may display the graphical indicator 424C to inform the user that the analytics server is minimizing or eliminating the effect of the breathing motion on the alignment treated area. For instance, when an analytics server does not employ at least one of the above-described motion management strategies, the analytics server or the operator may be more sensitive to the patient's alignment.

The analytics server may display graphical indicator 427D representing a safety feature associated with the treatment room. Safety features associated with the treatment room can include closing the door of the treatment room before the treatment is commenced, locking the position of the couch in the treatment room, hanging the pendant in the treatment room, and the like. Various graphical indicators (not shown) may be displayed representing safety features associated with the treatment room.

The graphical indicator 427C and/or 427D represent a safety feature that may be displayed by the analytics server in conjunction with a status indicator to convey what the analytics server has identified as the status of the safety feature. For instance, one safety feature may be the door to the treatment room. The graphical indicator representing the door to the treatment room in conjunction with a status indicator may be used to convey to a user that the door is open, closed, locked, and the like. The status indicator may be used to convey the status of the graphical indicator as discussed herein (e.g., with colors, shapes, borders).

In other embodiments, the graphical indicator 427D displayed by the analytics server may represent more than one safety feature associated with the treatment room. For example, graphical indicator 427D may represent that a treatment room has more than one safety feature (e.g., a lock to the treatment room, a lock for couch, a lock for various cabinets in the treatment room, an alert ensuring that the pendant is in a proper position). The status indicator may convey what the analytics server has identified as the status of the one or more safety features. In some instances, the status indicator may convey a binary determination. For example, the status indicator may convey that each of the one or more safety features indicated by graphical indicator 427D are proper or not proper.

The analytics server may display graphical indicator 428C representing machine alignment parameters (e.g., gantry, couch, and/or collimator parameters). The machine alignment parameters may be used, for instance, by a user to evaluate whether the gantry of the machine is aligned. For example, the analytics server may display graphical indicator 428C displaying a machine alignment parameter that indicates the gantry is at a zero position. The user may determine, based on the gantry position displayed via graphical indicator 428C, that the gantry is properly aligned.

Additionally, and/or alternatively, the analytics server displays patient and/or treatment information on a page. The treatment information may include the number of treatments left and a list of the patient's upcoming appointments (e.g., treatment appointments, doctor appointments). The displayed patient information may include PII including, but not limited to, the diagnoses of the patients, the name of the patient, the nickname of the patient, the birthdate of the patient, and one or more photos of the patient. Further, the analytics server may display one or more non-treatment related images. In some circumstances, the non-treatment related images may be selected by the patient based on the patient's preferences. In other circumstances, the non-treatment related image might be selected by a person other than the patient (e.g., the non-treatment related image might be a logo of the center in which the treatment is occurring).

At step 412, the analytics server displays a page on a GUI representing Stage Two. In this example, Stage Two relates to setting up the room based on the selected patient from step 410. In some circumstances, the room is set up before the patient arrives at the treatment room, the clinic where the treatment is being performed, and/or a waiting room. In other circumstances, the room is set up while the patient is in the treatment room, the clinic where the treatment is being performed, and/or a waiting room.

Setting up the room according to step 412 includes at least setting up the accessories and verifying machine parameters. The analytics server may display a graphical indicator (and a status indicator in conjunction with the graphical indicator) to inform the user whether the accessories required for the patient's treatment are within a predetermined proximity to the radiotherapy machine (or a specific location). As discussed in FIGS. 7A-7C, RFID or other technology may be implemented to identify the location of one or more accessories. The analytics server may also simplify displaying the location of the one or more accessories by merely indicating the status of the accessories. For instance, status indicators may be used to represent that the accessory is missing, the accessory is in an incorrect position, or that the accessory is present and placed properly. Further, the analytics server may display machine parameters. The machine parameters may be used by a user to verify that the machine is positioned correctly (e.g., that the gantry is at a zero position or the machine is aligned with the positions specified in the RT file). Additionally, or alternatively, the analytics server may display information relating to an initial couch position (e.g., a position of the couch that facilitates the user laying (or sitting) on the couch.

In some instances, if a user interacts with a pendant (as discussed as described in FIGS. 3A-3B), the analytics server proceeds to Stage Two of the workflow (e.g., Room Setup) in FIG. 4 (the page 400d). In other instances, a third party (e.g., a different technician, nurse, doctor) or the user (e.g., walking from the treatment room to a console) may interact with the console (as described in FIGS. 10A-10D) to indicate to the analytics server to proceed to Stage Two of the workflow (e.g., Room Setup) in FIG. 4 (the page 400*d*). Further, in other instances, the analytics server may proceed to Stage Two of the workflow (e.g., Room Setup) shown in FIG. 4D (the page 400*d*) based on a scheduled appointment time (determined by the analytics server, for instance, using the RT file).

As described throughout, the GUIs described as being displayed on the console monitors and the GUIs described as being displayed within the treatment room may be in-sync, such that accessing patient information (e.g., opening a patient file) in the treatment room ensures that data displayed on the console monitor is updated accordingly, and vice versa. This method also prevents opening of different (and sometimes incompatible) files at different locations.

The background 433D of the page 400*d* is a view of the couch. The analytics server may display a live view of the couch using a three-dimensional representation (e.g., animation) of the couch. Additionally, or alternatively, the analytics server may display a live feed view of the couch based on a received live stream of data from the one or more cameras. As discussed herein, the cameras may be placed on the gantry, at an end of the couch, on the ceiling, or generally within the room comprising the radiotherapy machine (e.g., FIGS. 2A-2F).

The page 400*d* includes a progress indicator 434D. As described herein, the progress indicator displayed on the page 400*d* indicates a progression of the stages. The progress indicator 434D may be displayed on the bottom of the page 400*d* horizontally. The analytics server indicates the current stage of the workflow 4341D (e.g., Stage Two, Room Setup). The current stage of the workflow is emphasized, for example, by the analytics server because the server displays the current stage of the workflow 4341D in a different color (e.g., white) from the other stages of the workflow (e.g., grey). The stages that have been completed 4342D, for example, are displayed in grey by the analytics server, in addition to stages preceding the current stage 4340D.

Display notes 436D displayed by the analytics server describes setup notes associated with the patient scheduled for treatment. The setup notes in the display notes 436D may be a portion of the setup notes (or a summary of setup notes). The setup notes may describe patient preferences, doctor comments, notes from prior treatment sessions, and the like. In the event the user needs more information about the setup notes, the user may navigate to an additional page of the Room Setup stage to consume additional information about room setup (e.g., FIGS. 4E-4G).

The analytics server may use graphical indicator 430D (including 430D1, 430D2) to display accessories necessary for patient treatment (e.g., as described in FIGS. 7A-7C). The analytics server displays the graphical indicators 430D representing the accessories (and the status of the accessories) on the side of the page 400*d* such that the accessories appear in a column. The analytics server may determine the accessories necessary for the patient according to the RT file or other one or more servers, databases, and/or files. Additionally, the analytics server may use status indicators in conjunction with the graphical indicator 430D. The status indicators in conjunction with graphical indicator 430D indicate the accessories necessary for treatment and convey whether the analytics server has located the accessory.

The analytics server may determine the location of the accessory using technology such as RFID technology (e.g., as described in FIGS. 7A-7C), or any other suitable technology as described above. A red status indicator shown in conjunction with the accessory indicated by the graphical indicator 430D2 may indicate that the wrong accessory is within a predetermined proximity from the couch. Additionally, or alternatively, an orange status indicator shown in conjunction with the accessory indicated by the graphical indicator 430D may indicate that Bolus 1 and Bolus 2 may be in an incorrect placement.

When using RFID technology, the analytics server may only detect whether the identified accessory is within a predetermined area (e.g., whether the accessory is present within the field of reception). Therefore, even though the exact location of the accessory may not be identified, the analytics server may determine whether the accessory is present.

The analytics server may display text 425D that describes identifying patient information. The identifying patient information may be derived from the RT file and/or memory of the analytics server. The identifying patient information may include PII, as discussed herein. For example, text 403C describes the patient's birthday. Text 411C describes the first and last name of the patient. Further, text 424D describes the patient identifier associated with the patient. The server may use the text 423D, 422D, and 424D alone or in combination to identify the patient. In other circumstances, other text identifying the patient may be displayed by the analytics server.

The graphical indicator 432D describes the areas of the patient requiring treatment. As shown, one patient may have multiple areas of the body requiring treatment. In the event that multiple areas of the body require treatment, the treatments may be performed consecutively. In such circumstances, one area of the body will be treated first, and upon treatment completion, the stages of the workflow may restart (or partially restart) such that the stages of the workflow are performed again with respect to the next area of the body to be treated. For example, the accessories required for one area of the body requiring treatment may be different from the accessories required for a different area of the body requiring treatment. The graphical indicator 432D describes the treatment areas with graphical indicator 409D describing the current area of the body being treated and graphical indicator 408D describes the next area of the body needing treatment. As shown, the analytics server is describing the Room Setup (Stage Two of the workflow) for the treatment of the right lung.

In some embodiments, the analytics server may display the same interlocks and machine alignment parameters on the Stage Two of the workflow as was displayed by the analytics server on Stage One of the workflow (e.g., graphical indicator 427C and 428C respectively). The graphical indicator displaying the interlocks by graphical indicator 427D may be beneficially displayed to the user, for instance, to indicate that the treatment room is closed. The graphical indicator displaying the machine alignment parameters by graphical indicator 428D may be beneficially displayed to the user, for instance, to indicate the alignment of the gantry. For example, the user may collide with the gantry as the user is carrying accessories so it may help the user to display machine alignment parameters such that the user can move the couch accordingly.

In some instances, the user may seek additional information related to the information on the page displayed by the analytics server. The analytics server may provide further information to the user in response to receiving various inputs. The user may interact with the screen on the radiotherapy machine (e.g., the display may be a touchscreen display). Additionally, or alternatively, the user may interact with the pendant (e.g., the pendant described in FIGS.

3A-3C). An example of the types additional information that the analytics server may provide based on the user input is displayed in example 400e of FIG. 4E.

The user may input the response 440E that indicates to the analytics server that the user is seeking additional setup information details. For instance, the user may swipe left on the display, press a left button on the pendant, swipe left on the trackpad of the pendant, or the like. In the event that the analytics server receives the response 440E, the analytics server may display page 400f or 400g associated with FIGS. 4F and 4G respectively.

The user may indicate to the analytics server that the user is seeking to perform an action. For instance, the user may perform an action (e.g., press a "back" button on the pendant, press a middle button on the pendant, press the trackpad on the pendant, press the middle of the display) to indicate to the analytics server that the user is seeking information on a workflow related stage (e.g., previous workflow stages, future workflow stages). Additionally, or alternatively, in the event the user has performed the tasks on the workflow related pages (e.g., pages that have workflow related tasks as opposed to pages that simply display additional user information) the user may input response 442E to advance the workflow. As shown, the user interacts with an interactive "Action" button to input response 442E.

The user may input the response 446E that indicates to the analytics server that the user is seeking additional patient information details. For instance, the user may swipe up on the display, press an up button on the pendant, swipe up on the trackpad of the pendant, or the like. In the event that the analytics server receives the response 446E, the analytics server may display page 400h associated with FIG. 4H.

The user may input the response 444E that indicates to the analytics server that the user is seeking additional machine details. For instance, the user may swipe right on the display, press a right button on the pendant, swipe right on the trackpad of the pendant, or the like. In the event that the analytics server receives the response 444E, the analytics server may display page 400i associated with FIG. 4I.

Additionally, or alternatively, the analytics server may display example 400e as a page on the screen on the radiotherapy machine in response to a user input (e.g., a "menu" button on the pendant and/or display). In such cases, the analytics server displays to the user the interactions (e.g., inputs 440E-446E) that the user must perform to consume additional information.

Referring now to FIGS. 4F and 4G, the analytics server may display additional setup information based on an input 440E as shown in FIG. 4E. For instance, pages 400f and 400g may be considered as examples of second pages of Stage Two (Room Setup). The setup information on page 400f may not be mandatory within the series of pages. That is, the user may never view page 400f and the analytics server may not display page 400f unless and until required by the user (e.g., by an input). For instance, because page 400f may not be mandatory, in some radiotherapy treatment sessions, the user may seek the additional setup information such that the analytics server will display page 400f. In other radiotherapy treatment sessions, the user may not seek the additional setup information such that the analytics server will not display page 400f. In contrast, during every radiotherapy treatment sessions using the workflow-oriented series of pages, the workflow related pages are displayed by the analytics server.

Page 400g is an alternate embodiment of page 400f. Because page 400g is an alternate embodiment of page 400f, page 400g is not mandatory. The page 400g may display additional or alternate information in additional or alternate layouts. The analytics server may also display the graphical indicator 432G indicating the treatment area. The analytics server may also display a list of accessories necessary, as depicted in graphical component 450G. The page 400g may also include setup notes, as depicted in the graphical component 453G and corresponding images 454G.

Some of the graphical indicators on pages 400f are similar to graphical indicators on various other pages. For instance, text 425F may describe identifying patient information. For example, the patient's first and last name, patient identifier associated with the patient, and birthdate may be displayed by the analytics server based on the RT file for the one or more patients and the patient scheduled for radiotherapy treatment. Further, graphical indicators 432F, describing the areas of the patient requiring treatment, may be displayed by the analytics server. Further, graphical indicators 430D indicating accessories necessary for patient treatment may be displayed by the analytics server. In some instances, the analytics server may use status indicators in conjunction with graphical indicator 430D to indicate whether the analytics server has located the accessories.

Display notes 453F displayed by the analytics server may provide setup note information. The display notes 436D in page 400d (e.g., FIG. 4D) displayed by the analytics server may be further explained in the display notes 453F in page 400f. Further, the treatment related images 454F might be displayed by the analytics server, for instance, to clarify the display notes 453F. For example, the treatment related images 454F might convey illustrative examples of an accessory on a particular patient being setup for treatment. Additionally, or alternatively, treatment related images 454F might convey illustrative examples of an accessory on a two-dimensional or three-dimensional representation (e.g., animation) of a patient being setup for treatment. The analytics server may also display the graphical indicator 432F indicating the treatment area. In some configurations, the information displayed within the graphical indicator 432F may be different for different treatment areas.

Graphical indicator 451F displayed by the analytics server may indicate an alert. For instance, an alert may be provided to the user to be aware of certain sensitive areas of the patient's body. The alert may be retrieved by the analytics server for instance, from the RT file. A user (e.g., a doctor) may identify certain sensitive areas of the patient's body or other treatment related information, and decide to alert a different user (e.g., a technician) to the supplemental treatment related information at particular stages in the workflow. The analytics server may display the alert, indicating to the user that supplemental treatment related information exists. The user may interact with the alert to receive the supplemental treatment related information. For instance, the analytics server may overlay the supplemental treatment related information on the current page or on a separate page. Additionally, or alternatively, the analytics server may indicate to the user where the user can retrieve the supplemental treatment related information indicated by the alert.

In some embodiments, the user who generated the alert may need to identify themselves. For instance, a doctor generating the alert may need to sign the alert with the doctor's name, date and time that the alert was generated. Alternatively, a technician may need to sign the alert with their identification information upon reviewing the supplemental treatment related information. Additionally, or alternatively, verification of the receipt of the supplemental treatment related information indicated by the alert may need to be verified by one or more users, system administrators, and/or supervisors before the user in the treatment room is allowed to progress to the subsequent stage in the workflow. For instance, a doctor may need to input a particular input to verify that the technician has reviewed the alert before the technician is allowed to progress to subsequent stages.

Some of the graphical indicators on pages 400g are similar to graphical indicators on various other pages. For instance, text 425G may describe identifying patient information. For example, the patient's first and last name, and picture may be displayed by the analytics server based on the RT file for the one or more patients and the patient schedule for radiotherapy treatment. Further, graphical indicators 432D, describing the areas of the patient requiring treatment, may be displayed by the analytics server. The analytics server may also display graphical indicator 451G indicating an alert related to the patient. Further, the analytics server may also display the graphical indicators 430D indicating accessories necessary for patient treatment. In some instances, the analytics server may use status indicators in conjunction with graphical indicator 430D to indicate whether the analytics server has located the accessories Display notes 453F displayed by the analytics server may provide setup note information. The display notes 436D in page 400d (e.g., FIG. 4D) displayed by the analytics server may be further explained in the display notes 453F in page 400g. Further, the analytics server may display the treatment related images 454F, for instance, to clarify the display notes 453F. For example, the treatment related images 454F might convey illustrative examples of the accessory on the particular patient being setup for treatment. Additionally, or alternatively, treatment related images 454F might convey illustrative examples of the accessory on a two-dimensional or three-dimensional representation (e.g., animation) of a patient being setup for treatment.

Referring now to FIG. 4H, the analytics server may display additional patient information on page 400h based on an input 446E as shown in FIG. 4E. For instance, page 400h may be considered a second page of Stage Two. The patient information in page 400h may not be mandatory within the series of pages. That is, the user may never view page 400h and the analytics server may not display page 400h unless and until required by the user (e.g., by an input). For instance, because page 400h may not be mandatory, in some radiotherapy treatment sessions, the user may seek the additional patient information such the analytics server will display page 400h. In other radiotherapy treatment sessions, the user may not seek the additional patient information such that the analytics server will not display page 400h. In contrast, during every radiotherapy treatment sessions utilizing the workflow-oriented series of pages, the workflow related pages are displayed by the analytics server.

Some of the graphical indicators on pages 400h are similar to graphical indicators on various other pages. For instance, text 425I1 may describe identifying patient information. For example, the patient's first and last name, patient identifier, date of birth, and picture may be displayed by the analytics server based on the RT file for the one or more patients and the patient schedule for radiotherapy treatment.

Display notes 460I1 displayed by the analytics server may provide alerts to the user. In some instances, the alerts may be extracted by the analytics server based on the RT file for the one or more patients and the patient scheduled for radiotherapy treatment. In other instances, the alerts may be based on doctor notes for the patient scheduled for radiotherapy treatment. The display notes 460I1 may display additional alert information associated with graphical indicator 451F and/or 451G.

Graphical indicator 462I1 displayed by the analytics server conveys to the user and/or patient the number of remaining radiotherapy treatments. In some instances, text may be displayed by the analytics server to convey to the user and/or patient the number of remaining radiotherapy treatments. The number of remaining radiotherapy treatments may be determined by one or more doctors as an estimation of the number of radiotherapy treatments the patient should undergo to rid the patient of their diagnoses. Additionally, or alternatively, the graphical indicator 462I1 may indicate the number of remaining radiotherapy treatments for multiple diagnosed areas of the body.

Text 464H may convey information about the patient's upcoming medical appointments. The upcoming medical appointments may be appointments with doctors, appointments for radiotherapy treatments, appointments for therapy, and the like. Text 464H may convey information about upcoming medical appointments on the same day as treatment. Alternatively, text 464H may convey information about upcoming medical appointments in the future.

Referring now to FIG. 4I, the analytics server may display additional machine information based on an input 444E as shown in FIG. 4E. For instance, page 400i may be considered another example of a second page of Stage Two. The machine information in page 400i may not be mandatory within the series of pages. That is, the user may never view page 400i and the analytics server may not display page 400i unless and until required by the user (e.g., by an input). For instance, because page 400i may not be mandatory, in some radiotherapy treatment sessions, the user may seek the additional patient information such the analytics server will display page 400i. In other radiotherapy treatment sessions, the user may not seek the additional machine information such that the analytics server will not display page 400i. In contrast, during every radiotherapy treatment sessions utilizing the workflow-oriented series of pages, the workflow related pages are displayed by the analytics server.

Graphical indicator 427I on page 400i may provide supplemental information to the information provided in graphical indicator 427D on page 400d. As discussed herein, in an embodiment, the graphical indicator 427D displayed by the analytics server may represent more than one safety feature associated with the treatment room. The analytics server may display various graphical indicators (427I1, 427I2, 427I3) associated with different interlocks. Status indicators may be displayed by the analytics server in conjunction with the graphical indicators (427I1, 427I2, 427I3). In an example, the graphical indicators (427I1, 427I2, 427I3) may convey various interlocks in the treatment room. However, status indicators displayed by the analytics server in conjunction with the (427I1, 427I2, 427I3) may display that a first interlock is open, a second interlock is locked, and a third interlock is open. In the depicted example, the graphical indicator 427I1 may represent a "beam not ready" status. The graphical indicator 427I2 may indicate whether the analytics server has detected an "accessory mismatch" and the graphical indicator 427I3 may indicate whether the treatment room is opened. As shown, none of the graphical indicators (427I1, 427I2, 427I3) are secure because the status indicators of each of the graphical indicators (427I1, 427I2, 427I3) are visually distinct (e.g., displayed as orange).

Because none of the graphical indicators (427I1, 427I2, 427I3) are secure, graphical indicator 427D on page 400d in FIG. 4D, representing the safety features generally, may have an orange status indicator. The orange status indicator associated with graphical indicator 427D on page 400*d* in FIG. 4D may be displayed by the analytics server to convey to the user that at least one graphical indicator (427I1, 427I2, 427I3) represented by graphical indicator 427D on page 400*d* in FIG. 4D is not secure. The user may transition to page 400*i* to determine which one or more safety features represented by graphical indicator 427D on page 400*d* in FIG. 4D is not secure.

Text 470I may convey information that identifies the radiotherapy machine performing the radiotherapy treatment. For instance, text 470I may convey the name of the radiotherapy machine, the model of the radiotherapy machine, a software version that the radiotherapy machine is operating on, and the like. Graphical indicator 478I may indicate the projected beam shape (e.g., an irradiated area) from the perspective of the collimator y. Graphical indicator 471J may also indicate the type of beam used during the radiotherapy treatment. Graphical indicator 476I may display a two-dimensional or three-dimensional representation (e.g., animation) representing the radiotherapy machine. Additionally, or alternatively, graphical indicator 476I may display a live view of the radiotherapy machine and/or the patient based on one or more cameras streaming live feed data to the analytics server.

Graphical indicator 472I may indicate the radiotherapy machine parameters. The radiotherapy machine parameters may indicate a satisfactory position of the couch for treatment. The analytics server may retrieve a position of the couch. A retrieved position of the couch may be one or more couch positions satisfactory for treatment. The retrieved position of the couch may be retrieved from memory of the analytics server, retrieved by the analytics server from a database, or retrieved from within the RT file. The retrieved position may be a three-dimensional image (or model) of the couch. The analytics server may employ various monitoring techniques (e.g., photogrammetry and/or triangulation, as discussed herein) to compare images of the satisfactory position of the couch for treatment to the retrieved position of the couch to determine position vectors that may be displayed on page 400*i*. The server may alternatively, or additionally, employ positional information retrieved from the treatment machine. As discussed herein, the analytics server may display the magnitude (e.g., extent of the difference) and direction (e.g., up, down, left, right, in, out, tilt in terms of pitch, roll to return the couch to the satisfactory position for treatment) based on the difference between the satisfactory position of the couch for treatment to the retrieved position of the couch using numbers, arrows, colors, or some combination. The analytics server may also display the numbers associated with the retrieved position of the couch and the satisfactory position of the couch for treatment. Graphical indicator 472I may be used to align the patient and/or a part of the patient with a satisfactory position on the couch.

Additionally, or alternatively, the analytics server may display the extent of difference between the satisfactory position of the gantry and/or couch for treatment to the retrieved position of the gantry and/or couch using colors. For instance, the color yellow may indicate a difference greater than 10 mm, the color orange may indicate a difference between the subsequent image and reference image from 5-10 mm, and the color grey may indicate a difference between the subsequent image and reference image from 0-5 mm. The colors and associated differences between the subsequent image and reference image may be determined by a user and/or system administrator.

As opposed to describing the alignment of hardware (e.g., graphical indicator 472I), text 473I may indicate software machine parameters such as whether the analytics server (or a device in communication with the analytics server) executes enhanced dynamic wedges. Additionally, or alternatively, text 473I may be represented by a graphical indicator. The analytics server may display on page 400*i* the software machine parameters based on received inputs (e.g., from a user in a different room, from a user using the pendant, from instructions contained in the RT file). The analytics server may display a status indicator (e.g., colors, shapes, borders) in conjunction with the graphical indicator (and/or text 473I).

Similarly, to the accessories displayed by the analytics server for the patient text 474I may indicate hardware accessories required for the radiotherapy machine. Additionally, or alternatively, text 474I may be represented by a graphical indicator. The analytics server may display (e.g., on page 400*i*) the hardware accessories to be used during the radiation based on received inputs (e.g., from a user in a different room, from a user using the pendant, from instructions contained in the RT file). In some embodiments, instead of listing the hardware accessories required for the radiotherapy machine, the analytics server may determine whether the hardware accessories are present on the radiotherapy machine.

For instance, the analytics server (or device in communication with the radiotherapy machine) may query one or more processors in the radiotherapy machine to perform a system check. Additionally, or alternatively, the analytics server may use the one or more cameras in the treatment room and perform object detection on the live feed of data received by the analytics server. For instance, the server may use object detection to determine whether hardware accessories are attached to the radiotherapy machine. In alternate embodiments, the analytics server may use RFID technology as discussed herein to determine whether the hardware accessories are within a predetermined proximity.

In response to the system check performed by the radiotherapy machine (or the object detection or RFID utilized by the analytics server) the analytics server may receive an indication of the attached hardware accessories present on the radiotherapy machine. The analytics server may display a status indicator (e.g., colors, shapes, borders) in conjunction with the graphical indicator (and/or text 473I) to display to the user the accessories detected on the radiotherapy machine. In some cases, the analytics server periodically or continuously queries the radiotherapy machine for the presence and/or status of the hardware accessories. In some cases, the analytics server queries the radiotherapy machine for the presence and/or status of the hardware accessories based on an input received by the analytics server. For instance, the input received by the analytics server may be from an interactive button pressed by the user on the pendant, a button pressed by a user on a console (the console discussed in FIGS. 10A-10D), a button pressed by a user on the screen on the gantry, and the like.

In one configuration, a user may interact with interactive button 475I to execute, by the analytics server, a dry run. In other embodiments, the dry run may be performed as a step just before treatment. That is, the analytics server may not display interactive button 475I and may not perform the dry run, or display information related to the dry run, until the next step (e.g., page 400*n* of FIG. 4N representing Stage Five, Patient Setup). In some embodiments, the dry run is a virtual dry run. In other embodiments, the dry run is a physical dry run. In other embodiments, the user may select the type of dry run to per executed by the analytics server (e.g., a virtual dry run or physical dry run). The virtual dry run is described herein (e.g., FIGS. 6A-6G).

A user may interact with interactive button 4771 to execute, by the analytics server, one or more predetermined presets. The one or more presets may be a collection of gantry and/or couch positions. For instance, a user may seek to maneuver the gantry and/or couch into various positions frequently. In the event the user interacts with interactive button 4771, the gantry and/or couch may automatically adjust to one or more predetermined presets. The user may progress through the stages of the workflow faster because various predetermined presets allow the radiotherapy machine to automatically adjust to various positions accurately and quickly. It may be beneficial for a user to progress through the stages of the workflow faster because the radiotherapy treatment may take less time and be less burdensome on the patient. A user and/or system administrator may determine the predetermined preset positions.

Referring back to FIG. 4D, the user may progress to the next stage in the workflow (e.g., the analytics server may display page 400*k* of FIG. 4K associated with Stage Three, Patient Identification) by completing the current stage. In a non-limiting example, placing all of the accessories in their appropriate positions may automatically trigger the analytics server to determine move to the next stage of the workflow. Additionally, or alternatively, an interactive button may appear (or light up) on the page 400*d* such that the user is encouraged to interact with the button In such instances, the analytics server may move to the next stage of the workflow in response to the user interacting with the interactive button.

FIG. 4J may be an alternate embodiment of FIG. 4I. For example, text 470J may provide additional and/or alternate identifying information about the radiotherapy machine as compared to text 470I in FIG. 4I. For instance, text 470J may convey to the user the name of the radiotherapy machine, the version of the software installed on the radiotherapy machine, the year the radiotherapy machine was built, the last inspection date of the radiotherapy machine, and the like. Text 471J may convey other identifying information about the radiotherapy machine such as the accessories used on the radiotherapy machine, the set radiation intensity of the scheduled radiotherapy treatment, and the like. Further text 473J may convey additional identifying information about the radiotherapy machine such as the degree of rotation that the radiotherapy machine is capable of and/or a predetermined range of rotation for the scheduled radiotherapy treatment. A user and/or system administrator may determine the range of rotation for the scheduled radiotherapy treatment.

The analytics server may display the set of graphical indicators 479J to help the medical professionals to identify needed accessories. As will be described below, the analytics server may retrieve a list of all accessories needed for the patient's treatment. Each graphical indicator within the set of graphical indicators 479J may correspond to one accessory. As described herein, the analytics server may track different accessories (e.g., via RFID tags or visual tags) and may represent the accessories located within a predetermined area as visually distinct. For instance, the analytics server may display the needed accessories that are located within a certain proximity to the radiotherapy machine in different colors. The analytics server may continuously or periodically monitor each accessory and may modify one or more of the graphical indicator within the set of graphical indicators 479J accordingly.

Graphical indicator 472J may indicate the radiotherapy machine parameters as arrows (or other directional indicators) indicating the direction of adjustment to reduce the difference between the satisfactory position of the couch for treatment to the retrieved position of the gantry and/or couch. As discussed herein, colors, graphical, and numerical representations conveying the difference between the satisfactory position of the gantry and/or couch for treatment to the retrieved position of the gantry and/or couch may be displayed by the analytics server (in conjunction with graphical indicator 472J as shown).

Further, some of the graphical indicators on pages 400*j* are similar to graphical indicators on various other pages herein. For instance, graphical indicator 478J may indicate the projected beam shape from the perspective of the collimator and/or the type of beam used during the radiotherapy treatment. Graphical indicator 476J may display a representation of the radiotherapy machine (e.g., two-dimensional model, three-dimensional model, live view, image, and the like).

Additionally, or alternatively, the analytics server may display the interactive button 475J. As a result of the user interacting with interactive button 475J, the analytics server may execute a dry run protocol. Further, interactive button 477J may be interacted with, executing by the analytics server, one or more predetermined presets.

At step 414, the analytics server displays a page on a GUI representing Stage Three. In this example, Stage Three relates to patient identification. The analytics server can display patient identification information (such as the patient's name and a photo) on the screen, increasing the likelihood that the user is engaged with the patient and the treatment room, as opposed to looking down at papers or interacting with the machine. The analytics server may display a portion of the treatment data associated with the patient scheduled to receive radiotherapy treatment. In some embodiments, the portion of the treatment data associated with the patient scheduled to receive radiotherapy treatment may help a user identify the patient.

The page 400*k* in FIG. 4K displays the page displayed by the analytics server that corresponds to Stage Three (Patient Identification). During the patient identification step, the patient may be allowed into the treatment room. In other embodiments, in the event the patient is already inside the treatment room, a user may match the patient in the treatment room with the patient identification information displayed on the screen.

Some of the graphical indicators on page 400*k* may be similar to graphical indicators on various other pages. For instance, text 425K may describe identifying patient information. For example, the analytics server may display the patient's first and last name, date of birth, and picture based on the RT file for the one or more patients and the patient schedule for radiotherapy treatment. Background 480K may be a non-treatment related image, a treatment related image, a solid color, a pattern, and the like. The patient will likely view the background 480K as the patient approaches the radiotherapy machine and views the screen.

In some embodiments, the analytics server will display the next stage in the workflow when the patient identity is verified. For instance, the analytics server may verify the patient using biometric identification (e.g., fingerprint, iris recognition, retina scanning). In some embodiments, the analytics server will display the next stage in the workflow when the user performs one or more actions (e.g., uses one or more interactive buttons to advance to the next stage).

At step 416, the analytics server displays a page on a GUI representing Stage Four. In this example, Stage Four relates to patient alignment. The analytics server may display information to facilitate the patient getting into a satisfactory position for treatment.

The user may progress to the next stage in the workflow (e.g., the analytics server may display page 400*l* of FIG. 4L associated with Stage Four, Patient Alignment) by completing the current stage. For example, walking the patient over to the radiotherapy machine. Additionally, or alternatively, an interactive button may appear (or light up) on the page 400*d* such that the user is encouraged to interact with the button In such instances, the analytics server may move to the next stage of the workflow in response to the user interacting with the interactive button. In other embodiments, the user may input any response to the analytics server to progress to the next stage in the workflow. In some configurations, the analytics server may execute a virtual dry run protocol. The analytics server may prevent the user to move to the next stage until and unless the virtual dry run protocol indicates that the patient will not collide with the radiation therapy machine.

The patient may be positioned in a satisfactory position for treatment. The satisfactory position for treatment may be indicated by positioning a particular area of the body in accordance with alignment data that is uniquely calculated for the patient. The alignment data may include various parameters indicating how a patient should be positioned on the couch. Therefore, alignment parameters are not limited to alignment angles. Although certain embodiments herein discuss displaying alignment angles, it is expressly understood that the methods herein apply to all alignment data and parameters. For instance, alignment may be expressed in terms on a distance and a corresponding direction (e.g., 5 mm to the right).

The reference material may be a plurality of reference surfaces, images and/or attributes of a patient indicating regions of the patient to be treated (e.g., needing radiotherapy treatment). The reference material may indicate that a part of the patient's body in a satisfactory position for treatment. The satisfactory position for treatment may be indicated by positioning a particular area of the body at an alignment angle(s) with reference to an isocenter or other reference points. The positioning of the particular area of the body at the alignment angle(s) allows the radiotherapy machine to radiate the positioned particular area of the body while minimizing radiation exposure to other parts of the body and avoiding collisions during the treatment (because the patient is aligned with respect to the reference position). The alignment angle(s) (and corresponding satisfactory position for treatment) may be predetermined by users and/or system administrators and retrieved by the analytics server (for example, from the radiation RT file) and/or received by the analytics server as an input from the users and/or system administrators. The analytics server may be monitoring the position of the patient based on object tracking, as discussed herein. The analytics server may determine that the position of the patient is acceptable if it is within a predetermined margin of error.

Alignment angle, as used herein, may refer to aligning the patient consistent with a patient position to receive optimal treatment. For instance, the patient's position may be aligned with a predetermined surface. Therefore, alignment angles refer to how the patient should be moved. These movements may sometimes be characterized in angles and sometimes in other forms. Furthermore, alignment parameters are not limited to alignment angles. For instance, the analytics server may display various alignment parameters instructing a technician to realign the patient accordingly. Therefore, even though certain embodiments herein discuss displaying alignment angles, it is expressly understood that the methods herein may apply to all alignment data and parameters.

In some embodiments, the analytics server may display a reference surface of a patient in an acceptable position for treatment. In some circumstances, the reference surface may be a "ghost image" or a shadow of the patient in the acceptable position for treatment. Other non-limiting examples of solutions may include joint position matching, body outline matching, and/or other surface matching techniques. The server may determine the position of the reference surface based on a retrieved reference surface. In some embodiments, the analytics server may retrieve the reference surface from memory (e.g., the memory of the analytics server may contain a library of acceptable positions for various treatment). For example, the analytics server may store a plurality of reference surfaces for patients needing radiotherapy to treat breast cancer in the left breast. Further, the server may store a plurality of reference surfaces for patients needing radiotherapy to treat breast cancer in the right breast. In other embodiments, the analytics server may retrieve the reference surface from a database in communication with the analytics server. In other embodiments, the server may determine the position of the reference surface based on prior images of the patient during the patient's diagnoses procedure or prior treatments. For example, the analytics server (or other server and/or device such as a camera) may have captured and stored an image of the patient during a first radiotherapy treatment. Additionally, or alternatively, the analytics server (or other server and/or device such as a camera) may have captured an image of the patient during a procedure associated with the patient's diagnoses (e.g., a CT scan). For medical purposes, it may be critical to treat the patient in the same position such that the same part of the body is treated, increasing the likelihood of successful treatments.

In other embodiments, the analytics server may retrieve a reference surface from one of the plurality of stored reference surfaces from the RT file. The retrieved reference surface by the analytics server from the RT file is based on the treatment for the patient scheduled to receive treatment (e.g., the selected patient in step 410). Additionally, or alternatively, a doctor or other user may save a reference surface (or plurality of reference surfaces) based on CT scan or other image to the analytics server. In the event the analytics server receives an image, the analytics server may convert the image into a three-dimensional reference surface.

The Patient Alignment stage facilitates the patient's correct position on the couch (e.g., not crooked, hands up, leg bent, and the like) to assist with receiving treatment at the proper location and angle and/or assist with avoiding interference with the radiotherapy machine.

In some instances, the reference surface may be overlaid on top of a two-dimensional or three-dimensional representation (e.g., animation) of the radiotherapy machine. In other instances, the reference surface may be overlaid on top of a live feed image of the radiotherapy machine (e.g., received by the analytics server from one or more cameras positioned on the gantry and/or in the treatment room). The analytics server may display the overlaid reference surface. In other embodiments, the analytics server may use the reference surface only for internal calculations.

A representation of the patient may be displayed on the screen such that the patient and/or the user can match the position of the patient to an acceptable position for treatment within a predetermined margin of error (the acceptable position of treatment determined by the reference surface). The representation of the patient may be a live view of the patient received by the analytics server from the one or more cameras positioned on the gantry and/or the treatment room. Additionally, or alternatively, the representation of the patient may be a two-dimensional or three-dimensional representation (e.g., animation).

The analytics server may compare the reference surface with the representation of the patient. As discussed herein, the analytics server may determine a position vector based on the comparison of the reference surface and the representation of the patient, indicating the difference in position of the patient to the reference surface. The analytics server may display the magnitude of the position vector using colors. For instance, the color red may indicate a difference greater than 10 mm, the color orange may indicate a difference between the subsequent image and reference image from 5-10 mm, and the color grey may indicate a difference between the subsequent image and reference image from 0-5 mm. The colors and associated differences between the subsequent image and reference image may be determined by a user and/or system administrator.

The analytics server may also overlay the representation of the patient with one or more colors, patterns, textures, and the like. The overlaid representation of the patient may be used to indicate the location of the patient relative to the reference surface. For example, a predetermined color may indicate that the patient is above the reference surface, and a different predetermined color may indicate that the patient is below the reference surface. Additionally, or alternatively, the analytics server may display the representation of the patient and the reference surface without overlaying the reference surface and/or representation of the patient respectively. For example, the analytics server may use the representation of the patient annotated and/or intersected with the reference surface.

The analytics server may also perform object tracking, as discussed herein, to track the position of the patient in three-dimensional space. The position of the patient may be compared to a three-dimensional reference surface such that the analytics server can determine how the position of the patient should be adjusted to match the position of the reference surface. The analytics server may display the position of the patient compared to the position of the reference surface such that the user and/or patient can see the adjustments that need to be made. Additionally, or alternatively, the analytics server may perform surface matching to match the image of the patient (e.g., the image of the patient in a frame) to the reference surface. The analytics server may map the structures of the image of the patient to the reference surface and use an optimization function such as the least square error to optimize the position of geometric attributes (such as metric, mean curvature, and textures) using the mapped image of the patient on the reference surface to determine how the image of the patient needs to be adjusted (e.g., in a next frame) according to the reference surface.

In the event that the analytics server determines the position of the patient matches the position of the reference surface (within a predetermined margin of error), the analytics server may overlay the portion of the patient that matches (within the predetermined margin of error) the reference surface a predetermined color.

Page 400*l* displays the page displayed by the analytics server that corresponds to Stage Four (Patient Alignment). The page 400*m* is an alternate embodiment of page 400*l*. The page 400*m* may display additional or alternate information in additional or alternate layouts.

Some of the graphical indicators on page 400*l* are similar to graphical indicators on various other pages. For instance, text 425L may describe identifying patient information. For example, the analytics serve may display the patient's first and last name, date of birth, and patient identifier based on the RT file for the one or more patients and the patient schedule for radiotherapy treatment. Further, as discussed herein, graphical indicator 432L describes the areas of the patient requiring treatment. As shown, one patient may have multiple areas of the body requiring treatment.

In addition, the analytics server may display graphical indicator 427L representing a safety feature associated with the treatment room. In some embodiments, the graphical indicator 427L may represent one or more safety features associated with the treatment room. In other embodiments, various graphical indicators 427L (not shown) represent one or more safety features in the treatment room. The graphical indicator 427L representing a safety feature may be displayed by the analytics server in conjunction with a status indicator to convey what the analytics server has identified as the status of the safety feature. The status indicator may convey what the analytics server has identified as the status of the more than safety features.

Further, as discussed herein, the analytics server may display graphical indicator 428L representing machine alignment parameters. The machine alignment parameters may be used, for instance, by a user to evaluate whether the gantry of the machine is aligned. In addition, graphical indicator 496L may indicate the radiotherapy machine parameters. The radiotherapy machine parameters may indicate a satisfactory position of the couch for treatment. As discussed herein, the analytics server may display the magnitude (e.g., extent of the difference between the satisfactory position of the couch for treatment to the retrieved position of the couch) and direction (e.g., up, down, left, right, in, out, tilt in terms of pitch, roll to return the couch to the satisfactory position for treatment).

Additionally, or alternatively, the analytics server may display the extent of difference between the satisfactory position of the gantry and/or couch for treatment to the retrieved position of the gantry and/or couch using colors. As shown, graphical indicator 496L is described using arrows to indicate the direction of adjustment and number to indicate the extent of adjustment to achieve the satisfactory position for treatment. Further, graphical indicator 496L uses colors to further emphasize the extent of adjustment to achieve the satisfactory position for treatment. The patient (or a portion of the patient) may be aligned on the couch using the graphical indicator 496L such that the patient (or a portion of the patient) is in a satisfactory position for treatment.

Further, as discussed herein, the analytics server may use graphical indicator 430L to display accessories necessary for patient treatment (e.g., as described in FIGS. 7A-7C). The analytics server displays the graphical indicators 430L representing the accessories (and the status of the accessories) on the side of the page 400*k* such that the accessories appear in a column. The analytics server may determine the accessories necessary for the patient according to the RT file associated with the one or more patients. Additionally, the analytics server may use status indicators in conjunction with the graphical indicator 430L indicating the accessories necessary for treatment to determine whether the analytics server has located the accessory. As shown, the status indicator is conveyed to a user by the color of the graphical indicators 430L. The analytics server may determine the location of the accessory using technology, such as RFID (e.g., as described in FIGS. 7A-7C).

Further, as discussed herein, the analytics server may display a progress indicator 434L to indicate the stages of the workflow. For example, the current stage of workflow (e.g., Stage Four, Patient Alignment) may be emphasized by the analytics server such that a user and/or patient can determine the current stage of the workflow from preceding or succeeding workflow stages displayed via the progress indicator 434L.

As discussed herein, Stage Four of the workflow beneficially facilitates the patient's correct position on the couch. The analytics server may overlay a reference surface on top of a two-dimensional or three-dimensional representation (e.g., animation) of the radiotherapy machine and/or on top of a live feed image of the radiotherapy machine. The analytics server may receive the live view of the patient on the couch from one or more cameras positioned on the gantry and/or the treatment room. In some instances, the analytics server may generate and display a three-dimensional model of the patient from the received live view data using various monitoring techniques (e.g., triangulation, time of flight, and/or photogrammetry as discussed herein). In other instances, the analytics server may display a live view feed of the patient on the couch. The displayed view of the patient on the couch (e.g., either as a three-dimensional model or as a live feed) may be overlaid with visually distinct areas 493L to facilitate the patient's correct position on the couch.

Visually distinct areas 493L are used to position the patient physically on the couch. For instance, the reference image may depict a patient with their arms above their head. The analytics server may display the reference image to the patient overlaid on the couch such that the patient is encouraged to match the position of the reference image. Overlaid visually distinct areas 493L on the patient may indicate adjustments required to position the patient according to the reference image. For instance, one color may indicate that part of the patient's body is below the reference surface. A different color may indicate that part of the patient's body is above the reference surface. The colors and the associated meanings may be determined by a user and/or system administrator.

The user may interact with interactive button 497L to advance the displayed page (e.g., 400l) to a next stage of the workflow (e.g., page 400n of FIG. 4N representing Stage Five, Patient Setup). As discussed herein, the analytics server may transition to a next workflow stage (e.g., page 400n of FIG. 4N) based on whether the analytics server determines that a predetermined portion of tasks displayed on page 400l have been completed. Additionally, or alternatively, the analytics server may transition to the next stage based on an input received from the user using a pendant and/or interacting with the displayed page 400l. The analytics server may use an interactive button such as button 497L to transition to the next stage of the workflow on page 400l because the next stage of the workflow, Stage Five, Patient Setup, involves the couch moving. Because Stage Five, Patient Setup involves the couch moving, it may be safer for the user to provide an input to the analytics server such that the user has time to talk to the patient before the couch and/or gantry begin moving.

For instance, in the event the analytics server transitions to a next stage based on the server determining that a predetermined portion of tasks have been completed (e.g., by determining that a certain number of flags and/or other indicators have been raised), the analytics server may transition to the next stage of the workflow and subsequently control the couch and/or gantry to begin moving upon the patient adjusting to a proper position (the proper position determined by the reference surface). The patient may be surprised by the sudden movement and consequently move, changing their position and undoing the alignment performed in Stage Four of the workflow, Patient Alignment.

Some of the graphical indicators on page 400m are similar to graphical indicators on various other pages. For instance, text 425M may describe identifying patient information. For example, the patient's first and last name, patient identifier, and picture may be displayed by the analytics server based on the RT file for the one or more patients and the patient schedule for radiotherapy treatment. Further, as discussed herein, graphical indicator 432M describes the areas of the patient requiring treatment. As shown, one patient may have multiple areas of the body requiring treatment.

Further, as discussed herein, the analytics server may display graphical indicator 498M representing machine alignment parameters. The machine alignment parameters may be used, for instance, by a user to evaluate whether the gantry of the machine is aligned. In addition, graphical indicator 496M may indicate the radiotherapy machine parameters. The radiotherapy machine parameters may indicate a satisfactory position of the couch for treatment. As discussed herein, the analytics server may display the magnitude (e.g., extent of the difference between the satisfactory position of the couch for treatment to the retrieved position of the couch) and/or direction (e.g., up, down, left, right, in, out, tilt in terms of pitch, roll to return the gantry and/or couch to the satisfactory position for treatment) of the machine parameters. The patient (or a portion of the patient) may be aligned on the couch using the graphical indicator 496M such that the patient (or a portion of the patient) is in a satisfactory position for treatment.

Additionally, or alternatively, the analytics server may display the extent of difference between the satisfactory position of the gantry and/or couch for treatment to the retrieved position of the gantry and/or couch using colors. As shown, the graphical indicator 496M is described using arrows to indicate the direction of adjustment and colors to emphasize the extent of adjustment to achieve the satisfactory position for treatment. For instance, the graphical indicator 496M may convey how the patient must move, such that the patient is aligned to receive treatment.

Further, as discussed herein, the analytics server may use graphical indicator 430M to display accessories necessary for patient treatment (e.g., as described in FIGS. 7A-7C). The analytics server displays the graphical indicators 430M representing the accessories (and the status of the accessories) on the side of the page 400l such that the accessories appear in a column. The analytics server may determine the accessories necessary for the patient according to the RT file associated with the one or more patients. Additionally, the analytics server may use status indicators in conjunction with the graphical indicator 430M indicating the accessories necessary for treatment to determine whether the analytics server has located the accessory. As shown, the status indicator is conveyed to a user by colored shapes contained within the graphical indicators 430M. The analytics server may determine the location of the accessory using technology, such as RFID (e.g., as described in FIGS. 7A-7C).

Further, as discussed herein, the analytics server may display a progress indicator 434M to indicate the stages of the workflow. For example, the current stage of workflow (e.g., Stage Four, Patient Alignment) may be emphasized by the analytics server such that a user and/or patient can determine the current stage of the workflow from preceding or succeeding workflow stages displayed via the progress indicator 434M.

Visually distinct areas 493M are used to position the patient physically on the couch. For instance, the reference image may depict a patient with their arms above their head. The analytics server may display the reference image to the patient overlaid on the couch such that the patient is encouraged to match the position of the reference image. Overlaid visually distinct areas 493M on the patient may indicate adjustments required to position the patient according to the reference image. For instance, one color may indicate that part of the patient's body is below the reference surface. A different color may indicate that part of the patient's body is above the reference surface. The colors and the associated meanings may be determined by a user and/or system administrator.

In some embodiments, the analytics server may utilize an interactive button 497M to advance the displayed page (e.g., 400m) to a next stage of the workflow (e.g., page 400n of FIG. 4N representing Stage Five, Patient Setup). As discussed herein, the analytics server may transition to a next workflow stage (e.g., page 400n of FIG. 4N) based on whether the analytics server determines that a predetermined portion of tasks displayed on page 400m have been completed. Additionally, or alternatively, the analytics server may transition to the next stage based on an input received from the user using a pendant and/or interacting with the displayed page 400m. The analytics server may use an interactive button such as button 497M to transition to the next stage of the workflow on page 400m because the next stage of the workflow, Stage Five, Patient Setup, involves the couch moving. Because Stage Five, Patient Setup involves the couch moving, it may be safer for the user provide an input to the analytics server such that the user has time to talk to the patient before the couch and/or gantry being moving. For instance, in the event the analytics server transitions to a next stage based on the server determining that a predetermined portion of tasks have been completed (e.g., by determining that a certain number of flags and/or other indicators have been raised), the analytics server may transition to the next stage of the workflow and subsequently control the couch and/or gantry to begin moving upon the patient adjusting to a proper position (the proper position determined by the reference surface). The patient may be surprised by the sudden movement and consequently move, changing their position and undoing the alignment performed in Stage Four of the workflow, Patient Alignment.

Additionally, or alternatively, the analytics server may receive an input from the user instructing the analytics server to execute a virtual dry run protocol. As a result, the analytics server may execute the methods described herein and determine whether the patient is projected to collide with one or more parts of the radiation therapy machine. If so, the analytics server may prevent the workflow from progressing to a subsequent stage unless/until the patient is no longer project to have a collision (e.g., the patient is realigned).

At step 417, the analytics server displays a page on a GUI representing Stage Five. In this example, Stage Five relates to patient setup. The analytics server refines the patient's position from the Patient Alignment Stage. During the Patient Setup Stage (Stage Five), the radiotherapy machine may automatically move the couch to refine the patient's manual position from the Patient Alignment Stage. The analytics server may refine the patient's manual position using the patient's position data analyzed, as described herein. For instance, the analytics server may execute surface matching techniques using patient images received via the cameras (e.g., as described in FIGS. 5A-5C) to calculate whether the patient must be realigned.

Figure 5A:
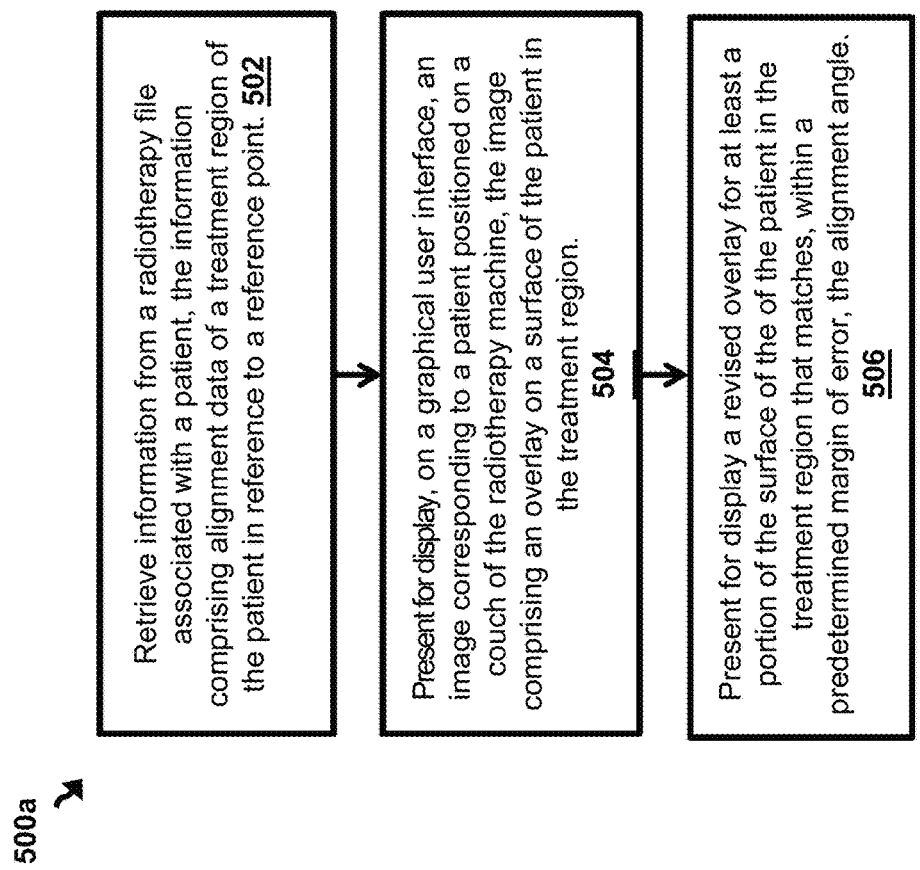
FIG. 5A illustrates a flow diagram executed in a workflow-oriented radiotherapy system, according to an embodiment.
Figure 5C:
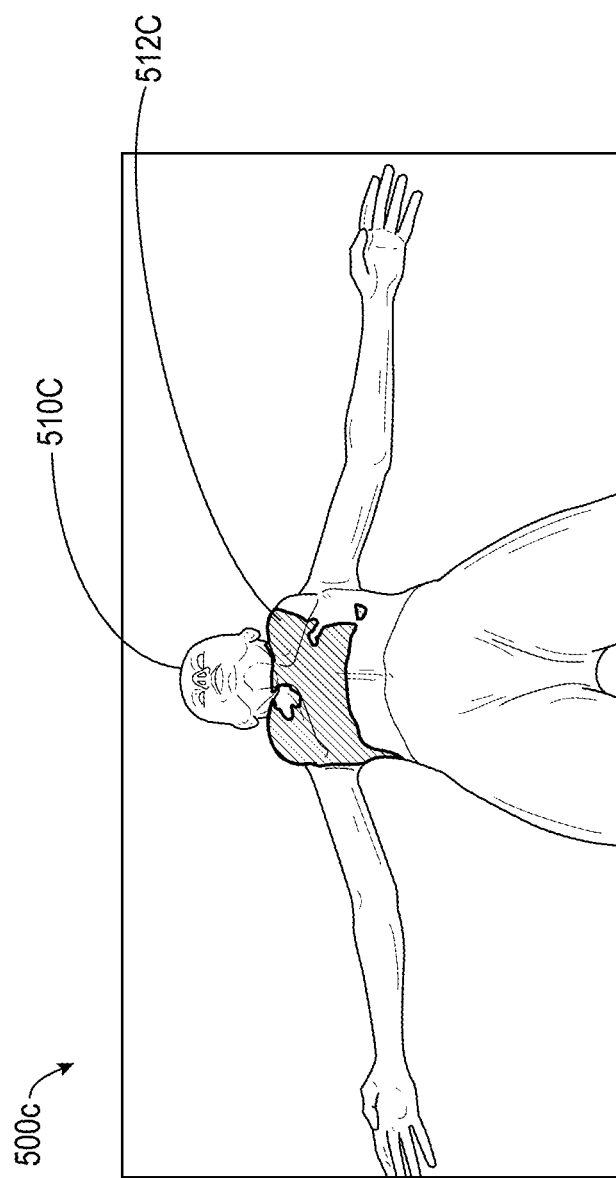

The analytics server may determine the movement of the gantry and/or couch based on surface matching described herein (e.g., FIGS. 5A-5C). In the event that surface matching is performed, the analytics server may display a representation of the two surfaces (e.g., the surface of the patient overlaid on a reference image), where the representation of the surface is displayed using an animation or using live feed data from the cameras in the treatment room and/or on the gantry (or some combination of live feed data and animation). The analytics server may move the couch based on the surface matching such that the surface of the patient matches (or is within a predetermined margin of error) the surface of the reference image. The surfaces that are not matched may be displayed by the analytics server using a color or other types of visualization techniques (e.g., overly and highlighting intersections). In the event that the couch adjusts their position such that the surface of the patient is matched (or is within a predetermined margin of error) with a reference image, the analytics server will not display any color on the surface of the patient.

Additionally, or alternatively, the surfaces that are matched may be displayed by the analytics server using a color. In the event that the couch adjusts their position such that the surface of the patient is matched (or is within a predetermined margin of error) with a reference image, the analytics server will display color over the entire surface of the patient. The analytics server may utilize other forms of indicators to indicate whether the patient of the surface is matched with the reference surface (e.g., shading, borders, texture, and shine).

Additionally, or alternatively, the analytics server determines the movement of the couch based on optical alignment. For example, the location on a patient's body that is to be treated may be indicated (e.g., a user may draw on the patient's body). For instance, the analytics server may display crosshairs drawn on the patient. In some cases, the analytics server adjusts (and/or communicates with another device to adjust) the couch such that the couch move to optically align the crosshairs with the radiation isocenter. In some embodiments, the analytics server may move the couch, such that the patient's position is closer to the required alignment whereby the user can realign the patient for treatment. Therefore, the analytics server's repositioning may be combined with the user's manual repositioning to align the patient accordingly.

In the event the analytics server adjusts (and/or communicates with another device to adjust) the couch according a predetermined margin of error with respect to the reference surface, the analytics server may change the displayed view of the patient. In some embodiments, the analytics server displays the new view of the patient according to cameras that are closer to the treatment site. The analytics server may further refine the position of the couch by adjusting the position of the couch (or being in communication with a device that adjusts the position of the couch) based on the data received from the new view of the patient.

Additionally or alternatively, the analytics server may receive inputs from the user upon the completion of the refined treatment position of the gantry and/or couch. For example, a user may further adjust the position of the couch (direct the gantry and/or couch up, down, left, right, in, out, tilt in terms of pitch, roll, and the like). These adjustments may be guided by the graphical indicators displayed by the analytics server (e.g., 472N). The user may input the adjusted positions of the gantry and/or couch using the pendant (as described in FIGS. 3A-3B).

The page 400n in FIG. 4N displays the page displayed by the analytics server that corresponds to Stage Five (Patient Setup). As discussed herein, Stage Five (Patient Setup) of the workflow. The focus of the page in Stage Five of the workflow may change to a focus on the patient. For instance, the perspective of page may change from a couch perspective shown in page 400d, page 400l, page 400m to a patient body perspective in page 400n.

The analytics server may guide (or communicate with a device that guides) the movement of the couch and/or gantry based on various guiding principles. For example, the analytics server may guide the couch and/or gantry based on surface matching (as described in FIGS. 5A-5C). In a different example, the analytics server may guide the couch and/or gantry based on optical alignment. As shown, page 400n describes an optical, laser-based, setup of a portion of the patient on the couch.

Graphical indicator 410N represents the analytics server executing surface matching on the patient on the couch to align the patient according to the satisfactory position for treatment (e.g., positional and angular alignment). As shown, graphical indicator 410N represents that the surfaces are not matched because analytics server is visually differentiating unmatched portions of a patient (or other representation of the patient) and a satisfactory position for treatment. In the event that the couch adjusts their position such that the surface of the patient is matched (or is within a predetermined margin of error) with the reference image, the analytics server will not visually differentiate any surface of the patient (or other representation of the patient). As discussed above, the analytics server may use a variety of methods to visualize the position discrepancies (e.g., overly and highlighting intersections).

In a non-limiting example, after the analytics server has performed surface matching and aligns the patient such that the patient is in the satisfactory position for treatment, the analytics server may capture the position of the patient. The analytics server may continuously monitor whether the patient adjusts from the captured position. In the event that a patient's adjustment exceed a predetermined margin of error (for instance, adjustments to the patient's position by breathing may be adjustments within the predetermined margin of error) the analytics server may display page 400o in FIG. 4O. Additionally, or alternatively, the analytics server may only display page 400o in FIG. 4O in the event that the patient's adjusted position exceeds a predetermined margin of error for a predetermined duration of time. For instance, if the patient takes a deep breath and exceeds the predetermined margin of error, but then returns back to the satisfactory position, the analytics server may not display page 400o in FIG. 4O.

The page 400o in FIG. 4O may include graphical indicators that are similar to graphical indicators on various other pages. For instance, display note 431O may use a graphical indicator (e.g., a hazard symbol) and text (e.g., a notice that the patient's position has changed) to convey to the user that the patient's exceed a predetermined margin of error. It should be noted that the display note may use other graphical indicators as described herein. Page 400o may also include text and/or graphical indicators conveying PII as shown in 425O, an indication of the one or more areas of the patient requiring treatment as shown in text 432O, machine alignment parameters as shown in graphical indicator 428O, radiotherapy machine parameters as shown in graphical indicator 472O, and a progress of the user in the treatment room as shown in progress indicator 434O (highlighting a current stage of the workflow progression and displaying succeeding/preceding stages). Referring back to FIG. 4N, some of the graphical indicators on page 400n are similar to graphical indicators on various other pages. For instance, text 425N may describe identifying patient information. For example, the analytics server may display the patient's first and last name, date of birth, and patient identifier based on the RT file for the one or more patients and the patient schedule for radiotherapy treatment. Further, as discussed herein, graphical indicator 432N describes the areas of the patient requiring treatment. As shown, one patient may have multiple areas of the body requiring treatment.

In addition, the analytics server may display graphical indicator 427N representing a safety feature associated with the treatment room. Graphical indicator 427N is displayed by the analytics server horizontally on a side of page 400n. The graphical indicator 427N may represent one or more safety features associated with the treatment room. In the event the user wanted to know what safety features were represented by graphical indicator 427N, the user may have to input a command to the analytics server such that the analytics server displays additional information regarding the safety features (e.g., input 444E in FIG. 4E). The graphical indicator 427N representing a safety feature may be displayed by the analytics server in conjunction with a status indicator to convey what the analytics server has identified as the status of the safety feature. The status indicator may convey what the analytics server has identified as the status of the more than safety features. As shown, the status of all of the safety features is acceptable (e.g., treatment door closed).

Further, as discussed herein, the analytics server may display graphical indicator 428N representing machine alignment parameters. The machine alignment parameters may be used, for instance, by a user to evaluate whether the gantry of the machine is aligned. Graphical indicator 428N is displayed by the analytics server horizontally on a side of the page 400n.

In addition, graphical indicator 472N may indicate the radiotherapy machine parameters. The radiotherapy machine parameters may indicate a satisfactory position of the couch for treatment. Graphical indicator 427N is displayed by the analytics server horizontally on a side of page 400n. As shown, graphical indicator 472N is described using arrows to indicate the direction of adjustment and number to indicate the extent of adjustment to achieve the satisfactory position for treatment. Further, graphical indicator 472N uses colors to further emphasize the extent of adjustment to achieve the satisfactory position for treatment. As shown, the patient is in a satisfactory position for treatment.

Further, as discussed herein, the analytics server may use graphical indicator 430N to display accessories necessary for patient treatment (e.g., as described in FIGS. 7A-7C). The analytics server displays the graphical indicators 430N representing the accessories (and the status of the accessories) horizontally on the side of the page 400n such that the accessories appear in a column. The analytics server may use status indicators in conjunction with the graphical indicator 430N to determine whether the analytics server has located the accessory. As shown, the status indicator is conveyed to a user by the color of the graphical indicators 430N. The status indicator in conjunction with graphical indicator 430N may convey that the accessory (Bolus 1) is not present.

The graphical indicators described herein may have two roles. Depending on the type of the setup, the "satisfactory position" may be defined differently. For instance, in an optical setup, the satisfactory position may be with respect to the initial patient position as calculated in Stage 4. In another example, the analytics server may use real-time feedback from the SGRT cameras to determine the satisfactory position. The graphical indicators may allow the user to minimize the discrepancy to the reference and ensure that the machine parameters are within the limits set in the treatment plan (indicated by orange highlights or otherwise visually distinct).

Further, as discussed herein, the analytics server may display a progress indicator 434N to indicate the stages of the workflow. For example, the current stage of workflow (e.g., Stage Four, Patient Alignment) may be emphasized by the analytics server such that a user and/or patient can determine the current stage of the workflow from preceding or succeeding workflow stages displayed via the progress indicator 434N. As shown, the progress indicator 434N is horizontally located on the bottom of page 400n.

Additionally, or alternatively, there may be an interactive button (not shown) that allows the user to perform a dry run (e.g., physical dry run, virtual dry run) or capture a setup position. In some embodiments, upon capturing a setup position, the analytics server may execute the virtual dry run to evaluate whether collisions will occur based on the setup position. In the event the analytics server determines that collisions will not occur, the analytics server may perform the steps associated with Stage Six.

At step 418, the analytics server performs the steps associated with Stage Six. In this example, Stage Six relates to treatment. The analytics server may turn off (or otherwise disable) the displays in the treatment room to prevent the displays from being damaged by radiation. Upon completion of Stage Five, the screen can display a notice that treatment is starting, and the screen can be disabled or turn off until Stage Six is complete.

The user may interact with interactive button 401N to advance the displayed page (e.g., 400n) to a next stage of the workflow (e.g., Stage Six, Treatment).

The analytics server shuts off the displayed screen on the gantry during the treatment stage of the workflow. Triggers for shutting off the displayed screen may include, but are not limited to, interacting with an interactive button (not shown), and closing the treatment door room. The analytics server turns on the screen on the gantry based on opening the treatment door room, receiving a trigger from a device (e.g., the console), and the like. The analytics server may display the screen corresponding to the current workflow stage.

In some embodiments, upon completion of the treatment, a portion of the workflow may repeat such that additional areas of the patient's body may be treated. For example, the workflow may restart at Stage Two, such that the patient is realigned to receive treatment for a second body part. The user may use various workflow oriented GUIs described herein to prepare the patient for additional treatments.

At step 419, the analytics server displays a page on a GUI representing Stage Seven. In this example, Stage Seven relates to unloading the patient. The analytics server adjusts (and/or communicates with another device to adjust) the couch and/or gantry into an ending position such that the patient is able to dismount from the couch.

In other embodiments, upon completion of the treatment, the workflow may proceed to Stage Seven, Unload. FIG. 4P illustrates page 400p of Stage Seven, Unloading, according to an embodiment. Some of the graphical indicators on page 400p are similar to graphical indicators on various other pages. For instance, text 425P may describe identifying patient information. For example, the patient's first and last name, date of birth, and patient identifier may be displayed by the analytics server based on the RT file for the one or more patients and the patient schedule for radiotherapy treatment.

Additionally, or alternatively, the workflow may proceed to Stage Seven at any time based on the user's input. For instance, the user (at any time) may interact with the unload button on the pendant (button 336) and the workflow proceeds to the unload stage. This option is available at any point in the workflow, such that the user is able to extract the patient from treatment position in case of emergency.

Graphical indicator 462P displayed by the analytics server conveys to the user and/or patient the number of remaining radiotherapy treatments. As shown, the graphical indicator 462P may indicate the number of remaining radiotherapy treatments for multiple diagnosed areas of the body. Further, graphical indicator 462P is displayed horizontally in the middle of the page. In alternate embodiments, the number of remaining radiotherapy treatments for multiple diagnosed areas may be vertically stacked instead of horizontal, as shown.

Text 464P may convey information about the patient's upcoming medical appointments. The upcoming medical appointments may be appointments with doctors, appointments for radiotherapy treatments, appointments for therapy, and the like. Text 464P may convey information about upcoming medical appointments on the same day as treatment. Alternatively, text 464P may convey information about upcoming medical appointments in the future.

Background 480P may be a non-treatment related image, a treatment related image, a solid color, a pattern, and the like. The patient will likely view the background 480P as treatment completes and the gantry and/or couch are being adjusted such that the patient can exit the radiotherapy machine. In some embodiments, background 480P may be the same background as in page 400k in FIG. K. In alternate embodiments, background 480P may be a different background as in page 400k in FIG. K.

Surface Matching

FIG. 5A illustrates a flowchart depicting operational steps performed by the analytics server in accordance with an embodiment. The method 500a describes how a server, such as the analytics server described in FIG. 1A, displays various interactive pages configured to display surface matching performed on a patient (e.g., a person to be treated by the radiotherapy machine). Even though the method 500a is described as being executed by the analytics server, the method 500a can be executed by any server(s) and/or performed locally using a computer/processor associated with the radiotherapy machine and/or the console (as discussed in FIGS. 11A-11L). Other configurations of the method 500a may comprise additional or alternative steps, or may omit and/or mix one or more steps altogether.

At step 502, the analytics server retrieves, from a RT file associated with a patient, information about a particular patient. The particular patient may be the patient being treated by the radiotherapy machine. The information about the particular patient may include surface matching information such as reference material. The reference material may include data associated with an alignment angle(s) for treatment of a region of a body. The RT file containing information about a particular patient may be retrieved from one or more medical databases (such as the medical database in FIG. 1A), servers, files, and the like.

The RT file may comprise a patient identifier. The patient identifier may be a series of numbers and/or letters to identify patients. A user (e.g., technician, doctor, nurse, or other professional) and/or system administrator may determine the patient identifiers and map the patient identifiers with particular patients. Additionally, or alternatively, the analytics server may update the RT file such that the RT file contains the mapped patient identifiers and associated patients. Additionally, or alternatively, the analytics server may store the mapped patient identifiers and associated patients.

The RT file may further include various treatment details associated with the patient's treatment. For instance, the RT file may include various couch/gantry attributes, such as couch angles, gantry rotation attributes (e.g., full or partial arcs), the number of partial arcs (if applicable), control points, and the like associated with each patient. In an example, the RT file may include the amount of dose delivered to the patient at each determined control point of the planned machine position.

In addition, the RT file may contain patient information, including PII such as the diagnoses of the patients, the name of the patient, nicknames of the patient, the birthdate of the patient, one or more photos of the patient, and the like. The RT file may also contain notes from one or more doctors regarding the patient and/or the diagnoses of the patient, and medical diagnoses tools such as x-ray scans, including computed tomography (CT) scans, ultrasound images, and the like. The RT file may also include whether the treatment is a VMAT treatment or IMRT treatment.

Additionally, or alternatively, the analytics server may retrieve information contained within the RT file from one or more source. For instance, the patient identifier may be retrieved by the analytics server from a medical database (such as the medical database in FIG. 1A), the treatment details associated with the patient's treatment may be retrieved from a doctor's file. Additionally, or alternatively, the analytics server may retrieve various portions of information from various source. For instance, patient identifiers and treatment details associated with the patient's treatment may be retrieved by the analytics server from a medical database (such as the medical database in FIG. 1A). Moreover, some PII may be retrieved by the analytics server from a patient file, while other PII may be retrieved by the analytics server from a library.

As discussed herein, the RT file may contain reference material. The analytics server may retrieve the reference material from the RT file. Additionally, or alternatively, the analytics server may generate reference material based on the various treatment details associated with the patient's treatment, patient attributes, and the like. For instance, the analytics server may be in communication with one or more servers, databases and/or devices to enable the analytics server access to files, notes, and the like. Additionally, or alternatively, the analytics server may receive the reference material from one or more third parties (e.g., vendors, other hospitals, other clinics, and the like).

The reference material may be a plurality of reference surfaces, images and/or attributes of a patient indicating regions of the patient to be treated (e.g., needing radiotherapy treatment). The reference material may indicate that a part of the patient's body in a satisfactory position for treatment. The satisfactory position for treatment may be indicated by positioning a particular area of the body at an alignment angle(s) with reference to an isocenter or other reference points. The positioning of the particular area of the body at the alignment angle(s) allows the radiotherapy machine to radiate the positioned particular area of the body while minimizing radiation exposure to other parts of the body and avoiding collisions during the treatment (because the patient is aligned with respect to the reference position). The alignment angle(s) (and corresponding satisfactory position for treatment) may be predetermined by users and/or system administrators and retrieved by the analytics server (for example, from the RT file) and/or received by the analytics server as an input from the users and/or system administrators.

The reference material may be various patient attributes. For example, the analytics server may use measurements of the patient's body to determine that the patient is aligned according to the alignment angle(s). The analytics server may determine the measurements of the patient's body based on one or more cameras or other devices feeding the analytics server images and/or live video data. Additionally, or alternatively, a user may input patient measurements such that the analytics server receives measurements of the patient's body. The analytics server may also retrieve measurements of the patient's body from the RT file or other one or more servers, files and/or databases.

The reference material may be a reference surface. For example, a reference surface may illustrate a proper position for treatment (determined by the alignment angle(s)) of treating a particular patient with breast cancer in their left breast. The reference surface may be a surface of the particular patient. For instance, the reference surface may be a three-dimensional model of the particular patient (e.g., an animation). The analytics server may retrieve a reference surface of the patient from the RT file, one or more databases, servers, files, third parties, and the like. Additionally, or alternatively, the analytics server may generate a reference surface of the patient based on information retrieved from RT file, one or more databases, servers, files, third parties, and the like.

Additionally, or alternatively, the reference surface may be a surface of a model patient. For instance, the model patient may be a patient being treated for breast cancer in their left breast (e.g., not the particular patient being treated for breast cancer in their left breast). Additionally, or alternatively, the model patient may be rendering of a patient positioned in a satisfactory position for treatment for treatment of cancer in the left breast and/or a user demonstrating a satisfactory position for treatment for breast cancer in the left breast. Additionally, or alternatively, the reference surface may be a three-dimensional model (e.g., an animation) of the model patient, in a satisfactory position for treatment of cancer in the left breast. Different perspectives of reference surfaces (e.g., of a model patient and/or particular patient to be treated) may be stored by the analytics server.

The reference material may be a two-dimensional image. The reference image may be based on, for instance, prior images of the patient during the patient planning. For example, the analytics server (or other server and/or device such as a camera) may have captured an image of the patient during a procedure associated with the patient planning (e.g., a CT scan). It is beneficial to treat the patient in the same position such that the same part of the body is treated, increasing the likelihood of successful treatments.

In the event the analytics server retrieves a reference image, the analytics server may convert the image into a three-dimensional reference surface using for instance, photogrammetry. In an example, the analytics server may execute photogrammetry to determine three-dimensional measurements from a reference image. The scale of the reference image may be determined, for instance, by measuring various distance of the patient (e.g., length of arms, length of legs, width of the torso, and the like) and/or using patent attributes. The analytics server may associate the measured distances of the patient and/or patient attributes with one or more reference images of patient. The analytics server may use the measured distances of the patient and/or patient attributes to construct depths in the reference image (e.g., converting the reference image into a reference surface).

Additionally, or alternatively, the reference material may be based on, for instance, a three-dimensional model of the patient generated using data collected from multiple perspectives of the patient's diagnoses material. For example, a plurality of cameras may capture continuous time series images of the patient during a procedure associated with the patient's diagnoses (e.g., a three-dimensional CT scan and/or four-dimensional CT scan imaging) from multiple perspectives. The plurality of cameras may also capture a stream of video data from multiple perspectives during the patient's diagnoses that the analytics server (or other device) may transform into frames. A frame can be considered a window of video data of a fixed duration of time.

Images of the patient may be captured using one or more cameras (or other devices capable of producing an image). The images of the patient may be captured when the patient is positioned on a couch of a radiotherapy machine. Additionally, or alternatively, a three-dimensional model of the patient positioned on the couch may be captured and/or generated by the analytics server based on the continuous time series images or frames of video data from multiple perspectives. Multiple perspectives of the patient may be captured by a plurality of cameras. As described in FIGS. 2A-2F, the analytics server may be in communication with a plurality of cameras (e.g., couch camera, gantry camera, or other cameras places within the radiotherapy room). The analytics server may use various methods (e.g., time of flight and/or triangulation) to generate a three-dimensional model of the patient from the plurality of cameras using continuous time series images or frames of video data.

In some configurations, the system may use structured light scanning technology, and/or time of flight technology, and/or any other known three dimensional imaging technology to analyze the patient's positions on the couch.

As an example, the analytics server may associate a two-dimensional pixel in the continuous time series images or frames of video data with a ray in three-dimensional space. Given multiple perspectives of the continuous time series images or frames of video data (e.g., at least two sets of continuous time series images or frames of video data capture the position of the patient from at least two different perspectives), a three-dimensional point can be obtained as the intersection of at least two rays from pixels of the continuous time series images or frames of video data.

The analytics server may execute various consistency functions to determine that the rays from the continuous time series images or frames of video data are associated with consistent pixels. For instance, a pixel from a first perspective of an image, mapped to a three-dimensional point using a ray based on the first perspective of the image, is consistent with a pixel from a second perspective of an image mapped to the same three-dimensional point using a ray from the second perspective of the image. The analytics server may determine from the consistency functions, whether the pixels used to determine the three-dimensional point are similar colors, for instance.

At step 504, the analytics server may present for display on a graphical user interface, an image corresponding to the patient positioned on a couch of a radiotherapy machine, the image comprising an overlay on a surface of the patient in the treatment region. The analytics server displays a graphical user interface (GUI) on a screen associated with the radiotherapy machine (e.g., the screen positioned on the gantry as described in FIGS. 2A-2F). The screen may be placed onto (other otherwise connected to) the radiotherapy machine itself, such as by placing the screen on the throat (or any other part) of the gantry. The screen may instead be placed in the treatment room (e.g., the same room as the radiotherapy machine). Various other screens may display the GUI displayed by the analytics server. For instance, screens in rooms outside of the treatment room (such as a room monitoring the treatment room) may display the GUI displayed by the analytics server. Additionally, or alternatively, the GUI may be displayed on various platforms. For instance, a user may view the GUI displayed by the analytics server on the various platforms by executing an application such as a browser application.

The analytics server may display on a page of the GUI a representation of the patient on a couch of the radiotherapy machine. The representation of the patient may be a three-dimensional model (revised in real time or near real time) of the patient generated by the analytics server, a live view of the patient received by the analytics server from one or more cameras, an image of the patient, or the like. The representation of the patient may capture the patient positioned on the couch of the radiotherapy machine.

The GUI may overlay (superimposed layers) the reference surface on top of the representation of the patient. For example, the reference surface may appear as a "ghost" surface (e.g., a translucent surface). Additionally, or alternatively, the representation of the patient may be overlaid on top of the reference surface. The GUI displays the overlaid reference surface and representation of the patient on a page of the GUI.

In one configuration, the GUI may not display the overlaid reference surface and representation of the patient on the page, and the analytics server may use the reference surface and representation of the patient for calculations and processing. The GUI may display either the reference surface or the representation of the patient on the page. Additionally, or alternatively, in such configurations, the analytics server may display either the reference surface or the representation of the patient on the page only in the event the surfaces are not matching within a predetermined error (e.g., the reference surface does not match within a predetermined error the representation of the patient). Additionally, or alternatively, the GUI could also display only selected information resulting from the calculation and processing that is relevant for the given stage of the treatment, e.g., breathing curve during gated or DIBH treatments.

In step 506, the analytics server may present for display, a visually distinct revised overlay for at least a portion of the surface of the patient in the treatment region that matches, within a predetermined margin of error, the alignment data. The analytics server may present a revised page for display. The revised page may indicate whether the position of the representation of the patient matches (within a predetermined margin of error) the reference surface. Additionally, or alternatively, the revised page may indicate whether the position of the reference surface matches (within a predetermined margin of error) the representation of the patient. The predetermined margin of error may be determined by a user and/or system administrator. For example, the area needing radiotherapy treatment (e.g., the treatment region) may be compared to the alignment angle(s) for treatment. The analytics server may perform surface matching to determine whether the position of the representation of the patient matches (within a predetermined margin of error) the reference surface (or whether the position of the reference surface matches (within a predetermined margin of error) the representation of the patient).

In one example, a surface of the patient derived from the position of the representation of the patient from the generated three-dimensional model may be matched to the reference surface because the two surfaces have the same underlying geometry. For instance, the underlying geometry of a treatment region of a male patient's torso likely will not change from being captured during planning (e.g., represented by a reference surface) to being captured in preparation for treatment (e.g., represented by a three-dimensional model representation of the patient on the couch).

In another example, a surface of the patient derived from the position of the representation of the patient from the live feed of the patient on the couch may be matched to the reference surface because the two surfaces have the same underlying geometry.

The analytics server may map the points from the generated three-dimensional model to corresponding points on the reference surface. For instance, points in a point cloud corresponding to a first model (e.g., the generated three-dimensional model) may be rotated and translated such that the points in the point cloud corresponding to the first model may be mapped to points in a point cloud of a second model (e.g., the reference surface). That is, the model of the patient may be rotated into the point cloud of the reference surface. In an example, the iterative closest point algorithm (ICP) maps and translates points of the first model to points in the second model by iteratively determining closest corresponding points of the first model on the second model. The determination of the closest corresponding points may be optimized using an optimization function such as the least square error to optimize the position of points every iteration. Other geometric attributes (such as metric, mean curvature, and textures) may be mapped from the first model to the second model.

The analytics server may perform surface matching in real time (or near real time) such that the patient and/or user can visually identify the differences between the positions of the representation of the patient (revised in real time and/or near real time based on the patient's movements) and the reference surface (e.g., the satisfactory position for treatment based on the alignment angle(s)). The analytics server may indicate the differences between the representation of the patient and the reference surface by overlaying the reference surface and/or representation of the patient using one or more colors. The one or more colors can be used on the GUI to represent whether the position of the representation of the patient matches (within the predetermined margin of error) the satisfactory position for treatment (indicated by the alignment angle(s) optimized for treatment represented by the reference surface). Additionally, or alternatively, the GUI can display an indication of the difference between the representation of the patient and the reference surface by overlaying the reference surface and/or representation of the patient with patterns (e.g., hatch, stripes, and dots), textures, shininess, opaqueness or any other appropriate method of visually distinguishing the reference surface from the representation of the patient.

Additionally, or alternatively, the GUI may indicate the difference between the representation of the patient and the reference surface by overlaying a surface and/or object on top of the reference surface and/or patient. The overlaid surface and/or object may be overlaid one or more colors to represent whether the position of the patient matches (within the predetermined margin of error) the satisfactory position for treatment (indicated by the alignment angle(s) for treatment represented by the reference surface). Additionally, or alternatively, the analytics server may display the representation of the patient and the reference surface without overlaying the reference surface and/or representation of the patient respectively. For example, the analytics server may use the representation of the patient annotated and/or intersected with the reference surface . . . .

Referring now to FIGS. 5B-5C, non-limiting examples of the analytics server displaying surface matching on a representation of a patient are depicted, according to an embodiment. In some embodiments, FIGS. 5B-5C are presented for display by the analytics server on a GUI. The GUI may be displayed on a screen associated with a radiotherapy machine.

FIG. 5B illustrates an example page 500*b* of the GUI displaying surface matching, according to an embodiment. Model 510B is a graphical representation of a patient. In some embodiments, model 510B may be a reference surface of the patient, where the reference surface derived from one or more alignment angle(s)/locations of the patient in a satisfactory position for treatment. In other embodiments, model 510B may be a live view of the patient from one or more cameras in the treatment room. As shown, model 510B is a three-dimensional (e.g., animation) of a patient positioned on a couch of the radiotherapy machine.

The GUI may display the indicators 512B as an overlay to the model 510B. The GUI may present an overlay on the model 510B with an object and/or surface having indicator 512B. Indicator 512B may be any suitable method of visually distinguishing alignment information. The alignment information may be determined from the surface matching performed by the analytics server. For instance, the alignment information may represent whether the representation of the position of the patient matches (or is within a predetermined margin of error) the reference surface.

Additionally, or alternatively, the alignment information, based on the results of the surface matching, may represent the extent to which the representation of the position of the patient matches (or is within a predetermined margin of error) the reference surface. The extent to which the representation of the position of the patient matches the reference surface may be evaluated using the number of iterations required for the ICP algorithm to map a closest point in the representation of the patient to a closest point in the reference surface. For example, in the event that the analytics server uses ICP to perform surface matching, one or more thresholds relating to the iterations in the ICP algorithm may be determined. The thresholds may be determined based on a user and/or system administrator. For instance, in the event that one-hundred or more iterations are required for the ICP algorithm to map a closest point in the representation of the patient to a closest point in the reference surface, the analytics server may determine that the position of the patient (represented by the representation of the patient) is for instance, 50 cm away from the satisfactory position for treatment.

As illustrated in this example, indicator 512B is a color (e.g., green) that is visually distinct from the surface color of the model 510B. In some embodiments, indicator 512B may be a pattern, texture, color(s), and the like that is visually distinct from a pattern, texture, color(s), and the like used to identify model 510B. In other embodiments, there may be multiple indicators. For example, an indicator with an associated visual pattern may indicate that part of the patient's body is below the reference surface. A different indicator with a different associated visual pattern may indicate that part of the patient's body is above the reference surface. The indicators and their associated meanings may be determined by a user and/or system administrator.

As shown in FIG. 5B, model 510B is nearly in a position satisfactory for treatment. A patient and/or user may determine that model 510B is nearly in a position satisfactory for treatment because indicator 512B is hardly visible. When the position of the patient is such that the representation of the patient (model 510B) matches the reference surface (or is within a predetermined margin of error), the GUI presents little or no indicator 512B. The analytics server can recognize when the patient is in a satisfactory position and indicate that position is satisfactory or that the next step is available.

Alternatively, when the position of the patient is such that the representation of the patient (model 510B) matches the reference surface (or is within a predetermined margin of error), the GUI can overlay the matched areas of the position of the patient to show a color indicating a match rather than removing an overlay color where there is no match.

FIG. 5C describes an example page 500c of the GUI displaying surface matching, according to an embodiment. Model 510C may be similar in operation and function as model 510B. Indicator 512C may be similar in operation and function as indicator 512B. Model 510C is a graphical representation of a patient, and indicator 512C is a color that is visually distinct from a color used to identify model 510C.

As shown in the example page 500c, model 510C is not in a position satisfactory for treatment. A patient and/or user may determine that model 510C is not in a position satisfactory for treatment because indicator 512C is very visible (e.g., there are significant portions of the patient's surface that covered in the overlay color. As shown, when the position of the patient is such that the representation of the patient (model 510C) does not match (or is not within a predetermined margin of error) with the reference surface, the GUI will display using indicator 512C (a color on the surface of the model 510C).

Alternatively, when the position of the patient is such that the representation of the patient (model 510C) does not match with the reference surface (or is not within a predetermined margin of error), the GUI can overlay the matched areas of the position of the patient to show a color indicating a match rather than removing an overlay color where there is no match.

Virtual Dry Run

Figure 6A:
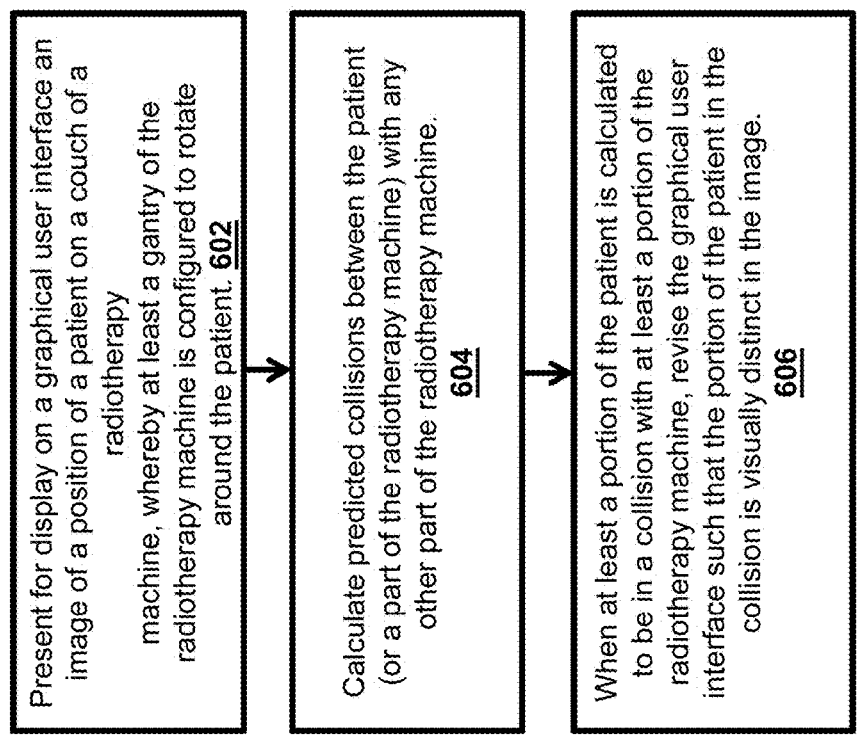
FIG. 6A illustrates a flow diagram executed in a workflow-oriented radiotherapy system, according to an embodiment.
Figure 6B:
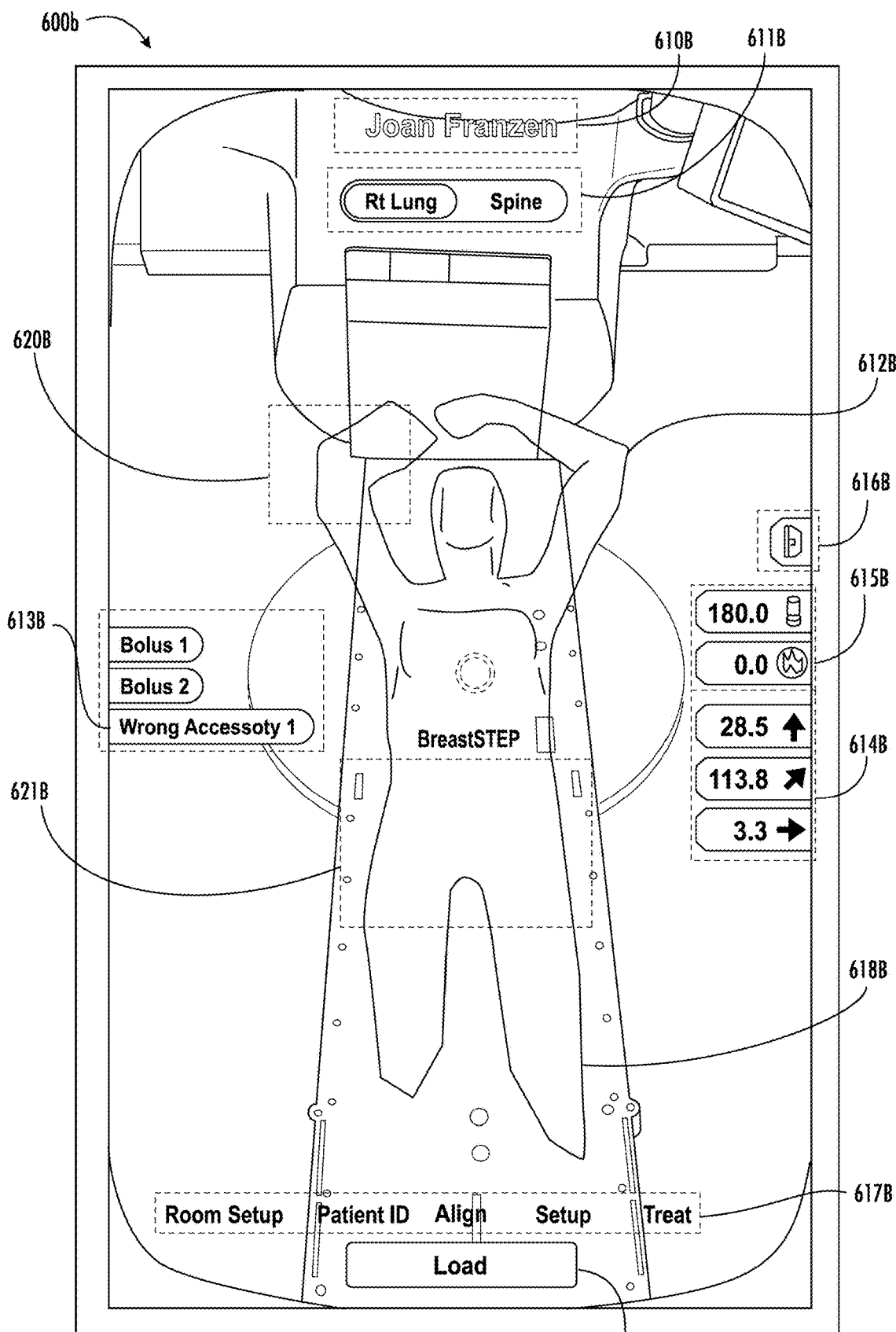
FIGS. 6B-6G illustrate pages displayed in a workflow-oriented radiotherapy system, according to an embodiment.

FIG. 6A illustrates a flowchart depicting operational steps performed by the analytics server in accordance with an embodiment. The method 600a describes how a server, such as the analytics server described in FIG. 1A, presents for display a GUI having various interactive pages corresponding to various stages of performing radiotherapy on a patient (e.g., a person being treated by the radiotherapy machine). Even though the method 600a is described as being executed by the analytics server, the method 600a can be executed by any server(s) and/or performed locally using a computer/processor associated with the radiotherapy machine and/or the console (as discussed in FIGS. 11A-11L). Other configurations of the method 600 may comprise additional or alternative steps, or may omit and/or mix one or more steps altogether.

Using the method 600a, the analytics server may determine whether the patient (or any devices attached to the patient) is projected to collide with any part of the radiotherapy machine, such as any part of the gantry, couch, imagers, accessories, or even any unknown object detected within the treatment room). Therefore, collision of the patient is not limited to the collision of the patient with the gantry. As used herein, a patient (or a part of the radiotherapy machine) is projected to collide with any part of the radiotherapy machine, when the patient (or a part of the radiotherapy machine) is within a planned trajectory of the radiotherapy machine.

The method 600a is not limited to projecting whether the patient is within the planned trajectory of the radiotherapy machine (e.g., collides with any part of the radiotherapy machine, such as the gantry, imager, or any other part of the radiotherapy machine). In some configurations, the analytics server may project that a part of the machine (e.g., imager) will collide with another part of the machine (e.g., couch).

At step 602, the analytics server may instruct one or more screens to display a page of the GUI. For example, the analytics server may present for display on a screen associated with the radiotherapy machine (e.g., the screen positioned on the gantry as described in FIGS. 2A-2F). The screen may be placed onto (other otherwise connected to) the radiotherapy machine itself, such as by placing the screen on the throat (or any other part) of the gantry. The screen may also be placed in the treatment room (e.g., the same room as the radiotherapy machine). Various other screens may display the pages presented by the analytics server. For instance, screens in rooms outside of the treatment room (such as a room monitoring the treatment room) may display the pages presented by the analytics server. Additionally, or alternatively, the GUI may be displayed on various platforms. For instance, a user (e.g., technician, doctor, nurse or other professional) or other third party may view the GUI on the various platforms by executing an application such as a browser application.

The radiotherapy machine allows adjustment of the gantry and/or the couch. For example, during non-coplanar treatment, both the couch and the gantry adjust to various positions to maximize the radiation exposure to areas of the body requiring treatment and limit the radiation exposure to areas of the body that are healthy. The radiotherapy machine may adjust positions of the couch and/or gantry for based on executing a virtual dry run. For instance, the analytics server may execute the virtual dry run protocol and determine that the patient is in risk of collision with the gantry. As a result, the analytics server may either prompt the user to move the couch (e.g., lower the couch by an amount to avoid the possible collision), automatically move the couch itself, or prompt the user to re-plan the treatment.

The analytics server may generate, receive, or retrieve a representation of a patient on the couch of the radiotherapy machine, representations of the gantry, and/or representations of the couch (e.g., FIGS. 4A-4P). The analytics server may present for display on the GUI the representations of the patient on the couch of the radiotherapy machine, representation of the gantry, and/or representation of the couch.

The analytics server is in communication with a plurality of cameras (e.g., camera at an end of the couch, gantry camera, or other cameras placed within the radiotherapy room and the like) to capture images, continuous time series images, point clouds, 3D surfaces, 3D models, or streams of video data from one or more perspectives of the patient, the accessories around the patient, the couch, and/or the gantry (e.g., FIGS. 4A-4P). The analytics server may use any appropriate method of generating models or images for the GUI to represent the patient on the couch of the radiotherapy machine, the couch, and/or the gantry. Additionally, or alternatively, the analytics server may use the live feed of data captured from the plurality of cameras from one or more perspectives as representations of the patient on the couch of the radiotherapy machine, the couch, and/or the gantry.

Even though certain aspects of embodiments described herein describe the analytics server receiving images and streams from the camera, it is expressly understood that the methods described herein are not limited to those embodiments. For instance, the analytics server may directly receive patient positioning data from the camera.

The analytics server may receive an input from a user to execute a virtual dry run or may automatically perform the dry run at appropriate times (e.g., between different stages). When the analytics server executes the virtual dry run, the analytics server virtually steps through satisfactory treatment positions of the couch position, gantry position, and/or the patient position that will be performed during treatment. As discussed herein, the treatment positions of the couch position, gantry position, and/or patient position may be retrieved and/or received by the analytics server (e.g., FIGS. 4A-4P). For example, satisfactory treatment positions, or machine trajectories, of the couch position, gantry position, and/or the patient position may be retrieved by the analytics server from one or more servers, databases, files, or the like.

The analytics server may predict collisions (or interference) that are likely to occur based on the virtual dry run. Collisions predicted may include, for example, collisions between the gantry and the couch, collisions between the gantry and the patient positioned on the couch, collisions between the gantry and one or more patient accessories required for treatment, collisions between the couch and the one or more patient accessories required for treatment, and collisions between the patient and the one or more patient accessories required for treatment.

At step 604, the analytics server may calculate one or more predicted collisions between a part of the radiotherapy machine and at least one of (a) the patient or (b) another part of the radiotherapy machine. The analytics server may determine whether any part of the patient (or the radiotherapy machine) is within the planned trajectory of the radiotherapy machine. The analytics server may project a collision based on the positon of the patient (or a part of the radiotherapy machine) and the planned trajectory. The analytics server may use various collision detection methodologies to determine whether the patient (or any part of the radiotherapy machine) is within the planned trajectory of the radiotherapy machine (e.g., gantry). For instance, the analytics server may determine a planned trajectory of the gantry based on the patient's treatment plan and further determine if any of the radiotherapy machine (e.g., imager) or the patient (e.g., patient's arm) is within that trajectory.

In some configurations, the collision detection may be based on a representation of the patient positioned on the couch and a representation of the gantry (couch, or patient accessory) or its planned trajectory. The representation of the patient positioned on the couch may be an image on the GUI of the patient positioned on the couch captured by one or more cameras. The representation of the patient positioned on the couch may also be a generated three-dimensional model of the patient positioned on the couch from the plurality of cameras using continuous time series images or frames of video data.

The representation of the patient positioned on the couch may also be retrieved from stored images and/or models. For example, an image stored by the analytics server may be one or more prior images of the patient positioned on the couch such as an image of the patient during the patient's diagnoses procedure(s). For example, the analytics server (or other server and/or device such as a camera) may have captured an image of the position of the patient during a procedure associated with the patient's diagnoses (e.g., a CT scan). Further, as opposed to using an image captured by the analytics server (or other server and/or device such as a camera) of an area of a particular patient to be treated, the image stored by the analytics server may be an image of a model patient in a position on the couch. The model patient may be a rendering of a patient being treated based on a similar diagnosis to the particular patient. Additionally, or alternatively, the stored image and/or model of the patient positioned on the couch (or a model patient positioned on the couch) may be retrieved by the analytics server from one or more third parties, servers, databases, files and the like.

Additionally, or alternatively, the images and/or models stored by the analytics server may be continuous time series images of the patient captured during a procedure associated with the patient's diagnoses (e.g., a CT scan) from multiple perspectives. The continuous time series images may be captured for instance, by one or more cameras from a plurality of cameras and/or other devices capable of capturing continuous time series images of the patient. Additionally, or alternatively, one or more cameras (e.g., out of the plurality of cameras) may capture a stream of video data from multiple perspectives during the patient's diagnoses procedure(s) that may be transformed into frames. Further, as opposed to using continuous time series images or frames of video data captured by one or more cameras from multiple perspectives of an area to be treated of a particular patient, the image stored by the analytics server may be based on a model patient in a position on the couch, or on a 3D model of the patient.

Additionally, or alternatively, the stored image and/or model of the patient positioned on the couch (or a model patient positioned on the couch) may be retrieved by the analytics server from one or more third parties, servers, databases, files and the like.

The representation of the gantry (couch, or patient accessories) may be an image captured by the one or more cameras. Additionally, or alternatively, the representation of the gantry (couch, or patient accessories) may be an image received by the analytics server by a vendor, user, in-house designer, and the like. In some embodiments, the analytics server may convert the image of the gantry (couch, or patient accessories) to a three-dimensional model of the gantry (couch, or patient accessories) using photogrammetry as described herein.

The representation of the gantry (couch, or patient accessories) may be a three-dimensional model generated by the analytics server employing various methods (e.g., time of flight and/or triangulation) on continuous time series images or frames of video data. Additionally, or alternatively, the representation of the gantry (couch, or patient accessories)

may be a three-dimensional model received by the analytics server by a third-party vendor, user, in-house designer, and the like.

In an example, the analytics server may use at least the representation of the gantry and the representation of the patient to determine whether a collision may occur between the gantry and the patient positioned on the couch. Additionally, or alternatively, the analytics server may use at least the representation of the gantry and the representation of the couch to determine whether a collision may occur between the gantry and the couch. In alternate embodiments, the analytics server may combine one or more representations (the representation of the couch, the representation of the patient). Additionally, or alternatively, the analytics server may modify one or more representations of the couch, gantry and patient before determining whether a collision will occur. For instance, a patient's clothing may become part of the representation of the patient and the patient's clothing may hang off the side of the couch, creating the appearance of a collision of the patient and the couch. The analytics server may crop and/or remove a portion of the model of the patient that extends below a plane of the couch.

As an alternative to a 3-D or 2-D model, the analytics server may project the possible collision using geometric representations of the couch, gantry, patient, and/or movement of the gantry. The analytics server may generate geometric shapes representing the patient, gantry, couch, and/or movement of the gantry. Additionally or alternatively, the analytics server may retrieve geometric shapes of the representation of the patient, gantry, couch and/or movement of the gantry from one or more servers, databases, files and the like. The analytics server may use these geometric shapes and apply various geometric models to determine whether the shapes (representing the patient and/or different parts of the radiotherapy machine) will collide.

The analytics server may determine whether a collision may occur between the gantry and the patient. The analytics server utilizes a geometric model of the gantry and a three-dimensional point cloud of the position of the patient, for instance, derived from the three-dimensional model of the patient and/or retrieved from the analytics server from one or more servers, databases, files, or the like. Additionally, or alternatively, the analytics server can evaluate whether various portions of the patient will collide (or likely collide) with various portions of the gantry or other components (e.g., accessory) of the radiotherapy machine.

The analytics server can determine whether a collision may occur between the gantry and the patient by iteratively checking points in the three-dimensional point cloud of the patient and determining, whether coordinates of the three-dimensional point cloud of the position of the patient are contained within (or intersect with) a portion of the gantry. For example, the head of the gantry may be geometrically modeled as a set of cylinders. The analytics server may determine whether points in the three-dimensional point cloud of the position of the patient are above a bottom surface of a cylinder and below a top surface of the cylinder.

The analytics server may determine that a collision may occur near a portion of the head of the gantry when the one or more points in the three-dimensional point cloud of the position of the patient are above the bottom surface of the cylinder and below the top surface of the cylinder. The analytics server may determine that a collision may not occur near a portion of the head of the gantry when the one or more points in the three-dimensional point cloud of the position of the patient are not above the bottom surface of the cylinder and below the top surface of the cylinder. The analytics server may determine that a collision may not occur near a portion of the head of the gantry when the one or more points in the three-dimensional point cloud of the position of the patient are above the bottom surface of the cylinder and not below the top surface of the cylinder Additionally, or alternatively, the analytics server may determine whether the patient is projected to have a collision by evaluating how close the points in the point cloud are to the surfaces of any part of the radiation therapy machine (e.g., a portion of the head of the gantry, couch, imagers, accessories or an unknown object detected within the treatment room). For example, whether the patient is projected to have a collision may be determined by the analytics server based on the proximity of the three-dimensional point cloud of the position of the patient to coordinates of the geometric shapes of the gantry. One or more thresholds may be defined by users to determine proximities indicative of collision or non-collision. The analytics server may use the ICP algorithm to iteratively loop through the points of the three-dimensional point cloud of the position of the patient point cloud.

The analytics server may iteratively check the three-dimensional point cloud of the position of the patient and the geometric shape representation of the gantry according to the treatment positions of both the gantry and the patient that will be executed during treatment. The treatment positions of the gantry such as the gantry angles may be determined from the treatment information retrieved from the RT file or the one or more servers, databases and files. The treatment positions of the patient such as the alignment angles may be determined from the treatment information retrieved from the RT file or the one or more servers, databases and files.

Additionally, or alternatively, the analytics server may iteratively check the three-dimensional point cloud of the position of the patient and the shape defined by the movement of the gantry. For instance, the shape defined by the movement of the gantry may be a cylinder in which one or more users have determined that anything inside of the cylinder will not result in a collision during treatment. That is, the analytics server may determine whether a collision is projected to occur using a collision-free envelope of the projected path of the gantry.

The description for step 604 includes non-limiting examples of how the analytics server can determine whether the patient may collide with the gantry during treatment. Other non-limiting examples of performing collision detection can be found in U.S. Pat. Nos. 9,886,534, 10,272,265, 10,166,406, 9,764,163, 10,493,298, 10,086,215, and 10,073, 438, and PCT application No. PCT/US2014/049078, each of which is incorporated by reference in its entirety.

At step 606, when a portion of the patient is calculated to be in a collision with the part of the radiotherapy machine, the analytics server may revise the graphical user interface such that the portion of the patient calculated to be in the collision is visually distinct in the image.

The analytics server may update (in real-time or near real-time) the image of the position of the patient on the couch of the radiotherapy machine. The analytics server may update the image of the position of the patient on the couch based on whether the analytics server determines that a collision will occur, as (or after) the analytics server determines whether collisions will occur. The GUI may display, on a page having the image of the position of the patient on the couch, whether the patient is projected to have a collision. The GUI may also display whether the analytics server has determined the patient, gantry and/or couch will collide.

For example, the GUI may display that the patient (or a portion of the patient) will collide (based on, for instance iteratively looping through points of the three-dimensional patient point cloud and determining whether the points are contained within the geometric shapes of portions of the gantry) by marking the area of collision on the displayed representation of the gantry (according to the geometric shape of the gantry). The analytics server may mark the area of collision on the displayed representation of the gantry using colors, patterns, shininess, opaqueness, textures or other visually distinctive identifiers. Additionally, or alternatively, the analytics server may mark the area of collision on the displayed representation of the patient using colors, patterns, shininess, opaqueness, textures or other visually distinctive identifiers.

The analytics server may continuously/periodically monitor the patient's position (and/or position of the couch, gantry, and patient accessories) and may revise the displayed representations of the position of the couch, gantry, and patient accessories described herein in real-time (or near real-time). For instance, if the patient moves (after being properly positioned on the couch by the technician), certain portions of the patient's body may potentially collide with the gantry and/or patient accessories. As a result, the analytics server may revise a page (e.g., upon receiving an instruction from the user, or upon determination that a collision will occur) on the GUI indicating that the patient's new position has created a collision hazard.

In some embodiments, the analytics server may halt (or revise, such as by changing the speed) the movement of the gantry and/or the couch based on determining that the patient will collide with any part of the radiotherapy machine.

Referring now to FIGS. 6B-6G, non-limiting examples of the analytics server displaying a GUI having pages based on a virtual dry run are depicted, according to an embodiment. In other embodiments, the analytics server may not display all of the pages described herein and/or all the components of the page. For instance, the analytics server may display some (but not all) of the features described herein. The analytics server may display various combinations and configurations of the pages depicted herein.

The pages depicted in FIGS. 6B-6G illustrate one or more pages displayed by the analytics server via a display on a gantry, as described in FIG. 1A. The pages 600*b*-600*f* may use the same (or similar) graphical elements as discussed herein. For example, graphical elements displayed by the analytics server may include graphical indicators, status indicators, progress indicators, treatment related images, non-treatment related images, backgrounds, live feeds of the radiotherapy machine, and notes as discussed herein.

For instance, page 600*b* may include text 610B, conveying PII, text 611B indicating one or more areas of the patient requiring treatment, graphical indicator 616B (in conjunction with status indicators) indicating one or more safety features associated with the treatment room and/or console room, text 613B conveying hardware accessories (including medical devices), graphical indicator 615B representing machine alignment parameters, and progress indicator 617B indicating the progress of the user in the treatment workflow (e.g., highlighting a current stage of a workflow progression and displaying succeeding/preceding stages) as described similarly to the graphical elements in FIGS. 4A-4P.

Additionally, or alternatively, models 612B-D and 612F may represent the patient on the couch of the radiotherapy machine displayed by the analytics server. As shown, models 612B-D and 612F are three-dimensional animation representations of the patient. However, models 612B-D and 612F may also be a live feed image of the patient as positioned on the couch (or any other representation of the patient).

The analytics server may also employ one or more interactive buttons. Additionally, or alternatively, the analytics server may employ one or more interactive buttons with multiple functions. For example, interactive button 619B may initiate the virtual dry run, pause the virtual dry run program, restart the virtual dry run, and the like.

In the event the analytics server determines that a collision may occur, the analytics server may provide recommendations to the user to reduce the likelihood of the collision and/or eliminate the chance of collision. That is, the analytics server may coach (in real-time and/or near real time) the user using visual indicators, such that the patient, for instance, is realigned accordingly. The analytics server may accomplish this task using a variety of methods.

Figure 6C:
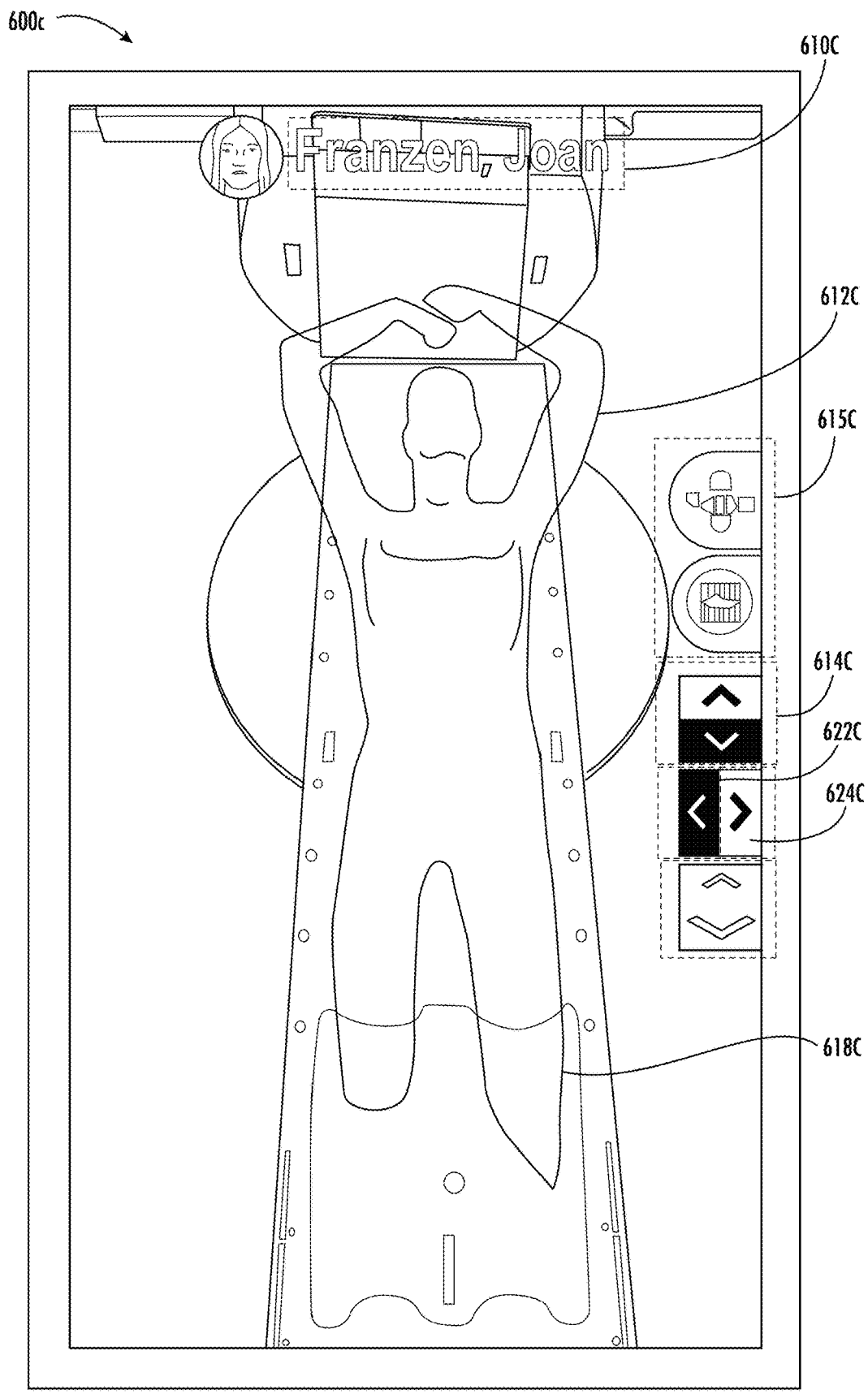
Figure 6D:
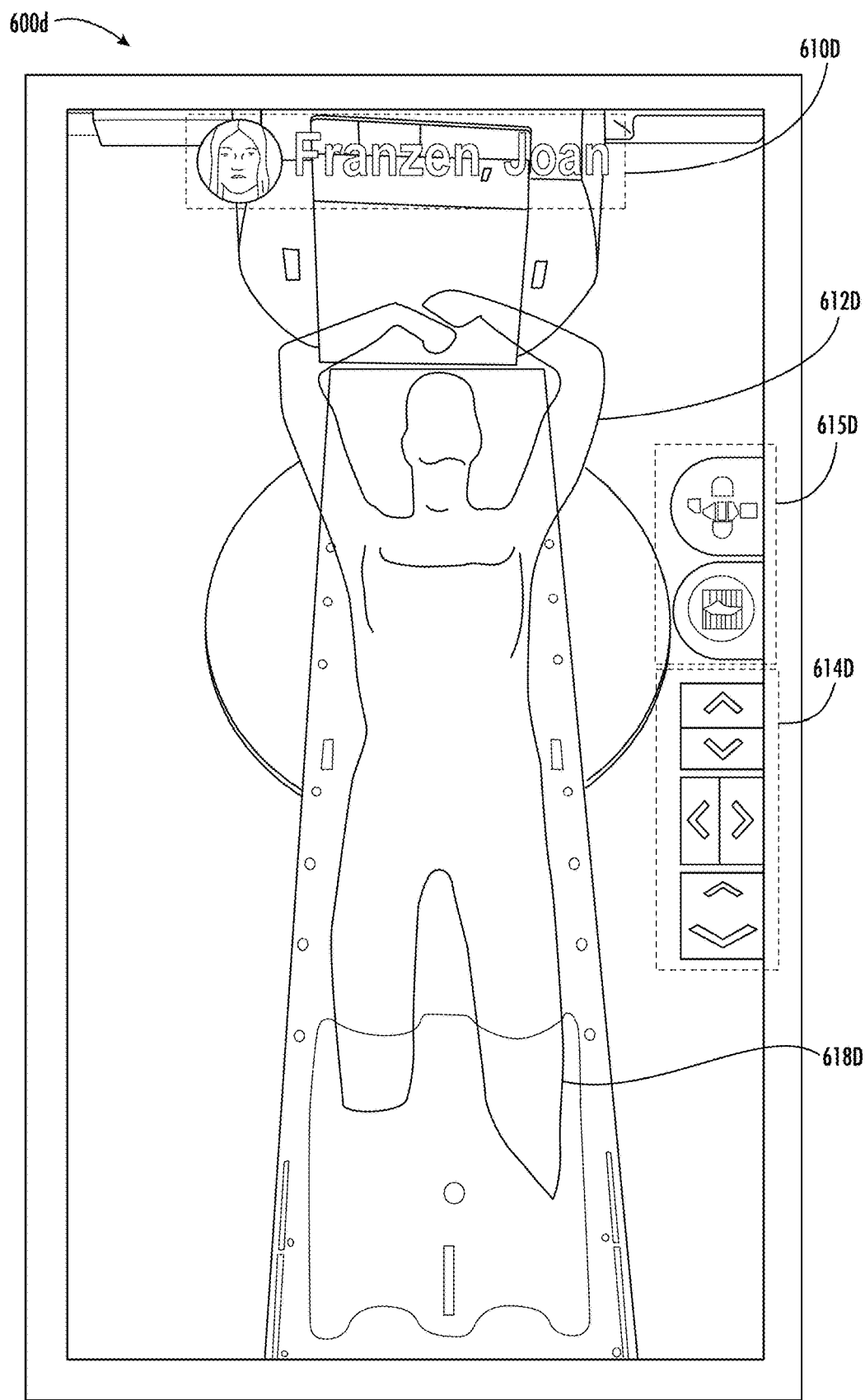
Figure 6E:
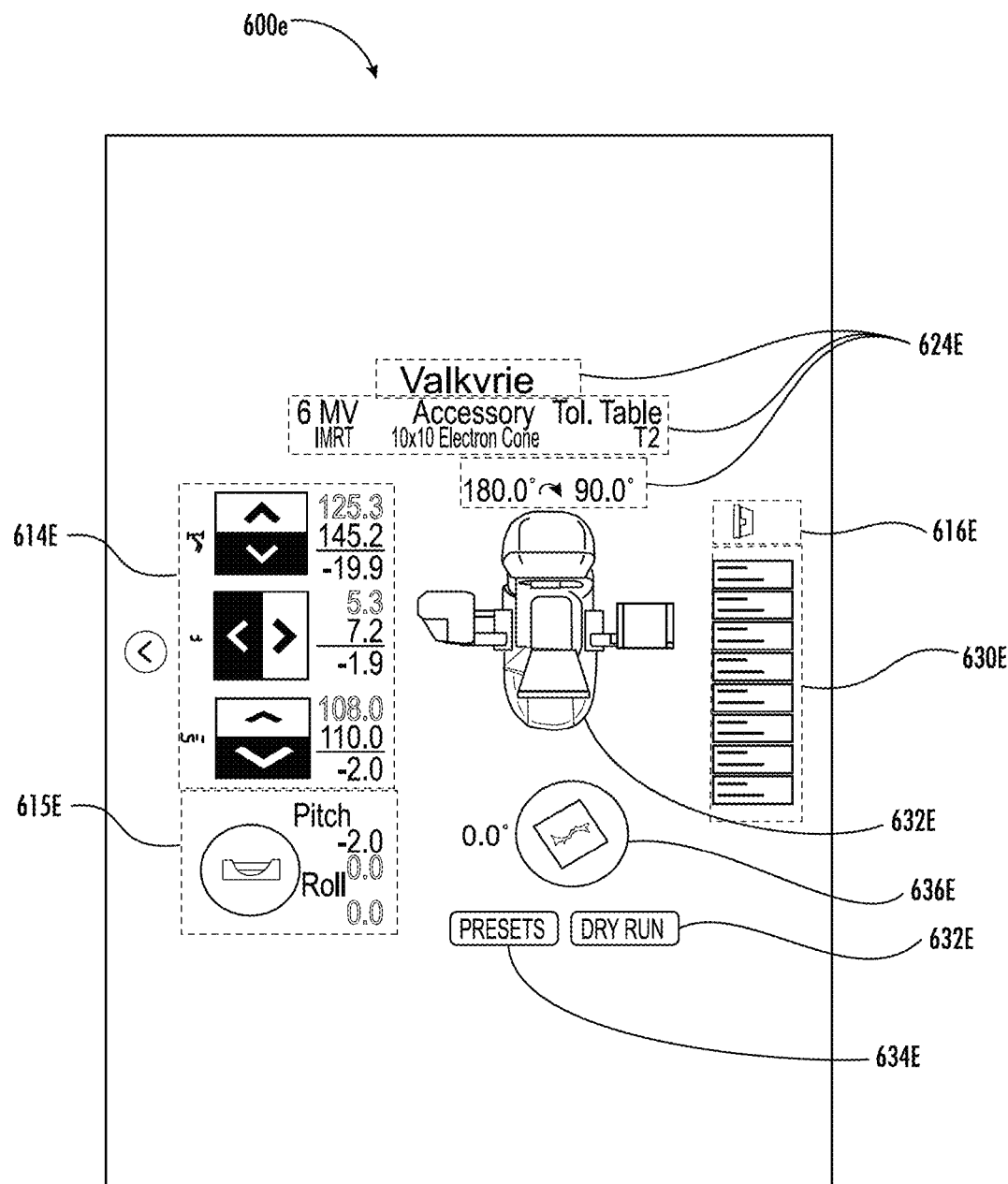
Figure 6F:
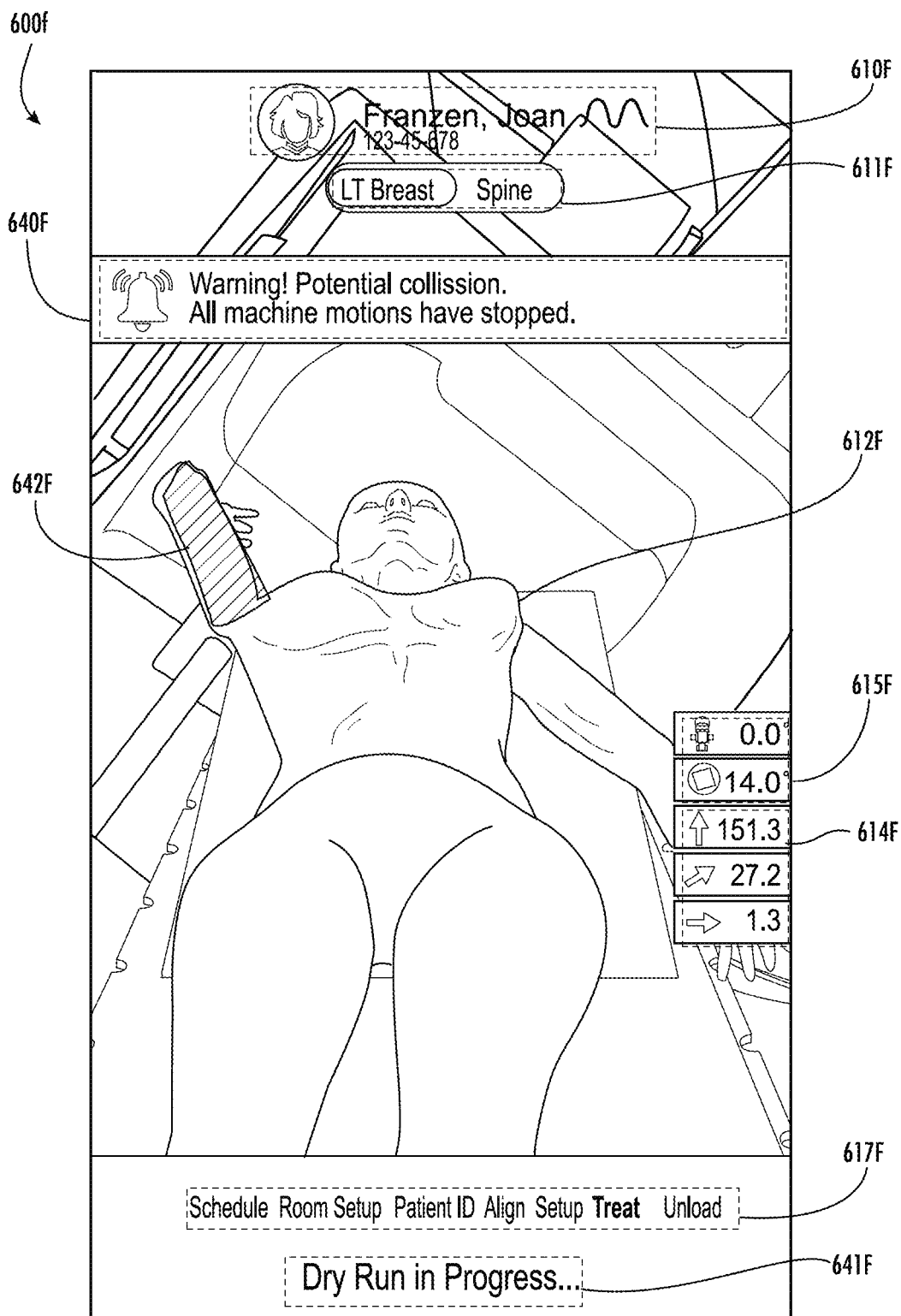

In one example, the analytics server may identify a specific area of the patient that would potentially collide with the gantry based on the results of the virtual dry run as shown in page 600*f* in FIG. 6F as discussed herein. The analytics server may then display the identified area of the patient that might potentially collide with the gantry in a visually distinct manner that highlights the hazard. For instance, the analytics server may display the identified area of the patient in a different color (or any other visually distinct manner, such as hatch patterns).

In another example, the analytics server may display a list of one or more areas of the patient that could potentially collide with the gantry. For example, the analytics server may display using text "left arm" on the page 600*b* and/or 600*c*.

In yet another example, the analytics server may display the graphical indicators 614B that can provide recommendations regarding how to realign the patient such that the risk of a possible collision is eliminated/reduced. For instance, the analytics server may display graphical indicators 614B as realignment parameters, coaching a user and/or patient on a direction and extent of direction (e.g., magnitude and direction of a position vector determined by the analytics server using information associated with the virtual dry run) to realign the patient, or a portion of the patient, on the couch. For example, the guidance provided by the analytics server may be focused on a particular body part (e.g., move the elbow inwards).

In the event the risk of a possible collision is not eliminated/reduced, for instance, because a user does not realign the patient, the user may not progress to a subsequent workflow stage (e.g., following the workflow stages described in FIGS. 4A-4P)

As described above, the analytics server may visually identify any area of the patient that could collide with the gantry. For instance, visual indicators 618B-D may be displayed by the analytics server (in real time or near real time) in response to the virtual dry run results.

For example, as the analytics server determines whether a collision may occur between the patient and the gantry, the analytics server may overlay visual indicator 618B on the model 612B such that a user and/or patient is visually aware of areas of collision and/or likely collision. The user and/or patient is made visually aware by the analytics server because the analytics server uses visually distinct patterns (e.g., hatch, stripes, and dots), textures, shininess, opaqueness or any other appropriate method of visually distinguishing the model 612B from the visual indicator 618B. For example, as depicted, the analytics server displays the area 620B using a different color than area 621B because the analytics server has determined that the area 620B has a high risk of collision with the gantry and area 621B has a low risk of a collision with the gantry. Additionally, or alternatively, the analytics server may identify one or more potential collision areas (e.g., 620B, 621B) with labels.

In some embodiments, as depicted in FIG. 6C, the analytics server may only display a direction in which the patient (e.g., model 612C) should be moved for realignment. For instance, the graphical indicators 614C indicate that the patient must be realigned in a specific direction (e.g., realignment directions). For instance, graphical indicator 622C indicates that the patient must be moved to the left. The graphical indicator 622 may be visually distinct from the graphical indicator 624C (using different colors or any other method). The visual differences between graphical indicator 622C and graphical indicator 624C may indicate that the patient must be moved in a direction corresponding to the graphical indicator 622C. As described herein, the analytics server may continuously monitor the patient's position. When the patient is realigned, such that the analytics server no longer projects that patient is going to collide with the gantry, the analytics server may revise the graphical indicator 614C (in real-time or near real-time), such that it no longer indicates a necessity to realign the patient. For instance, the analytics server may display the graphical indicator 614D on page 600d in FIG. 6D.

Page 600c may also include graphical elements displayed by the analytics server such as graphical indicators, status indicators, progress indicators, treatment related images, non-treatment related images, backgrounds, live feeds of the radiotherapy machine, and notes as discussed herein.

For instance, page 600c may include text 610C, including text that conveys PII, and graphical indicator 615C representing machine alignment parameters, as described similarly to the graphical elements in FIGS. 4A-4P.

The analytics server may display a graphical indicator in orange, which conveys that the patient is projected to have a collision unless the patient is realigned. When the patient is realigned, the analytics server may recalculate whether the patient will have a collision and may dynamically change the color of the graphical indicator. For instance, an orange left arrow indicates that the patient must be moved to the left or the patient will have a collision. When the patient is moved to the left, the analytics server may remove the orange color from the graphical indicator. Additionally, or alternatively, various visual differences may distinguish an extent of realignment. For example, a graphical indicator displayed in a particular color may indicate that the patient move a significant amount to reduce the likelihood of collision. In contrast, a graphical indicator displayed in a different color may indicate that the patient move a smaller amount to reduce the likelihood of collision. The patient may be considered aligned when the graphical indicators no longer display orange.

As show in page 600d, the patient and the couch have adjusted according to the guidance provided by the analytics server such that the radiotherapy machine parameters (e.g., graphical indicators 614D) and machine alignment parameters (e.g., 615D) convey to a user and/or patient that the likelihood of collision is smaller (or that the analytics server does not predict that a collision will occur).

Page 600d may also include graphical elements displayed by the analytics server such as graphical indicators, status indicators, progress indicators, treatment related images, non-treatment related images, backgrounds, live feeds of the radiotherapy machine, and notes as discussed herein.

For instance, page 600d may include text 610D, including text that conveys PII, and graphical indicator 615D representing machine alignment parameters, as described similarly to the graphical elements in FIGS. 4A-4P.

In some configurations, the analytics server may display additional information regarding realignment of the patient. The realignment of the patient may not be limited to realigning the patient. For instance, realignment recommendations may include realigning the machine as well. For instance, realignment parameters 614B-F may refer to the realignment of the patient and/or the realignment of the machine (including the gantry and/or couch). For example, graphical indicator 615E may refer to the realignment of the couch with respect to the pitch and roll of the couch. When the analytics server receives a request from the user, the analytics server may display the additional realignment information, as depicted in FIG. 6E.

Page 600e may also include text 624E that conveys identifying information about the radiotherapy machine. The graphical indicator 616E (in conjunction with status indicators) may represent one or more safety features associated with the treatment room and/or console room. The page 600e may also include text 630E and graphical indicator 632E displaying a representation of the radiotherapy machine, graphical indicator 636E indicating the projected beam spread from the perspective of the collimator positioned on the gantry and/or the type of beam used during the radiotherapy treatment.

Figure 6G:
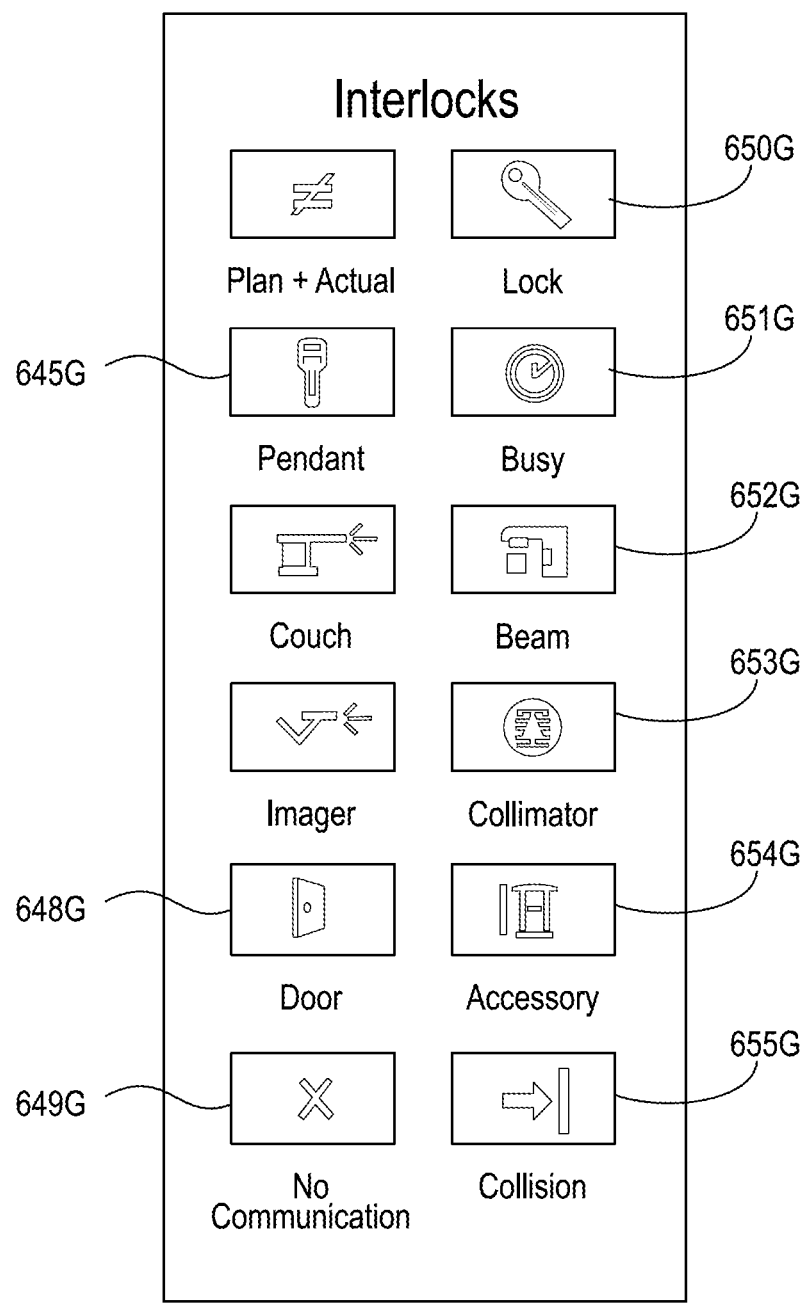

The graphical indicators 630E may represent interlocks and treatment attributes. A non-limiting list of some possible different interlocks is depicted in FIG. 6G. An interlock may represent an attribute of the radiotherapy machine, the treatment, and/or the treatment room. Interlocks may be customizable by a system administrator, clinic administrator, and/or a medical professional. The analytics server may display the graphical indicators 645G and 648G-655G depending on whether each corresponding interlock has been satisfied. For instance, when an interlock is satisfied or present (e.g., conditions regarding the interlock has been met), the analytics server may display a corresponding graphical indicator or may distinguish the corresponding indicator (e.g., highlight or color change).

The graphical indicator 645G indicates whether the analytics server is in communication with the pendant and/or whether the pendant has been placed correctly on its holder within the treatment room. Proper placement of the pendant eliminates the chance of wire entanglement and/or damage by the machine motion, pendant dropping, and the like.

The graphical indicator 648G indicates whether the treatment room door is closed. The graphical indicator 649G indicates that the analytics server has lost communication with one or more devices/features described herein (e.g., radiotherapy machine, pendant, imaging apparatus, clinic server, and/or the console computers). The graphical indicator 650G indicates whether the input elements (e.g., console computers or the pendant) has been "locked," such that users are no longer able to interacts with the input elements to adjust the patient's treatment and/or one or more attributes of the radiotherapy machine.

The graphical indicator 651G indicates that the analytics server is processing (e.g., analyzing data) and will shortly provide results (e.g., provide new alignment angles). The graphical indicator 652G indicates that the gantry is not set up properly (e.g., beam not ready). The graphical indicator 653G indicates that the collimator is not set up (e.g., not initialized). The graphical indicator 654G indicates that at least one accessory is missing or cannot be identified by the analytics server. The graphical indicator 655G indicates that the patient (and/or a medical device connected to the patient) may collide (or has collided) with the gantry if the patient is not repositioned before the treatment begins. As will be described below, the analytics server may use various methods to determine a possible collision between the gantry and the patient.

Referring now to FIG. 6E, The page 600e may also include the interactive button 632E executing by the analytics server a physical dry run and/or a virtual dry run, and interactive button 634E executing by the analytics server, one or more predetermined presets as described similarly to the graphical elements in FIGS. 4A-4P. The analytics server may also display realignment parameters 614E as described herein.

Additionally, or alternatively, the user may interact with interactive button 632E to repeat the virtual dry run process. As a result, the analytics server may reevaluate whether the patient is projected to have a collision with the gantry, couch, and/or accessories. The user may select one or more virtual dry runs to execute using the analytics server.

Page 600f in FIG. 6F illustrates the GUI identifying a specific area of the patient that may potentially collide with the gantry based on the results of the virtual dry run, according to an embodiment. Graphical indicator 642F is a message shown overlaying a portion of model 612F representing the patient. As shown, graphical indicator 624F is a visually distinguished from model 612F because the analytics server has overlaid a color on graphical indicator 624F. A user and/or patient viewing the dry run page may be informed by display note 640F that a potential collision may occur on the right arm of the patient. Graphical indicator 640F as shown includes graphical components (e.g., an alarm bell) and text (e.g., a warning conveying that a potential collision). However, the message may use other graphical elements (e.g., treatment related images, live feed data, backgrounds, and the like) to convey to the patient and/or user that a collision is likely to occur based on the dry run results. Text 641F may convey to the user and/or patient that the page displayed by the analytics server is a virtual dry run. The page 600f may also include realignment parameters as depicted 614F.

Page 600f may also include text 610F identifying the patient, conveying PII, text 611F indicating one or more areas of the patient requiring treatment, and graphical indicator 615F representing machine alignment parameters. The page 600f may also include progress indicator 617F indicating the progress of the user in the treatment room (e.g., highlighting a current stage of a workflow progression and displaying succeeding/preceding stages) as described similarly to the graphical elements in FIGS. 4A-4P.

Identifying Required Accessories

FIG. 7A illustrates a flowchart of a method 700 depicting operational steps performed by a server, such as the analytics server described in FIG. 1A, in accordance with an embodiment. The method 700 describes how the analytics server displays various interactive pages on a GUI configured to identify one or more accessories needed for a patient's treatment. Even though the method 700 is described as being executed by the analytics server, the method 700 can be executed by any server and/or performed locally using a computer/processor associated with the radiotherapy machine and/or the console. Other configurations of the method 700 may comprise additional or alternative steps, or may omit and/or mix one or more steps altogether.

At step 710, the analytics server may retrieve radiotherapy file associated with a patient, the radiotherapy file comprising information associated with one or more accessories associated with the patient's radiation therapy treatment. The analytics server may retrieve an RT file associated with a patient, the RT file comprising an accessory associated with the patient's radiotherapy treatment. As described above, the analytics server may retrieve information associated with the patient and the patient's treatment. The analytics server may query and retrieve a RT file associated with the patient identifier. The RT file may include various treatment details associated with the patient's treatment. For instance, the RT file may include various couch/gantry attributes, such as couch angles, gantry rotation attributes (e.g., full or partial arcs), control points, the number of partial arcs (if applicable), and the like. In some configurations, the RT file may also include whether the treatment is a VMAT treatment or IMRT treatment.

The RT file may also include a list of accessories needed to conduct the patient's treatment. Accessories may refer to any medical equipment required to treat the patient, for example to position and align the patient in accordance with alignment angles. Non-limiting examples of accessories may include bolus material that is used during high-energy photon and electron radiation treatments and placed over the treated region to deliver the full-prescribed dose to the skin surface as well as underlining tissue. Other non-limiting examples accessories may include tungsten shields, grip rings, various other shields, skin care accessories, preloaded markers, clamps, digital level, skin markers, calipers, transfer boards, straps, fixing apparatus used to immobilize particular regions of the patient, isocenter-alignment apparatus, and the like.

The list of accessories may be previously inputted by a treating physician, clinician, or any other medical professional. For instance, a treating oncologist may directly input the accessory name and attributes (e.g., size, shape, classification, type, and configurations) into a platform where the data is captured and retrieved by the analytics server. In some configurations, the list of accessories are determined and inputted by a technician. For instance, a technician may review the patient's treatment plan and identify one or more accessories needed to implement the patient's treatment.

Additionally, or alternatively, the analytics server may automatically populate/determine the list of needed accessories for the patient based the patient's treatment plan. The analytics server may analyze the treatment attributes retrieved (step 710) and may execute one or more predetermined rules, protocols, and thresholds to identify a list of necessary accessories. For instance, the analytics server may determine that straps and isocenter alignment apparatus is needed for a patient who is receiving radiotherapy on his chest.

At step 720, the analytics server may present for display on the graphical user interface, a graphical indicator corresponding to each of the one or more accessories. The analytics server may display an image of a radiotherapy machine on a page. The analytics server may instruct the GUI associated with the radiotherapy machine to display a series of pages on a screen associated with the radiotherapy machine. As described above, the screen may be placed onto (other otherwise communicatively coupled to) the radiotherapy machine itself, such as by placing the screen on the throat (or any other part) of the gantry. The screen may also be placed in the treatment room (e.g., the same room as the radiotherapy machine). In some embodiments, the screen displaying the page may refer to the screen of monitoring devices placed in a separate room (e.g., console placed outside of the treatment room, such as a monitoring room).

Various pages associated with the method 700 may be a part of a series of pages described herein (e.g., stage-based pages described in FIGS. 4A-4P) or may be a standalone page that can be separately displayed (e.g., not as a part of a series of pages). Furthermore, the pages describe herein may be displayed on multiple screens in a synchronous or asynchronous manner. For instance, the analytics server may displays the pages described herein on a GUI on the throat of the gantry, radiotherapy room screen, and/or console monitors, in a simultaneous or near simultaneous manner, such that one or more users can monitor the technician's actions.

The GUI may display an image of the radiotherapy machine (e.g., couch). As described above, the analytics server may be in communication with one or more cameras (e.g., camera on the couch, gantry camera, or other cameras places within the radiotherapy room). The analytics server may utilize a feed from the one or more cameras to display a live feed of the radiotherapy machine (e.g., live feed of the couch with or without the patient).

At step 730, the analytics server may present for display on the page a graphical indicator corresponding to the accessory. The page may display a graphical indicator associated with each accessory identified within the RT file. The graphical indicator, as used herein, may correspond to any graphical component (e.g., graphical icon or text) displayed on a page that indicates the need for a particular accessory. Non-limiting examples of a graphical indicator may include icons in different shapes (e.g., rectangular, square, and circle) and/or in different colors (e.g., black, white, red, orange, and can be solid, opaque, or translucent).

The graphical indicator may include an indication corresponding to the accessory identified as necessary for the patient's treatment. For instance, the analytics server may display a name associated with the accessory. In other example, the analytics server may display a shape corresponding to the needed accessory. For instance, the analytics sever may assign different shapes for different accessories (e.g., circle for grip rings and triangles for boluses). Different shapes and their corresponding accessories may be predetermined (e.g., system default) or may be inputted by the end user (e.g., technician). The shapes and their corresponding accessories may be revised by the end user (e.g., system administrator or technician).

At step 740, the analytics server may scan a set of accessories within a predetermined proximity to the radiotherapy machine. The analytics server may utilize various location tracking/scanning methods to determine one or more accessories within a predetermined proximity to the radiotherapy machine. The analytics server may use a default predetermined proximity set up by a system administrator or specific to a clinic. The analytics server may also receive the predetermined proximity and its reference point (e.g., two feet from the couch) from the system administrator or a technician or any other electronic device/feature descried in FIG. 1A. In some embodiments, the predetermine proximity may refer to a specific location on the couch.

In one configuration, the analytics server may use RFID technology to identify the locations of one or more accessories nearby (e.g., within a predetermined proximity to the radiotherapy machine). More specifically, the analytics server may use electromagnetic fields to automatically identify and track RFID tags attached to different accessories. An RFID tag consists of a radio transponder, a radio receiver, and transmitter. When triggered by an electromagnetic interrogation pulse from a nearby RFID reader device, the RFID tag may transmit data back to the reader. The data may include a number (or other identifier) unique to a particular accessory. The analytics server may utilize active and/or passive RFID tags to identify locations of the accessories. The RFID technology may include near field communication (NFC) or other related configurations. Alternatively, although the example utilizes RFID, other technology for determining the presence of a nearby object may be used, such as Bluetooth, beacons, ultra-wide band RTLS, GPS, Wi-Fi, computer vision, and the like.

The analytics server may be in communication with one or more nearby RFID readers, which can in turn communicate with one or more RFID tags placed onto each accessory devices. The analytics server may identify a location and a range of each RFID reader. The analytics server identifies and accessory's location when the accessory's RFID tag is detected within a particular RFID reader's range. In a non-limiting example, the analytics server queries/activates an RFID reader placed on the couch. As a result, the RFID reader communicates with all RFID tags within the RFID reader's range and transmits RFID tag numbers/identifiers to the analytics server. The analytics server then queries a data table to identify an accessory associated with each received RFID number to identify the corresponding accessory.

The analytics server may continuously or periodically monitor location of the accessories (or a list of accessories within a predetermined proximity to the radiotherapy machine), such that the analytics server possesses real time (or near real time) location information for each accessory.

Additionally, or alternatively, the analytics server may use visual tags to identify a location of one or more accessories. The analytics server may scan one or more visual tags present within the images of the radiotherapy (received from the cameras described herein) to identify whether the necessary accessory is within a predetermined proximity to the radiotherapy machine. Visual tag, as used herein, may refer to encoded images placed on the accessories, such as barcodes, quick response (QR) codes, and the like. The encoded images may represent data associated with its corresponding accessory (e.g., type, category, and model). The encoded image may be in a machine-readable format, such that the analytics server can identify and scan the visual tag within the received images and identify the corresponding accessories present within the image.

In a non-limiting example, the analytics server receives a live feed of the couch from a camera placed on the gantry. The analytics server continuously/periodically scan the live feed to identify any present visual tags. The analytics server scans the visual tags present within the live feed received from the camera. The analytics server may also scan other live feeds received from other camera (e.g., camera placed on the couch, such as at depicted in FIG. 2E). The analytics server then queries a data table to identify the corresponding accessory. If the visual tag for a particular accessory is identified within the frame (e.g., the visual tag is present within the live feed of the couch), the analytics server determines that the accessory is present within the predetermined proximity to the radiotherapy machine/couch.

Additionally or alternatively, the analytics server may use beacon technology to identify location of different accessories. Each accessory may include a beacon receiver configured to receive a unique identifier of a beacon transmitter placed at different locations within the treatment room (e.g., on the radiotherapy machine or in other corners of the room). The analytics server may use the unique identifier, signal strength, and/or triangulation to identify the location of each accessory (e.g., beacon receiver placed on each accessory). In a non-limiting example, the analytics server receives three unique identifiers and signal strengths from three different beacon receivers. The analytics server then queries a data table to identify an accessory associated with each beacon receiver (e.g., each beacon receive may also have an identifier that is unique to a particular accessory). The analytics server then identifies the location of each identified accessory based on the signal strength received from each beacon receiver.

At step 750, when the analytics server does not detect one or more of the one or more accessories in proximity to the radiotherapy machine or when one or more of the one or more accessories is not within a predetermined location, revising, by one or more servers, the graphical indicator corresponding to that accessory. When the analytics server does not detect the accessory in proximity to the radiotherapy machine, the analytics server may revise the graphical indicator on the GUI corresponding to the accessory. If the analytics server determines that the necessary/needed accessory (identified in step 710) is not within the predetermined proximity to the radiotherapy machine, the analytics server may revise the graphical indicator associated with the accessory. The analytics server may revise the graphical indicator on the GUI, such that the technician or other end user operating the radiotherapy machine and/or viewing the page is notified that the accessory is missing.

Additionally, or alternatively, the analytics server may generate and transmit a notification to one or more electronic devices described herein (e.g., described in FIG. 1A). For instance, the analytics server may notify the end user by displaying a prompt on the page displayed in step 720 or other pages (e.g., page on the console GUIs). In another example, the analytics server may notify a second device (e.g., physician or clinician computing device). The notification may be visual, haptic, auditory, and the like. Therefore, even though aspects of the method 700 are described in terms of visual notifications, they are not limited to such embodiments.

Referring now to FIGS. 7B and 7C, non-limiting examples of the analytics server displaying and/or revising pages of the GUI based on necessary accessories are depicted. In one example, the analytics server may instruct a screen associated with a radiotherapy machine to display the page depicted in FIG. 8 on a screen associated with a radiotherapy machine, such as on the gantry, on a screen of the radiotherapy room, and/or on a console or any other monitoring screen. Furthermore, as described above, the analytics server may display the pages depicted herein in conjunction (e.g., as a part of a series) with other stage-based pages.

As depicted in FIG. 7A, the analytics server may display a live feed of a radiotherapy machine. For instance, the analytics server may receive a live feed from a camera placed on the couch and display a graphical component 769 corresponding to a live feed of the patient positioned on the couch. The graphical component 769 may be an actual image (revised in real time as the patient moves) and/or a two-dimensional or three-dimensional representation (e.g., animation) representing the patient.

The analytics server may also display patient information, such as the patient's name or an identifier, date of treatment, and the like. For instance, the analytics server displays the patient's name in a graphical component 766. The analytics server may further display various other treatment and/or radiotherapy machine attributes, such as depicted in a graphical component 768.

The analytics server may use the methods and systems described herein to identify a list of necessary accessories for the patient depicted in the graphical component 766. As a result, the analytics server may display a graphical indicator 760-764 where each graphical indicator corresponds to one accessory needed for the patient. More specifically, the analytics server identifies that the patient needs a breast board, 1 cm bolus, and a knee wedge. As a result, the analytics server may display the graphical indicators 760-764 respectively. Each indicator may also include a status indicator 760A-764A. Each status indicator may correspond to a status of each respective accessory. For instance, as described above, the analytics server uses a variety of methods and systems to identify whether an accessory is present within the predetermined proximity to the radiotherapy machine (e.g., the couch).

The status indicator of each accessory may convey/identify whether the analytics server has identified the accessory to be present within the predetermined proximity. The status indicator may correspond to different colors, shapes, hatch patterns, words, or any other method of indicating whether an accessory is present. In the depicted embodiment, the analytics server uses colors (e.g., orange) to identify that an accessory is not present. For instance, the status indicator 760A indicates that the breast board is not present within the predetermined proximity to the couch (e.g., two feet or any other proximity set by the system administrator and/or the end user). In other embodiments, the analytics server may display text indicating whether each accessory is present. In some embodiments, the analytics server may display a particular shape indicating whether an accessory is present (e.g., circle status indicator to identify presence and triangle to indicate missing accessories). The analytics server may determine both proximity and/or position of the accessories relative to machine/couch and signal the status accordingly.

Referring now to page depicted in FIG. 7C, the analytics server may display similar features on the GUI as described in FIG. 7B. For instance, a graphical indicator 776 displays the patient's name and a graphical indicator 778 displays treatment and/or radiotherapy attributes associated with the patient's treatment. Moreover, the GUI may display a representation (or the actual image) of the patient positioned on the couch. The GUI may display graphical components 770-774 where each graphical component corresponds to an accessory needed for the patient's treatment. The GUI may display each indicator in a different color, such that the color indicates whether the accessory is present within the predetermined proximity to the radiotherapy machine. For instance, as depicted, the GUI displays the graphical component 770 (bolus 1) and the graphical component 772 (bolus 2) in orange to indicate that bolus 1 and bolus 2 are not present within the predetermined proximity.

Additionally, or alternatively, the GUI may display a status indicator identifying that an accessory identified within the pre-determined proximity is the wrong accessory. As a result, the analytics server may revise the graphical and/or status indicator (in real time or near real time) to identify that the wrong accessory is being used. For instance, the graphical indicator 774 in red may indicate that its corresponding accessory is not within the list of accessories needed for the patient's treatment (e.g., retrieved from the RT file or otherwise received by the analytics server).

The analytics server may continuously/periodically monitor locations of one or more accessories and determine whether a needed accessory is located within the predetermined proximity to the radiotherapy machine. Therefore, the analytics server may revise the status indicators in real time or near real time to indicate their presence. For instance, when the technician places a required accessory on the couch, the analytics server may revise its status indicator in real time such that the status indicator identifies that the required accessory is within the predetermined proximity.

For instance, when the analytics server determines that bolus 1 is located within the predetermined proximity, the analytics server may revise the status indicator of the graphical component 770 on the GUI, such as by changing the orange color to green or translucent. In another embodiment, when the technician moves the wrong accessory corresponding to the graphical indicator 774 away from the radiotherapy machine, the analytics server may revise the graphical indicator 774 by removing it, changing its color, shape, or any other manner that is visually distinct.

In some configurations, the analytics server may not allow the end user to move to a subsequent stage until and unless all needed medical accessories are placed within the predetermined proximity. For instance, if the analytics server identifies that the patient needs a knee wedge, the analytics server may disable one or more graphical components within the depicted pages, such that the technician cannot move to a next page until the analytics server identifies the knee wedge is within the predetermined proximity.

Additionally, or alternatively, the analytics server may be programmed, such that it only displays accessories present within the predetermined proximity. For instance, the analytics server may monitor location of one or more accessories within the predetermined proximity and may display on the GUI a graphical indicator for each accessory placed within the predetermined proximity. In some other embodiments, the GUI may display a translucent indicator corresponding to one or more needed accessories. The analytics server may then change the status indicator (and/or change the color of each translucent indicator) based on whether its corresponding accessory is within the predetermined proximity. Additionally, or alternatively, the analytics server may only display the graphical indicator for each missing and/or incorrect accessories.

Features on the GUI

Figure 8:
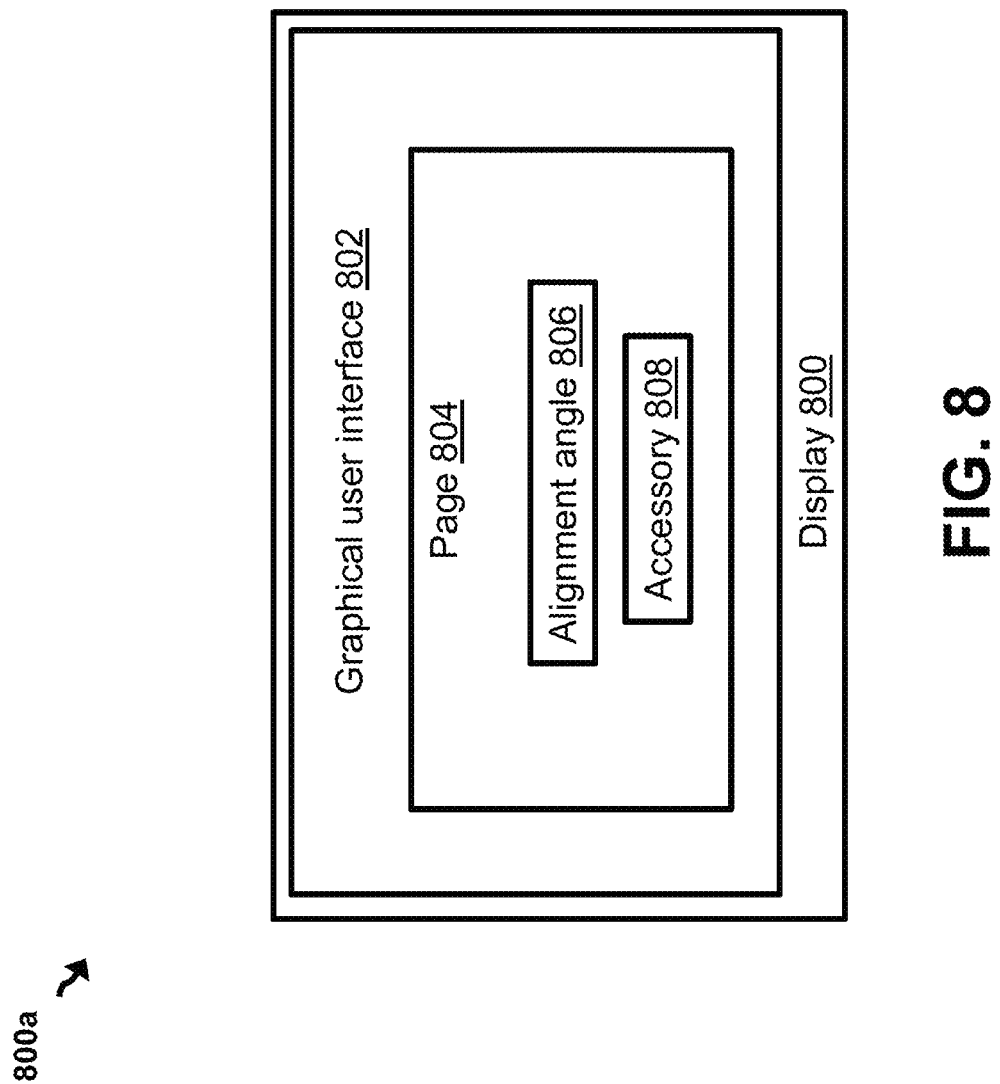
FIG. 8 illustrates a flow diagram executed in a workflow-oriented radiotherapy system, according to an embodiment.

FIG. 8 illustrates a schematic of a GUI 802 that is capable of communicating with the analytics server and displaying various interactive pages that contain various graphical elements, such as those presented in FIGS. 7B and 7C. The GUI 802 presents a page 804 on a display 800.

The GUI 802 is presents information from the analytics server on the display 800, such as a screen on a gantry (e.g., on a throat of the gantry as described in FIGS. 2A-2F), a console display, a mobile phone, monitor, or other computing device. The analytics server may asynchronously or synchronously display the pages on one or more screens outside the treatment room and on various devices using various platforms. At some time before the treatment begins (e.g., the radiotherapy machine begins treating the patient with radiation), the analytics server may disable the screen.

The page presented by the analytics server may be a page associated with radiotherapy treatment of a patient (e.g., a person to be treated by the radiotherapy machine). Some of the pages presented by the analytics server may correspond to stage within a workflow (e.g., as discussed in FIGS. 4A-4P). The analytics server may display only relevant information on each page. Relevant information, as used herein, may refer to a subset of all information used to treat the patient at a given stage in the workflow. The relevant information may be consumed by the user while the user performs tasks at a given stage of workflow. The analytics server displays the relevant information for the current stage of workflow on a page. The analytics server may also display various graphical elements on the pages of the page. For example, graphical elements on various pages may include progress indicators, treatment related images, non-treatment related images, backgrounds, live feeds of the radiotherapy machine, and notes as discussed herein.

The GUI 802 allows transition of the page 804 to at least a second page so that a user (e.g., technician) can navigate the GUI 802 and ensure proper configuration for treatment. The second page of the GUI 802 presented by the analytics server may contain additional information about the first page, as described in FIG. 4E. For instance, one or more graphical elements of the second page may relate to and/or contain additional information of one or more graphical elements on the first page. The progress indicator may indicate whether the page displayed by the analytics server is associated with a stage of the workflow and/or is associated with supplemental information of a page in the workflow. Additionally, or alternatively, the progress indicator may indicate succeeding and/or preceding stages in the workflow.

In this example, the page 804 has a graphical component for an alignment angle 806 and a graphical component for an accessory 808. These graphical components 806, 808 can be positioned on an edge of the page, in the middle of the page, or upon activating a button (e.g., clicking a button or otherwise interacting with the button) on the page. The graphical components 806, 808 can include indicators and/or text to illustrate status, action items, alerts, issues, etc., associated with the alignment angle or one or more accessories.

On the one or more pages of the GUI 802 presented by the analytics server, the alignment angle graphical component 806 indicates a satisfactory position for treatment. As discussed herein, the satisfactory position for treatment, as determined by one or more predetermined alignment positions allows the radiotherapy machine to radiate the positioned particular area of the body while minimizing radiation exposure to other parts of the body. The predetermined alignment angle(s) may be determined by a user and/or system administrator.

In the event that the position of the patient is different from the satisfactory position for treatment (e.g., the position of the patient is not within a predetermined margin of error), the analytics server may visually distinguish, using various graphical elements such as models and other graphical indicators as discussed herein, the position of the patient from the satisfactory position for treatment. The analytics server visually distinguish the position of the patient from the satisfactory position for treatment using colors, patterns, textures, shininess, opaqueness, and the like.

On the one or more pages of the GUI 802 presented by the analytics server, the accessory graphical component 808 can identify to a user whether the analytics server has determined that the necessary accessories for the radiotherapy treatment of the patient are located. The analytics server may also use graphical indicators to indicate radiotherapy machine parameters and adjustments such that a patient may become aligned with satisfactory positions for treatment.

As discussed herein, the analytics server may use status indicators to visually distinguish whether the analytics server has determined that the necessary accessories for radiotherapy treatment of the patient are located. For instance, various colors, shapes, borders and the like may distinguish the analytics server displaying that an accessory is in a proper position or that an accessory is not within a predetermined proximity.

Various features of one or more pages described herein are detailed with reference to FIGS. 4A-12B. For instance, visualization of the alignment angle(s) and different non-limiting examples of revising the position of the patient based on the alignment angle(s) are described in FIGS. 5A-5C. Moreover, visual representation of accessories (e.g., how the analytics server identifies the needed accessories and how it visually indicates the presence/absence of each needed accessory) is detailed in FIGS. 7A-C.

Navigation Using Pendant

Figure 9:
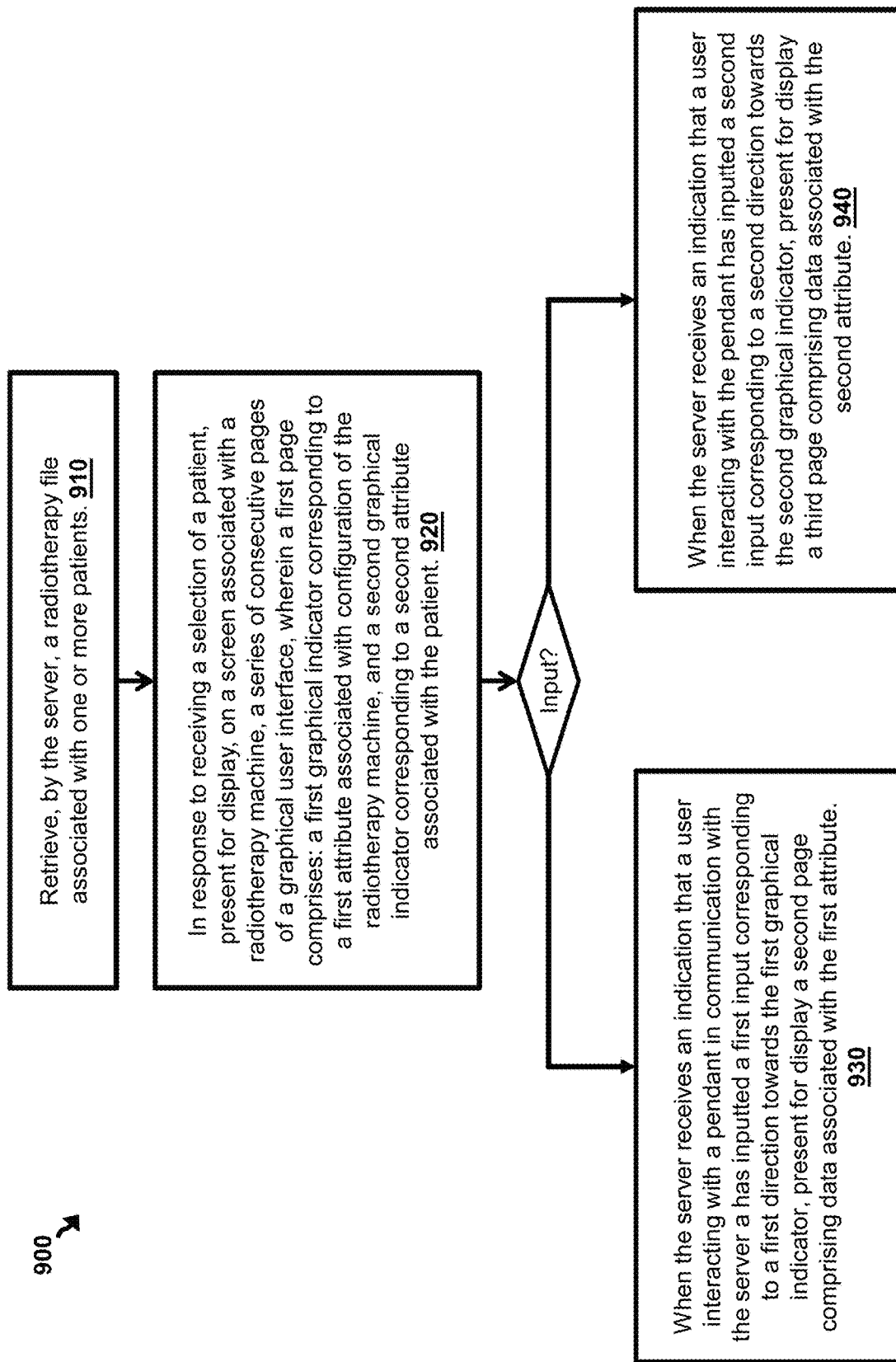
FIG. 9 illustrates a flow diagram executed in a workflow-oriented radiotherapy system, according to an embodiment.

Referring now to FIG. 9, a flowchart depicting operational steps performed by an analytics server is depicted, in accordance with an embodiment. The method 900 describes how a server, such as the analytics server described in FIG. 1A, may allow a user to navigate various interactive pages of a GUI configured to display various stages of performing radiotherapy on a patient. Even though the method 900 may be described as being executed by the analytics server, the method 900 can be executed by any server(s) and/or performed locally using a computer/processor associated with a radiotherapy machine and/or a console (e.g., such as the radiotherapy machine and the console depicted in FIG. 1A). Other configurations of the method 900 may comprise additional or alternative steps, or may omit and/or mix one or more steps altogether.

At step 910, the analytics server may retrieve a RT file associated with one or more. RT file may be retrieved from one or more a medical databases (such as the medical database in FIG. 1A), servers, files, and the like. As described herein, the analytics server may retrieve various treatment information associated with the patient's treatment from a variety of data sources. For instance, the analytics server may retrieve a file that may include all treatment information (e.g., treatment attributes including type of treatment and field geometry, such as alignment angles, accessories, and other attributes). In some configurations, the analytics server may retrieve the data from multiple sources.

At step 920, in response to receiving a selection of a patient within the one or more patients, the analytics server may display on a screen associated with a radiotherapy machine (e.g., a screen on a gantry of the radiotherapy machine), a series of consecutive pages. A first page within the series of consecutive pages may include a first graphical indicator corresponding to a first attribute associated with configuration of the radiotherapy machine and a second graphical indicator corresponding to a second attribute associated with the patient.

Steps 910 or 920 describe an embodiment where the analytics server retrieves RT files associated with multiple patients and then receives a selection from an operator of the radiotherapy machine (e.g., technician in the treatment room). Upon receiving the selection, the analytics server identifies treatment data (RT file(s)) associated with the selected patient and displays the GUIs described herein. Therefore, the method 900 is specific to the patient who is being treated.

In response to receiving a selection of a patient from the one or more in the RT file, the GUI displays a page associated with the selected patient. The GUI may be a series of consecutive pages, wherein a first page within the series of consecutive pages comprises a first graphical indicator corresponding to a first attribute associated with configuration of the radiotherapy machine and a second graphical indicator corresponding to a second attribute associated with the patient.

The response (e.g., displaying the pages) by the server may be generated by a user input (e.g., an input from a pendant as discussed in FIGS. 3A-3B), and the like. For instance, a user may select a patient to be treated using a page displayed by the analytics server. Additionally, or alternatively, the response by the server may be in response to a timing trigger (e.g., the time at which the patient is expected to begin an appointment with the radiotherapy machine).

The analytics server may present for displaying (e.g., instruct a display screen associate with the radiotherapy to display) the page on the display screen associated with of the radiotherapy machine (e.g., the display positioned on the gantry as described in FIGS. 2A-2F). The display screen may be placed onto (other otherwise connected to) the radiotherapy machine itself, such as by placing the display screen on the throat (or any other part) of the gantry. The display screen may also be placed in the treatment room (e.g., the same room as the radiotherapy machine). Various other display screens may display the pages displayed by the analytics server. For instance, display screens in rooms outside of the treatment room (such as a room monitoring the treatment room) may display the pages displayed by the analytics server. Additionally, or alternatively, the page may be displayed on various platforms. For instance, a user may view the pages displayed by the analytics server on the various platforms by executing an application such as a browser application. Therefore, the GUIs described herein are not limited to being displayed on the display located on the radiotherapy machine or the console monitors.

Various pages associated with the method 900 and displayed by the analytics server may be a part of a workflow-oriented series of pages described herein. Additionally, or alternatively, the various pages associated with the method 900 may be standalone pages that can be separately displayed (e.g., not as a part of the workflow-oriented series of pages). The workflow-oriented series of pages associated with the method 900 can be modified (e.g., with respect to content, with respect to order, with respect to the number of stages) by a system administrator and/or user.

The analytics server may display a room setup page on the GUI. As discussed in greater detail in FIG. 4D, the room setup may include a live view of the couch, the setup notes, the patient information, the required accessories, and the machine parameters.

The pages of GUIs described herein may be displayed on multiple screens (and on various platforms) in a synchronous or asynchronous manner. For instance, the analytics server may display the pages described herein on the throat of the gantry, radiotherapy room screen, console monitors, and/or a physician device in a simultaneous or near simultaneous manner, such that one or more users can monitor the actions of the user in the treatment room. For instance, the actions performed by a technician in the treatment room may be monitored by another technician using the console monitors.

Additionally, or alternatively, the analytics server may receive one or more inputs that may cause an alert and/or indicator on the page displayed to the user in the treatment room. The alert and/or indicator may be visual and/or audible. For instance, a user may notify the user in the treatment room that the user in the treatment room may be missing something (e.g., an accessory) and/or did not complete a task. The analytics server may also receive one or more inputs that have a net effect of changing the displayed page in the treatment room. For instance, the displayed page may change to display a different page.

The analytics server presents for display a series of consecutive pages onto the display screen. The series of consecutive pages may include a first page including a first graphical indicator corresponding to a first attribute associated with a configuration of the radiotherapy machine. The first attribute may include any data associated with the radiotherapy machine. The data associated with the radiotherapy machine may include, but is not limited to, the radiotherapy machine alignment parameters, software machine parameters, gantry position, couch position, and the camera positions. The data associated with the radiotherapy machine may also include received inputs from the pendant, the console monitor, and the system administrator computer.

The first page may also include a second graphical indicator corresponding to a second attribute associated with the patient. The second attribute may include any known parameter regarding the patient used for, but not limited to, the alignment of the patient, the current surface matching of the patient, and the position of the patient. The second attribute may include data corresponding to aligning the patient with a predetermined alignment angle.

At step 930, when the server receives an indication that a user interacting with a pendant having a processor in communication with the server has inputted a first input corresponding to a first direction towards the first graphical indicator, the server causes the display screen to display a second page comprising data associated with the first attribute.

If the server receives an indication that a user interacting with a pendant having a processor in communication with the server and the radiotherapy machine has inputted a first input corresponding to a first direction towards the first graphical indicator, displaying, on the gantry, a second page comprising data associated with the first attribute. The second page may include alphanumerical values retrieved from the RT file. The alphanumerical values may correspond to aligning the patient based on a predetermined alignment angle.

The analytics server may receive an indication that the user may be interacting with a pendant (e.g., the pendant as depicted in FIGS. 3A-3B). The user may indicate a desire to see more detailed information regarding the first graphical indicator. As a result, the user may submit an input corresponding to a direction towards the first graphical indicator. For instance, the user may interact with an input element of the pendant (e.g., interact with the track pad (e.g., swipe), interact with the wheel, and/or interact with (e.g., click) a button in the direction of the first graphical indicator using the pendant). As a result, the analytics server may direct the user to a new page (referred to herein as the second page). The second page may include data associated with the first attribute. A non-limiting example of an input in a first direction is illustrated in FIG. 4E.

As discussed in greater detail in FIG. 4E, the user may swipe in a direction (or input the direction using any other method, such as by clicking a button in the pendant). This causes the analytics server to transition to a new page (second page) that displays detailed information regarding the first indicator. For example, if the user swipes the touch pad of the pendant in a specific direction, the analytics server may then display the setup information details.

FIGS. 4F-4G depicts an example of a second page. As described in more detail in FIGS. 4F-4G, the displayed pages may provide additional accessory information for the user. The setup notes may include setup photos, setup notes, and the accessories for the selected patient. The analytics server may display the pages depicted in FIGS. 4F-4G when the user clicks (or other interacts with the GUIs) towards the graphical indicator 430 depicted in FIG. 4D.

As discussed herein, the user may navigate each of the pages using the pendant. The pendant may include a processor and may be communicatively coupled with the radiotherapy machine and/or the analytics server. The user may input to the pendant the first input that indicates to the analytics server that the user may be seeking additional information/details. For instance, the user may press a left button on the pendant, swipe left on the trackpad of the pendant, or the like. In the event that the analytics server receives an indication of the user's interaction, the analytics server may display the second page on the gantry.

Referring back to FIG. 9, at step 940, when the analytics server receives an indication that a user interacting with the pendant has inputted a second input corresponding to a second direction towards the second graphical indicator, the server causes the display screen to display a third page including data associated with the second attribute.

If the server receives an indication that a user interacting with the pendant has inputted a second input corresponding to a second direction towards the second graphical indicator, displaying, by the server on the gantry, a third page comprising data associated with the second attribute. The third page may include alphanumerical values retrieved from the RT file. The alphanumerical values may correspond to aligning the patient based on a predetermined alignment angle.

The analytics server may receive an indication that the user may be interacting with the pendant. The user may indicate a desire to see more detailed information regarding the second graphical indicator. As a result, the user may submit an input corresponding to a direction towards the second graphical indicator. For instance, the user may interact with an input element of the pendant (e.g., interact with the track pad (e.g., swipe), interact with the wheel, and/or interact with (e.g., click) a button in the direction of the second graphical indicator). As a result, the analytics server may direct the user to a new page (referred to herein as the third page). The third page may include data associated with the second attribute. A non-limiting example of an input in a second direction is illustrated in FIG. 4E.

As discussed in greater detail in FIG. 4E, the user may swipe in a direction. This causes the analytics server to display the respective page. For example, if the user swipes their finger from the action button to the machine details, the analytics server may then display the machine details.

FIG. 4I depicts an example of the third page. As described in more detail in FIG. 4I, the displayed page may provide additional setup information for the user such as setup notes and machine parameters. The analytics server may display the page 400i depicted in FIG. 4I when the user clicks (or otherwise interacts with the pendant) towards the graphical indicator 428D depicted in FIG. 4D. In another non-limiting example, when the user clicks towards the direction of the graphical indicator 421 depicted in FIG. 4D, the GUI directs the user towards the page 400h depicted in FIG. 4H.

Additionally, or alternatively, the analytics server may display the third page on the display screen in response to a user's second input (e.g., a "menu" button on the pendant and/or display). For instance, the analytics server may display to the user the interactions that the user must perform to receive additional information. For example, if the user presses the menu button, the third page may display to the user the different menu options available to the user. In some configurations, a designated button may be customized to direct the user to the second or third pages. For instance, a button on the pendant may be customized, such that when pressed, the analytics server directs the user to another page displaying information that is more detailed.

For example, as described in FIG. 3B, the pendent may have a customized home button such that a user's interaction with the home button may navigate the user to go to a home page. The home page may be the first page of the workflow. Additionally or alternatively, the home page may be the first page of the stage of the workflow the user is currently in. Further, the pendent may have a customized return button (e.g., back button). The return button may cause the workflow to return back a step. For example, if the technician would like to return to a prior step of the workflow, the technician may press the return button. Further, the pendent may have a customized safety button. The safety button may prevent the accidental repositioning of the couch if the set of buttons are unintentionally pressed by a user.

Console Monitors

Figure 10A:
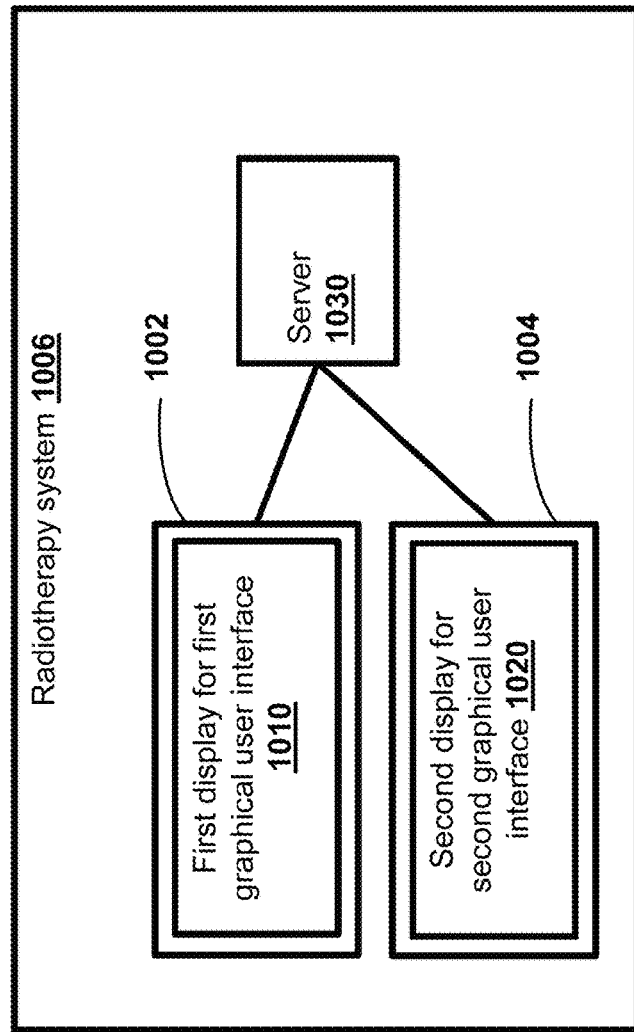
FIG. 10A illustrates a diagram of a console monitor used in a workflow-oriented radiotherapy system, according to an embodiment.
Figure 10B:
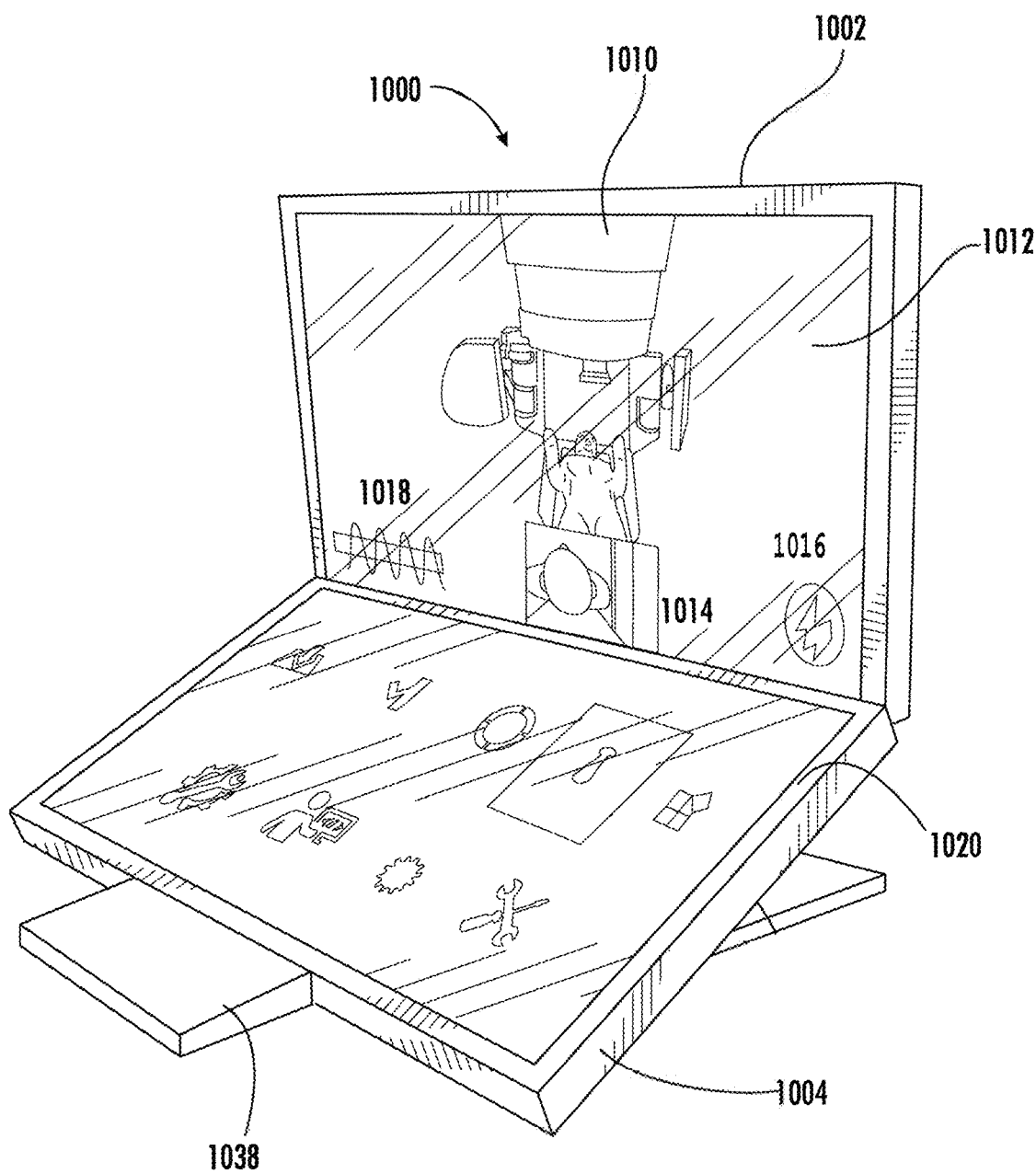
FIGS. 10B-10D illustrate console monitors used in a workflow-oriented radiotherapy system, according to an embodiment.
Figure 10C:
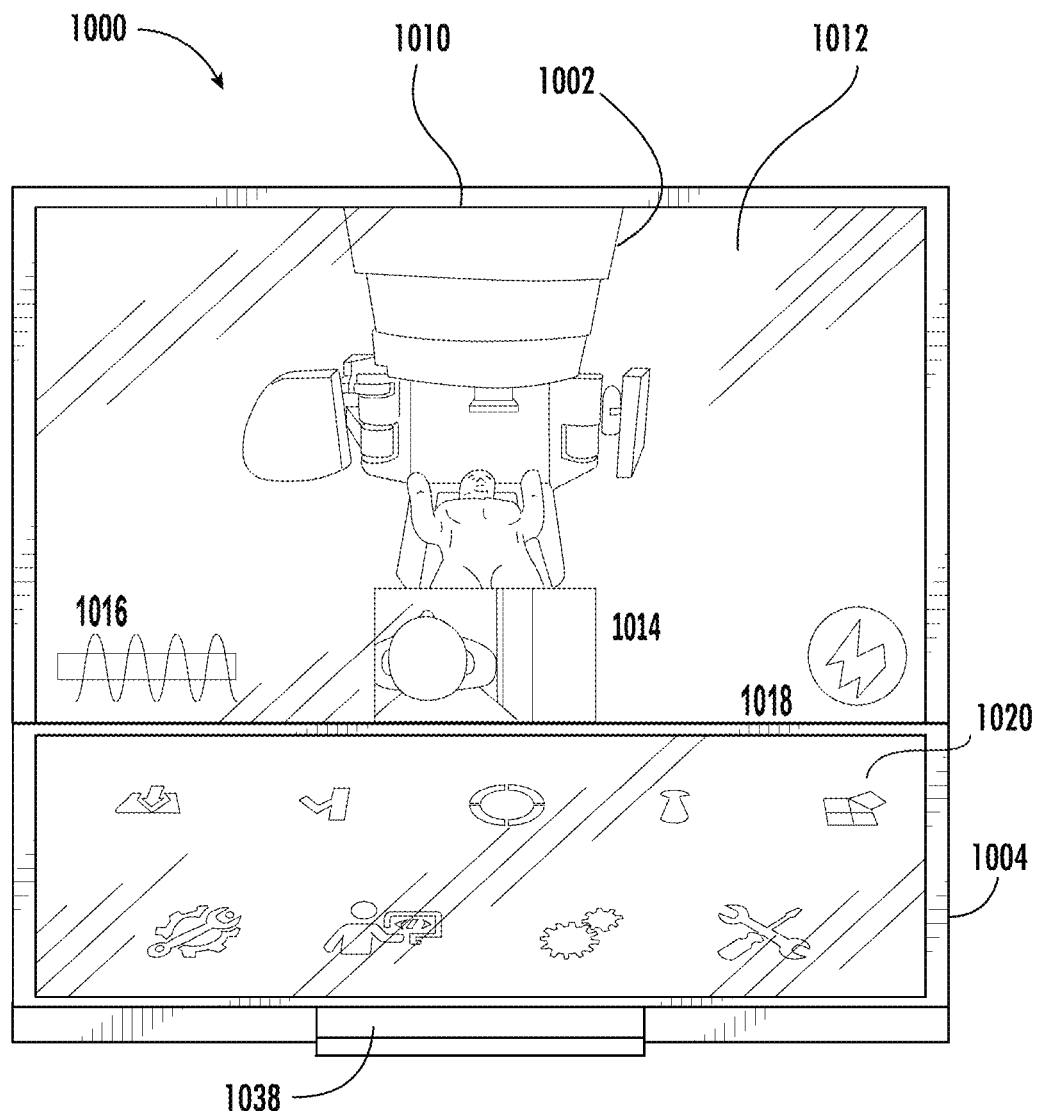
Figure 10D:
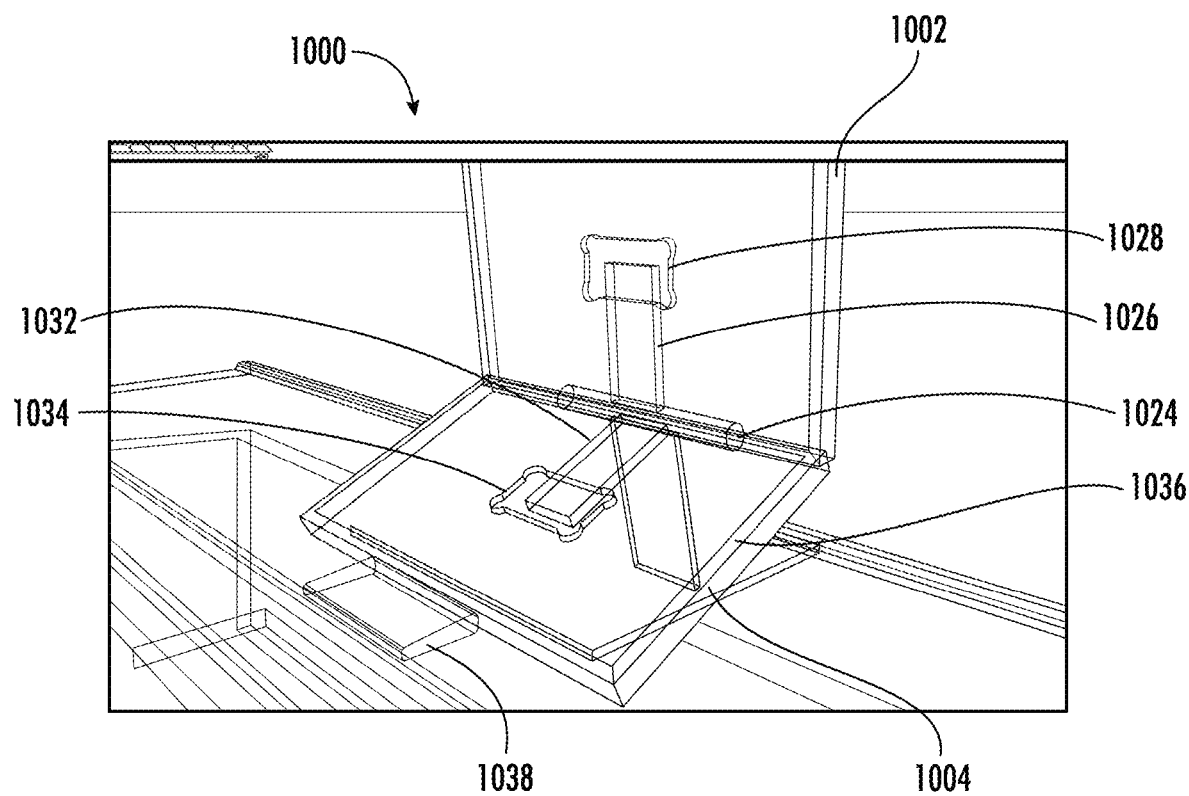

Referring now to FIGS. 10A-10D, various embodiments describing the console monitor (such as the console monitors 150 depicted and described in FIG. 1A) are provided. FIG. 10A, in conjunction with FIGS. 10B-D, illustrate various components of console system 1000 having two monitors 1002 and/or 1004 used in a radiotherapy system 1006. The radiotherapy system 1006 may be similar to the radiotherapy system depicted in FIG. 1A. The console monitors 1002, 1004 may be positioned outside of the treatment room, such as in a console room. The console monitors 1002, 1004 allow a user (e.g., technician, doctor, nurse, or other professional) to monitor a patient while the patient is receiving treatment. Although the example embodiment shows console monitor 1002 used for patient monitoring or other controls, other configurations may allow patient monitoring or other controls using console monitor 1004 in addition to or instead of console monitor 1002. Throughout the disclosure, controls described as being utilized on one of the console monitors can be implemented on the other console monitor. Through various pages of a GUI provided by the analytics server, the user can determine whether the radiotherapy system 1006 has been set-up properly. The user can also view the current machine parameters of the radiotherapy system 1006. The user may be able to use the console monitors 1002, 1004 to control the radiotherapy system 1006. The console monitors may include a dedicated input element (e.g., keyboard 1038) that can control the radiotherapy system 1006.

The console monitors 1002, 1004 may include a processing unit and a non-transitory machine-readable storage medium. The processing unit may include a processor with a computer-readable medium, such as a random access memory coupled to the processor. The console monitors 1002, 1004 may be executing algorithms or computer executable program instructions, which may be executed by a single processor or multiple processors in a distributed configuration. The console monitors 1002, 1004 may be configured to interact with one or more software modules of a same or a different type operating within the radiotherapy system 1006.

Non-limiting examples of the processor may include a microprocessor, an application specific integrated circuit, and a field programmable object array, among others. The console monitors 1002, 1004 may be capable of executing data processing tasks, data analysis tasks, and valuation tasks. Non-limiting examples of the console monitors 1002, 1004 may include a desktop computer, a server computer, a laptop computer, a tablet computer, and the like. However, some embodiments may include a plurality of server computing devices capable of performing various tasks described herein. The one or more processors may communicate with the analytics server to display various pages described herein.

The console monitor 1002 may be in communication with a server 1030 (e.g., such as the analytics server depicted in FIG. 1). Non-limiting examples of 1002 may include a desktop monitor, a tablet, a television monitor, and the like. In some configurations, the console monitor 1002 may be a touch screen (e.g., touch sensitive).

The console monitor 1002 may be configured to display a first GUI 1012. The first display 1010 may display a live view of the radiotherapy machine using one or more of the cameras described herein (e.g., camera placed on the couch, gantry, or on the walls/ceiling of the treatment room). For instance, the GUI 1012 may include a live view of the patient resting on the couch (on first display 1010) that is received from a camera at an end of the couch of the radiotherapy machine. The GUI 1012 may also include a secondary live view of the treatment room, as depicted in the live view box 1014. Therefore, the GUI 1012 may be a picture-in-picture display of the treatment room. The live feed depicted in the live view box 1014 may also be received from any of the cameras described herein.

The GUI 1012 may be customized by the operator. In some configurations, the operator may select a desired camera and the analytics server may revise the GUI 1012 such that the live feed corresponds to the camera selected by the operator. In some embodiments, the picture-in-picture may include two live feeds of the same camera.

The analytics server may display, on the console monitor 100, a live feed of a first camera and a second camera from a set of cameras (e.g., a first camera and second camera from a set of cameras as depicted in FIGS. 2E-2G). The analytics server may provide the live feed of the first camera and the second camera simultaneously (or near simultaneously) to the console monitor 1002. In a non-limiting example, the console monitor 1002 may display a live view of the couch (from any of the cameras pointed towards the couch, such as a room camera) where the live feed is not cropped or otherwise manipulated. The console monitor 1002 may also display a second live feed derived from the same camera. The second display may be manipulated (e.g., cropped), such that the second display highlights a particular portion of the image received from the camera.

In some configurations, the analytics server may perform the image manipulation (e.g., cropping) dynamically. For instance, the analytics server may crop the live feed received and automatically adjust the cropping box, such that the feed displayed on the console monitor 1002 stays focused on a particular area (e.g., the patient's chest wall or the patient's face).

The operator may also change the placement of the live view box 1014. For instance, the live view box may be displayed at any other location within the console monitor 1002 (e.g., bottom left or top right). The GUI 1012 may also include a motion monitoring indicator 1016 and a beam delivery progress indicator 1018. The operator may also revise the type and/or the placement of these indicators. For instance, a user may display a "collision" or a "beam on" indicator instead of the motion monitoring indicator 1016.

The GUI 1012 may be placed in a "locked" mode, such that the live view of the patient and/or the radiotherapy machine within the treatment room is always displayed. Therefore, the console system 1000 may be required to display a live feed of the radiotherapy machine regardless of the workflow steps described herein. This safety feature allows the user operating the console system 1000 to consistently monitor the treatment room on one monitor while progressing through the workflow described herein on another monitor.

While the analytics server is displaying a live view of the patient and/or the treatment room on the GUI 1012, the analytics server may display a series of workflow-oriented pages on the console monitor 1004 (as depicted in FIGS. 11C-11M). The console monitor 1004 may be in communication with a server (e.g., such as the analytics server depicted in FIG. 1A). Non-limiting examples of the console monitor 1004 may include a desktop monitor, and the like. In some embodiments, the second display 1020 may be a touch screen (e.g., touch sensitive).

The console monitor 1004 may be configured to display a GUI 1020. The GUI 1020 may display various pages associated with radiation treatment. For example, the GUI 1020 may be directed to the workflow-oriented series of pages described herein. In another example, the GUI 1020 may display an image of the radiotherapy machine during treatment. Additionally, or alternatively, the analytics server may display a live feed of the radiotherapy machine (e.g., live feed of the couch with or without the patient) on the GUI 1020.

The GUI 1020 may display various graphical indicators, as depicted in FIG. 10B. For instance, the GUI 1020 may include a graphical indicator that represents the analytics server executing surface matching on the patient resting on the couch. The graphical indicator may indicate that the surfaces are not matched as described herein.

In another example, the GUI 1020 may include graphical indicators that are displayed by the analytics server to provide setup note information. For example, the setup note information may convey illustrative examples of an accessory on a particular patient being setup for treatment. Additionally, or alternatively, setup note information may convey illustrative examples of an accessory on a two-dimensional or three-dimensional representation (e.g., animation) of a patient being setup for treatment. A non-limiting example of the second GUI is depicted in FIG. 11D.

The GUI 1020 may include graphical indicators that describe the areas of the patient requiring treatment. A patient may have multiple areas of the body requiring treatment. In the event that multiple areas of the body require treatment, the treatments may be performed consecutively. A non-limiting example of the second GUI is depicted in FIG. 11C.

The GUI 1020 may include graphical indicators that indicate the radiotherapy machine parameters. The radiotherapy machine parameters may indicate a satisfactory position of the gantry and/or couch for treatment. A non-limiting example of a second page is depicted in FIG. 11E-F.

In some configurations, the operator may customize the GUIs described herein, such that the console monitor 1004 displays the live view of the treatment room and the console monitor 1002 displays one or more pages, such as the workflow-oriented series of pages described herein.

As illustrated in FIG. 10D, the first monitor 1002 and the second monitor 1004 may be coupled to one another via a hinge 1024. The hinge 1024 may be disposed at the bottom end of the first monitor 1002 and the top end of the second monitor 1004. This configuration places the first monitor 1002 vertical to the second monitor 1004. In some embodiments, the hinge 1024 may be disposed at a first side of the first monitor 1002 and a first side of the second monitor 1004 so that the first monitor 1002 and the second monitor 1004 are disposed horizontally.

The hinge 1024 may include a first arm 1026 (e.g., extension). The first arm 1026 may extend from the hinge 1024 to along the rear of the first monitor 1002. The hinge 1024 may be coupled to a first monitor center 1028. The first monitor center 1028 may be disposed on and coupled to the rear of the first monitor 1002. The first monitor center 1028 and the first arm 1026 may co-facilitate the movement of the first monitor 1002 during the rotation of the hinge 1024. In operation, if a user adjust the first monitor 1002 to raise the height from the console, the first monitor 1002 and the second monitor 1004 will actuate from the hinge to increase the angle between the monitors 1002, 1004 but keeps them in a vertically-oriented position respective to each other.

The hinge 1024 may also include a second arm 1032 (e.g., extension). The second arm 1032 may extend from the hinge 1024 to the rear of the second monitor 1004. The hinge 1024 may couple to a second monitor center 1034. The second monitor center 1034 may dispose on and coupled to the rear of the second monitor 1020. The second monitor center 1034 and the second arm 1032 may co-facilitate the movement of the second monitor 1004 during the rotation of the hinge 1024.

The hinge 1024 may also include a stand 1036 (e.g., support). The stand provides structural support to the hinge 1024 so that at different set points (e.g., stop point) of the hinge 1024, the first monitor 1002 and the second monitor 1004 are provided support by the stand. In some embodiments, the stand 1036 incorporates linear actuators. In some embodiments, the hinge 1024 may include linear actuators to facilitate the travel of the first monitor 1002 and the second monitor 1004. In other embodiment, the stand 1036 may be coupled to pivoting members. In some embodiments, the hinge 1024 may be hydraulically coupled to the stand 1036.

In some embodiments, the actuators may be linked to a user's login information, such that upon the user logging in, the actuator automatically adjusts itself based on the user's preferences.

The console monitors 1002, 1004 may also include a keyboard 1038 (sometimes referred to as the "dedicated keyboard"). The keyboard 1038 may be an auxiliary component. In some embodiments, the keyboard 1038 may be integrated into the console monitors 1002, 1004. The keyboard 1038 may also be coupled to either one of the monitors or the stand (actuator), such that the keyboard 1038 moves along with one/two monitors and/or the actuator/stand of the console system 1000. The keyboard 1038 may be configured to control the radiotherapy machine (e.g., adjust machine parameters, move the couch/gantry, start/stop the treatment/radiation).

Console GUI

Figure 11A:
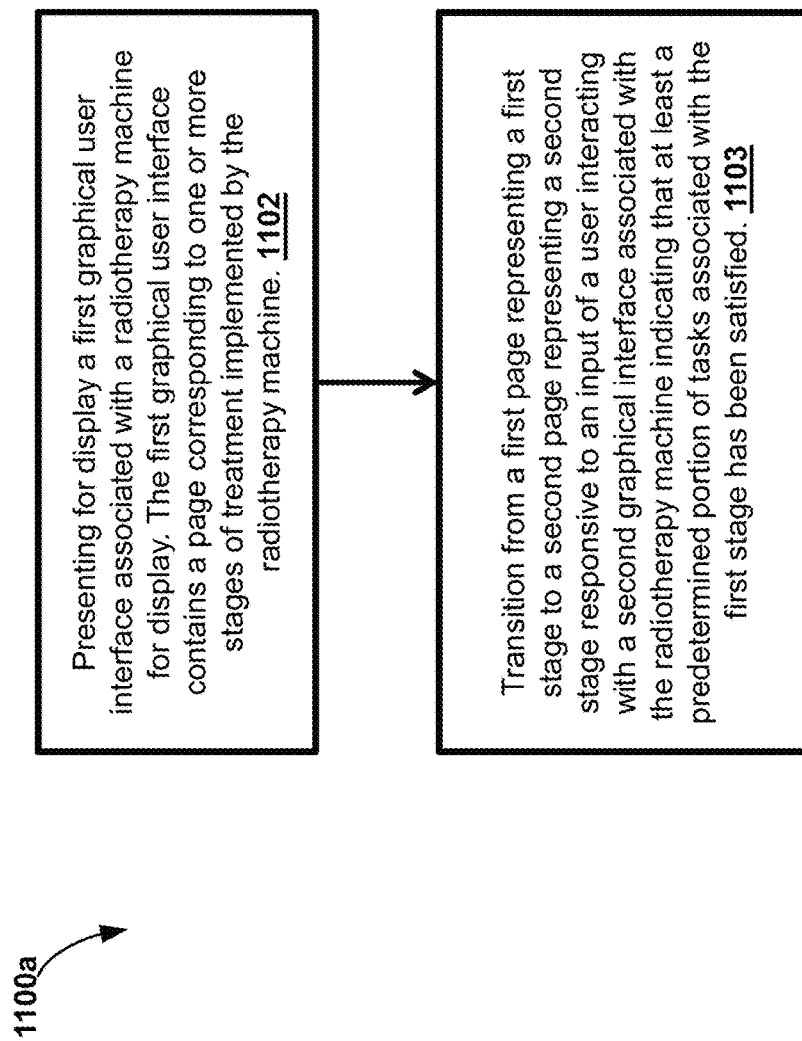
FIG. 11A illustrates a flow diagram executed in a workflow-oriented radiotherapy system, according to an embodiment.

FIG. 11A illustrates a flowchart depicting operational steps performed by a server, such as the analytics server described in FIG. 1A, displaying various interactive pages of a GUI configured to display various stages of performing radiotherapy on a patient. Even though the method 1100a is described as being executed by the analytics server, the method 1100a can be executed by any server(s) and/or performed locally using a computer/processor associated with the radiotherapy machine and/or the console (as discussed in FIGS. 10A-10D). Other configurations of the method 1100a may comprise additional or alternative steps, or may omit and/or mix one or more steps altogether.

At step 1102, the analytics server may present a first page of a first GUI associated with a radiotherapy machine. As discussed herein, the analytics server may asynchronously or synchronously display the pages on one or more screens outside the treatment room (including on one or more screens on a console as described in FIGS. 10A-10D), inside the treatment room (including on the gantry) and on various devices using various platforms. The first GUI presented by the analytics server on the one or more screens on the console may coordinate with the second GUI presented by the analytics server in a treatment room.

The first GUI presented by the analytics server may contain a page associated with radiotherapy treatment of a patient (e.g., a person to be treated by the radiotherapy machine), as shown in 1102. Some of the pages on the pages of the first GUI presented by the analytics server may correspond to different stages within a workflow (e.g., as discussed in FIGS. 4A-4P). Each page may contain a plurality of pages to progress a user (e.g., technician, doctor, nurse or other professional) through one or more stages. There may be five predetermined stages. A user and/or system administrator may determine the number of stages and the content associated with each of the stages. One or more pages may be used to describe the workflow stages to treat a patient using a radiotherapy machine. As described herein, the workflow progress (presented by the analytics server using pages) describes the work performed by a user to treat a patient using the radiotherapy machine. In an example, a first page (corresponding to a first page) may be a first stage of the workflow. As discussed herein, the analytics server may display only relevant information on each page. Relevant information, as used herein, may refer to a subset of all information used to treat the patient relevant at a given stage in the workflow. The relevant information is information that a user (e.g., a technician, nurse, doctor or other professional) consumes while viewing the displayed page.

The analytics server's presentation of the first GUI on the screen transitions from a first page (showing a first page) to a second page (showing a second page) based on an input received by the analytics server, as shown in step 1103. The analytics server may transition between the pages displayed to the user in response to one or more triggers. Triggers may include a user's interaction at the console GUI (e.g., FIGS. 4A-4P), a user's interaction with the dedicated keyboard (e.g., FIG. 10B), a user's one or more actions performed in the treatment room (e.g., FIGS. 4A-4P), a user's interaction with the pendent (e.g., FIG. 3B), or the analytics server determining a completion of one or more tasks performed in the treatment room (e.g., FIGS. 4A-4P).

As discussed herein, the second page may contain information belonging to a stage on the first page. For example, the second page may contain additional information about the stage on the first page. Additionally, or alternatively, the second page may not contain information associated with the stage on the first page. For example, the second page may progress to a subsequent stage.

The input received by the analytics server may be an input generated by a user using a console (e.g., console described in FIGS. 10A-10D) in a different location (e.g., a console room located away from the treatment room). The analytics server may use the input generated by the user from the different location to transition both the GUI displayed on the console and the GUI displayed in the treatment room. In the event the analytics server is displaying the GUI on additional monitors, the analytics server may use the input generated by the user from the different location to transition the GUIs displayed on any additional monitors. Additionally, or alternatively, the analytics server may use the input generated by the user in the different area to transition only the GUIs displayed on the screen of the console. For instance, the user in the different area may be viewing a different GUI than the user in the treatment room. Additionally, or alternatively, in the event the console is displaying one or more GUIs on various screens, the input generated by the user in the different area may transition one or more of the GUIs displayed on the various screens.

In one example, a console room has a display, and a radiotherapy machine has a display on a gantry. An analytics server presents a first GUI on the console room display and presents a second GUI on the radiotherapy machine display. Each of the first and second GUIs can transition between pages based upon the stages of treatment. In some instances, such as a transition to a next stage, as the second GUI changes on the radiotherapy machine display, the first GUI on the console room display will also change. An input to or an action affecting the second GUI (e.g., indicating that at least a predetermined portion of tasks associated with a stage has been satisfied) may cause the second GUI to transition from a first page of a first stage to a second page of a second stage, and the first GUI will also transition accordingly.

Additionally, or alternatively, as discussed herein, the analytics server may deny the user using the radiotherapy machine (e.g., the user in the treatment room) from transitioning to the second page from the first page in response to one or more inputs by a user (or system administrator, third party, supervisor, or the like) in the different area. The user in the different area may also effectively "pause" the workflow progression in the treatment room by denying the user in the treatment room from progressing to the second page. In some embodiments, the user may still navigate to, view, and/or edit the data in the other pages but the progress for that page is paused. That is, the analytics server will not track the executed and/or completed steps for the second page. The duration of the "pause" of the workflow progression may be for a predetermine period of time. For instance, the analytics server may "pause" the workflow progression for 10 minutes. In the event the "pause" of the workflow progression is determined to be a predetermined period of time, the user in the different area may "un-pause" the "paused" workflow progression by inputting one or more inputs to the analytics server.

Additionally, or alternatively, the analytics server may transition to a second page from the first page based on an input from the user in the different area. For instance, even in the event that the analytics server determines that the predetermined portion of tasks have been completed (e.g., using, for instance, the flag threshold as discussed in FIGS. 4A-4P), the analytics server may not transition to the second page from the first page unless the user in the different area confirms that the predetermined portion of tasks have been completed. The user in the different area will hereinafter be called the user in the console room, but it should be appreciated that the user may not necessarily be in the console room (e.g., the user may be viewing one or more various screens such as the screens displayed by the analytics server on one or more platforms).

Additionally, or alternatively, the analytics server may transition from a first page to a second page in the event the screen displaying the page in the treatment room transitions from the first page to the second page. The pages in the treatment room may be transitioned as discussed herein (e.g., as described in FIGS. 4A-4P).

Additionally, or alternatively, the analytics server may transition from a first page to a second page on one or more screens in the event the analytics server, monitoring the treatment room, determines that a predetermined portion of tasks have been completed in the treatment room, as discussed herein (e.g., as described in FIGS. 4A-4P).

Additionally, or alternatively, the analytics server may transition from a first page to a second page on one or more screens in the event that the analytics server receives an input from a user (e.g., a user in the treatment room). For instance, the user in the treatment room may interact with a page displayed by the analytics server on the screen on a radiotherapy machine.

Figure 11B:
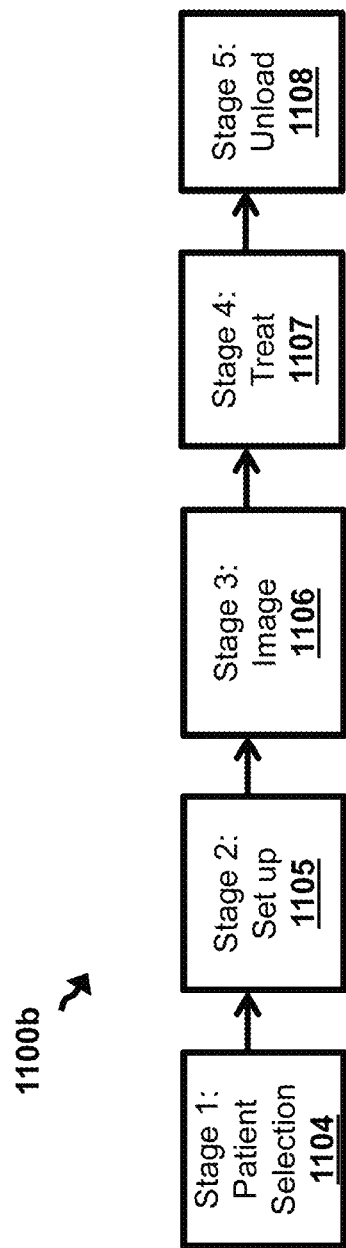
FIGS. 11B-11N illustrate pages displayed in a workflow-oriented radiotherapy system, according to an embodiment.
Figure 11C:
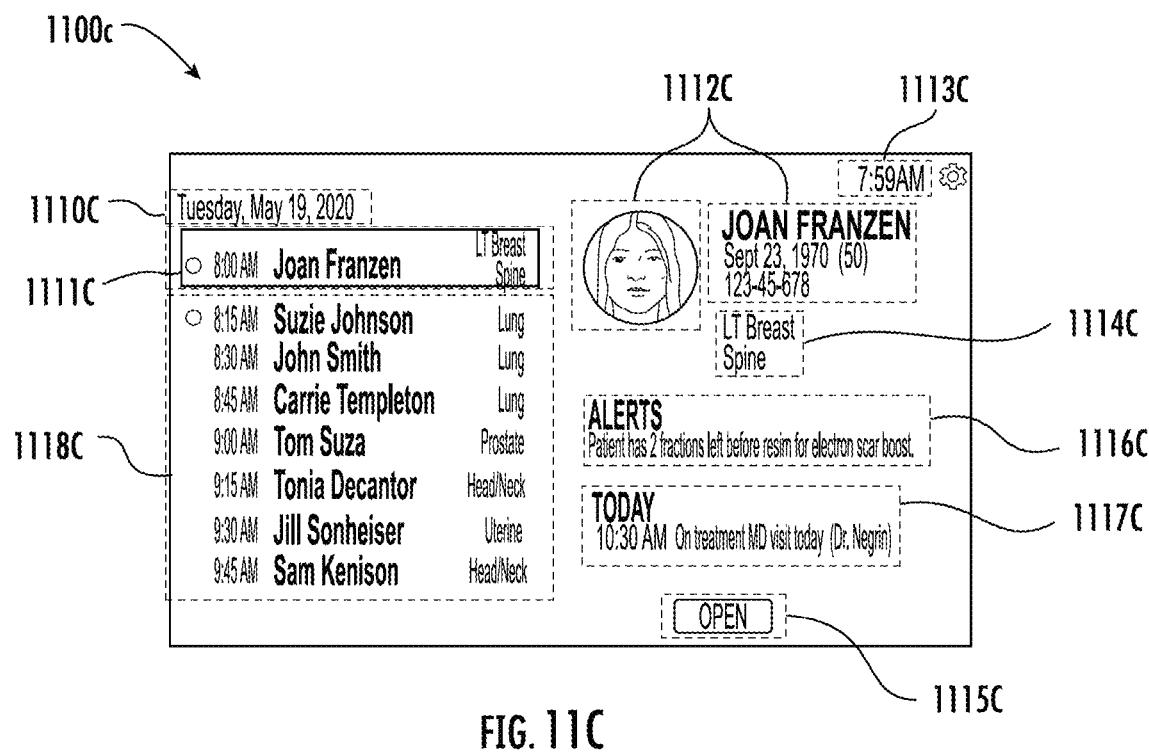
Figure 11D:
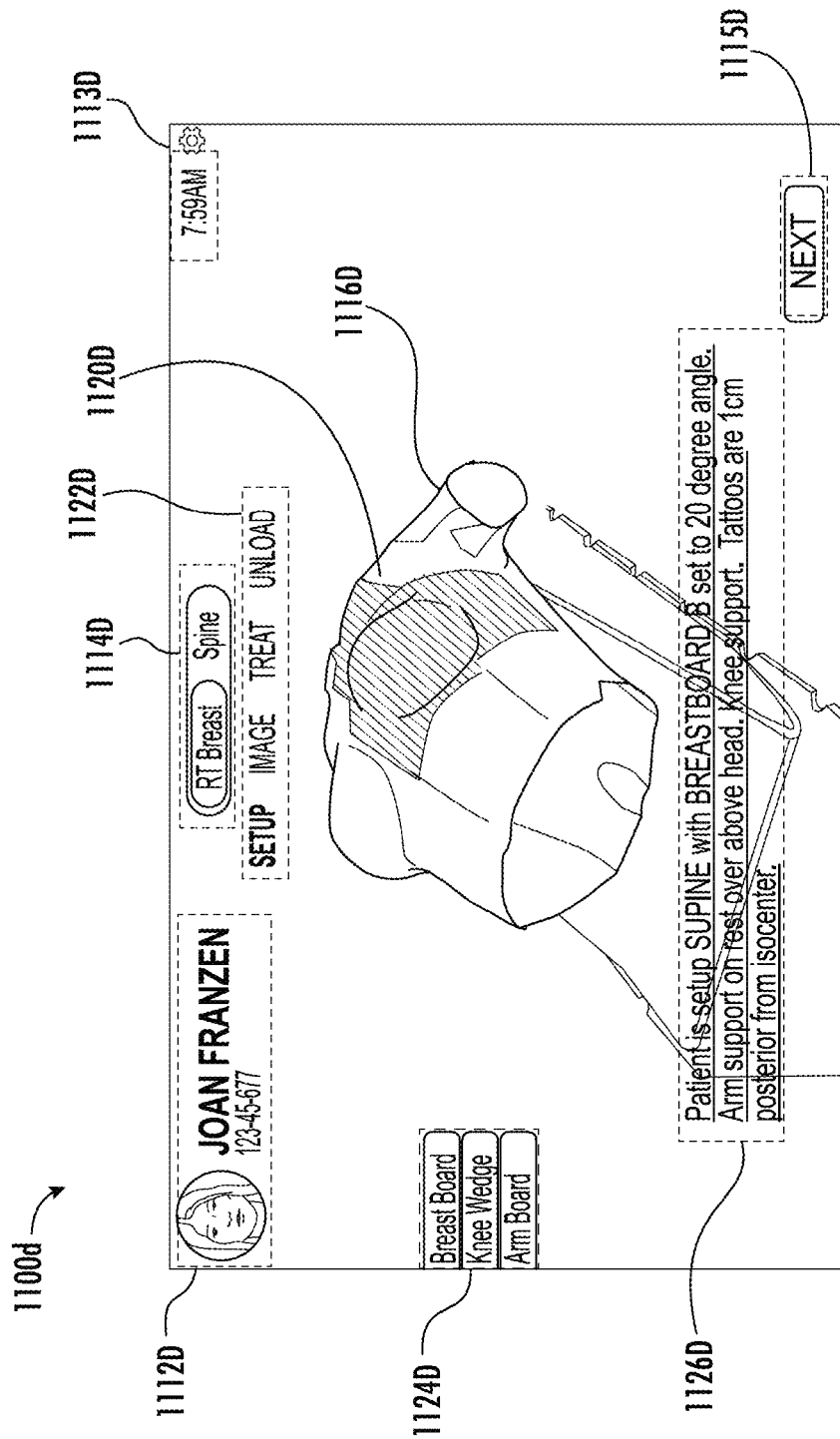
Figure 11E:
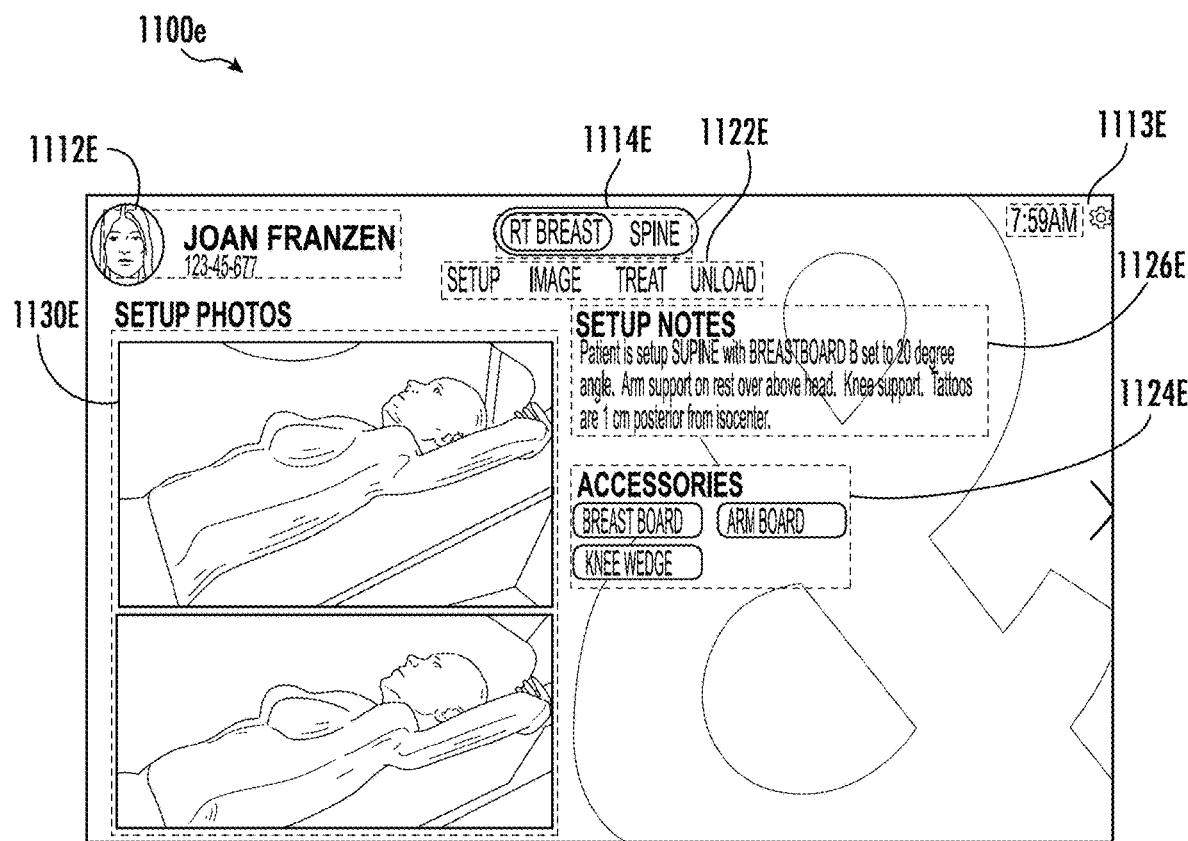
Figure 11F:
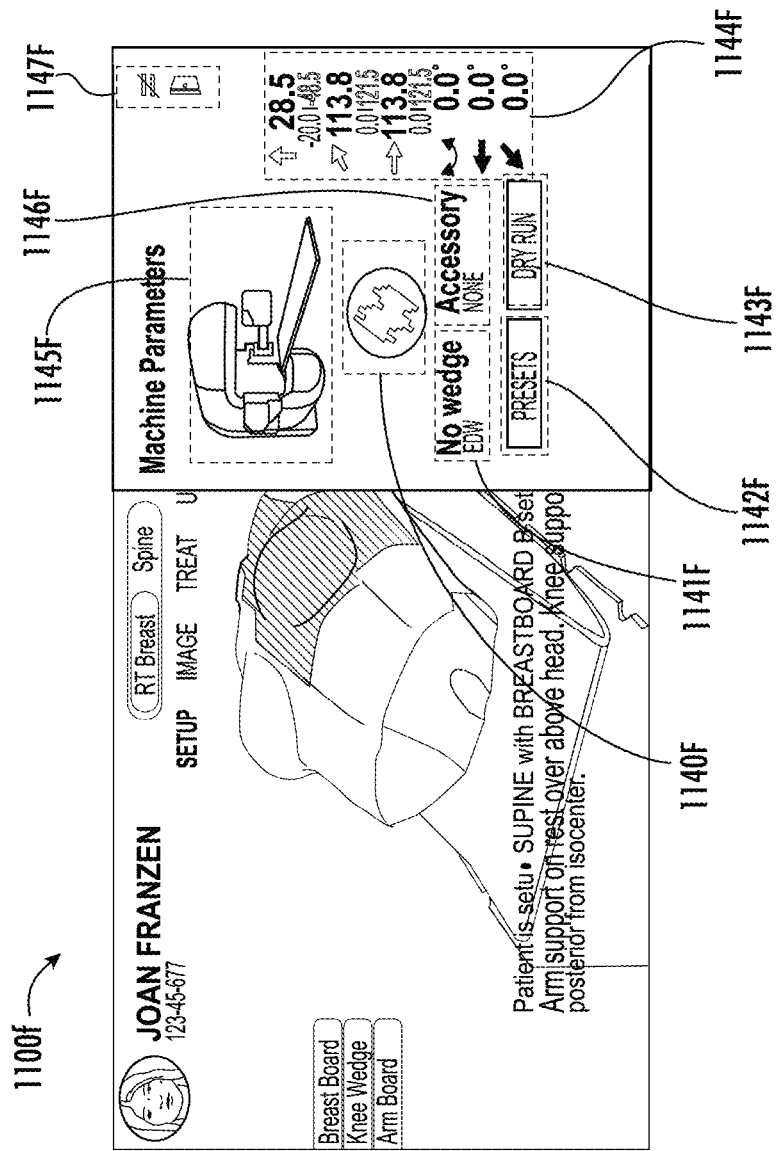

FIG. 11B illustrates the five stages of workflow for a console to be performed for a successful execution of treating a patient with radiation using a radiotherapy machine, in accordance with an embodiment. Although five stages are shown, it is intended that the workflow can comprise any number of stages and/or sub-stages. The method $1100b$ describes the workflow stages of performing radiotherapy on a patient displayed by a server, such as the analytics server described in FIG. 1A. The workflow stages displayed by the analytics server are displayed on various interactive workflow-oriented series of pages configured to display the various stages. Even though the method $1100b$ is described as being executed by the analytics server, the method $1100b$ can be executed by any server(s) and/or performed locally using a computer/processor associated with the console. Other configurations of the method $1100b$ may comprise additional or alternative stages, or may omit and/or mix one or more stages altogether. Further, each of the five stages of workflow represented in method $1100b$ may be standalone stages displayed by the analytics server on standalone pages.

Referring to FIGS. 11C-11M, non-limiting examples of the analytics server displaying pages based on a user's progression through the stages of the workflow are depicted. Even though FIGS. 11C-11M illustrate a progression in sequential pages, in some configurations the analytics server may display the depicted pages in another order. Moreover, the analytics server may not display one or more of the pages described herein. The analytics server may display various combinations and configurations of the pages depicted herein.

The pages depicted in FIGS. 11C-11M illustrate one or more pages displayed by the analytics server on a console (or other separate screen). The analytics server may use the methods and systems described herein to display workflow-oriented series of pages (e.g., pages $1100c$-$1100m$, in FIGS. 11C-11M respectively) such that a user progresses through the workflow to successfully treat a patient using a radiotherapy machine.

As discussed herein, the analytics server may generate, receive, and/or retrieve a representation of a patient on the couch of the radiotherapy machine, representations of the gantry, representations of the couch, and/or representations of patient accessories (e.g., FIGS. 4A-4P). Additionally, or alternatively, the analytics server may monitor the patient on the couch of the radiotherapy machine, gantry, couch, patient accessories and user in the treatment room. The analytics server may display the generated, received, retrieved, and/or monitored information regarding the patient, couch, gantry, and radiotherapy machine in the treatment room on one or more pages displayed using one or more screens.

For example, the analytics server may be in communication with a plurality of cameras (e.g., camera at an end of the couch, gantry camera, or other cameras places within the radiotherapy room and the like) to capture images, continuous time series images, or streams of video data from one or more perspectives of the patient, the accessories around the patient, the couch, and/or the gantry (e.g., FIGS. 4A-4P). The analytics server may use any appropriate method of generating models or images to represent the patient on the couch of the radiotherapy machine, the couch, and/or the gantry. Additionally, or alternatively, the analytics server may use the live feed of data captured from the plurality of cameras from one or more perspectives as representations of the patient on the couch of the radiotherapy machine, the couch, and/or the gantry.

At step 1104, the analytics server displays Stage One, which represents the stage related to patient selection. Stage One of the console workflow (e.g., step 1104 in FIG. 11B) may be similar in structure and operation to Stage One of the treatment room workflow (e.g., step 410 in FIG. 4B). For instance, Stage One displayed by the analytics server on the console room may contain the same information as Stage One displayed by the analytics server on a screen on the gantry.

In FIG. 11C, page $1100c$ (Stage One, Patient Selection) displayed on a GUI by the analytics server may use the same (or similar) graphical elements as discussed herein with respect to a GUI on a radiotherapy machine. For example, graphical elements displayed by the analytics server may include graphical indicators, status indicators, progress indicators, treatment related images, non-treatment related images, backgrounds, live feeds of the radiotherapy machine, and notes as discussed herein.

For instance, page $1100c$ may include text 1110C conveying the date, text 1118C conveying the a patient time (e.g., the time of the patient scheduled for upcoming treatment, the time the patient is expected to arrive at the treatment area, the time the patient may begin treatment, the time the patient is expected to check-in, the wait time), text 1111C emphasizing the patient schedule for upcoming treatment, graphical elements 1112C, including both non-treatment related images and text that convey PII, text 1113C conveying the current time, text 1114C indicating one or more areas of the patient requiring treatment, text 1116C conveying an alert, text 1117C conveying information about the patient's upcoming medical appointments, as described similarly to the graphical elements in FIGS. 4A-4P. Page $1100c$ may also include interactive button 1115C that opens/displays the treatment information and/or beings the treatment workflow associated with the emphasized patient scheduled for upcoming treatment in text 1111C.

In some embodiments, a user may interact with the page and/or an interactive button on the page (not shown), triggering the analytics server to display one or more machine parameters in detail.

At step 1105, the analytics server displays Stage Two, which represents the stage related to setting up the selected patient from step 1104 for radiotherapy treatment.

In FIG. 11D, page $1100d$ (Stage Two, Setup) depicts summary information that may provide the user with a visual representation of what area of the patient is to be treated and a technique that is to be used to treat the patient. The page $1100d$ may use the same (or similar) graphical elements as discussed herein. For example, graphical elements displayed by the analytics server may include graphical indicators, status indicators, progress indicators, treatment related images, non-treatment related images, backgrounds, live feeds of the radiotherapy machine, and notes as discussed herein.

For instance, page $1100d$ may include graphical elements 1112D, including both non-treatment related images and text that convey PII, text 1113D conveying the current time, text 1114D indicating one or more areas of the patient requiring treatment, progress indicator 1122D indicating the progress of the user in the treatment room (e.g., highlighting the current stage and displaying the subsequent stages) and graphical indicators 1124D (in conjunction with status indicators) conveying accessories located by the radiotherapy machine as described similarly to the graphical elements in FIGS. 4A-4P.

The analytics server may display the model 1116D as a representation of the patient surface as known at the time of planning (or other time) and overlay graphical indicator 1120D to indicate to the user what area of the patient is to be treated. Graphical indicator 1120D may indicate the treatment beam projection overlaid on the model 1116D. The graphical indicator 1120D may be extracted by the analytics server from user notes, images during patient planning, and the like. The analytics server may also receive graphical indicator 1120D (e.g., as an input from a user, from a database). As described herein, the representation of the patient may be a three-dimensional representation of the patient at the time of planning, a two-dimensional representation at the time of planning, and the like. In the event the patient has entered the treatment room and positioned themselves on the couch, the representation of the patient may be a live feed view of the patient and/or a two-dimensional/three-dimensional representation of the patient on the couch.

Page 1100d may also include interactive button 1115D that when interacted with, may result in a next page being displayed by the analytics server. The analytics server may display pages in the console room independently from the displayed pages in the treatment room. For instance, a user in the console room may view a different page from a user in the treatment room.

Additionally, or alternatively, the analytics server may display notes 1126D that convey to the user (either in the treatment room or in the console room) information regarding setting up the patient on the couch. A user in the console room may view or edit the display notes 1126D in real time (e.g., while the user in the treatment room is setting up the patient). The analytics server may display the revised display notes 1126D on one or more screens in various other areas (e.g., on a screen in the treatment room). Additionally, or alternatively, the user in the console room may edit the display notes 1126D before or after the treatment scheduled with the patient.

In the event the user seeks addition information related to the information on the page displayed by the analytics server, the user may direct the analytics server to transition to other pages using various inputs. For instance, the user may interact with the console to generate inputs provided to the analytics server. An example of the types of additional information that the analytics server may provide based on the user input is displayed in example 1100N of FIG. 11N. Additionally, or alternatively, as discussed herein, the analytics server may display example 1100N as a page on the console in response to a user input (e.g., a "menu" button on the console).

As discussed herein, for instance, similar to the inputs used in example 400e in FIG. 4E, the user may input the response 1190N to indicate to the analytics server that the user is seeking additional setup information details, the user may input the response 1191N to indicate to the analytics server that the user is seeking to perform an action, the user may input the response 1194N to indicate to the analytics server that the user is seeking additional patient information details, and the user may input the response 1192N to indicate to the analytics server that the user is seeking additional machine details.

Figure 11G:
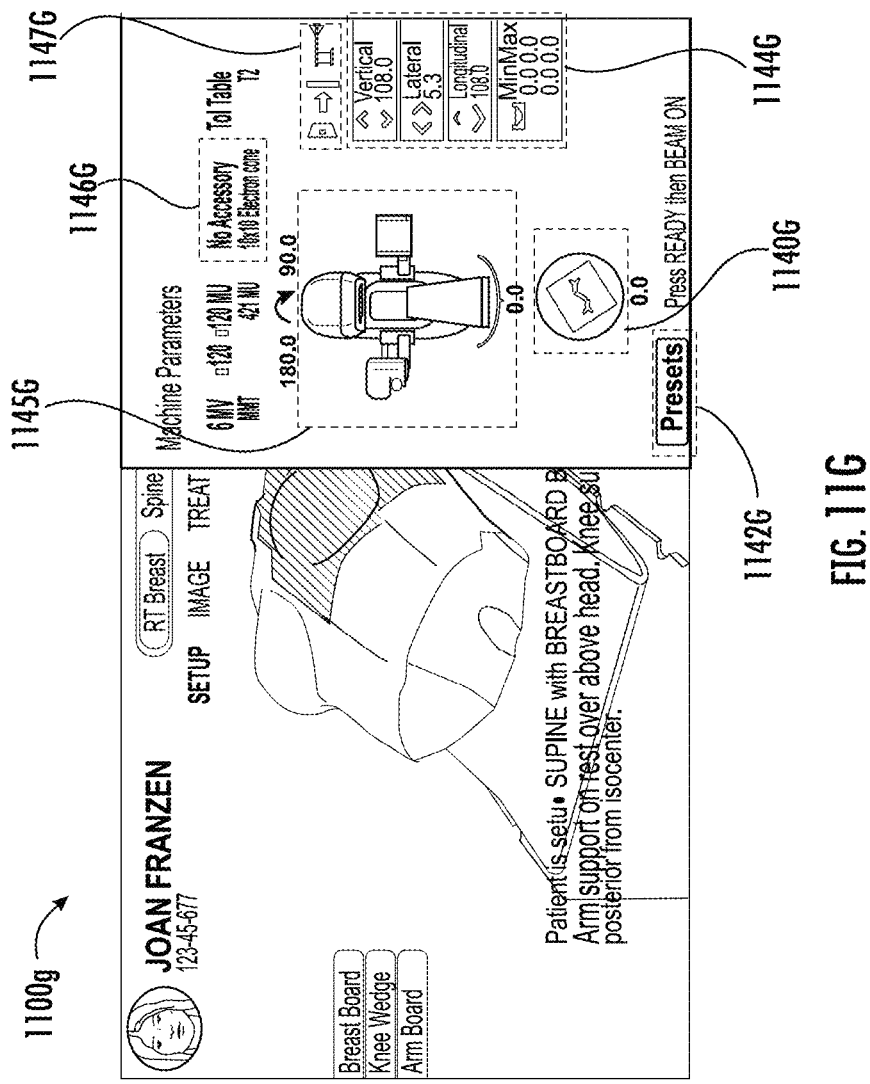
Figure 11H:
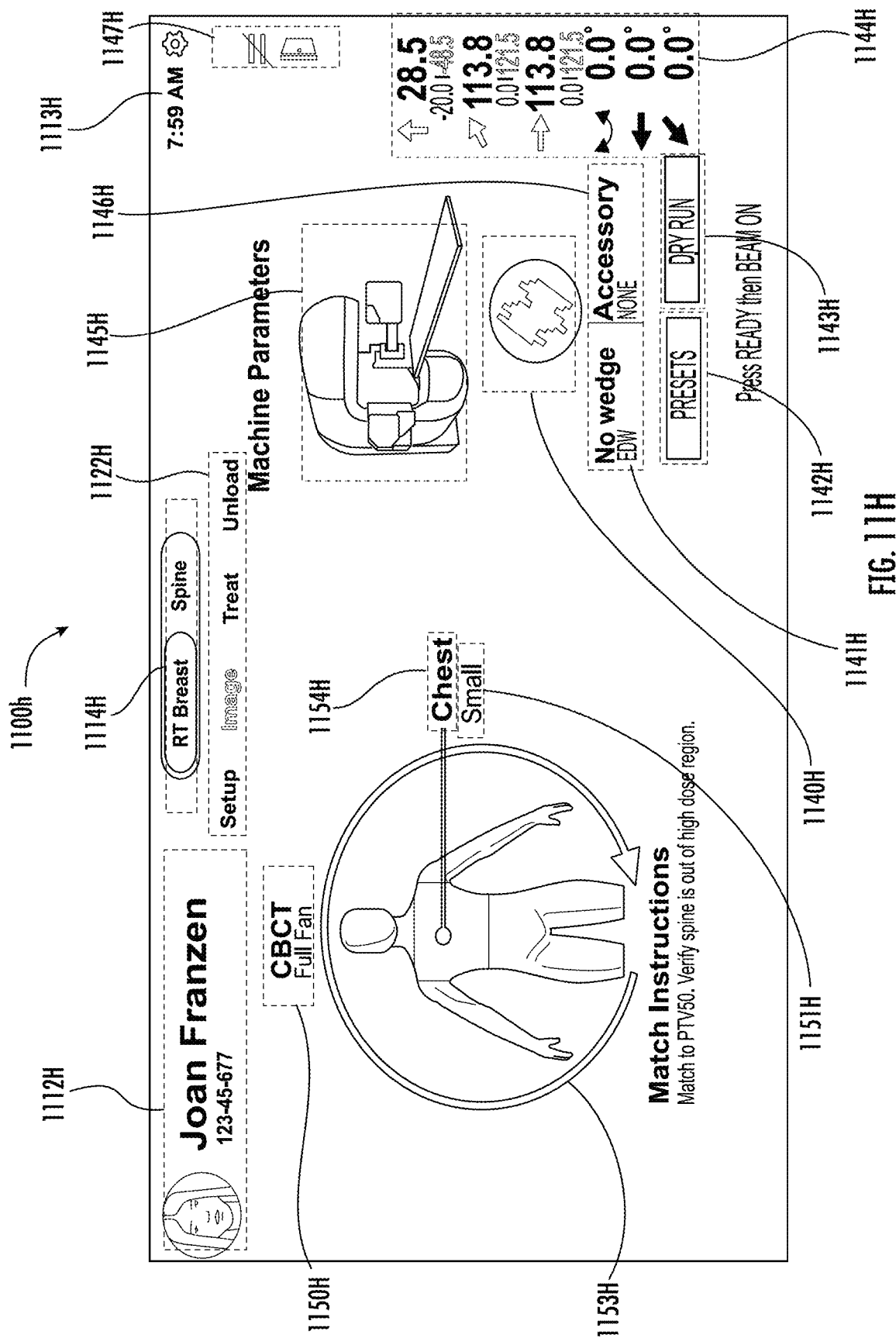
Figure 11I:
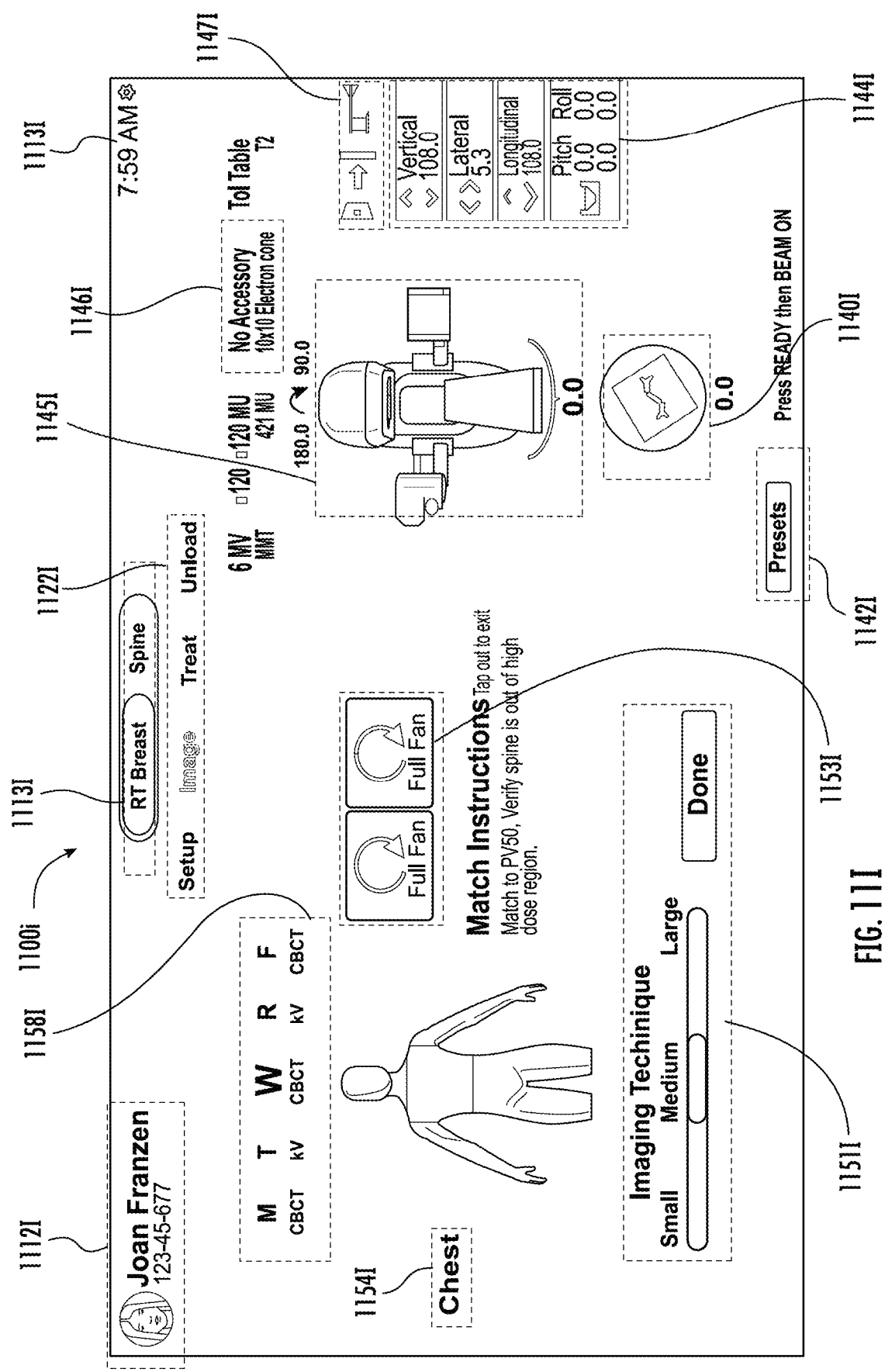
Figure 11J:
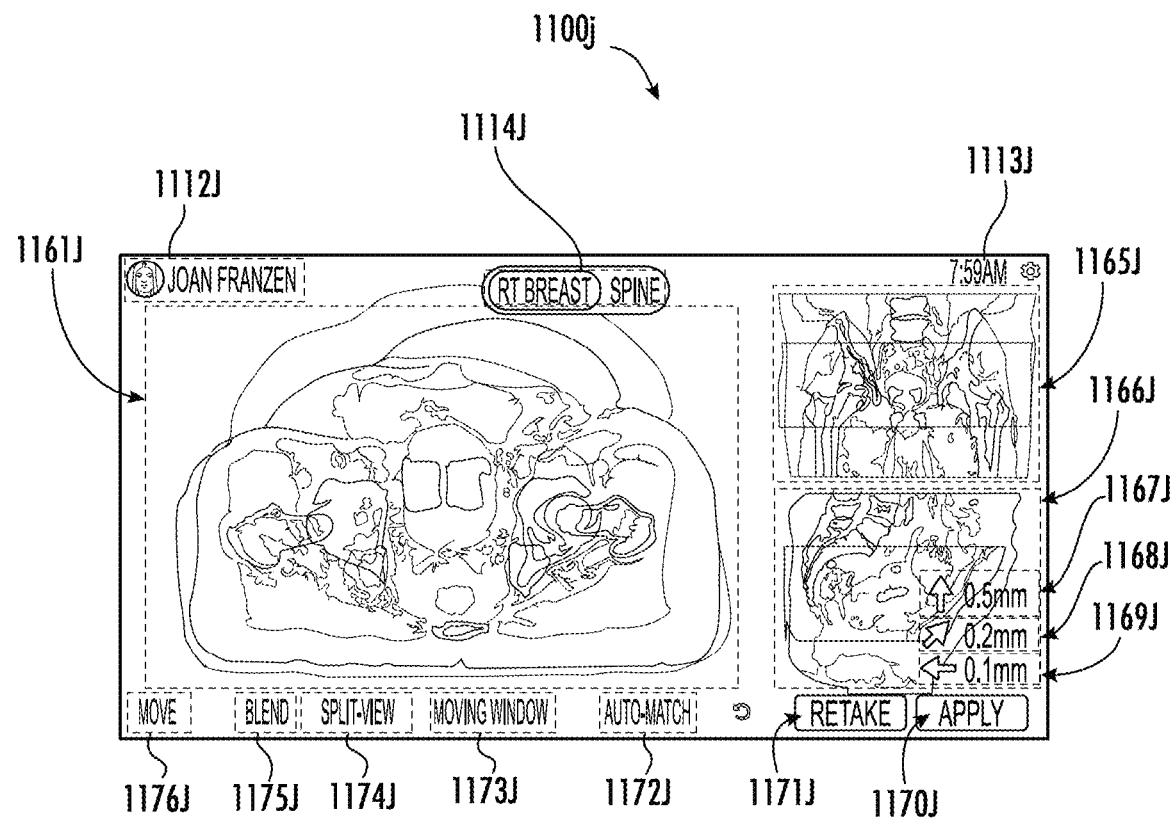
Figure 11K:
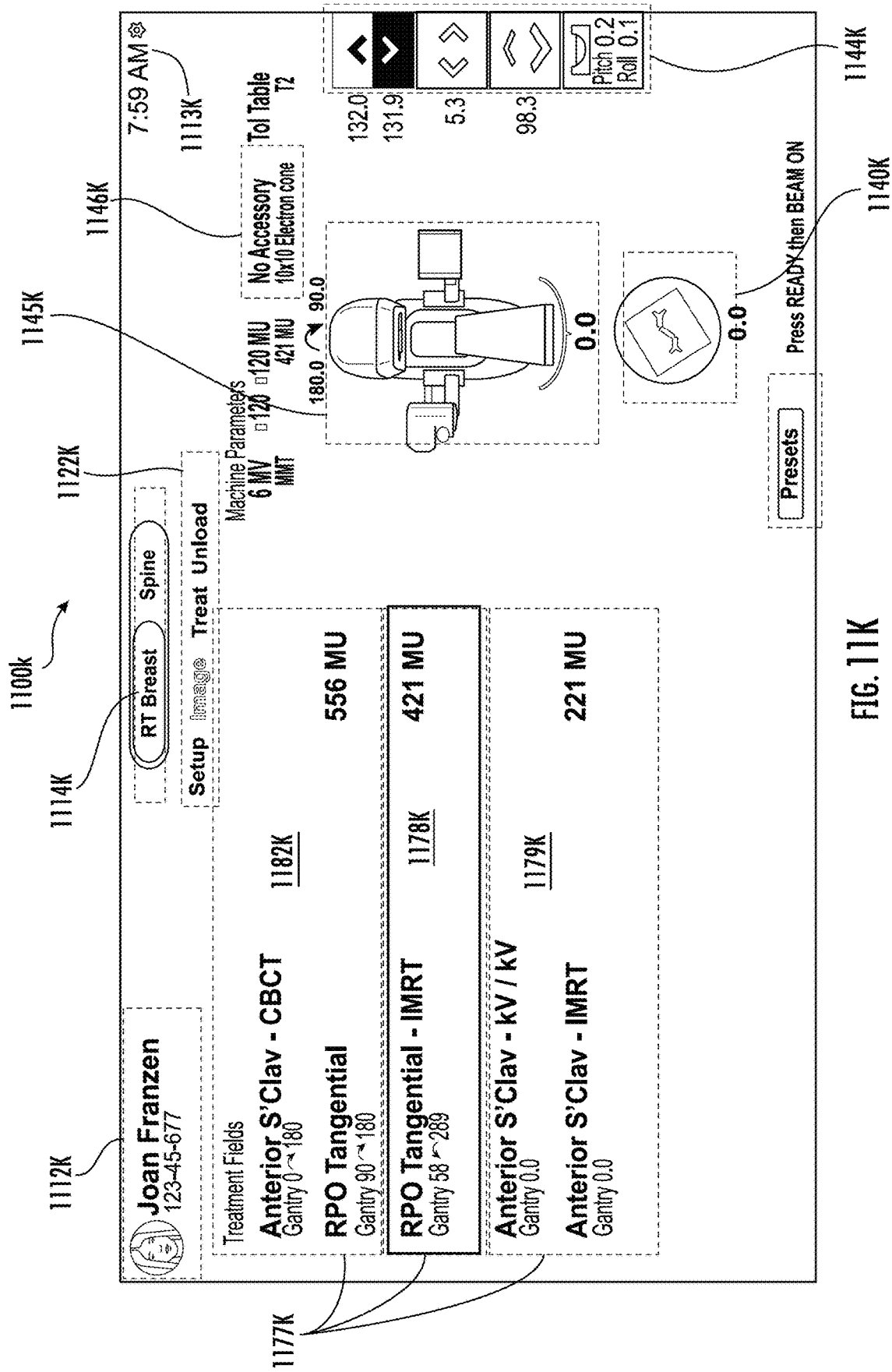
Figure 11L:
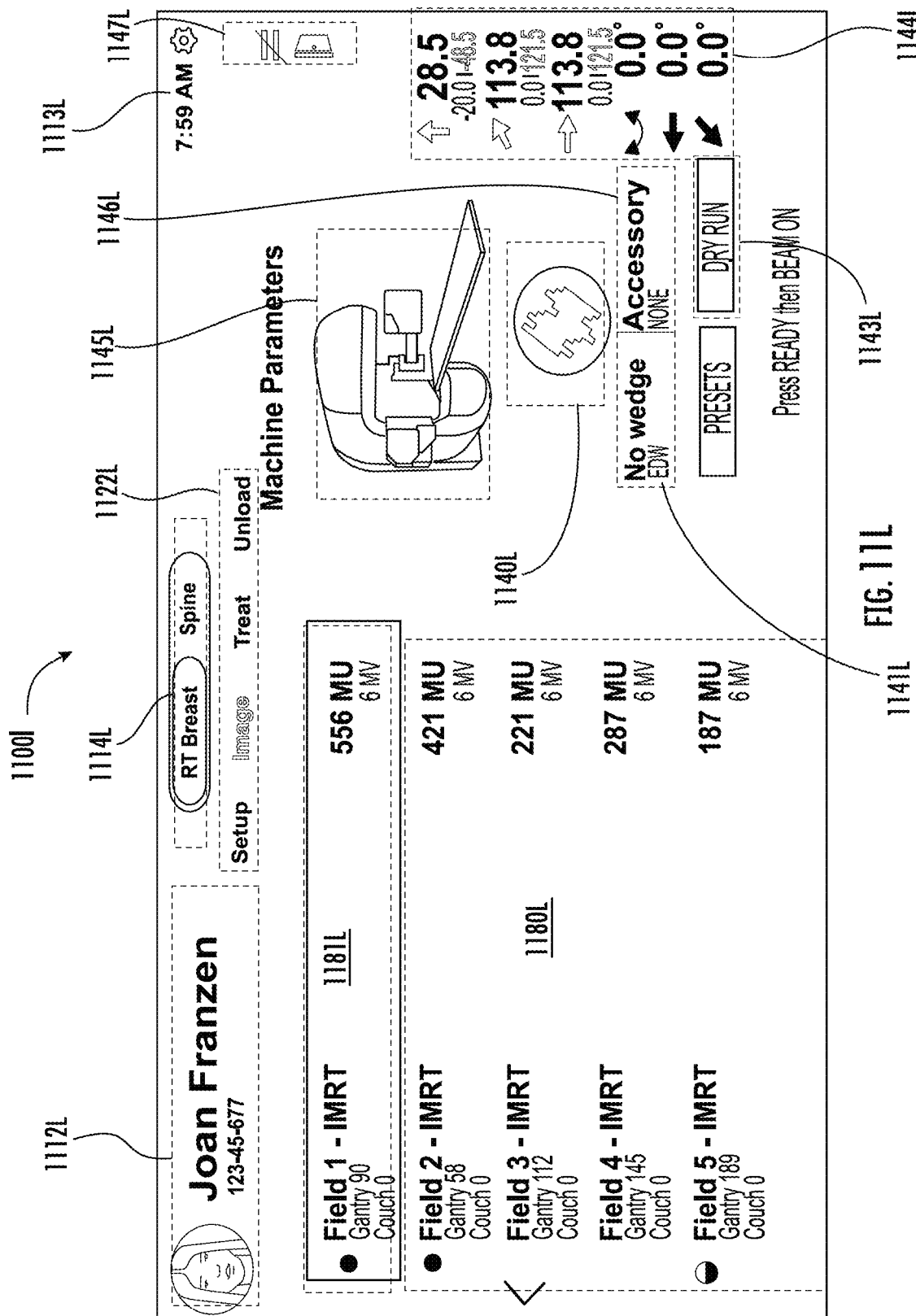
Figure 11M:
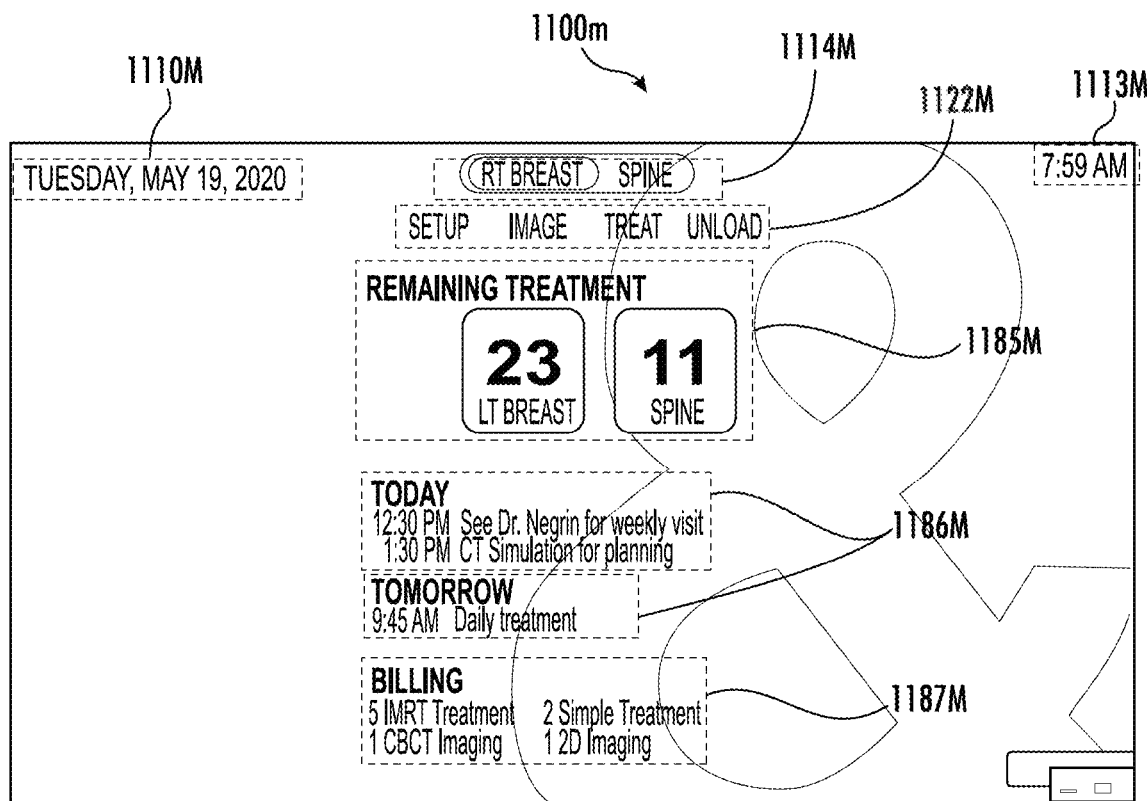
Figure 11N:
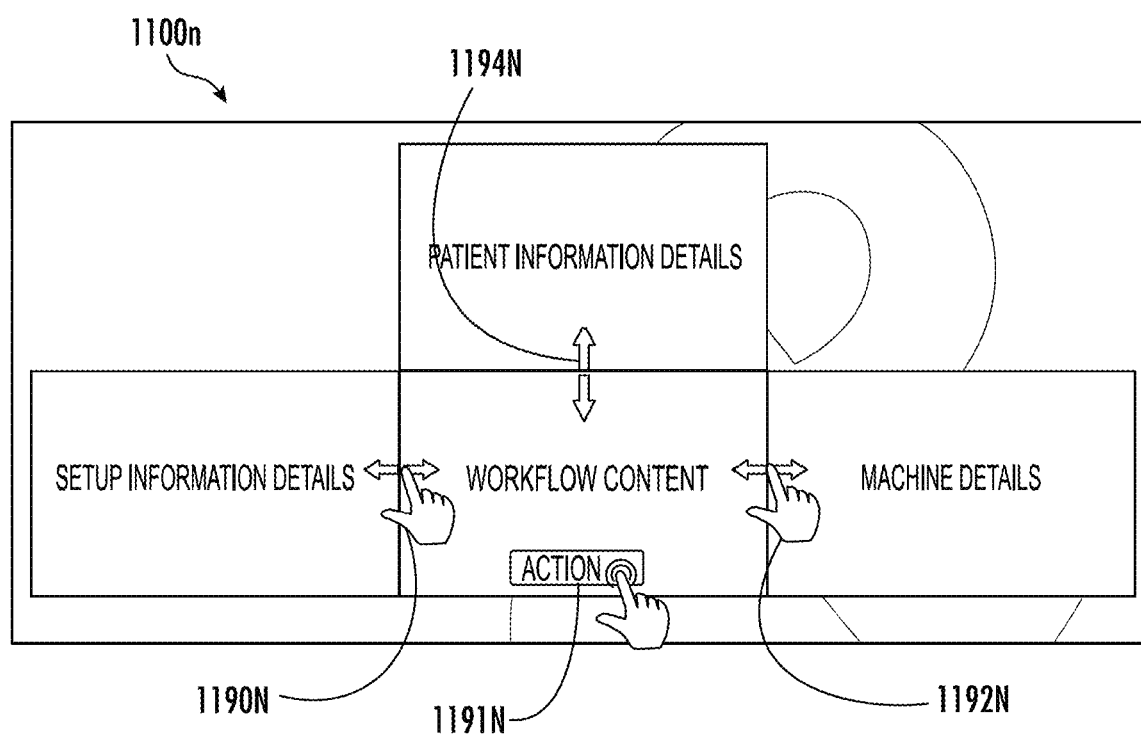

Referring now to FIG. 11E the analytics server may display additional setup information based on an input 1190N as shown in FIG. 11N. Additionally, or alternatively, the analytics server may display other information supplemental information related to the current stage of the workflow. For example, during the imaging stage of the workflow (Stage Three), in response to receiving input 1190N, the analytics server may display image acquisition settings. Similarly, during the treatment stage of the workflow (Stage Five), in response to receiving input 1190N, the analytics server may display treatment details. As discussed herein, the setup information on page 1100e may not be mandatory within the series of page. That is, the user may never view page 1100e and the analytics server may not display page 1100e unless and until required by the user (e.g., by an input). The page 1100e may use the same (or similar) graphical elements as discussed herein. For example, graphical elements displayed by the analytics server may include graphical indicators, status indicators, progress indicators, treatment related images, non-treatment related images, backgrounds, live feeds of the radiotherapy machine, and notes as discussed herein For instance, page 1100e may include graphical elements 1112E, including both non-treatment related images and text that convey PII, text 1113E conveying the current time, text 1114E indicating one or more areas of the patient requiring treatment, progress indicator 1122E indicating the progress of the user in the treatment room (e.g., highlighting the current stage and displaying the subsequent stages), display notes 1126E providing setup note information, graphical indicators 1124E (in conjunction with status indicators) conveying accessories located by the radiotherapy machine, and treatment related images 1130E may be to clarify the display notes 452, as similarly described similarly to the graphical elements in FIGS. 4A-4P.

Referring now to FIGS. 11F-11G, the analytics server may display additional information based on an input 1192N as shown in FIG. 11N. As discussed herein, the setup information on pages 1100f-1100g may not be mandatory within the series of pages. That is, the user may never view pages 1100f-1100g and the analytics server may not display pages 1100f-1100g unless and until required by the user (e.g., by an input). The pages 1100f-1100g may use the same (or similar) graphical elements as discussed herein. For example, graphical elements displayed by the analytics server may include graphical indicators, status indicators, progress indicators, treatment related images, non-treatment related images, backgrounds, live feeds of the radiotherapy machine, and notes as discussed herein.

For instance, page 1100f may include graphical elements 1145F displaying a three-dimensional representation (e.g., animation) representing the radiotherapy machine and/or patient, graphical indicator 1147F (in conjunction with status indicators) representing more than one safety feature associated with the treatment room and/or console room, graphical indicator 1140F indicating the projected beam shape from the collimator and/or the type of beam, text 1141F conveying software machine parameters/accessories, text 1146F conveying hardware accessories, graphical indicators 1144F indicating the radiotherapy machine parameters (including the position of the couch in the treatment room compared to a predetermined satisfactory position for treatment of the couch and one or more suggested adjustments based on the comparison), interactive button 1143F initiating a dry run (either a physical dry run or a virtual dry run as discussed herein), and interactive button 1142F initiating one or more preset positions of the couch and/or gantry, as described similarly to the graphical elements in FIGS. 4A-4P. Additionally, or alternatively, the analytics server may display a representation of the patient (e.g., two-dimensional/three-dimensional images of the patient and/or the patient and the couch).

Similarly, page 1100g may include graphical elements 1145G (an alternate representation of 1145F) displaying a three-dimensional representation (e.g., animation) representing the radiotherapy machine and/or patient, graphical indicator 1147G (in conjunction with status indicators) representing more than one safety feature associated with the treatment room and/or console room, graphical indicator 1140G (an alternate representation of 1140F) indicating the projected beam spread from the collimator and/or the type of beam, text 1146G (an alternate representation of 1146F) conveying hardware accessories, graphical indicators 1144G (an alternate representation of 1145F) indicating the radiotherapy machine parameters (including the position of the couch in the treatment room compared to a satisfactory position for treatment of the couch and one or more suggested adjustments based on the comparison), and interactive button 1142G initiating one or more preset positions of the couch and/or gantry, as described similarly to the graphical elements in FIGS. 4A-4P.

At step 1106, the analytics server displays Stage Three, which represents the stage related to imaging the patient based on the patient in a position for treatment from step 1105. Stage Three may include image acquisition (e.g., pages 1100h, 1100i, 1100k displayed in FIGS. 11H, 11I, 11K) and image matching (e.g., page 1100j displayed in FIG. 11J). The image matching may be similar in structure and operation to a procedure for determining whether a patient's internal organs are properly aligned for treatment (e.g., FIGS. 12A-12B).

Pages 1100h-1100k (Stage Three, Image) displayed in FIGS. 11H-11K illustrate the pages associated with preparing to capture and capturing an image of the patient. For instance, the analytics server may prepare to capture an x-ray image, a CT scan, a four-dimensional CT scan, fluoroscopy images and the like. The pages 1100h-1100k may use the same (or similar) graphical elements as discussed herein. For example, graphical elements displayed by the analytics server may include graphical indicators, status indicators, progress indicators, treatment related images, non-treatment related images, backgrounds, live feeds of the radiotherapy machine, and notes as discussed herein.

For instance, page 1100h may include graphical elements 1112H, including both non-treatment related images and text that convey PII, text 1113E conveying the current time, text 1114H indicating one or more areas of the patient requiring treatment, progress indicator 1122H indicating the progress of the user in the treatment room (e.g., highlighting the current stage and displaying the succeeding/preceding stages), 1145H displaying a three-dimensional representation (e.g., animation) representing the radiotherapy machine, graphical indicator 1147H (in conjunction with status indicators) representing more than one safety feature associated with the treatment room and/or console room, graphical indicator 1140H indicating the projected beam spread from the collimator and/or the type of beam, text 1141H conveying software machine parameters and/or accessories, text 1146H conveying hardware accessories, graphical indicators 1144H indicating the radiotherapy machine parameters (including the position of the gantry and/or couch in the treatment room compared to a satisfactory position for treatment of the gantry and/or couch and one or more suggested adjustments based on the comparison), interactive button 1143H initiating a dry run (either a physical dry run or a virtual dry run as discussed herein), and interactive button 1142H initiating one or more preset positions of the couch and/or gantry, as described similarly to the graphical elements in FIGS. 4A-4P.

Additionally, or alternatively, the analytics server may display text 1150H indicating one or imaging techniques. For instance, cone-beam computed tomography (CBCT), may be employed by the radiotherapy machine to capture images of the patient. A user may select an imaging technique for the patient. Additionally, or alternatively, the imaging technique may be predetermined by a user and/or system administrator. The analytics server may also display graphical indicator 1153H indicating a type of fan scan. For instance, half fan or full fan scan types may be employed by the radiotherapy machine. A user may select the fan type for the patient. Additionally, or alternatively, the fan type may be predetermined by a user and/or system administrator. As shown, the type of fan is indicated using the indicator itself. For instance, in the event a half fan was to be employed by the radiotherapy machine, the graphical indicator 1153H may be a half-circle around a representation of the patient.

Text 1154H may convey an area of the patient's body (e.g., using a representation of the patient such as a live view feed and/or a three-dimensional animation) to be captured using the imaging technique. Text 1151 may convey the size of the patient. A user may select and/or input the size of the patient to the analytics server. The analytics server may, based on the received size of the patient, determine various imaging parameters (for instance, the type of fan as shown in graphical indicator 1153H). The analytics server may receive a mapping of various patient sizes and various patient parameters. A user and/or system administrator may generate the map mapping the patient sizes to the patient parameters.

Similarly, page 1100i may include graphical elements graphical elements 1112I, including both non-treatment related images and text that convey PII, text 1113I conveying the current time, text 1114I indicating one or more areas of the patient requiring treatment, progress indicator 1122I indicating the progress of the user in the treatment room (e.g., highlighting the current stage and displaying the succeeding/preceding stages), 1145I (an alternate representation of 1145H) displaying a three-dimensional representation (e.g., animation) representing the radiotherapy machine, graphical indicator 1147I (in conjunction with status indicators) representing more than one safety feature associated with the treatment room and/or console room, graphical indicator 1140I (an alternate representation of 1140H) indicating the projected beam spread from the collimator and/or the type of beam, text 1146I (an alternate representation of 1146H) conveying hardware accessories, graphical indicators 1144I (an alternate representation of 1145H) indicating the radiotherapy machine parameters (including the position of the gantry and/or couch in the treatment room compared to a satisfactory position for treatment of the gantry and/or couch and one or more suggested adjustments based on the comparison), and interactive button 1142I initiating one or more preset positions of the couch and/or gantry, as described similarly to the graphical elements in FIGS. 4A-4P.

Additionally, or alternatively, the analytics server may display text 1158I to convey an imaging schedule for the patient. For instance, various days of the week may be associated with various imaging techniques. It may be beneficial to schedule the imaging techniques because it may be beneficial to keep track of and/or record the patient's radiation intake (for instance, including the radiation the patient receives as part of the imaging performed during the treatment setup) As shown, Monday is mapped to CBCT imaging, Tuesday is mapped to kilo voltage (kv) imaging, Wednesday is mapped to CBCT imaging, Thursday is mapped to kv and Friday is mapped to CBCT imaging. A user may determine the imaging schedule. The imaging schedule may vary from week to week.

Graphical indicator 1153I may be an alternate embodiment of graphical indicator 1153H. Graphical indicator 1153I may indicate the type of fan. The selected fan type may appear visually distinguished from the one or more other fan types. As disclosed herein, visually distinguished may include identifying graphical indicator 1153I using a color, texture, shine, opacity, pattern, and the like. As shown, a full fan is selected for imaging the patient. Graphical indicator 1151I be an alternate embodiment of text 1151I1. Graphical indicator 1153I may be used by a user to select the size of the patient. As shown, the user may slide a scale based on the appearance of the patient. As discussed herein, the analytics server may modify the imaging parameters based on the selected size of the patient. Additionally, or alternatively, a user may set the imaging parameters in addition to selecting the size of the patient. Text 1154I be an alternate embodiment of text 1154H. Text 1154I may convey an area of the patient's body to be captured using the imaging technique.

Additionally, or alternatively, the analytics server may display on pages 1100h-1100i a planned image acquisition. The analytics server may also overlay the image acquisition on the representation of the patient, a topogram, and the like.

Page 1100j may convey the imaging information received by the analytics server according to one or more appropriate methods of imaging internal organs (e.g., x-ray, CT scan, and the like). For instance, page 1100j may include graphical elements 1112J, including both non-treatment related images, treatment related images, and text that convey PII, text 1113J conveying the current time, text 1114J indicating one or more areas of the patient requiring treatment, treatment related image 1161J, 1165J and 1166J displaying and overlaying one or more instances of reference images and acquired images of a target organ from different angles, graphical indicators 1167J, 1168J, and 1169J characterizing internal organ misalignment in different axes and directions, graphical indicators, graphical indicators 1176J, 1175J, 1174J, 1173J and 1172J displaying various tools that a user may interact with to adjust, evaluate, and align the image of the target organ, interactive button 1171J to retake an image, and interactive button 1170J accepting an alignment displayed by the analytics server, as described similarly to the graphical elements in FIGS. 12A-12B. Page 1100k may be an alternate embodiment of page 1100i. For instance page 1100k may include graphical elements graphical elements 1112K, including both non-treatment related images and text that convey PII, text 1113K conveying the current time, text 1114K indicating one or more areas of the patient requiring treatment, progress indicator 1122K indicating the progress of the user in the treatment room (e.g., highlighting the current stage and displaying the succeeding/preceding stages), 1145K (an alternate representation of 1145I) displaying a three-dimensional representation (e.g., animation) representing the radiotherapy machine, graphical indicator 1147K (in conjunction with status indicators) representing more than one safety feature associated with the treatment room and/or console room, graphical indicator 1140K (an alternate representation of 1140I) indicating the projected beam spread from the collimator and/or the type of beam, text 1146K (an alternate representation of 1146I) conveying hardware accessories, graphical indicators 1144K (an alternate representation of 1145I) indicating the radiotherapy machine parameters (including the position of the gantry and/or couch in the treatment room compared to a satisfactory position for treatment of the gantry and/or couch and one or more suggested adjustments based on the comparison), and interactive button 1142K initiating one or more preset positions of the couch and/or gantry, as described similarly to the graphical elements in FIGS. 4A-4P.

Additionally, or alternatively, the analytics server may display the graphical indicators 1177K indicating a schedule of treatment. Each indicator may have a corresponding text that identifies different field geometry necessary to conduct the patient's treatment. In some embodiment, the patient's treatment may be performed in different segments where each segment requires different treatment attributes (e.g., alignment angles or field geometry). Each indicator within the graphical indicators 1177K may correspond to each segment of the patient's treatment. For instance, text 1177K may include the area of the body to be treated, the treatment type used, the treatment attribute (e.g., intensity), the gantry and/or couch positions for satisfactory images, and the like. For instance, 1177K may include text 1182K indicating a first field geometry of the patient's treatment and its corresponding attribute (e.g., treatment data).

The analytics server may also display other field geometries (e.g., 1178K and 1179K). As depicted, when the end user (medical professional) selects a particular field geometry or treatment segment, the analytics server may dynamically revise the 1100k and display data corresponding to that particular field geometry. For instance, as depicted, the medical professional has selected the text 1182K and the other features described within the GUI 1100k may correspond to the text 1182K.

At step 1107, the analytics server displays Stage Four, which represents the stage related to treatment (e.g., when the radiotherapy machine is actively radiating target areas of the patient). The user may monitor the patient by the analytics server capturing data from one or more cameras in the treatment room (e.g., as described in FIGS. 2A-2F) and displaying a form of the captured data on one or more screens on the console. At any moment during treatment, a user may pause treatment using, for example, the dedicated keyboard. In response to receiving an input to pause the treatment, the analytics server may turn off the radiotherapy machine such that the radiotherapy machine is not actively radiating target areas of the patient.

Page 1100l (Stage Four, Treat) displayed in FIG. 11L illustrates the page associated with treatment. The page 1100l may use the same (or similar) graphical elements as discussed herein. For example, graphical elements displayed by the analytics server may include graphical indicators, status indicators, progress indicators, treatment related images, non-treatment related images, backgrounds, live feeds of the radiotherapy machine, and notes as discussed herein For instance, page 1100l may include graphical elements 1112L, including both non-treatment related images and text that convey PII, text 1113L conveying the current time, and the text 1114L indicating one or more areas of the patient requiring treatment. The page 1100l may also include the progress indicator 1122L indicating the progress of the user in the treatment room (e.g., highlighting the current stage and displaying the succeeding/preceding stages), 1145L displaying a three-dimensional representation (e.g., animation) representing the radiotherapy machine, and the graphical indicator 1147L (in conjunction with status indicators) representing more than one safety feature associated with the treatment room and/or console room. The page 1100*l* may also include the graphical indicator 1140L indicating the projected beam spread from the collimator and/or the type of beam. The page 1100*l* may also include accessory information (11140L).

The page 1100*l* may also include the graphical indicator 1140L indicating the projected beam spread from the collimator and/or the type of the beam being used. "Beam spread," as used herein may refer to any complete irradiated area outline. The shape depicted in the graphical indicator 1140L (and similar indicators, such as 1140G, 1140H, 1140I, and 1140K) may correspond to an opening of the collimator that forms the beam/radiation used for the patient's treatment. The opening (e.g., sometimes referred to as the "jaw opening") may be adjusted by the medical professional depending on the target organ (e.g., size of the tumor) and the shape depicted in the graphical indicator 1140L may correspond to the shape of the opening of the collimator. The medical professional may use the graphical indicator to monitor the jaw opening shape and determine whether the shape of the jaw opening is correct (e.g., matches predetermined attributes of the patient's treatment).

The page 1100*l* may also include text 1141L conveying software machine parameters, text 1146L conveying hardware accessories, graphical indicators 1144L indicating the radiotherapy machine parameters (including the position of the gantry and/or couch in the treatment room compared to a satisfactory position for treatment of the gantry and/or couch and one or more suggested adjustments based on the comparison), interactive button 1143L initiating a dry run (either a physical dry run or a virtual dry run as discussed herein), and interactive button 1142L initiating one or more preset positions of the couch and/or gantry, as described similarly to the graphical elements in FIGS. 4A-4P.

Additionally, or alternatively, the analytics server may display text 1180L conveying various one or more labeled fields of radiation employed by the radiotherapy machine during treatment. Text 1180L may additionally, or alternatively convey the intensity of the radiation, the gantry position, and the couch position. Text 1181L may emphasize the field of radiation that may be actively employed to treat the patient. Text 1181L may be visually distinct (e.g., highlighted) from the text 1180L to better to convey to a user the radiation that is actively treating the patient. As shown, the MU counter indicates the radiation treating the patient.

At step 1108, the analytics server displays Stage Five, which represents the stage related to unloading the patient from the radiotherapy machine. Stage Five of the console workflow (e.g., step 1108 in FIG. 11B) may be similar in structure and operation to Stage Five of the treatment room workflow (e.g., step 419 in FIG. 4B).

Page 1100*m* (Stage Five, Unload, as depicted by "unload" graphical element 1112M) displayed in FIG. 11M illustrates the page associated with unloading the patient. The page 1100*m* may use the same (or similar) graphical elements as discussed herein. For example, graphical elements displayed by the analytics server may include graphical indicators, status indicators, progress indicators, treatment related images, non-treatment related images, backgrounds, live feeds of the radiotherapy machine, and notes as discussed herein For instance, page 1100*m* may include text 1114M indicating one or more areas of the patient requiring treatment, progress indicator 1122M indicating the progress of the user in the treatment room (e.g., highlighting the current step and displaying the previous steps) text 1113M conveying the current time, and text 1110M conveying the date. The page 1100*m* may also include the graphical indicator 1185M conveying the number of remaining radiotherapy treatments for one or more diagnosed areas of the body, and text 1186M conveying information about the patient's upcoming medical appointments, as described similarly to the graphical elements in FIGS. 4A-4P.

Additionally, or alternatively, the analytics server may display text 1187M displaying billing information. For instance, the analytics server may record the occurrence of several predetermined billing items and display on page 1100*m* the recorded billing items. For example, in the event the analytics server captures an image of the patient using the imager, the analytics server may raise a flag associated with the images. Upon completion of the treatment of the patient, the analytics server may tally the raised flags associated with images.

Additionally, or alternatively, the billing information may be predetermined by a user and/or system administrator. For instance, a user may determine that two medical images will be captured throughout the scheduled treatment of the patient. The billing information may include bills that have been accumulated during the recently completed (scheduled) radiotherapy treatment. Additionally, or alternatively, the billing information may include bills that have been unpaid from previous one or more radiotherapy treatment sessions using radiotherapy machines. The billing information may include a number of images captured, a number of treatments performed, the dates of the images captures, the dates of the treatments performed, the cost of the images captured, the cost of the treatments performed, a total cost, and the like.

Additionally, or alternatively, the analytics server may display radiotherapy machine parameters (e.g., the position of the couch), machine alignment parameters (e.g., position of the gantry and/or collimator), and the like.

Alignment Page

Figure 12A:
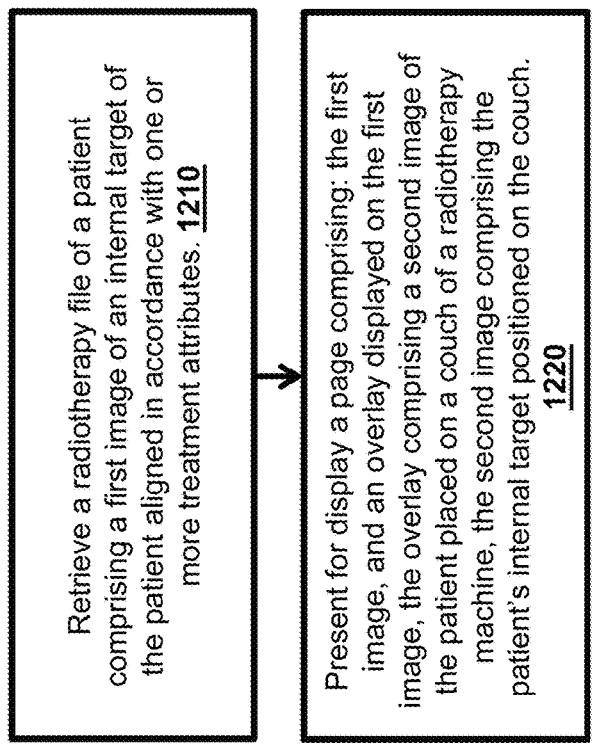
FIG. 12A illustrates a flow diagram executed in a workflow-oriented radiotherapy system, according to an embodiment.
Figure 12B:
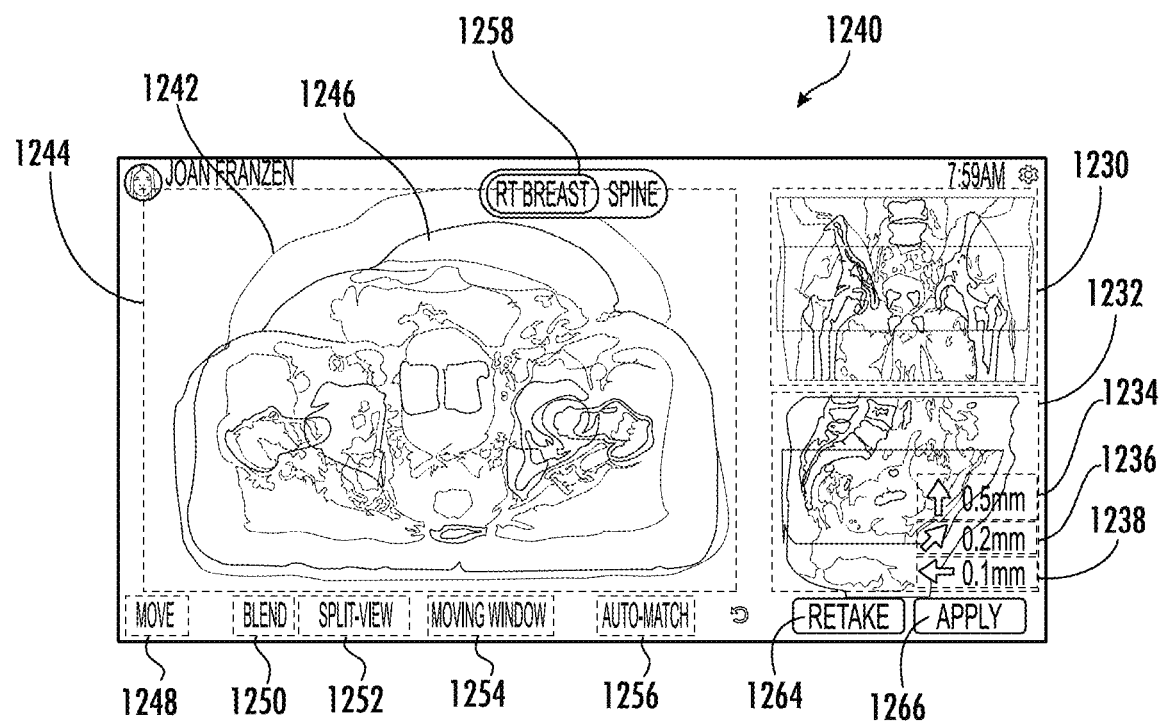
FIG. 12B illustrates a page displayed in a workflow-oriented radiotherapy system, according to an embodiment.

As discussed above, the analytics server may identify one or more alignment attributes (e.g., alignment angles, dimensions, magnitudes, and/or surfaces for the patient) associated with the patient and the patient's treatment. The alignment angles may indicate the patient's optimum alignment/position on the couch, such that the effects of the radiotherapy machine (e.g., radiation emitted from the gantry) is optimized. Using the alignment information provided by the analytics server, such as by displaying on the workflow-oriented series of pages described herein, the technician may align the patient's body on the couch. However, the alignment angles only indicate an optimum alignment angle for the patient's extremities and not interior organs. For instance, the alignment angle may indicate that the patient's arm must be moved to the left by a predetermined amount/magnitude in a particular direction (e.g., angle). However, the alignment angles do not identify, and the technician may be unable to determine whether the patient's target organs receiving the radiations are positioned to receive optimal treatment. To rectify this problem, the analytics server may execute the method 1200 and display on the GUI a page 1240, as depicted in FIGS. 12A-B.

The method 1200 is not limited to identifying internal positioning of target organs. The method 1200 may also be applicable to mutual position of the target organ and the other organs (sometimes referred to as organs at risk or OARs). The organs at risk may be organs near the target organ that may inevitably receive radiation when the target organs receives radiation. Using the method 1200 and the GUIs described herein, the user may evaluate how the organs at risk are positioned, such that these organs at risk receive minimal radiation during the patient's treatment. In a non-limiting example, the method 1200 and the GUIs described herein can be used, such that the patient is realigned based on the alignment of his/her organs at risk that are near his/her target organ. Therefore, the method 1200 is applicable to any internal target of the patient (e.g., target organ and other targets).

As used herein, the method 1200 and the page 1240 are described in the context of analyzing and displaying images. It is intended that images includes any medical images received that represents the patient's organs using any medical imaging techniques and protocols, such as x-ray, CT scan, 4D CT scan, fluoroscopy imaging, ultrasound, and the like.

The page 1240 may be a part of a stage-by-stage or workflow-oriented series of pages. For instance, the analytics server may display the page 1240 as a part of the workflow-oriented series of pages described herein. In a non-limiting example, the analytics server may display the page 1240 after the patient's body has been aligned using the alignment angles (e.g., set up stage), such that a technician or any other medical professional operating the console monitors may determine whether the patient's internal organs are properly aligned for treatment. That is, the analytics server may compare the presentation of the target organ (e.g., image of the target organ) with optimal treatment orientation determined by other medical professionals (e.g., treating oncologist).

In other non-limiting examples, the page 1240 may be displayed after the technician has completed the workflow and before the patient's treatment is commenced. For instance, a technician may use the workflow-oriented series of pages described herein (displayed in the treatment room) and may leave the treatment room before the radiotherapy machine starts treatment. However, before the treatment has begun, the technician (or another medical professional) operating the console monitors placed in a different room may be required to confirm the patient's alignment. Therefore, the console monitors may display the page 1240 and the technician or the other medical professional may confirm that the patient is aligned properly or delay the treatment to realign the patient. When the page 1240 is displayed as a part of a workflow-oriented series of pages, the workflow may not proceed to a subsequent stage (e.g., radiation therapy) unless the patient's internal organs (target organ and/or OARs) are aligned within an acceptable tolerance (error threshold).

Due to the hazardous nature of medical imaging, the analytics server may ensure that the imager of the radiotherapy machine does not operate while the technician is still in the treatment room. Therefore, the display of the page 1240 may be delayed, such that the technician has left the treatment room and the image can operate, at which time the analytics server received the image from the imager and displays the page 1240.

In some embodiments, the page 1240 may be displayed on one or both of the console monitors as a standalone page. For instance, the page 1240 may not be a part of the workflow-oriented series of pages. For instance, a medical professional operating the console monitor, screen of the radiotherapy machine, or any other electronic device configured to display the pages described herein (e.g., physician device or an administrative device) may view the page 1240 to confirm that the patient's internal organs are aligned properly. Medical professionals may access and view the page 1240 any time before the treatment has begun.

Additionally, or alternatively, the analytics server may capture images of the target organ and/or the organs at risk during the treatment or during any period of the workflow described herein. These captured images may be subsequently reviewed by other medical professionals after the treatment of the patient.

Referring now to FIG. 12A, at step 1210, the analytics server may retrieve, from a radiotherapy file of a patient, a first image of an internal target of the patient aligned in accordance with one or more treatment attributes. The analytics server may retrieve a RT file of the patient that includes a first image of a target organ aligned in accordance with one or more treatment attributes. As discussed herein, RT file may include various treatment attributes including machine attributes and patient alignments to provide an optimum radiotherapy treatment to the patient. Among other things described herein, the RT file may include various alignment data indicating orientation attributes of a target organ (e.g., the organ receiving treatment) or organs at risk (OARs). The RT file may also include an image of the target organ properly aligned to receive treatment.

In some embodiments, the analytics server may retrieve alignment data from other electronic data sources. For instance, the analytics server may query one or more databases and/or electronic devices (e.g., physician electronic device) to identify one or more alignment attributes/angles. In some configurations, the RT file may not include an image. Therefore, the analytics server either may retrieve the image from a different data source or may execute a protocol that generates an image resembling an image of the target organ aligned properly for treatment.

At step 1220, the analytics server may receive a second image of the internal target of the patient on a couch of a radiotherapy machine. The analytics server may then overlay, on a first page of the plurality of pages, the first image and the second image, wherein the first page displays a direction to position the internal target in the second image to align with the internal target in the first image. Moreover, when the when the internal target is aligned, presenting, by the server, a second page of the plurality of pages corresponding to a subsequent stage of the radiotherapy treatment for the patient.

The analytics server may present a page comprising the first image, and an overlay displayed on the first image. The overlay may comprise a second image (or a series/sequence of images, such as fluoroscopy, triggered imaging, and/or 4DCT) of the patient placed on the couch of a radiotherapy machine, the second image comprising the patient's target organ and/or OARs. The analytics server may display a page that includes the first image of the patient's target organ overlaid by a second image displaying the patient's target organ as currently positioned on the couch. The technician or any other medical professional operating and viewing the page may use the two images to identify any discrepancies. For instance, the technician may visually inspect misalignments (e.g., alignment differences) between the patient's internal organ at its current position and the patient's internal organ as required by the treating physician.

As discussed above, the GUIs described herein are not limited to displaying target organs. For instance, in alternative embodiments, the analytics server may display other organs (e.g., organs at risk) in addition to or instead of the target organ.

Referring to FIG. 12B, the analytics server may display a GUI having page 1240. The page 1240 may include various graphical indicators and features each interactive and configured to allow the user to customize the page 1240. As described above, the analytics server may visually represent misalignments of the patient's interior organs such that these misalignments are easily identifiable to the technician or any other medical professional viewing the page 1240. The page 1240 may include the graphical indicator 1258 displaying treatment regions and/or organs associated with the patient's treatment. If the patient is receiving treatment on more than one treatment sites, the analytics server may display the toggle 1258, such that the user can switch between different target organs. For instance, as depicted, the analytics server identifies that the patient is receiving radiotherapy on the patient's right breast and spine. As a result, the analytics server displays the toggle 1258 indicating each treatment organ. The embodiment depicted in page 1240 displays the patient's anatomy (e.g., spine or any other organ dictated/requested by the user).

The analytics server may capture a separate image (e.g., at a different couch position) to show each treatment site alignment. Alternatively, the workflow of FIG. 11 may be repeated for each treatment site. The analytics server may align several organs identified in one set of images and then allow an analysis of the overall patient alignment based on the individual organ alignments. Therefore, there could be different "views" of one image pair to review generated at each treatment site.

The page 1240 includes three main regions, though any configuration may be utilized. The graphical components 1244, 1230, 1232 each display and overlays one or more instances of reference images and acquired images (e.g., x-ray images, 2D x-ray images or 2D images reconstructed from 3D (or 4D) x-ray image (or CT images)) of the selected target organ. For instance, the graphical component 1244 displays cross-sectional images of the patient's anatomy, the graphical component 1230 displays front view images of the patient's anatomy, and the graphical component 1232 displays a side view images of the patient's anatomy. In some configurations, the patient's target organ may have dimensionality, such that showing the entire target organ may be inefficient and/or unnecessary. For instance, spinal treatments may be limited to a particular area of the patient's anatomy. In those embodiments, and as depicted in the page 1240, the analytics server may only display an image corresponding to the portion of the target organ to be treated. For instance, as depicted in the graphical components 1230, 1232, the analytics server may display only the relevant portions of the patient's anatomy.

The analytics server may display these graphical components in the same page. As depicted, the page 1240 includes the graphical components 1234, 1230, 1232 where the graphical component 1244 is larger than the graphical components 1230, 1234. However, this configuration may be changed such that another graphical component is larger or they are all displayed as the same size. In some configurations, the user may instruct the analytics server to only show one graphical component (e.g., images of one area or one view) at a time.

Each image displayed in the page 1240 may be one of the first image (e.g., a medical image of the patient's target organ aligned properly, a reference image) and second image (e.g., current target organ, an acquired image) discussed above. For instance, the analytics server may retrieve the first image from the patient's RT file. The analytics server may then instruct one or more imaging devices operatively in communication with the analytics server to generate an image of the patient's target organ. For instance, the analytics server may transmit an instruction to the radiotherapy machine to generate an image of the patient (or a particular region of the patient). As a result, one or more imaging devices associated or otherwise in communication with the radiotherapy machine may generate an image of the patient (in his/her current position) and transmit the image to be displayed on the page 1240. Therefore, the second image, as used herein, refers to the target organs current and "actual" position before shifting to the optimized position for treatment.

In some embodiments, the analytics server may instruct the imaging apparatus to generate periodic images of the patient. For instance, the analytics server may transmit an instruction to medical imaging machine attached or otherwise in communication with a radiotherapy machine to generate real-time or near real-time images of the patient, such that the user viewing the page 1240 can have the latest image associated with the patient's target organ. That is, the analytics server may update the second image in real time or near real time.

The analytics server may display the first or the second image as an overlay. For instance, the images displayed within the graphical component 1244 may include the first image 1242 and the second image 1246. The analytics server may overlay (superimpose) the first image 1242 and the second image 1246, such that the viewer can visually identify misalignments and differences between features of each image. For instance, the viewer can identify that a region of the patient's interior (from the second image representing the patient's current position) does not align with the same region as indicated within the first image (e.g., representing the how the patient should be positioned).

The analytics server may also display graphical indicators 1234, 1236, 1238 that represent quantity of misalignment in different axes and directions. For instance, the graphical indicator 1234 indicates that the target organ should be moved 0.5 mm in the direction identified by its corresponding arrow (upward direction). The graphical indicator 1236 indicates that the target organ should be moved 0.2 millimeters in the direction identified by its corresponding arrow (upwards and to the right). The graphical indicator 1238 indicates that the target organ should be moved 0.1 mm in the direction indicated by its corresponding arrow (left).

The end-user may use the tools indicated by graphical indicators 1248-1256 to revise and modify the target organ's alignment (by moving re-aligning the patient on the couch). In order to better identify misalignments, the end-user may move each image using the graphical indicator 1248 or blend the images using the graphical indicator 1250. The end-user may also split the images using the graphical indicator 1252, such that each image is separated and displayed independently.

The graphical indicator 1254 may refer to another tool for reviewing the images. Using the graphical indicator 1254, the user may resize and/or move a crop of one image over anther image.

In some embodiments, the user may instruct the analytics server to automatically match the first image and the second image such that misalignments are visually distinct, as depicted in the graphical component 1244. The user may accomplish this task by interacting with the graphical indicator 1256.

The end-user may also interact with the graphical indicator 1264 to retake the second image. When a discrepancy or misalignment is identified, the user may use his/her judgment and/or the graphical indicators 1234-1238 to realign the patient (or instruct the patient to be realigned).

For instance, the user viewing the page 1240 may instruct the patient to move in a direction that would align his/her target organ closer to the alignment depicted in the first image. The user may then generate a new second image of the patient's new position on the couch using the graphical indicator 1264. The user may then reassess the patient's re-oriented target organ using the newly generated second image. The user may repeat this process until the user is satisfied with the alignment of the patient's target organ with the target predetermined organs alignment (e.g., first image). In some embodiments, if the user cannot visually identify misalignments, the user may interact with the graphical component 1256 where the analytics server identifies and highlights small misalignments.

When the user is satisfied with the alignment of the patient's target organs, the user may interact with the graphical indicator 1266 to accept the alignment (e.g., patient's current position/alignment on the couch). If the page 1240 is displayed as a part of a workflow-oriented series of pages, the analytics server may move to the next stage. The analytics server may also transmit a prompt to one or more computing devices. For example, the analytics server may notify the page displayed on the radiotherapy machine, physician device, or any other electronic device discussed in FIG. 1A. The user may also use the graphical indicator 1266 to overwrite results displayed in the page 1240. For instance, if the end-user visually identifies misalignments, the end-user may overwrite the misalignment by interacting with the graphical component 1266.

The foregoing method descriptions and the process flow diagrams are provided merely as illustrative examples and are not intended to require or imply that the steps of the various embodiments must be performed in the order presented. The steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, and the like. When a process corresponds to a function, the process termination may correspond to a return of the function to a calling function or a main function.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:
1. A method comprising:
   retrieving, by one or more servers, a radiotherapy file associated with a patient, the radiotherapy file comprising information associated with one or more acces- sories associated with the patient's radiation therapy treatment, the one or more accessories corresponding to one or more objects to be used during the patient's radiotherapy treatment;

presenting, by one or more servers, for display on the graphical user interface, a graphical indicator corresponding to each of the one or more accessories;

scanning, by one or more servers, a set of accessories within a predetermined proximity to the radiotherapy machine within a treatment room; and when the server does not detect one or more of the one or more accessories in proximity to the radiotherapy machine or when one or more of the one or more accessories is not within a predetermined location, revising, by one or more servers, the graphical indicator corresponding to that accessory.

2. The method of claim 1, wherein the one or more servers receives an input corresponding to a value of the predetermined proximity.

3. The method of claim 1, wherein revising the graphical indicator corresponding to the accessory comprises changing a color of the graphical indicator corresponding to the accessory.

4. The method of claim 1, wherein revising the graphical indicator corresponding to the accessory comprises changing a shape of the graphical indicator corresponding to the accessory.

5. The method of claim 1, wherein revising the graphical indicator corresponding to the accessory comprises displaying, by the server, an additional graphical indicator associated with the graphical indicator corresponding to the accessory.

6. The method of claim 1, wherein the graphical user interface is displayed on a screen on a gantry of the radiotherapy machine.

7. The method of claim 1, wherein scanning, by one or more servers, the set of accessories within the predetermined proximity to the radiotherapy machine comprises scanning a radio frequency identification tag associated with each accessory.

8. The method of claim 1, wherein scanning, by one or more servers, the set of accessories within the predetermined proximity to the radiotherapy machine comprises scanning a visual tag associated with each accessory.

9. The method of claim 1, further comprising presenting, by the one or more servers, for display a status of each of the one or more accessories associated with the patient's radiation therapy treatment.

10. The method of claim 1, wherein the graphical user interface is displayed on a console computer associated with the radiotherapy machine.

11. A system comprising:
one or more servers comprising a processor and a non-transitory computer-readable medium containing instructions that when executed by the processor causes the processor to perform operations comprising:

retrieve a radiotherapy file associated with a patient, the radiotherapy file comprising information associated with one or more accessories associated with the patient's radiation therapy treatment, the one or more accessories corresponding to one or more objects to be used during the patient's radiotherapy treatment;

present for display on the graphical user interface, a graphical indicator corresponding to the each of the one or more accessories;

scan a set of accessories within a predetermined proximity to the radiotherapy machine within a treatment room; and when the server does not detect one or more of the one or more accessories in proximity to the radiotherapy machine or when one or more of the one or more accessories is not within a predetermined location, revise the graphical indicator corresponding to that accessory.

12. The system of claim 11, wherein the one or more servers receives an input corresponding to a value of the predetermined proximity.

13. The system of claim 11, wherein revising the graphical indicator corresponding to the accessory comprises changing a color of the graphical indicator corresponding to the accessory.

14. The system of claim 11, wherein revising the graphical indicator corresponding to the accessory comprises changing a shape of the graphical indicator corresponding to the accessory.

15. The system of claim 11, wherein revising the graphical indicator corresponding to the accessory comprises displaying, by the one or more servers, an additional graphical indicator associated with the graphical indicator corresponding to the accessory.

16. The system of claim 11, wherein the graphical user interface is displayed on a screen on a gantry of the radiotherapy machine.

17. The system of claim 11, wherein scanning the set of accessories within the predetermined proximity to the radiotherapy machine comprises scanning a radio frequency identification tag associated with each accessory.

18. The system of claim 11, wherein scanning the set of accessories within the predetermined proximity to the radiotherapy machine comprises scanning a visual tag associated with each accessory.

19. The system of claim 11, wherein the one or more servers presents for display a status of each of the one or more accessories associated with the patient's radiation therapy treatment.

20. The system of claim 11, wherein the graphical user interface is displayed on a console computer associated with the radiotherapy machine.

* * * * *